US011959141B2

(12) United States Patent
Otto et al.

(10) Patent No.: US 11,959,141 B2
(45) Date of Patent: Apr. 16, 2024

(54) MULTIGENE ANALYSIS OF TUMOR SAMPLES

(71) Applicant: FOUNDATION MEDICINE, INC., Cambridge, MA (US)

(72) Inventors: Geoffrey Alan Otto, Cambridge, MA (US); Michelle Nahas, Cambridge, MA (US); Doron Lipson, Cambridge, MA (US)

(73) Assignee: Foundation Medicine, Inc., Boston, MA (US)

( * ) Notice: Subject to any disclaimer, the term of this patent is extended or adjusted under 35 U.S.C. 154(b) by 526 days.

(21) Appl. No.: 15/529,237

(22) PCT Filed: Dec. 4, 2015

(86) PCT No.: PCT/US2015/064044
§ 371 (c)(1),
(2) Date: May 24, 2017

(87) PCT Pub. No.: WO2016/090273
PCT Pub. Date: Jun. 9, 2016

(65) Prior Publication Data
US 2017/0356053 A1  Dec. 14, 2017

Related U.S. Application Data

(60) Provisional application No. 62/088,457, filed on Dec. 5, 2014.

(51) Int. Cl.
*C12Q 1/68* (2018.01)
*C12N 15/10* (2006.01)
*C12Q 1/6806* (2018.01)
*C12Q 1/6886* (2018.01)
*G16B 25/00* (2019.01)
*G16B 25/10* (2019.01)
*G16B 30/00* (2019.01)
*G16B 30/10* (2019.01)
*G16B 45/00* (2019.01)

(52) U.S. Cl.
CPC ....... *C12Q 1/6886* (2013.01); *C12N 15/1065* (2013.01); *C12Q 1/6806* (2013.01); *G16B 25/00* (2019.02); *G16B 25/10* (2019.02); *G16B 30/00* (2019.02); *G16B 30/10* (2019.02); *G16B 45/00* (2019.02); *C12Q 2600/156* (2013.01); *C12Q 2600/158* (2013.01); *C12Q 2600/16* (2013.01)

(58) Field of Classification Search
CPC ............... C12Q 1/6886; C12Q 1/6806; C12Q 2600/156; C12Q 2535/122; C12Q 2537/159; C12Q 2563/131; C12N 15/1065
See application file for complete search history.

(56) References Cited

U.S. PATENT DOCUMENTS

| | | | |
|---|---|---|---|
| 7,244,567 B2 | 7/2007 | Chen et al. | |
| 7,381,526 B2 | 6/2008 | Polansky | |
| 9,340,830 B2 | 5/2016 | Lipson et al. | |
| 9,598,731 B2 | 3/2017 | Talasaz | |
| 9,792,403 B2 | 10/2017 | Sun et al. | |
| 9,834,822 B2 | 12/2017 | Talasaz | |
| 9,840,743 B2 | 12/2017 | Talasaz | |
| 9,850,523 B1 | 12/2017 | Chudova et al. | |
| 9,902,992 B2 | 2/2018 | Talasaz et al. | |
| 9,920,366 B2 | 3/2018 | Eltoukhy et al. | |
| 10,041,127 B2 | 8/2018 | Talasaz | |
| 11,118,213 B2 | 9/2021 | Lipson et al. | |
| 11,136,619 B2 | 10/2021 | Lipson et al. | |
| 11,421,265 B2 | 8/2022 | Lipson et al. | |
| 2003/0134274 A1 | 7/2003 | Wood et al. | |
| 2005/0209787 A1 | 9/2005 | Waggener et al. | |
| 2006/0246497 A1 | 11/2006 | Huang et al. | |
| 2006/0275779 A1 | 12/2006 | Li et al. | |
| 2007/0087362 A1 | 4/2007 | Church et al. | |
| 2007/0194225 A1 | 8/2007 | Zorn | |
| 2008/0131887 A1 | 6/2008 | Stephan et al. | |
| 2009/0221438 A1 | 9/2009 | Kitzman et al. | |
| 2010/0029498 A1 | 2/2010 | Gnirke et al. | |
| 2010/0105052 A1 | 4/2010 | Drmanac et al. | |
| 2010/0216648 A1 | 8/2010 | Staehler et al. | |
| 2010/0286143 A1 | 11/2010 | Dias-Santagata et al. | |
| 2011/0236903 A1 | 9/2011 | McClelland et al. | |
| 2012/0208706 A1* | 8/2012 | Downing ............... | G16B 20/00 506/2 |
| 2013/0136799 A1* | 5/2013 | Faham ................. | C12Q 1/6883 424/577 |
| 2013/0338933 A1 | 12/2013 | Deciu et al. | |

(Continued)

FOREIGN PATENT DOCUMENTS

| | | |
|---|---|---|
| CN | 101619350 A | 1/2010 |
| JP | 2008017853 A | 1/2008 |

(Continued)

OTHER PUBLICATIONS

Ye, K., et al., "Pindel: A Pattern Growth Approach to Detect Break Points of Large Deletions and Medium Sized Insertions from Paired-End Short Reads," Bioinformatics, 25(21):2865-71 (2009).
Zerbino, D.R. and Birney, E., "Velvet: Algorithms for De Novo Short Read Assembly Using De Bruijn Graphs," Genome Res., 18:821-829 (2008).
Extended European Search Report for European Application No. 15866246.0, dated Sep. 28, 2018, 12 pages.
"Foundation Medicine and Collaborators to Present New Clinical Data on FoundationOne® and FoundationOne Heme at the 2014 ASCO Annual Meeting" Press Release dated May 14, 2014.

(Continued)

*Primary Examiner* — Sahana S Kaup
(74) *Attorney, Agent, or Firm* — MORRISON & FOERSTER LLP

(57) ABSTRACT

Methods of evaluating or providing a clonal profile of a subject interval, e.g., a subgenomic interval, or an expressed subgenomic interval (or of a cell containing the same), in a subject, are disclosed.

25 Claims, 7 Drawing Sheets

Specification includes a Sequence Listing.

(56) References Cited

U.S. PATENT DOCUMENTS

| | | | |
|---|---|---|---|
| 2014/0186848 A1* | 7/2014 | Robins | C12Q 1/6881 |
| | | | 435/6.12 |
| 2014/0272976 A1 | 9/2014 | Lee et al. | |
| 2014/0315725 A1* | 10/2014 | Faham | C12Q 1/6886 |
| | | | 506/2 |
| 2014/0336996 A1 | 11/2014 | Sun et al. | |
| 2016/0032396 A1 | 2/2016 | Diehn et al. | |
| 2019/0032118 A1 | 1/2019 | Lipson et al. | |
| 2019/0119733 A1 | 4/2019 | Lipson et al. | |
| 2019/0136301 A1 | 5/2019 | Lipson et al. | |
| 2020/0149097 A1 | 5/2020 | Otto et al. | |
| 2023/0148412 A1 | 5/2023 | Lipson et al. | |

FOREIGN PATENT DOCUMENTS

| | | | | |
|---|---|---|---|---|
| JP | 2013524849 A | 6/2013 | | |
| JP | 2014507133 A | 3/2014 | | |
| JP | 2018502563 A | 2/2018 | | |
| WO | 2009099602 A1 | 8/2009 | | |
| WO | 2010028098 A2 | 3/2010 | | |
| WO | WO-2010141955 A2 | 12/2010 | | |
| WO | 2011139371 A1 | 11/2011 | | |
| WO | WO-2011139371 A1 | 11/2011 | | |
| WO | 2012092426 A1 | 7/2012 | | |
| WO | WO-2012092426 A1 | 7/2012 | | |
| WO | WO-2013028817 A1 | 2/2013 | | |
| WO | 2013190441 A2 | 12/2013 | | |
| WO | 2014008447 A1 | 1/2014 | | |
| WO | WO-2014130975 A1 | 8/2014 | | |
| WO | 2014164486 A1 | 10/2014 | | |
| WO | 2014165785 A2 | 10/2014 | | |
| WO | WO-2014183078 A1 | 11/2014 | | |
| WO | WO-2015002908 A1 * | 1/2015 | | C12Q 1/686 |
| WO | WO-2015021080 A2 | 2/2015 | | |
| WO | WO-2016090273 A1 | 6/2016 | | |
| WO | WO-2017151524 A1 | 9/2017 | | |

OTHER PUBLICATIONS

"Foundation Medicine and Memorial Sloan-Kettering Cancer Center Announce Partnership to Advance Patient Care in Hematologic Cancers" Press Release dated May 2, 2013.
"Foundation Medicine Launches FoundationOne™ Heme, Developed in Collaboration with Memorial Sloan-Kettering Cancer Center" Press Release dated Dec. 7, 2013.
"FoundationOne™ Heme Enables Identification of Genomic Alterations Not Identified by Conventional Methods Across Hematologic Malignancies" Press Release dated Dec. 9, 2013.
"Novel and Previously Reported Genomic Alterations Identified in Clinical Multiple Myeloma Cases Using FoundationOne™ Heme" Press Release dated Dec. 10, 2013.
Albers, C.A., et al., "Dindel: Accurate Indel Calls from Short-Read Data," Genome Res. (Oct. 27, 2010) epub ahead of print.
Aslanidis and de Jong, "Ligation-Independent Cloning of PCR Products (LIC-PCR)," Nucleic Acids Res. 18:6069-6074 (1990).
Bazan, et al., "Specific Condon 13 K-ras Mutations are Predictive of Clinical Outcome in Colorectal Cancer Pateients, whereas Codon 12 K-ras Mutations are Associated with Mucinous Histotype", Annals. Oncol., 13(1438-1446, Especially p. 1440, col. 2 para. 1-2, Sep. 2002.
Berger, et al., "Integrative Analysis of the Melanoma Transcriptome," Genome Res., 20(4):413-427 (2010) (PMID 20179022).
Blumenstiel, B., et al., "Targeted Exon Sequencing by In-Solution Hybrid Selection," Curr. Protoc. Hum. Genet., Chapter 18.4, (2010).
Braggio et al. "Lessons from next-generation sequencing analysis in hematological malignancies" Blood Cancer Research (2013) vol. 3, e127, pp. 1-10.
Branton, D., et al., "The Potential and Challenges of Nanopore Sequencing," Nat. Biotechnol. 26(10):1146-1153 (2008).
Browning, B.L. and Yu, Z., "Simultaneous Genotype Calling and Haplotype Phasing Improves Genotype Accuracy and Reduces False-Positive Associations for Genome-Wide Association Studies," Am. J. Hum. Genet., 85(6):847-861 (2009).
Butler, J., et al., "ALLPATHS: De Novo Assemly of Whole-Genome Shotgun Microreads," Genome Res., 18:810-820 (2008).
Craig, David W., et al., "Identification of Genetic Variants Using Bar-Coded Multiplexed Sequencing", Nature Methods, 5(10), Oct. 1, 2008, pp. 887-893.
Dahl, Fredrik et al., "Multigene Amplification and Massively Parallel Sequencing for Cancer Mutation Discovery", Proceedings of the National Academy of Sciences, 104(22), May 29, 2007, pp. 9387-9392.
Ding, L., et al., "Analysis of Next-Generation Genomic Data in Cancer: Accomplishments and Challenges", Human Molecular Genetics, 19(R2), Sep. 15, 2010, pp. R188-R196.
Drilon et al. "Broad, Hybrid Capture-Based Next-Generation Sequencing Identifies Actionable Genomic Alternations in Lung Adenocarcinomas Otherwise Negative for Such Alterations by Other Genomic Testing Approaches" Clinical Cancer Research (2015) vol. 21 No. 16 pp. 3631-3639.
Edwards, J.R., et al., "Mass-Spectrometry DNA Sequencing," Mut. Res. 573(1-2):3-12 (2005).
Frampton et al. "Development and validation of a clinical cancer genomic profiling test based on massively parallel DNA sequencing" Nature Biotechnology (2013) vol. 31, No. 11, pp. 1023-1031.
Garber, et al., "Computational Methods for Transcriptome Annotation and Quantification Using RNA-seq," Nat. Methods. 8(6):469-477 (2011) (PMID21623353).
Gazzola et al. "The evolution of clonality testing in the diagnosis and monitoring of hematological malignancies" Therapeutic Advances in Hematology (2014) vol. 5, No. 2, pp. 35-47.
Georgiou et al "The promise and challenge of high-throughput sequencing of the antibody repertoire" Nature Biotechnology (2014) vol. 32, No. 2, pp. 158-168.
Gnirke, A., et al., "Solution Hybrid Selection with Ultra-long Oligonucleotides for Massively Parallel Targeted Sequencing," Nat. Biotechnol. 27(2):182-189 (2009).
Hanna, G.J., et al., "Comparison of Sequencing by Hybridization and Cycle Sequencing for Genotype of Human Immunodeficiency Virus Type 1 Reverse Transcriptase," J. Clin. Microbiol., 38(7):2715-21 (2000).
He et al. "Integrated genomic DNA/RNA profiling of hematologic malignancies in the clinical setting" Blood (2016) vol. 127, No. 24, pp. 3004-2014.
Hutchinson et al. "BRAF Fusions Define a Distinct Molecular Subset of Melanomas with Potential Sensitivity to MEK Inhibition" Clinical Cancer Research (2013) vol. 19 No. 24 pp. 6696-6702.
Mielinski et al., "Mapping the Hallmarks of Lung Adenocarcinoma with Massively Parallel Sequencing" Cell (2012) vol. 150 pp. 1107-1120.
International Search Report and Written Opinion for International Application No. PCT/US2015/064044 dated Apr. 8, 2016.
International Search Report for PCT/US11/67725 dated Apr. 27, 12.
Lavinder et al. "Next-generation sequencing and protein mass spectrometry for the comprehensive analysis of human cellular and serum antibody repertoires" Current Opinion in Chemical Biology (2015) vol. 24, pp. 112-120.
Le, S.Q. and Durbin, R., "SNP Detection and Genotyping from Low-Coverage Sequencing Data on Multiple Diploid Samples," Genome Res., Oct. 27, 2010, epub ahead of print.
Levin, et al., "Targeted Next-Generation Sequencing of a Cancer Transcriptome Enhances Detection of Sequence Variants and Novel Fusion Transcripts," Genome Biol., 10(10):R115 (PMID19835606) (2009).
Li, H. and Durbin, R., "Fast and Accurate Long-Read Alignment with Burrows-Wheeler Transform," Bioinformatics, 26(5):589-595 (2010).
Li, H., et al., "The Sequence Alignment/Map Format and SAMtools," Bioinformatics, 25(16):2078-2079 (2009).
Li, Y., et al., "Genotype Imputation," Annu. Rev. Genomics Hum. Genet., 10:387-406 (2009).

(56) References Cited

OTHER PUBLICATIONS

Logan et al. "High=throughput VDJ sequencing for quantification of minimal residual disease in chronic lymphocytic leukemia and immune reconstitution assessment" PNAS (2011) vol. 108, No. 52, pp. 21194-21199.
Lunter, G. and Goodson, M., "Stampy: A Statistical Algorithm for Sensitive and Fast Mapping of Illumina Sequence Reads," Genome Res. epub ahead of print (2010).
McKenna, A., et al., "The Genome Analysis Toolkit: A MapReduce Framework for Analyzing Next-Generation DNA Sequencing Data," Genome Res., 20(9):1297-1303 (2010).
Mullighan et al. "Genome sequencing of lymphoid malignancies" Blood (2013) vol. 122, No. 24, pp. 3899-3907.
Rhei et al., Mutation Analysis of the Putative Tumor Supressor Gene PTEN/MMAC1 in Primary Breast Carcinomas., Cancer Res., 57(17):3657-3659, Sep. 1, 1997.
Singapore Search Report dated Oct. 8, 2014 from Singapore Application No. 201305122.2.
Singapore Written Opinion dated Nov. 18, 2014 from Singapore Application No. 201305122.2.
Summerer D., et al., "Targeted high Throughput Sequencing of a Cancer-Related Exome Subset by specific Sequence Capture with a Fully Automated Microarray Platform", Genomics, 95(4), Apr. 1, 2010, pp. 241-246.
Supplemental European Search Report dated Apr. 24, 2014 from European Application No. 11853462.
Teer, J.K., et al., "Systematic Comparison of Three Genomic Enrichment Methods for Massively Parallel DNA Sequencing", Genome Research, 20(10), Sep. 1, 2010, pp. 1420-1431.
Trapnell, C. and Salzberg, S.L., "How to Map Billions of Short Reads Onto Genomes," Nature Biotech., 27:455-457 (2009).
Warren, R., et al., "Assembling Millions of Short DNA Sequences Using SSAKE," Bioinformatics, 23:500-501 (2007).
Wong, K.K., et al., "Use of Tagged Random Hexamer Amplification (TRHA) to Clone and Sequence Minute Quantities of DNA-Application to a 180 kb Plasmid Isolated from Sphingomonas F199," Nucleic Acids Res. 24(19):3778-3783 (1996).
Written Opinion of the International Searching Authority for PCT/US 11/67725 dated Apr. 27, 2012.
Agilent Technologies, Inc. (2011). "Sure Select Target Enrichment System From Sample to Analysis," 8 pages.
Agilent Technologies, Inc. (2011). "Sure Select Target Enrichment System, Sure Select Catalogue," 13 pages.
Bashford-Rogers et al., (2014). "Capturing needles in haystacks: a comparison of B-cell receptor sequencing methods," BMC Immunology, 15:29, 9 pages.
Jiang et al., (2014). "Deep sequencing reveals clonal evolution patterns and mutation events associated with relapse in B-cell lymphomas," Genome Biology, 15:432, 17 pages.
Walker, et al., (2013). "Characterization of IGH Locus Breakpoints in Multiple Myeloma Indicates a Subset of Translocations Appear to Occur in Pregerminal Center B Cells," Blood, 121(17):3413-3419.
Hui et al., (2015). "Differences in attitudes and beliefs toward end-of-life care between hematologic and solid tumor oncology specialists," Annals of Oncology, 26:1440-1446.
LeBlanc et al., (2015). "What is Different About Patients With Hematologic Malignancies? A Retrospective Cohort Study of Cancer Patients Referred to a Hospice Research Network," Journal of Pain and Symptom Management, 49(3):505-512.
Extended European Search Report received for European Patent Application No. 22168503.5, dated Nov. 14, 2022, 7 pages.
[No Author Listed] College of American Pathologists Molecular Pathology Checklist, draft dated Jun. 15, 2010, 64 pages.
[No Author Listed] Illumina Technical Note, Improved Accuracy for ELAND and Variant Calling, published Oct. 18, 2011, 8 pages.
Affidavit of S. Wang in Support of Patent Owner's Motion for Pro Hac Vice Admission submitted before the USPTO Patent Trial and Appeal Board case IPR2017-01170, U.S. Pat. No. 9,340,830, dated Dec. 1, 2017, 7 pages.
Affidavit of S. Wang in Support of Patent Owner's Motion for Pro Hac Vice Admission submitted before the USPTO Patent Trial and Appeal Board case IPR2017-01447, U.S. Pat. No. 9,340,830, dated Dec. 1, 2017, 7 pages.
Affidavit of S. Wang in Support of Patent Owner's Motion for Pro Hac Vice Admission submitted before the USPTO Patent Trial and Appeal Board case IPR2017-01448, U.S. Pat. No. 9,340,830, dated Dec. 1, 2017, 7 pages.
Agilent Technologies, Inc. (2009). "SureSelect Target Enrichment System: Illumina Single-End Sequencing Platform Library Prep—Protocol," Agilent Technologies, Inc. Protocols, 54 pages.
Agreed Claim Constructions U.S. Pat. No. 9,340,830 in *Foundation Medicine, Inc.* v. *Guardant Health, Inc.*, C.A. No. 2:16-cv-00523-JRG-RSP, filed Mar. 2, 2017, 2 pages.
Albert et al., (2007). "Direct selection of human genomic loci by microarray hybridization," Nat. Methods, 4(11):903-5.
Ali et al., (2015). "Prospective Comprehensive Genomic Profiling of Advanced Gastric Carcinoma Cases Reveals Frequent Clinically Relevant Genomic Alterations and New Routes for Targeted Therapies," The Oncologist, 20:499-507.
Ali et al., (2016). "Comprehensive Genomic Profiling Identifies a Subset of Crizotinib-Responsive ALK-Rearranged Non-Small Cell Lung Cancer Not Detected by Fluorescence In Situ Hybridization," The Oncologist, 21:762-770.
Amended Scheduling Order submitted before the USPTO Patent Trial and Appeal Board case IPR2017-01447, U.S. Pat. No. 9,340,830, filed Dec. 5, 2017, 3 pages.
Amended Scheduling Order submitted before the USPTO Patent Trial and Appeal Board case IPR2017-01448, U.S. Pat. No. 9,340,830, filed Dec. 5, 2017, 3 pages.
Amended Scheduling Order, submitted before the USPTO Patent Trial and Appeal Board case IPR2017-01170, U.S. Pat. No. 9,340,830, filed Dec. 5, 2017, 8 pages.
Astrazeneca, (2011). "AstraZeneca updates on olaparib and TC-5214 development programmes," available online at <https://www.astrazeneca.com/media-centre/press-releases/2011/AstraZeneca-updates-on-olaparib-and-TC-5214-development-programmes-20122010.html#!>, accessed on Feb. 13, 2018, 5 pages.
Barlesi et al., (2016). "Routine molecular profiling of patients with advanced non-small-cell lung cancer: results of a 1-year nationwide programme of the French Cooperative Thoracic Intergroup (IFCT)," Lancet, 387:1415-26.
Barve et al., (2017). "Case Report: Immune Checkpoint Inhibitor Elicited Complete Response in a Heavily Pretreated Patient with Metastatic Endometrial Carcinoma with a High Tumor Mutation Burden (TMB)," Mol. Med: Current Aspects, 1(1):1-4.
Baum, (2013). "11 health companies make the World Economic Group tech pioneer list," available online at <https://medcitynews.com/2013/08/what-does-a-technology-pioneer-in-medtech-look-like-here-are-11/>, accessed on Feb. 8, 2018, 9 pages.
Bezak et al., (2017). "Comprehensive Genomic Profiling of Central Giant Cell Lesions Identifies Clinically Relevant Genomic Alterations," J. Oral Maxillofac. Surg., 75:955-961.
Bridge, J. A. (2008). "Advantages and Limitations of Cytogenetic, Molecular Cytogenetic, and Molecular Diagnostic Testing in Mesenchymal Neoplasms," J. Orthop. Sci., 13:273-282.
Budowle et al., (2008). "Forensically relevant SNP classes," BioTechniques, 44(5):603-610.
Business Wire, (2017). "FDA Approves Foundation Medicine's FoundationOne CDx, the First and Only Comprehensive Genomic Profiling Test for All Solid Tumors Incorporating Multiple Companion Diagnostics," available online at <https://www.foundationmedicine.com/press-releases/f2b20698-10bd-4ac9-a5e5-c80c398a57b5>, 5 pages.
Business Wire, (2018). "Foundation Medicine Reports Preliminary 2017 Results," available online at <https://www.businesswire.com/news/home/20180108005713/en/Foundation-Medicine-Reports-Preliminary-2017-Results>, 4 pages.
Business Wire, (2018). "Foundation Medicine's New Liquid Biopsy Assay Granted Breakthrough Device Designation by U.S. Food and Drug Administration," available online at <https://www.foundationmedicine.com/press-releases/991ce685-7dbf-400a-aa33-eb4f9d411ed3>, 3 pages.

(56) References Cited

OTHER PUBLICATIONS

Campbell, P. J. et al. (2008). "Subclonal phylogenetic structures in cancer Revealed by Ultra-deep Sequencing," PNAS, 105(35):12 pages.
Canada's Michael Smith Genome Sciences Centre. (2009). "Slider II Results of SNPs concordance comparison to Maq," Available online at <http://www.bcgsc.ca/platform/bioinfo/software/Sliderll>, 9 pages.
Carr et al., (2016). "Defining actionable mutations for oncology therapeutic development," Nature Reviews Cancer, 16(5) 319-29.
Center for Devices and Radiological Health, (2015). "Expedited Access for Premarket Approval and De Novo Medical Devices Intended for Unmet Medical Need for Life Threatening or Irreversibly Debilitating Diseases or Conditions," 45 pages.
Centerwatch, "FDA Approved Drugs for Oncology," available online at <https://www.centerwatch.com/drug-information/fda-approved-drugs/therapy>, accessed on Feb. 15, 2018, 19 pages.
Chalmers et al., (2017). "Analysis of 100,000 human cancer genomes reveals the landscape of tumor mutational burden," Genome Medicine, 9(34):1-14.
Chin et al., (2011). "Making sense of cancer genomic data," Genes & Development, 25:534-555.
Chiu et al. (2008). "Noninvasive prenatal diagnosis of fetal chromosomal aneuploidy by massively parallel genomic sequencing of DNA in maternal plasma," PNAS, 105(51):20458-20463.
Chmielecki et al., (2017). "Genomic Profiling of a Large Set f Diverse Pediatric Cancers Identifies Known and Novel Mutations across Tumor Spectra," Cancer Res., 77(2):509-519.
Chmielecki, J. et al. (2010). "Targeted Next-Generation Sequencing of DNA Regions Proximal to a Conserved GXGXXG Signaling Motif Enables Systematic Discovery of Tyrosine Kinase Fusions in Cancer," Nucleic Acids Research, 38(20): 6985-6996.
Claim Construction Memorandum Opinion and Order for *Foundation Medicine, Inc. v. Guardant Health, Inc.*, Civil Action No. 2:16-CV-00523-JRG-RSP, filed May 19, 2017, 27 pages.
Clean Version of the Modified Default Protective Order by Foundation Medicine, Inc., submitted before the USPTO Patent Trial and Appeal Board for Case Nos. IPR2017-01170, IPR2017-01447, and IPR2017-01448, U.S. Pat. No. 9,340,830, filed Feb. 16, 2018, 8 pages.
ClinicalTrials.gov, (2016). "Pbi-shRNA WS/FLI1 Type 1 LPX in Subjects with Advanced Ewing's Sarcoma, NCT02736565," available online at <https://clinicaltrials.gov/ct2/show/NCT02736565>, accessed on Feb. 9, 2018. 7 pages.
Cloonan et al., "RNA-mate: a recursive mapping strategy for high-throughput RNA-sequencing data," Bioinformatics (2009) vol. 25, No. 19, pp. 2615-2616.
Complaint for Patent Infringement by Plaintiff in *Foundation Medicine, Inc. v. Guardant Health, Inc.*, Case 1:17-cv-00607-LPS-CJB, filed May 25, 2017, 10pages.
Complaint for Patent Infringement by Plaintiff in *Foundation Medicine, Inc. v. Guardant Health, Inc.*, Civil Action No. 2:16-CV-00523, filed May 17, 2016, 11pages.
Confidential Videotaped Deposition of John Quackenbush, Ph.D. in *Foundation Medicine, Inc. v. Guardant Health, Inc.*, C.A. No. 2:16-cv-00523-JRG-RSP, filed Apr. 6, 2017, 6 pages.
Cronin et al., (2004). "Measurement of gene expression in archival paraffin-embedded tissues: development and performance of a 92-gene reverse transcriptase-polymerase chain reaction assay," Am J Pathol., 164(1):35-42.
Cummings, N. et al. (2010). "Combining Target Enrichment with Barcode Multiplexing for High Throughput SNP Discovery," BMC Genomics, 11: 8 pages.
Curriculum Vitae of Dr. J. Quackenbush, dated Mar. 27, 2017, submitted before the USPTO Patent Trial and Appeal Board for U.S. Pat. No. 9,340,830, 45 pages.
Day et al., (2014). "Targeted Sequencing of Large Genomic Regions with CATCH-Seq," PLOS ONE, 9(10):1-11.
Decision—Denying Patent Owner's Motion for Protective Order, submitted before the USPTO Patent Trial and Appeal Board cases IPR2017-01170, IPR2017-01447, and IPR2017-01448, U.S. Pat. No. 9,340,830, filed Apr. 4, 2018, 5 pages.
Decision—Denying Patent Owner's Request for Rehearing, submitted before the USPTO Patent Trial and Appeal Board case IPR2017-01170, U.S. Pat. No. 9,340,830, filed Nov. 8, 2017, 7 pages.
Decision—Granting Joint Motion for Entry of a Modified Protective Order 37 C.F.R. sec 42.14, submitted before the USPTO Patent Trial and Appeal Board cases IPR2017-01170, IPR2017-01447, and IPR2017-01448, U.S. Pat. No. 9,340,830, filed Apr. 27, 2018, 3 pages.
Decision—Granting Patent Owner's Unopposed Renewed Motion to Seal 37 C.F.R. sec 42.14, submitted before the USPTO Patent Trial and Appeal Board cases IPR2017-01170, IPR2017-01447, and IPR2017-01448, U.S. Pat. No. 9,340,830, filed Apr. 27, 2018, 5 pages.
Decision—Granting-in-Part Patent Owner's Motion to Seal, submitted before the USPTO Patent Trial and Appeal Board cases IPR2017-01170, IPR2017-01447, and IPR2017-01448, U.S. Pat. No. 9,340,830, filed Apr. 4, 2018, 6 pages.
Decision—Institution of Inter Partes Review submitted before the USPTO Patent Trial and Appeal Board case IPR2017-01448, U.S. Pat. No. 9,340,830, filed Nov. 28, 2017, 31 pages.
Decision—Institution of Inter Partes Review, submitted before the USPTO Patent Trial and Appeal Board case IPR2017-01170, U.S. Pat. No. 9,340,830, filed Oct. 11, 2017, 27 pages.
Decision Granting Patent Owner's Unopposed Motion to Seal 37 C.F.R. § 42.14, submitted before the USPTO Patent Trial and Appeal Board cases IPR2017-01170, IPR2017-01447, and IPR2017-01448, U.S. Pat. No. 9,340,830, filed Jun. 5, 2018, 4 pages.
Decision Granting Patent Owner's Motion to Submit Supplemental Information Pursuant to 37 C.F.R. § 42.123(b), submitted before the USPTO Patent Trial and Appeal Board cases IPR2017-01170, IPR2017-01447, and IPR2017-01448, U.S. Pat. No. 9,340,830, filed May 29, 2018, 4 pages.
Decision submitted before the USPTO Patent Trial and Appeal Board case IPR2017-01447, U.S. Pat. No. 9,340,830, filed Nov. 28, 2017, 28 pages.
Declaration by Dr. J. Nemunaitis submitted before the USPTO Patent Trial and Appeal Board for cases IPR2017-01170, U.S. Pat. No. 9,340,830, filed Feb. 16, 2018, 107 pages.
Declaration by Dr. J. Nemunaitis submitted before the USPTO Patent Trial and Appeal Board for cases IPR2017-01447, U.S. Pat. No. 9,340,830, filed Feb. 16, 2018, 107 pages.
Declaration by Dr. J. Nemunaitis submitted before the USPTO Patent Trial and Appeal Board for cases IPR2017-01448, U.S. Pat. No. 9,340,830, filed Feb. 16, 2018, 107 pages.
Declaration of Dr. J. Quackenbush submitted before the USPTO Patent Trial and Appeal Board for U.S. Pat. No. 9,340,830, filed Mar. 30, 2017, 106 pages.
Declaration of E. Reines in Support of Petitioner Guardant Health, Inc.'s Motion for Pro Hac Vice Admission submitted before USPTO Patent Trial and Appeal Board for case IPR2017-01170, U.S. Pat. No. 9,340,830, dated Mar. 16, 2018, 7 pages.
Declaration of E. Reines in Support of Petitioner Guardant Health, Inc.'s Motion for Pro Hac Vice Admission submitted before USPTO Patent Trial and Appeal Board for case IPR2017-01447, U.S. Pat. No. 9,340,830, dated Mar. 16, 2018, 7 pages.
Declaration of E. Reines in Support of Petitioner Guardant Health, Inc.'s Motion for Pro Hac Vice Admission submitted before USPTO Patent Trial and Appeal Board for case IPR2017-01448, U.S. Pat. No. 9,340,830, dated Mar. 16, 2018, 7 pages.
Demichelis et al., (2008). "SNP panel identification assay (SPIA): a genetic-based assay for the identification of cell lines," Nucleic Acids Research, 36(7):2446-2456.
Deposition of Dr. J. Quackenbush, (Jan. 31, 2018) in *Guardant Health, Inc. v. Foundation Medicine, Inc.*: Case Nos. IPR2017-01170, IPR2017-01447, and IPR2017-01448, 342 pages.
Deposition of Dr. S. Gabriel, (Mar. 24, 2017) for *Foundation Medicine, Inc. v. Guardant Health, Inc.*, Civil Action No. 2:16-CV-00523-JRG-RSP, 146 pages.

(56) References Cited

OTHER PUBLICATIONS

Deposition of Stacey Gabriel Ph.D. on Mar. 24, 2017 in *Foundation Medicine, Inc. v. Guardant Health, Inc.*, C.A. No. 2:16-cv-00523-JRG-RSP, filed Apr. 20, 2017, 54 pages.
DePristo et al., (2011). "A framework for variation discovery and genotyping using next-generation DNA sequencing data," Nature Genetics, 43(5):491-500.
Disputed Claim Constructions U.S. Pat. No. 9,340,830 in *Foundation Medicine, Inc. v. Guardant Health, Inc.*, C.A. No. 2:16-cv-00523-JRG-RSP, filed May 4, 2017, 10 pages.
Dowsett, M. et al. (2008). "Emerging Biomarkers and New Understanding of Traditional Markers in Personalized Therapy for Breast Cancer," Clin. Cancer. Res., 14(24):8019-8026.
Drilon et al., (2013). "Response to Cabozantinib in Patients with RET Fusion-Positive Lung Adenocarcinomas," Cancer Discovery, 3(6):1-7.
Egholm et al., (1993). "PNA hybridizes to complementary oligonucleotides obeying the Watson-Crick hydrogen-bonding rules," Nature, 365(6446):566-8.
Evidentiary Declaration of P. Medley, submitted before the USPTO Patent Trial and Appeal Board for U.S. Pat. No. 9,340,830, filed Mar. 30, 2017, 6 pages.
Expert Declaration of John Quackenbush, Ph.D. in *Foundation Medicine, Inc. v. Guardant Health, Inc.*, C.A. No. 2:16-cv-00523-JRG-RSP, filed Apr. 6, 2017, 41 pages.
Extended European Search Report received for European Patent Application No. 19157180.1, dated Sep. 24, 2019, 13 pages.
Extended European Search Report received for European Patent Application No. 19820152.7, dated Feb. 15, 2022, 13 pages.
FDA, (2017). "FDA announces approval, CMS proposes coverage of first breakthrough-designated test to detect extensive number of cancer biomarkers," available online at <https://www.fda.gov/NewsEvents/Newsroom/PressAnnouncements/ucm587273.htm>, accessed on Feb. 8, 2018, 4 pages.
FDA, (2017). "FDA approves first cancer treatment for any solid tumor with a specific genetic feature," available online at <https://www.fda.gov/newsevents/newsroom/pressannouncements/ucm560167.htm>, accessed on Jan. 29, 2018, 3 pages.
File history for U.S. Appl. No. 13/339,986, filed Dec. 29, 2011, 1,453 pages.
Forbes et al., (2008). "The Catalogue of Somatic Mutations in Cancer (COSMIC)," Current Protocols in Human Genetics, 10.11.1-10.11.26, 26 pages.
Forbes et al., (2011). "COSMIC: mining complete cancer genomes in the Catalogue of Somatic Mutations in Cancer," Nucleic Acids Research, 39:D945-D950, 6 pages.
Foundation Medicine, Inc., "FoundationOne CDx Technical Information," submitted before the USPTO Patent Trial and Appeal Board for Case Nos. IPR2017-01170, IPR2017-01447, and IPR2017-01448, U.S. Pat. No. 9,340,830, filed Feb. 16, 2018, 36 pages.
Foundation Medicine, Inc., (2017). "FDA Approves Foundation Medicine's FoundationOne CDx™, the First and Only Comprehensive Genomic Profiling Test for All Solid Tumors Incorporating Multiple Companion Diagnostics," available online at <https://www.businesswire.com/news/home/20171130006320/en/>, accessed on Feb. 8, 2018, 6 pages.
Foundation Medicine, Inc.'s Opening Claim Constructions Brief in *Foundation Medicine, Inc. v. Guardant Health, Inc.*, C.A. No. 2:16-cv-00523-JRG-RSP, filed Apr. 6, 2017, 27 pages.
Foundation Medicine, "Bait Set Design Summary," Exhibit 1 of Redacted Deposition of Dr. S. Gabriel in *Guardant Health, Inc. v. Foundation Medicine, Inc.* Case Nos. IPR2017-01170, IPR2017-01447, and IPR2017-01448, U.S. Pat. No. 9,340,830, filed May 8, 2018, 5 pages.
Foundation Medicine's Power of Attorney Under 37 C.F.R. §42.10 submitted before the USPTO Patent Trial and Appeal Board case IPR2017-01447, U.S. Pat. No. 9,340,830, filed Jun. 6, 2017, 2 pages.
Foundation Medicine's Power of Attorney Under 37 C.F.R. §42.10, submitted before the USPTO Patent Trial and Appeal Board case IPR2017-01170, U.S. Pat. No. 9,340,830, filed Apr. 21, 2017, 2 pages.
Foundation Smart Trials, "An End-to-End Partner for Clinical Trials," submitted before the USPTO Patent Trial and Appeal Board for Case Nos. IPR2017-01170, IPR2017-01447, and IPR2017-01448, U.S. Pat. No. 9,340,830, filed Feb. 16, 2018, 8 pages.
Garber, K., (2008). "Fixing the Front End," Nature Biotechnology, 26(10):1101-1104.
Goya et al., (2010). "SNVMix: predicting single nucleotide variants from next-generation sequencing of tumors," Bioinformatics, 26(6):730-736.
Granting Petitioner's Motion for Pro Hac Vice Admission of Edward R. Reines 37 C.F.R. §42.10, submitted before the USPTO Patent Trial and Appeal Board cases IPR2017-01170, IPR2017-01447, and IPR2017-01448, U.S. Pat. No. 9,340,830, filed Mar. 22, 2018, 3 pages.
Griffith et al., (2015). "Optimizing cancer genome sequencing and analysis," Cell Syst., 1(3):210-223.
Groisberg et al., (2017). "Clinical genomic profiling to identify actionable alterations for investigational therapies in patients with diverse sarcomas," Oncotarget, 14 pages.
Guardant Health, Inc.'s Responsive Claim Construction Brief for *Foundation Medicine, Inc. v Guardant Health, Inc.*: Case Nos. 2:16-CV-00523-JRG, dated Feb. 2, 2017, 172 pages.
Guardant Health, Inc.'s Responsive Claim Construction Brief in *Foundation Medicine, Inc. v. Guardant Health, Inc.*, C.A. No. 2:16-cv-00523-JRG-RSP, filed Apr. 20, 2017, 31 pages.
Guardant's Notice of Deposition of Dr. J. Nemunaitis submitted before the USPTO Patent Trial and Appeal Board case IPR2017-01447, U.S. Pat. No. 9,340,830, filed Mar. 23, 2018, 3 pages.
Guardant's Notice of Deposition of Dr. John Nemunaitis, M.D. submitted before the USPTO Patent Trial and Appeal Board case IPR2017-01448, U.S. Pat. No. 9,340,830, filed Mar. 23, 2018, 3 pages.
Guardant's Notice of Deposition of Dr. John Nemunaitis, M.D., submitted before the USPTO Patent Trial and Appeal Board case IPR2017-01170, U.S. Pat. No. 9,340,830, filed Mar. 23, 2018, 3 pages.
Guardant's Notice of Deposition of Dr. S. Gabriel submitted before the USPTO Patent Trial and Appeal Board case IPR2017-01447, U.S. Pat. No. 9,340,830, filed Mar. 23, 2018, 3 pages.
Guardant's Notice of Deposition of Dr. Stacey Gabriel, Ph.D. submitted before the USPTO Patent Trial and Appeal Board case IPR2017-01448, U.S. Pat. No. 9,340,830, filed Mar. 23, 2018, 3 pages.
Guardant's Notice of Deposition of Dr. Stacey Gabriel, Ph.D., submitted before the USPTO Patent Trial and Appeal Board case IPR2017-01170, U.S. Pat. No. 9,340,830, filed Mar. 23, 2018, 3 pages.
Gubin et al., (2015). "CANCER. The odds of immunotherapy success," Science, 350:158-9.
Hodges et al., (2007). "Genome-wide in situ exon capture for selective resequencing," Nat. Genet., 39(12):1522-7.
In Re E. Reines for US Court of Appeals for the Federal Circuit Case 14-MA004, filed Nov. 5, 2014, 19 pages.
Initial Declaration of Stacey Gabriel, Ph.D. in Support of Foundation Medicine, Inc.'s Proposed Claim Constructions in *Foundation Medicine, Inc. v. Guardant Health, Inc.*, C.A. No. 2:16-cv-00523-JRG-RSP, filed Apr. 6, 2017, 26 pages.
International Search Report received for PCT Patent Application No. PCT/US2011/67725, dated Apr. 27, 2012, 4 pages.
International Search Report and Written Opinion issued in PCT/US2019/036555, dated Aug. 28, 2019, 14 pages.
Jemal et al., (2011). "Global Cancer Statistics," CA Cancer J. Clin., 61:69-90.
Johnson et al., (2017). "Comprehensive Genomic Profiling of 282 Pediatric Low- and High-Grade Gliomas Reveals Genomic Drivers, Tumor Mutational Burden, and Hypermutation Signatures," The Oncologist, 22:1478-1490.

(56) References Cited

OTHER PUBLICATIONS

Joint Claim Construction Chart Pursuant to Patent Local Rule 4-5 in *Foundation Medicine, Inc.* v. *Guardant Health, Inc.*, C.A. No. 2:16-cv-00523-JRG-RSP, filed May 4, 2017, 3 pages.
Joint Motion for Entry of a Modified Protective Order submitted before the USPTO Patent Trial and Appeal Board case IPR2017-01447, U.S. Pat. No. 9,340,830, filed Apr. 23, 2018, 4 pages.
Joint Motion for Entry of a Modified Protective Order submitted before the USPTO Patent Trial and Appeal Board case IPR2017-01448, U.S. Pat. No. 9,340,830, filed Apr. 23, 2018, 4 pages.
Joint Motion for Entry of a Modified Protective Order, submitted before the USPTO Patent Trial and Appeal Board case IPR2017-01170, U.S. Pat. No. 9,340,830, filed Apr. 23, 2018, 4 pages.
Joint Motion to Keep Confidential and Separate Under 35 U.S.C. § 317(b) and 37 C.F.R. § 42.74( c), submitted before the USPTO Patent Trial and Appeal Board cases IPR2017-01170, IPR2017-01447, and IPR2017-01448, U.S. Pat. No. 9,340,830, filed Jul. 2, 2018, 3 pages.
Joint Motion to Terminate Under 35 U.S.C. § 317(a), submitted before the USPTO Patent Trial and Appeal Board cases IPR2017-01170, IPR2017-01447, and IPR2017-01448, U.S. Pat. No. 9,340,830, filed Jul. 2, 2018, 6 pages.
Joint Stipulation to Modify the Scheduling Order submitted before the USPTO Patent Trial and Appeal Board case IPR2017-01447, U.S. Pat. No. 9,340,830, filed Apr. 20, 2018, 4 pages.
Joint Stipulation to Modify the Scheduling Order submitted before the USPTO Patent Trial and Appeal Board case IPR2017-01448, U.S. Pat. No. 9,340,830, filed Apr. 20, 2018, 4 pages.
Joint Stipulation to Modify the Scheduling Order, submitted before the USPTO Patent Trial and Appeal Board case IPR2017-01170, U.S. Pat. No. 9,340,830, filed Apr. 20, 2018, 4 pages.
Kaur et al., (2006). "Thermodynamic, Counterion, and Hydration Effects for the Incorporation of Locked Nucleic Acid Nucleotides into DNA Duplexes," Biochemistry, 45(23):7347-55.
Kenny, E. M. et al. (2011). "Multiplex Target Enrichment Using DNA Indexing for Ultra-High Throughput SNP Detection," DNA Research, 18:31-38.
Kidd et al., "A Human Genome Structural Variation Sequencing Resource Reveals Insights into Mutational Mechanisms," Cell (2010) vol. 143, pp. 837-847.
Koboldt, et al. (2010). "Challenges of Sequencing Human Genomes," Briefings in Bioinformatics, 11(5):484-498.
Leary et. al. (2010). "Development of Personalized Tumor Biomarkers Using Massively Parallel Sequencing," Sci Transl Med, 2(20): 20ra14.
Leary et. al. (2012). "Detection of Chromosomal Alterations in the Circulation of Cancer Patients with Whole-Genome Sequencing," Sci Transl Med, 4(162):162ra154.
Ledermann (2014). "Olaparib maintenance therapy in patients with platinum-sensitive relapsed serous ovarian cancer: a preplanned retrospective analysis of outcomes by BRCA status in a randomised phase 2 trial," Lancet Oncol., 15:852-861.
Lek et al. (2016). "Analysis of protein-coding genetic variation in 60,706 humans," Nature 536(7616):285-291, 33 pages.
Ley et al., (2008). "DNA Sequencing of a Cytogenetically Normal Acute Myeloid Leukaemia Genome," Nature, 456:66-72, and Supplementary Information, 39 pages.
Li et al., "A survey of sequence alignment algorithms for next-generation sequencing," Briefings in Bioinformatics (2010) vol. 2, No. 5, pp. 473-483.
Li, et al. (2009). "Fast and Accurate Short Read Alignment with Burrows-Wheeler Transform," Bioinformatics, 25(14):1754-1760.
Liang et al., (2014). "Short intronic repeat sequences facilitate circular RNA production," Genes & Development, 28:2233-2247.
Life Technologies Corporation. (2011). "RecoverAll Total Nucleic Acid Isolation Protocol," Ambion, Cat. No. 10 AM 1975, 29 pages.
Lindeman et al., (2013). "Molecular Testing Guideline for Selection of Lung Cancer Patients for EGFR and ALK Tyrosine Kinase Inhibitors," J. Thorac. Oncol., 8(7):823-859.
Lipson et al., (2012). "Identification of new ALK and RET gene fusions from colorectal and lung cancer biopsies," Nat. Med., 18(3):382-384.
Lozano et al., (2012). "Global and regional mortality from 235 causes of death for 20 age groups in 1990 and 2010: a systematic analysis for the Global Burden of Disease Study 2010," Lancet, 380:2095-128.
Magi et al., (2010). "Bioinformatics for Next Generation Sequencing Data," Genes, 1:294-307.
Malhis, et al. (2010). "High Quality SNP Calling Using Illumina Data at Shallow Coverage," Bioinformatics, 26(8):1029-1035.
Mamanova, L. et al. (2010). "Target-Enrichment Strategies for Next Generation Sequencing," Nature Methods, 7(2):111-118.
Mardis, (2008). "Next-Generation DNA Sequencing Methods," Annu. Rev. Genomics Hum. Genet., 9:387-402.
Mardis, et al. (2009). "Recurring Mutations Found by Sequencing an Acute Myeloid Leukemia Genome," The New England Journal of Medicine, 361:1058-1066.
Marsh, S. et al. (2007). "Pharmacogenetic Analysis of Paclitaxel Transport and Metabolism Genes in Breast Cancer," The Pharmacogenomics Journal, 7:362-365.
Masuda et al., (1999). "Analysis of chemical modification of RNA from formalin-fixed samples and optimization of molecular biology applications for such samples," Nucleic Acids Res., 27(22):4436-4443.
McBride et. al. (2010). "Use of Cancer-Specific Genomic Rearrangements to Quantify Disease Burden in Plasma from Patients with Solid Tumors," Genes Chromosomes Cancer, 49(11):1062-1069.
Meldrum et al., (2011). "Next-Generation Sequencing for Cancer Diagnostics: a Practical Perspective," Clin. Biochem Rev., 32:177-195.
Mertes et al., (2011). "Targeted enrichment of genomic DNA regions for next-generation sequencing," Briefings in Functional Genomics, 10(6):374-386.
Metzker, M., (2010). "Sequencing Technologies—the Next Generation," Nature Reviews, 11:31-46.
Meyerson et al., (2010). "Advances in understanding cancer genomes through second-generation sequencing," Nature Reviews Genetics, 11(10):685-696.
Miklos, (2005). "The Human Cancer Genome Project-one more misstep in the war on cancer," Nature Biotechnology, 23(5):535-537.
Morlan, J. et al. (2009). "Mutation Detection by Real-Time PCR: A Simple, Robust and Highly Selective Method," PLoS ONE, 4(2):e4584, 11 pages.
Motion for Protective Order submitted before the USPTO Patent Trial and Appeal Board case IPR2017-01447, U.S. Pat. No. 9,340,830, filed Feb. 16, 2018, 8 pages.
Motion for Protective Order submitted before the USPTO Patent Trial and Appeal Board case IPR2017-01448, U.S. Pat. No. 9,340,830, filed Feb. 16, 2018, 8 pages.
Motion for Protective Order, submitted before the USPTO Patent Trial and Appeal Board case IPR2017-01170, U.S. Pat. No. 9,340,830, filed Feb. 16, 2018, 8 pages.
National Human Genome Research Institute, "The Cost of Sequencing a Human Genome," available online at <https://www.genome.gov/sequencingcosts/>, accessed on Jul. 7, 2017, 4 pages.
Negrini, S. et al. (2010). "Genomic Instability—an Evolving Hallmark of Cancer," Nature Reviews Molecular Cell Biology, 11:220-228.
New England Biolabs. "Master Mixes," available online at <http://www.neb.sg/products/pcr ..qpcr-and-amplification-technologies/master-mixes/master-mixes>, accessed on Jul. 6, 2017, 3 pages.
Ngeow, J. et al. (2016). "Precision Medicine in Heritable Cancer: When Somatic Tumour Testing and Germline Mutations Meet," Genomic Medicine, 3 pages.
NGS Alignment Programs. (2009). Available online at <http://lh3lh3.users.sourceforge.net/NGSalign.shtml>, 4 pages.
Nord, A. S. et al., (2011). "Accurate and Exact CNV Identification from Targeted High-throughput Sequence Data," BMC Genomics, 12:184, 10 pages.

(56) References Cited

OTHER PUBLICATIONS

Notice of Deposition of Dr. J. Quackenbush submitted before the USPTO Patent Trial and Appeal Board case IPR2017-01447, U.S. Pat. No. 9,340,830, filed Jan. 5, 2018, 3 pages.
Notice of Deposition of Dr. John Quackenbush submitted before the USPTO Patent Trial and Appeal Board case IPR2017-01447, U.S. Pat. No. 9,340,830, filed Apr. 27, 2018, 4 pages.
Notice of Deposition of Dr. John Quackenbush submitted before the USPTO Patent Trial and Appeal Board case IPR2017-01448, U.S. Pat. No. 9,340,830, filed Apr. 27, 2018, 4 pages.
Notice of Deposition of Dr. John Quackenbush submitted before the USPTO Patent Trial and Appeal Board case IPR2017-01448, U.S. Pat. No. 9,340,830, filed Jan. 5, 2018, 3 pages.
Notice of Deposition of Dr. John Quackenbush, submitted before the USPTO Patent Trial and Appeal Board case IPR2017-01170, U.S. Pat. No. 9,340,830, filed Apr. 27, 2018, 4 pages.
Notice of Deposition of Dr. John Quackenbush, submitted before the USPTO Patent Trial and Appeal Board case IPR2017-01170, U.S. Pat. No. 9,340,830, filed Jan. 5, 2018, 3 pages.
Notice of Deposition of Dr. John Quackenbush, submitted before the USPTO Patent Trial and Appeal Board case IPR2017-01170, U.S. Pat. No. 9,340,830, filed Nov. 16, 2017, 3 pages.
Notice of Filing Date Accorded to Petition and Time for Filing Patent Owner Preliminary Response submitted before the USPTO Patent Trial and Appeal Board case IPR2017-01447, U.S. Pat. No. 9,340,830, filed Jun. 6, 2017, 5 pages.
Notice of Filing Date Accorded to Petition and Time for Filing Patent Owner Preliminary Response submitted before the USPTO Patent Trial and Appeal Board case IPR2017-01448, U.S. Pat. No. 9,340,830, filed Jun. 6, 2017, 5 pages.
Notice of Filing Date Accorded to Petition and Time for Filing Patent Owner Preliminary Response, submitted before the USPTO Patent Trial and Appeal Board case IPR2017-01170, U.S. Pat. No. 9,340,830, filed Apr. 12, 2017, 4 pages.
Notice of Joint Stipulation to Revised Schedule submitted before the USPTO Patent Trial and Appeal Board case IPR2017-01447, U.S. Pat. No. 9,340,830, filed Jan. 9, 2018, 3 pages.
Notice of Joint Stipulation to Revised Schedule submitted before the USPTO Patent Trial and Appeal Board case IPR2017-01448, U.S. Pat. No. 9,340,830, filed Jan. 9, 2018, 3 pages.
Notice of Joint Stipulation to Revised Schedule, submitted before the USPTO Patent Trial and Appeal Board case IPR2017-01170, U.S. Pat. No. 9,340,830, filed Jan. 9, 2018, 3 pages.
Okou et al., (2007). "Microarray-based genomic selection for high-throughput resequencing," Nat. Methods, 4(11):907-9.
Omega Bio-tek, (2019). "E.Z.N.A.® FPPE DNA Kit Product Manual," Product Nos. D3399-00, D3399-01, and D3399-02, 20 pages.
Order—Patent Owner's Motion for Pro Hac Vice Admission of Sophie F. Wang—37 CFR 42.10 submitted before the USPTO Patent Trial and Appeal Board case IPR2017-01448, U.S. Pat. No. 9,340,830, filed Dec. 5, 2017, 3 pages.
Order—Patent Owner's Motion for Pro Hac Vice Admission of Sophie F. Wang—37 CFR 42.10, submitted before the USPTO Patent Trial and Appeal Board case IPR2017-01170, U.S. Pat. No. 9,340,830, filed Dec. 5, 2017, 3 pages.
Order Granting Guardant Health, Inc.'s Motion to Dismiss Foundation Medicine, Inc.'s Complaint in *Foundation Medicine, Inc.* v. *Guardant Health, Inc.*, C.A. No. 2:16-cv-00523-JRG-RSP, filed Jun. 12, 2017, 1 page.
Order Granting Patent Owner's Unopposed Motion to Expunge, 37 C.F.R. § 42.56, submitted before the USPTO Patent Trial and Appeal Board cases IPR2017-01170, IPR2017-01447, and IPR2017-01448, U.S. Pat. No. 9,340,830, filed Aug. 10, 2018, 3 pages.
Order Patent Owner's Motion for Pro Hac Vice Admission of Sophie F. Wang 37 CFR 42.10 submitted before the USPTO Patent Trial and Appeal Board case IPR2017-01447, U.S. Pat. No. 9,340,830, filed Dec. 5, 2017, 3 pages.

Order Trial Hearing 37 C.F.R. § 42.70, submitted before the USPTO Patent Trial and Appeal Board cases IPR2017-01170, IPR2017-01447, and IPR2017-01448, U.S. Pat. No. 9,340,830, filed May 25, 2018, 4 pages.
P.R. 4-3 Joint Claim Construction and Prehearing Statement in *Foundation Medicine, Inc.* v. *Guardant Health, Inc.*, C.A. No. 2:16-cv-00523-JRG-RSP, filed Mar. 2, 2017, 4 pages.
Pao transcript of "Emerging new targets and new drugs in non-small cell lung cancer: Discussion: Inhibition of immune checkpoint programmed death protein—1 (PD-1) in NSCLC," American Society of Clinical Oncology (Jun. 2, 2012), video available at <http://meetinglibrary.asco.org/record/71618/video>, submitted before the USPTO Patent Trial and Appeal Board for Case Nos. IPR2017-01170, IPR2017-01447, and IPR2017-01448, U.S. Pat. No. 9,340,830, filed Feb. 16, 2018, 14 pages.
Parties' Proposed Preliminary Claim Constructions U.S. Pat. No. 9,340,830 in *Foundation Medicine, Inc.* v. *Guardant Health, Inc.*, C.A. No. 2:16-cv-00523-JRG-RSP, filed Mar. 2, 2017, 19 pages.
Patent Owner's Unopposed Motion for Pro Hac Vice Admission Under 37 C.F.R. § 42.10( c ), submitted before the USPTO Patent Trial and Appeal Board case IPR2017-01170, U.S. Pat. No. 9,340,830, filed Nov. 22, 2017, 4 pages.
Patent Owner's Unopposed Motion for Pro Hac Vice Admission Under 37 C.F.R. § 42.10(c) submitted before the USPTO Patent Trial and Appeal Board case IPR2017-01448, U.S. Pat. No. 9,340,830, filed Dec. 1, 2017, 4 pages.
Patent Owner's First Amended Mandatory Notices Under 37 C.F.R. §42.8 submitted before the USPTO Patent Trial and Appeal Board case IPR2017-01447, U.S. Pat. No. 9,340,830, filed Dec. 12, 2017, 8 pages.
Patent Owner's First Amended Mandatory Notices Under 37 C.F.R. §42.8, submitted before the USPTO Patent Trial and Appeal Board case IPR2017-01170, U.S. Pat. No. 9,340,830, filed Jun. 21, 2017, 8 pages.
Patent Owner's First Amended Mandatory Notices Under 37 C.F.R. sec. 42.8 submitted before the USPTO Patent Trial and Appeal Board case IPR2017-01448, U.S. Pat. No. 9,340,830, filed Dec. 12, 2017, 8 pages.
Patent Owner's Mandatory Notices Under 37 C.F.R. §42.8 submitted before the USPTO Patent Trial and Appeal Board case IPR2017-01447, U.S. Pat. No. 9,340,830, filed Jun. 6, 2017, 8 pages.
Patent Owner's Mandatory Notices Under 37 C.F.R. §42.8, submitted before the USPTO Patent Trial and Appeal Board case IPR2017-01170, U.S. Pat. No. 9,340,830, filed Apr. 21, 2017, 8 pages.
Patent Owner's Mandatory Notices Under 37 C.F.R. sec. 42.8 submitted before the USPTO Patent Trial and Appeal Board case IPR2017-01448, U.S. Pat. No. 9,340,830, filed Jun. 6, 2017, 8 pages.
Patent Owner's Motion to Seal submitted before the USPTO Patent Trial and Appeal Board case IPR2017-01447, U.S. Pat. No. 9,340,830, filed Feb. 16, 2018, 5 pages.
Patent Owner's Motion to Seal submitted before the USPTO Patent Trial and Appeal Board case IPR2017-01448, U.S. Pat. No. 9,340,830, filed Feb. 16, 2018, 5 pages.
Patent Owner's Motion to Seal, submitted before the USPTO Patent Trial and Appeal Board case IPR2017-01170, U.S. Pat. No. 9,340,830, filed Feb. 16, 2018, 5 pages.
Patent Owner's Motion to Submit Supplemental Information Pursuant to 37 C.F.R. § 42.123(b), submitted before the USPTO Patent Trial and Appeal Board case IPR2017-01170, U.S. Pat. No. 9,340,830, filed May 7, 2018, 11 pages.
Patent Owner's Motion to Submit Supplemental Information Pursuant to 37 C.F.R. § 42.123(b) submitted before the USPTO Patent Trial and Appeal Board case IPR2017-01447, U.S. Pat. No. 9,340,830, filed May 7, 2018, 10 pages.
Patent Owner's Motion to Submit Supplemental Information Pursuant to 37 C.F. R. sec. 42.123(b) submitted before the USPTO Patent Trial and Appeal Board case IPR2017-01448, U.S. Pat. No. 9,340,830, filed May 7, 2018, 10 pages.

(56) References Cited

OTHER PUBLICATIONS

Patent Owner's Objections to Evidence Pursuant to 37 C.F.R. § 42.64 submitted before the USPTO Patent Trial and Appeal Board case IPR2017-01447, U.S. Pat. No. 9,340,830, filed Dec. 12, 2017, 4 pages.
Patent Owner's Objections to Evidence Pursuant to 37 C.F.R. § 42.64, submitted before the USPTO Patent Trial and Appeal Board case IPR2017-01170, U.S. Pat. No. 9,340,830, filed Oct. 25, 2017, 4 pages.
Patent Owner's Objections to Evidence Pursuant to 37 C.F.R. sec. 42.64 submitted before the USPTO Patent Trial and Appeal Board case IPR2017-01448, U.S. Pat. No. 9,340,830, filed Dec. 12, 2017, 4 pages.
Patent Owner's Objections to Petitioner's Oral Hearing Demonstratives, submitted before the USPTO Patent Trial and Appeal Board cases IPR2017-01170, IPR2017-01447, and IPR2017-01448, U.S. Pat. No. 9,340,830, filed Jun. 8, 2018, 3 pages.
Patent Owner's Power of Attorney submitted before the USPTO Patent Trial and Appeal Board case IPR2017-01447, U.S. Pat. No. 9,340,830, filed Dec. 12, 2017, 2 pages.
Patent Owner's Power of Attorney submitted before the USPTO Patent Trial and Appeal Board case IPR2017-01448, U.S. Pat. No. 9,340,830, filed Dec. 12, 2017, 2 pages.
Patent Owner's Power of Attorney Under 37 C.F.R. sec. 42.10 submitted before the USPTO Patent Trial and Appeal Board case IPR2017-01448, U.S. Pat. No. 9,340,830, filed Jun. 6, 2017, 2 pages.
Patent Owner's Power of Attorney, submitted before the USPTO Patent Trial and Appeal Board case IPR2017-01170, U.S. Pat. No. 9,340,830, filed Dec. 12, 2017, 2 pages.
Patent Owner's Preliminary Response submitted before the USPTO Patent Trial and Appeal Board case IPR2017-01447, U.S. Pat. No. 9,340,830, filed Sep. 6, 2017, 72 pages.
Patent Owner's Preliminary Response submitted before the USPTO Patent Trial and Appeal Board case IPR2017-01448, U.S. Pat. No. 9,340,830, filed Sep. 6, 2017, 71 pages.
Patent Owner's Preliminary Response, submitted before the USPTO Patent Trial and Appeal Board case IPR2017-01170, U.S. Pat. No. 9,340,830, filed Jul. 12, 2017, 70 pages.
Patent Owner's Request for Oral Argument submitted before the USPTO Patent Trial and Appeal Board case IPR2017-01447, U.S. Pat. No. 9,340,830, filed May 22, 2018, 4 pages.
Patent Owner's Request for Oral Argument submitted before the USPTO Patent Trial and Appeal Board case IPR2017-01448, U.S. Pat. No. 9,340,830, filed May 22, 2018, 4 pages.
Patent Owner's Request for Oral Hearing, submitted before the USPTO Patent Trial and Appeal Board case IPR2017-01170, U.S. Pat. No. 9,340,830, filed May 22, 2018, 4 pages.
Patent Owner's Request for Rehearing Pursuant to 37 C.F.R. § 42.71(d), submitted before the USPTO Patent Trial and Appeal Board case IPR2017-01170, U.S. Pat. No. 9,340,830, filed Oct. 25, 2017, 14 pages.
Patent Owner's Response submitted before the USPTO Patent Trial and Appeal Board case IPR2017-01447, U.S. Pat. No. 9,340,830, filed Feb. 16, 2018, 80 pages.
Patent Owner's Response submitted before the USPTO Patent Trial and Appeal Board case IPR2017-01448, U.S. Pat. No. 9,340,830, filed Feb. 16, 2018, 80 pages.
Patent Owner's Response, submitted before the USPTO Patent Trial and Appeal Board case IPR2017-01170, U.S. Pat. No. 9,340,830, filed Feb. 16, 2018, 80 pages.
Patent Owner's Revocation of Power of Attorney With New Power of Attorney Under 37 C.F.R. §42.10, submitted before the USPTO Patent Trial and Appeal Board case IPR2017-01170, U.S. Pat. No. 9,340,830, filed Jun. 21, 2017, 2 pages.
Patent Owner's Second Amended Mandatory Notices Under 37 C.F.R. §42.8, submitted before the USPTO Patent Trial and Appeal Board case IPR2017-01170, U.S. Pat. No. 9,340,830, filed Dec. 12, 2017, 8 pages.

Patent Owner's Unopposed Motion for Pro Hac Vice Admission Under 37 C.F.R. § 42.10( c ) submitted before the USPTO Patent Trial and Appeal Board case IPR2017-01447, U.S. Pat. No. 9,340,830, filed Dec. 1, 2017, 4 pages.
Patent Owner's Unopposed Motion to Expunge Unredacted Versions of Exhibits2077, 2026, 1052, 1053, and 1054 and Petitioner's Reply, submitted before the USPTO Patent Trial and Appeal Board cases IPR2017-01170, IPR2017-01447, and IPR2017-01448, U.S. Pat. No. 9,340,830, filed Aug. 8, 2018, 6 pages.
Patent Owner's Unopposed Motion to Seal, submitted before the USPTO Patent Trial and Appeal Board cases IPR2017-01170, IPR2017-01447, and IPR2017-01448, U.S. Pat. No. 9,340,830, filed May 31, 2018, 9 pages.
Patent Owner's Unopposed Renewed Motion to Seal submitted before the USPTO Patent Trial and Appeal Board case IPR2017-01447, U.S. Pat. No. 9,340,830, filed Apr. 23, 2018, 7 pages.
Patent Owner's Unopposed Renewed Motion to Seal submitted before the USPTO Patent Trial and Appeal Board case IPR2017-01448, U.S. Pat. No. 9,340,830, filed Apr. 23, 2018, 7 pages.
Patent Owner's Unopposed Renewed Motion to Seal, submitted before the USPTO Patent Trial and Appeal Board case IPR2017-01170, U.S. Pat. No. 9,340,830, filed Apr. 23, 2018, 7 pages.
Patent Owner's Updated Exhibit List submitted before the USPTO Patent Trial and Appeal Board case IPR2017-01447, U.S. Pat. No. 9,340,830, filed Apr. 17, 2018, 11 pages.
Patent Owner's Updated Exhibit List submitted before the USPTO Patent Trial and Appeal Board case IPR2017-01447, U.S. Pat. No. 9,340,830, filed Apr. 23, 2018, 11 pages.
Patent Owner's Updated Exhibit List submitted before the USPTO Patent Trial and Appeal Board case IPR2017-01448, U.S. Pat. No. 9,340,830, filed Apr. 17, 2018, 11 pages.
Patent Owner's Updated Exhibit List submitted before the USPTO Patent Trial and Appeal Board case IPR2017-01448, U.S. Pat. No. 9,340,830, filed Apr. 23, 2018, 11 pages.
Patent Owner's Updated Exhibit List, submitted before the USPTO Patent Trial and Appeal Board case IPR2017-01170, U.S. Pat. No. 9,340,830, filed Apr. 17, 2018, 11 pages.
Patent Owner's Updated Exhibit List, submitted before the USPTO Patent Trial and Appeal Board case IPR2017-01170, U.S. Pat. No. 9,340,830, filed Apr. 23, 2018, 11 pages.
Payseur et al., (2010). "A Genomic Portrait of Human Microsatellite Variation," Mol. Biol. Evol., 28(1):303-312.
Peled et al., (2012). "Next Generation Sequencing Identifies and Immunohistochemistry Confirms a Novel Crizotinib Sensitive ALK Rearrangement in a Patient with Metastatic Non-small Cell Lung Cancer," J. Thorac. Oncol., 7(9):1-5.
Pengelly et al., (2013). "A SNP profiling panel for sample tracking in whole-exome sequencing studies," Genome Medicine, 5(89):1-7.
Personal Statement of E. Reines for US Court of Appeals for the Federal Circuit Case 14-MA004, filed Jul. 7, 2014, 2 pages.
Petition for Inter Partes Review of U.S. Pat. No. 9,340,830 submitted before the USPTO Patent Trial and Appeal Board case IPR2017-01447, U.S. Pat. No. 9,340,830, filed May 17, 2017, 75 pages.
Petition for Inter Partes Review of U.S. Pat. No. 9,340,830 submitted before the USPTO Patent Trial and Appeal Board case IPR2017-01448, U.S. Pat. No. 9,340,830, filed May 17, 2017, 77 pages.
Petition for Inter Partes Review of U.S. Pat. No. 9,340,830 submitted before the USPTO Patent Trial and Appeal Board case IPR2017-01170, U.S. Pat. No. 9,340,830, filed Mar. 30, 2017, 73 pages.
Petitioner Guardant Health Inc.'s Updated Exhibit List submitted before the USPTO Patent Trial and Appeal Board case IPR2017-01448, U.S. Pat. No. 9,340,830, filed May 31, 2018, 8 pages.
Petitioner Guardant Health, Inc.'s Motion for Pro Hac Vice Admission Under 37 C.F.R. §42.10( c ) submitted before the USPTO Patent Trial and Appeal Board case IPR2017-01447, U.S. Pat. No. 9,340,830, filed Motion for Pro Hac Vice Admission, filed Mar. 16, 2018, 13 pages.

(56) References Cited

OTHER PUBLICATIONS

Petitioner Guardant Health, Inc.'s Motion for Pro Hac Vice Admission Under 37 C.F.R. §42.10( c) submitted before the USPTO Patent Trial and Appeal Board case IPR2017-01448, U.S. Pat. No. 9,340,830, filed Mar. 16, 2018, 14 pages.
Petitioner Guardant Health, Inc.'s Motion for Pro Hac Vice Admission Under 37 C.F.R. §42.10( c), submitted before the USPTO Patent Trial and Appeal Board case IPR2017-01170, U.S. Pat. No. 9,340,830, filed Mar. 16, 2018, 14 pages.
Petitioner Guardant Health, Inc.'s Power of attorney submitted before the USPTO Patent Trial and Appeal Board case IPR2017-01447, U.S. Pat. No. 9,340,830, filed May 17, 2017, 2 pages.
Petitioner Guardant Health, Inc.'s Power of attorney submitted before the USPTO Patent Trial and Appeal Board case IPR2017-01448, U.S. Pat. No. 9,340,830, filed May 17, 2017, 2 pages.
Petitioner Guardant Health, Inc.'s Power of attorney, submitted before the USPTO Patent Trial and Appeal Board case IPR2017-01170, U.S. Pat. No. 9,340,830, filed Mar. 30, 2017, 2 pages.
Petitioner Guardant Health, Inc.'s Reply to Patent Owner Response submitted before the USPTO Patent Trial and Appeal Board case IPR2017-01447, U.S. Pat. No. 9,340,830, filed May 8, 2018, 36 pages.
Petitioner Guardant Health, Inc.'s Reply to Patent Owner Response submitted before the USPTO Patent Trial and Appeal Board case IPR2017-01448, U.S. Pat. No. 9,340,830, filed May 8, 2018, 37 pages.
Petitioner Guardant Health, Inc.'s Reply to Patent Owner Response, submitted before the USPTO Patent Trial and Appeal Board case IPR2017-01170, U.S. Pat. No. 9,340,830, filed May 8, 2018, 36 pages.
Petitioner Guardant Health, Inc.'s Updated Exhibit List submitted before the USPTO Patent Trial and Appeal Board case IPR2017-01447, U.S. Pat. No. 9,340,830, filed May 31, 2018, 8 pages.
Petitioner Guardant Health, Inc.'s Updated Exhibit List, submitted before the USPTO Patent Trial and Appeal Board case IPR2017-01170, U.S. Pat. No. 9,340,830, filed May 31, 2018, 8 pages.
Petitioner's List of Proposed Motions submitted before the USPTO Patent Trial and Appeal Board case IPR2017-01447, U.S. Pat. No. 9,340,830, filed Dec. 4, 2017, 4 pages.
Petitioner's List of Proposed Motions submitted before the USPTO Patent Trial and Appeal Board case IPR2017-01448, U.S. Pat. No. 9,340,830, filed Dec. 4, 2017, 4 pages.
Petitioner's List of Proposed Motions, submitted before the USPTO Patent Trial and Appeal Board case IPR2017-01170, U.S. Pat. No. 9,340,830, filed Oct. 23, 2017, 4 pages.
Petitioner's Notice of Objection to Evidence submitted before the USPTO Patent Trial and Appeal Board case IPR2017-01447, U.S. Pat. No. 9,340,830, filed Feb. 26, 2018, 6 pages.
Petitioner's Notice of Objection to Evidence submitted before the USPTO Patent Trial and Appeal Board case IPR2017-01448, U.S. Pat. No. 9,340,830, filed Feb. 26, 2018, 6 pages.
Petitioner's Notice of Objection to Evidence, submitted before the USPTO Patent Trial and Appeal Board case IPR2017-01170, U.S. Pat. No. 9,340,830, filed Feb. 26, 2018, 6 pages.
Petitioner's Notice of Objection to Evidence, submitted before the USPTO Patent Trial and Appeal Board cases IPR2017-01170, IPR2017-01447, and IPR2017-01448, U.S. Pat. No. 9,340,830, filed May 14, 2018, 4 pages.
Petitioner's Opposition to Patent Owner's Motion for Protective Order submitted before the USPTO Patent Trial and Appeal Board case IPR2017-01447, U.S. Pat. No. 9,340,830, filed Mar. 5, 2018, 9 pages.
Petitioner's Opposition to Patent Owner's Motion for Protective Order submitted before the USPTO Patent Trial and Appeal Board case IPR2017-01448, U.S. Pat. No. 9,340,830, filed Mar. 5, 2018, 9 pages.
Petitioner's Opposition to Patent Owner's Motion for Protective Order, submitted before the USPTO Patent Trial and Appeal Board case IPR2017-01170, U.S. Pat. No. 9,340,830, filed Mar. 5, 2018, 9 pages.
Petitioner's Opposition to Patent Owner's Motion to Seal submitted before the USPTO Patent Trial and Appeal Board case IPR2017-01447, U.S. Pat. No. 9,340,830, filed Mar. 5, 2018, 7 pages.
Petitioner's Opposition to Patent Owner's Motion to Seal submitted before the USPTO Patent Trial and Appeal Board case IPR2017-01448, U.S. Pat. No. 9,340,830, filed Mar. 5, 2018, 7 pages.
Petitioner's Opposition to Patent Owners Motion to Seal, submitted before the USPTO Patent Trial and Appeal Board case IPR2017-01170, U.S. Pat. No. 9,340,830, filed Mar. 5, 2018, 7 pages.
Petitioner's Opposition to Patent Owner's Motion to Submit Supplemental Information submitted before the USPTO Patent Trial and Appeal Board case IPR2017-01447, U.S. Pat. No. 9,340,830, filed May 21, 2018, 10 pages.
Petitioner's Opposition to Patent Owner's Motion to Submit Supplemental Information submitted before the USPTO Patent Trial and Appeal Board case IPR2017-01448, U.S. Pat. No. 9,340,830, filed May 21, 2018, 10 pages.
Petitioner's Opposition to Patent Owner's Motion to Submit Supplemental Information, submitted before the USPTO Patent Trial and Appeal Board case IPR2017-01170, U.S. Pat. No. 9,340,830, filed May 21, 2018, 10 pages.
Petitioner's Request for Oral Argument Pursuant to 37 C.F.R. § 42.70 submitted before the USPTO Patent Trial and Appeal Board case IPR2017-01447, U.S. Pat. No. 9,340,830, filed May 22, 2018, 3 pages.
Petitioner's Request for Oral Argument Pursuant to 37 C.F.R. § 42.70, submitted before the USPTO Patent Trial and Appeal Board case IPR2017-01170, U.S. Pat. No. 9,340,830, filed May 22, 2018, 3 pages.
Petitioner's Request for Oral Argument Pursuant to 37 C.F.R. sec. 42.70 submitted before the USPTO Patent Trial and Appeal Board case IPR2017-01448, U.S. Pat. No. 9,340,830, filed May 22, 2018, 3 pages.
Petitioner's Updated Exhibit List submitted before the USPTO Patent Trial and Appeal Board case IPR2017-01447, U.S. Pat. No. 9,340,830, filed Jun. 6, 2017, 7 pages.
Plaintiff Foundation Medicine, Inc.'s Opposition to Defendant's Motion to Dismiss Complaint Pursuant to Fed. R. Civ. P. 12(B)(6), Civil Action No. 2:16-CV-00523-JRG-RSP, filed Aug. 25, 2016, 10 pages.
Plaintiff Foundation Medicine's First Preliminary Infringement Contentions in *Foundation Medicine, Inc.* v. *Guardant Health, Inc.*, C.A. No. 2:16-cv-00523-JRG-RSP, filed Aug. 25, 2016, 91 pages.
Plaintiff's P.R. 4-2 Preliminary Claim Constructions in *Foundation Medicine, Inc.* v. *Guardant Health, Inc.*, C.A. No. 2:16-cv-00523-JRG-RSP, filed Apr. 20, 2017, 8 pages.
Promega, (2015). "Maxwell® 16 Cell LEV Total RNA Purification Kit Technical Bulletin," Promega Literature #TB351, 18 pages.
Promega, (2017). "Maxwell® 16 FFPE Plus LEV DNA Purification Kit Technical Manual," Promega Literature #TM349, 13 pages.
Promega, (2017). "Maxwell® 16 LEV Blood DNA Kit and Maxwell® 16 Buccal Swab LEV DNA Purification Kit Technical Manual," Promega Literature #TM333, 11 pages.
Proposed Clean Version of the Modified Default Protective Order by Foundation Medicine, Inc., submitted before the USPTO Patent Trial and Appeal Board for Case Nos. IPR2017-01170, IPR2017-01447, and IPR2017-01448, U.S. Pat. No. 9,340,830, filed Apr. 23, 2018, 6 pages.
Proposed Redline Version of the Modified Default Protective Order by Foundation Medicine, Inc., submitted before the USPTO Patent Trial and Appeal Board for Case Nos. IPR2017-01170, IPR2017-01447, and IPR2017-01448, U.S. Pat. No. 9,340,830, filed Apr. 23, 2018, 6 pages.
Protective Order, submitted before the USPTO Patent Trial and Appeal Board cases IPR2017-01170, IPR2017-01447, and IPR2017-01448, U.S. Pat. No. 9,340,830, filed May 31, 2018, 9 pages.
Qiagen, (2020). "QIAamp® DNA FFPE Tissue Handbook," Qiagen, Cat. No. 37625, 28 pages.
Rebuttal Declaration of Dr. S. Gabriel in Support of Foundation Medicine, Inc.'s Proposed Claim Constructions for *Foundation Medicine, Inc.* v. *Guardant Health, Inc.*, Civil Action No. 2:16-CV-00523-JRG-RSP, dated Mar. 17, 2017, 11 pages.

(56) References Cited

OTHER PUBLICATIONS

Rebuttal Declaration of Stacey Gabriel, Ph.D. in Support of Foundation Medicine, Inc.'s Proposed Claim Constructions in *Foundation Medicine, Inc. v. Guardant Health, Inc.*, C.A. No. 2:16-cv-00523-JRG-RSP, filed Apr. 6, 2017, 12 pages.
Record of Oral Hearing held on Jun. 13, 2018, submitted before the USPTO Patent Trial and Appeal Board cases IPR2017-01170, IPR2017-01447, and IPR2017-01448, U.S. Pat. No. 9,340,830, filed Jun. 13, 2018, 88 pages.
Redacted Deposition of Dr. J. Nemunaitis (Apr. 5, 2018) in *Guardant Health, Inc. v. Foundation Medicine, Inc.* Case Nos. IPR2017-01170, IPR2017-01447, and IPR2017-01448, U.S. Pat. No. 9,340,830, 166 pages.
Redacted Deposition of Dr. S. Gabriel (Apr. 3, 2018) in *Guardant Health, Inc. v. Foundation Medicine, Inc.* Case Nos. IPR2017-01170, IPR2017-01447, and IPR2017-01448, U.S. Pat. No. 9,340,830, filed May 31, 2018, 287 pages.
Redacted Deposition of Dr. S. Gabriel (Apr. 3, 2018) in *Guardant Health, Inc. v. Foundation Medicine, Inc.* Case Nos. IPR2017-01170, IPR2017-01447, and IPR2017-01448, U.S. Pat. No. 9,340,830, filed May 8, 2018, 287 pages.
Redacted Expert Declaration of Dr. S. Gabriel submitted before the USPTO Patent Trial and Appeal Board for case IPR2017-01170, U.S. Pat. No. 9,340,830, filed Apr. 23, 2018, 88 pages.
Redacted Expert Declaration of Dr. S. Gabriel submitted before the USPTO Patent Trial and Appeal Board for case IPR2017-01170, U.S. Pat. No. 9,340,830, filed Feb. 16, 2018, 88 pages.
Redacted Expert Declaration of Dr. S. Gabriel submitted before the USPTO Patent Trial and Appeal Board for case IPR2017-01447, U.S. Pat. No. 9,340,830, filed Apr. 23, 2018, 88 pages.
Redacted Expert Declaration of Dr. S. Gabriel submitted before the USPTO Patent Trial and Appeal Board for case IPR2017-01447, U.S. Pat. No. 9,340,830, filed Feb. 16, 2018, 88 pages.
Redacted Expert Declaration of Dr. S. Gabriel submitted before the USPTO Patent Trial and Appeal Board for case IPR2017-01448, U.S. Pat. No. 9,340,830, filed Apr. 23, 2018, 88 pages.
Redacted Expert Declaration of Dr. S. Gabriel submitted before the USPTO Patent Trial and Appeal Board for case IPR2017-01448, U.S. Pat. No. 9,340,830, filed Feb. 16, 2018, 88 pages.
Redline Version of the Modified Default Protective Order by Foundation Medicine, Inc., submitted before the USPTO Patent Trial and Appeal Board for Case Nos. IPR2017- 01170, IPR2017-01447, and IPR2017-01448, U.S. Pat. No. 9,340,830, filed Feb. 16, 2018, 8 pages.
Reply in Support of Patent Owner's Motion for Protective Order submitted before the USPTO Patent Trial and Appeal Board case IPR2017-01447, U.S. Pat. No. 9,340,830, filed Mar. 12, 2018, 8 pages.
Reply in Support of Patent Owner's Motion for Protective Order submitted before the USPTO Patent Trial and Appeal Board case IPR2017-01448, U.S. Pat. No. 9,340,830, filed Mar. 12, 2018, 8 pages.
Reply in Support of Patent Owner's Motion for Protective Order, submitted before the USPTO Patent Trial and Appeal Board case IPR2017-01170, U.S. Pat. No. 9,340,830, filed Mar. 12, 2018, 8 pages.
Reply in Support of Patent Owner's Motion to Seal submitted before the USPTO Patent Trial and Appeal Board case IPR2017-01447, U.S. Pat. No. 9,340,830, filed Mar. 12, 2018, 8 pages.
Reply in Support of Patent Owner's Motion to Seal submitted before the USPTO Patent Trial and Appeal Board case IPR2017-01448, U.S. Pat. No. 9,340,830, filed Mar. 12, 2018, 8 pages.
Reply in Support of Patent Owner's Motion to Seal, submitted before the USPTO Patent Trial and Appeal Board case IPR2017-01170, U.S. Pat. No. 9,340,830, filed Mar. 12, 2018, 8 pages.
Reporter's Transcription of Teleconference Board Meeting, (Apr. 16, 2018) in *Guardant Health, Inc. v. Foundation Medicine, Inc.*: Case Nos. IPR2017-01170, IPR2017-01447, and IPR2017-01448, 22 pages.

Rosell et al., (2009). "Screening for Epidermal Growth Factor Receptor Mutations in Lung Cancer," N. Engl. J. Med, 361:958-67.
Ross et al., (2013). "Comprehensive genomic profiling of epithelial ovarian cancer by next generation sequencing-based diagnostic assay reveals new routes to targeted therapies," Gynecologic Oncology, 130:554-559.
Ross et al., (2017). "ALK Fusions in a Wide Variety of Tumor Types Respond to Anti-ALK Targeted Therapy," The Oncologist, 22:1444-1450.
Roy, et al. (2006). "Survival Advantage from Imatinib Compared with the Combination Interferon-alpha plus Cytarabine in Chronic-Phase Chronic Myelogenous Leukemia: Historical Comparison Between Two Phase 3 Trials," Blood, 108(5): 1478-1484.
Sakharkar et al., (2004). "Distributions of Exons and Introns in the Human Genome," In Silico Biology, 4:387-393.
Sambrook et al., (2001). "In Vitro Amplification of DNA by the Polymerase Chain Reaction," Molecular Cloning: A Laboratory Manual, 3rd edition, 2:6-28.
Scheduling Order submitted before the USPTO Patent Trial and Appeal Board case IPR2017-01447, U.S. Pat. No. 9,340,830, filed Nov. 28, 2017, 7 pages.
Scheduling Order submitted before the USPTO Patent Trial and Appeal Board case IPR2017-01448, U.S. Pat. No. 9,340,830, filed Nov. 28, 2017, 7 pages.
Scheduling Order, submitted before the USPTO Patent Trial and Appeal Board case IPR2017-01170, U.S. Pat. No. 9,340,830, filed Oct. 11, 2017, 7 pages.
Schuster, (2008). Next-generation sequencing transforms today's biology, Nature Methods, 5(1):16-18.
Second Amended Scheduling Order submitted before the USPTO Patent Trial and Appeal Board case IPR2017-01447, U.S. Pat. No. 9,340,830, filed Dec. 12, 2017, 3 pages.
Second Amended Scheduling Order submitted before the USPTO Patent Trial and Appeal Board case IPR2017-01448, U.S. Pat. No. 9,340,830, filed Dec. 12, 2017, 3 pages.
Second Amended Scheduling Order, submitted before the USPTO Patent Trial and Appeal Board case IPR2017-01170, U.S. Pat. No. 9,340,830, filed Dec. 12, 2017, 3 pages.
Shah et al., (2009). "Mutational Evolution in a Lobular Breast Tumour Profiled at Single Nucleotide Resolution," Nature, 461:809-813, and Supplementary Information, 1021 pages.
Shah et al., (2012). "The clonal and mutational evolution spectrum of primary triple-negative breast cancers," Nature, 486:395-399.
Shepherd et al., (2005). "Erlotinib in Previously Treated Non-Small-Cell Lung Cancer," N. Engl. J. Med, 353:123-32.
Sherry et al., (2001). "DbSNP: the NCBI database of genetic variation," Nucleic Acids Res., 29(1):308-311.
Shum, J. et al. (2009). "Chemically Modified Primers for Improved Multiplex PCR," Anal. Biochem., 388(2):15 pages.
Specht et al., (2001). "Quantitative Gene Expression Analysis in Microdissected Archival Formalin-Fixed and Paraffin-Embedded Tumor Tissue," Am J Pathol., 158(2):419-429.
Stephens, et al., (2009). "Complex Landscapes of Somatic Rearrangement in Human Breast Cancer Genomes," Nature, 462: 8 pages.
Stratton et al., (2009). "The cancer genome," Nature, 458: 6 pages.
Sucker et al., (2017). "Acquired IFNgamma resistance impairs anti-tumor immunity and gives rise to T-cell-resistant melanoma lesions," Nature Communications, 8(154):1-15.
Summerer et al., "Microarray-based multicycle-enrichment of genomic subsets for targeted next generation sequencing," Genome Research (2009) vol. 19, pp. 1616-1621.
Summerer et al., (2010). "Supplementary Information Targeted High Throughput Sequencing of a Cancer-related Exome Subset by Specific Sequence Capture with a Fully Automated Microarray Platform," Genomics, 95(4), Apr. 1, 2010, 9 pages.
Summerer et al., (2010). "Targeted high Throughput Sequencing of a Cancer-Related Exome Subset by specific Sequence Capture with a Fully Automated Microarray Platform", Genomics, 95(4):241-246.
Summerer, (2009). "Enabling technologies of genomic-scale sequence enrichment for targeted high-throughput sequencing," Genomics, 94:363-368.

(56) References Cited

OTHER PUBLICATIONS

Sun et al., (2014). "Abstract 1893: A computational method for somatic versus germline variant status determination from targeted next-generation sequencing of clinical cancer specimens without a matched normal control," Cancer Research, 74(19S):1893.

Sun et al., (2018). "A computational approach to distinguish somatic vs. germline origin of genomic alterations from deep sequencing of cancer specimens without a matched normal," PLoS Comput Biol., 14(2):e1005965, 13 pages.

Taylor et al., (2011). "Clinical cancer genomics: how soon is now?" The Journal of Pathology, 223(2):319-327.

Taylor, (2017). "Foundation Medicine gets FDA, CMS nods for pan-cancer genomic test," available online at <https://www.fiercebiotech.com/medtech/foundation-medicine-gets-fda-cms-nods-for-pan-cancer-genomic-test>, accessed on Feb. 16, 2018, 3 pages.

Termination, Terminating the Proceeding 37 C.F.R. sec. 42.72, submitted before the USPTO Patent Trial and Appeal Board cases IPR2017-01170, IPR2017-01447, and IPR2017-01448, U.S. Pat. No. 9,340,830, filed Jul. 10, 2018, 3 pages.

Tewhey et al., (2009). "Enrichment of Sequencing Targets from the Human Genome by solution Hybridization," Genome Biology, 10:R116, 13 pages.

The 1000 Genomes Project Consortium, (2012). "An integrated map of genetic variation from 1,092 human genomes," Nature, 491:56-65.

The Cancer Genome Atlas Network, (2015). "Genome Classification of Cutaneous Melanoma" Cell Press, 161:1681-1696.

Third Party Observations Filed in Australian Patent Application No. 2011352070, Jan. 30, 2017, 4 pages.

Timmermann et al., "Somatic Mutation Profiles of MSI and MSS Colorectal Cancer Identified by Whole Exome Next Generation Sequencing and Bioinformatics Analysis," PLOS One (2010) vol. 5, Issue 12, Article e15661, 10 pages.

Wang et al., (2012). "A quick and simple FISH protocol with hybridization-sensitive fluorescent linear oligodeoxynucleotide probes," RNA, 18:166-175.

Wilkerson et al., (2014). "Integrated RNA and DNA sequencing improves mutation detection in low purity tumors," Nucleic Acids Research, e107, 12 pages.

World Health Organization, (2014). "World Cancer Report 2014," WHO Press, World Health Organization, 19 pages.

Wu, D. et al. (1989). "Allele-Specific Enzymatic Amplification of β-Globin Genomic DNA for Diagnosis of Sickle Cell Anemia," Proc. Natl. Acad. Sci. USA, 86:2757-2760.

Yassour, M. et al. (2009). "Ab Initio Construction of a Eukaryotic Transcriptome by Massively Parallel mRNA Sequencing," PNAS, 106(9):13 pages.

Coronella et al., (2002). "Antigen-Driven Oligoclonal Expansion of Tumor-Infiltrating B Cells in Infiltrating Ductal Carcinoma of the Breast," J. Immunol., 169(4):1829-1836.

Thor Straten et al., (2004). "T-cell clonotypes in cancer," Journal of Translational Medicine, 2:11, 10 pages.

Woodsworth et al., (2013). "Sequence analysis of T-cell repertoires in health and disease," Genome Medicine, 5:98, 13 pages.

Clement et al., (2010). "The GNUMAP algorithm: unbiased probabilistic mapping of oligonucleotides from next-generation sequencing," Bioinformatics, 26(1):38-45.

De Bona et al., (2008). "Optimal spliced alignments of short sequence reads," Bioinformatics, 24(16):i174-i180.

Eaves et al., (2009). "MOM: maximum oligonucleotide mapping," Bioinformatics, 25(7):969-70.

Fahlgren et al., (2009). "Computational and analytical framework for small RNA profiling by high-throughput sequencing," RNA, 15:992-1002.

Homer et al., (2009). "BFAST: An Alignment Tool for Large Scale Genome Resequencing," PLOS One, 4(11):e7767, 12 pages.

Jiang et al., (2008). "SeqMap: mapping massive amount of oligonucleotides to the genome," Bioinformatics, 24:2395-2396.

Kent, (2002). "BLAT—the BLAST-like alignment tool," Genome Res., 12(4):656-64.

Kim et al., (2009). "ProbeMatch: rapid alignment of oligonucleotides to genome allowing both gaps and mismatches," Bioinformatics, 25(11):1424-5.

Krishnakumar et al., (2008). "A comprehensive assay for targeted multiplex amplification of human DNA sequences," Proc. Natl. Acad. Sci. USA, 105:9296-9310.

Langmead et al., (2009). "Ultrafast and memory-efficient alignment of short DNA sequences to the human genome," Genome Biol., 10(3):R25, 10 pages.

Lasken, (2007). "Single-cell genomic sequencing using Multiple Displacement Amplification," Curr Opin Microbiol., 10(5):510-6.

Li et al., (2008). "Mapping short DNA sequencing reads and calling variants using mapping quality scores," Genome Res., 18(11):1851-8.

Li et al., (2008). "SOAP: short oligonucleotide alignment program," Bioinformatics, 24(5):713-4.

Li et al., (2009). "SOAP2: an improved ultrafast tool for short read alignment," Bioinformatics, 25(15):1966-7.

Malhis et al., (2009). "Slider-maximum use of probability information for alignment of short sequence reads and SNP detection," Bioinformatics, 25(1):6-13.

Muller et al., (2001). "Non-symmetric score matrices and the detection of homologous transmembrane proteins," Bioinformatics, 17 Suppl 1:S182-9.

Ning et al., (2001). "SSAHA: a fast search method for large DNA databases," Genome Res., 11(10):1725-9.

Ondov et al., (2008). "Efficient mapping of Applied Biosystems SOLiD sequence data to a reference genome for functional genomic applications," Bioinformatics, 24(23):2776-7.

Porreca et al., (2007). "Multiplex amplification of large sets of human exons," Nature Methods, 4:931-936.

Prufer et al., (2008). "PatMaN: rapid alignment of short sequences to large databases," Bioinformatics, 24(13):1530-1.

Rumble et al., (2009). "SHRiMP: Accurate Mapping of Short Color-space Reads," PLoS Comput. Biol., 5(5):e1000386, 11 pages.

Salmela, (2010). "Correction of sequencing errors in a mixed set of reads," Bioinformatics, 26(10):1284-90.

Schatz, (2009). "CloudBurst: highly sensitive read mapping with MapReduce," Bioinformatics, 25(11):1363-9.

Shi et al., (2010). "A parallel algorithm for error correction in high-throughput short-read data on CUDA-enabled graphics hardware," J Comput Biol., 17(4):603-15, 20 pages.

Smith et al., (2009). "Updates to the RMAP short-read mapping software," Bioinformatics, 25(21):2841-2.

Tewhey et al., (2009). "Microdroplet-based PCR enrichment for large-scale targeted sequencing," Nature Biotech., 27:1025-1031, 24 pages.

Turner et al., (2009). "Massively parallel exon capture and library-free resequencing across 16 genomes," Nature Methods, 6:315-316, 5 pages.

Weese et al., (2009). "RazerS—fast read mapping with sensitivity control," Genome Research, 19:1646-1654.

Wong et al., (1996). "Use of tagged random hexamer amplification (TRHA) to clone and sequence minute quantities of DNA—application to a 180 kb plasmid isolated from Sphingomonas F199," Nucleic Acids Res., 24(19):3778-83.

Wu et al., (2005). "GMAP: a genomic mapping and alignment program for mRNA and EST sequences," Bioinformatics, 21(9):1859-75.

Wu et al., (2010). "Fast and SNP-tolerant detection of complex variants and splicing in short reads," Bioinformatics, 26(7):873-81.

\* cited by examiner

SEQUENCE LISTING

```
<160> NUMBER OF SEQ ID NOS: 3

<210> SEQ ID NO 1
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (16)..(135)
<223> OTHER INFORMATION: a, c, t, g, unknown or other

<400> SEQUENCE: 1
atcgcaccag cgtgtnnnnn nnnnnnnnnn nnnnnnnnnn nnnnnnnnnn nnnnnnnnnn     60
nnnnnnnnnn nnnnnnnnnn nnnnnnnnnn nnnnnnnnnn nnnnnnnnnn nnnnnnnnnn    120
nnnnnnnnnn nnnnncactg cggctcctca                                     150

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aatgatacgg cgaccaccga gat                                             23

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caagcagaag acggcatacg a                                               21
```

MULTIGENE ANALYSIS OF TUMOR SAMPLES

CROSS REFERENCE TO RELATED APPLICATIONS

This application is the U.S. National Phase Application under 35 U.S.C. § 371 of International Application No. PCT/US2015/064044, filed Dec. 4, 2015, which claims the benefit of U.S. Provisional Application No. 62/088,457, filed Dec. 5, 2014. The contents of the aforementioned application are hereby incorporated by reference in their entirety.

SEQUENCE LISTING

The instant application contains a Sequence Listing which has been submitted electronically in ASCII format and is hereby incorporated by reference in its entirety. Said ASCII copy, created on Dec. 3, 2015, is named F2036-7056WO-_SL.txt and is 1,172 bytes in size.

FIELD OF INVENTION

The invention relates to optimized methods for analyzing nucleic acids from tumor samples, e.g., methods having integrated optimized nucleic acid selection, read alignment, and mutation calling.

BACKGROUND OF THE INVENTION

Genomic testing of cancer cells shows significant promise towards developing better understanding of cancers and managing more effective treatment approaches. Genomic testing involves the sequencing of the genome of a patient's cancer cells and identifying any genomic alteration in those cells. Genomic alterations can include, for example, mutations, base substitutions, rearrangements, deletions, insertions, among other options. Understanding these genomic alterations as they are found in a specific patient's cancer may also help develop better treatments and help identify the best approaches for treating specific cancer variants using genomic alteration information.

SUMMARY OF THE INVENTION

Methods described herein provide for the use of hybridization of sample nucleic acid to a bait set to evaluate a region of interest, e.g., to evaluate the clonal profile of a region of interest, in the sample. E.g., a method described herein allows analysis of the abundance or structure of loci that are subject to somatic change, e.g., rearrangement or somatic hypermutation. Methods described herein allow for the evaluation of the rearrangement and expression of selected sequences, e.g., V segments, or other sequences, e.g., immunoglobulin sequences, B cell receptor (BCR) sequences, or T cell receptor (TCR) sequences. Methods described herein allow for clonal analysis, e.g., providing the relative abundance of selected signatures or cells containing them. A typical, non-limiting application is evaluating the V, D, or J segment usage in somatically rearranged antibody, and B cell receptor or T cell receptor genes. The method can be conducted at the genomic level (e.g., the analysis of chromosomal DNA) or at the level of transcription (e.g., analysis of mRNA) or both. In an embodiment, the method provides the clonal profile of a first subject interval and the sequence of a second preselected subject interval, e.g., the clonal profile of V segments and the occurrence or absence of a mutation in another gene, e.g., an oncogene. In an embodiment, the clonal profile of the first subject interval in a first cell type is provided. In another embodiment, the sequence of the second subject interval in a second cell type is provided. For example, the first cell type can be a non-malignant cell, e.g., a tumor-infiltrating lymphocyte (TIL), and the second cell type can be a malignant cell. The first cell type and the second cell type can be obtained from the same sample, e.g., tumor sample, from a patient. Thus, the method provides integrated analysis of a clonal profile and somatic mutations, e.g., somatic mutations associated with disease, e.g., cancer.

Accordingly, in an aspect, the invention features a method of evaluating or providing a clonal profile of a subject interval, e.g., a subgenomic interval, or an expressed subgenomic interval (or of a cell containing the same), in a subject, comprising:

(a) acquiring a nucleic acid library comprising a plurality of members, each member of the plurality comprising a nucleic acid from the subject, e.g., a plurality of tumor members from a solid tumor or hematologic malignancy (or premalignancy) sample;

(b) contacting the library with a bait set to provide a plurality of selected members, each of which comprises the subject interval, or a portion thereof (sometimes referred to herein as a library catch);

optionally, (c) amplifying each member of the plurality of selected members, e.g., to provide an amplified sequence of the subject interval;

(d) acquiring the sequence of one or more occurrences of the subject interval;

thereby providing or evaluating the clonal profile of a subject interval.

In an embodiment, step (a) comprises fragmenting, e.g., shearing, a nucleic acid from the subject.

In an embodiment, step (b) comprises contacting the library with the bait set under conditions of solution hybridization.

In an embodiment, step (b) comprises contacting the library with the bait set under conditions of surface-based hybridization.

In an embodiment, step (b) comprises contacting the library with the bait set on a surface, e.g., a bait set disposed on a substrate comprising a plurality of baits.

In an embodiment, step (c) comprises amplifying each member of the plurality of selected members by a method that relies on or comprises a sequence specific interaction with a target/subject nucleic acid in the member, e.g., by amplifying each member of the plurality of selected members with a primer that binds to a target/subject nucleic acid in the member.

In an embodiment, step (c) comprises amplifying each member of the plurality of selected members with a primer pair, wherein at least one member of the primer pair does not bind to a target/subject nucleic acid in the member.

In an embodiment, step (c) comprises amplifying each member of the plurality of selected members by a method that does not rely on or comprise a sequence specific interaction with a target/subject nucleic acid in the member.

In an embodiment, step (c) comprises amplifying each member of the plurality of selected members by amplifying each member of the plurality of selected members with a primer pair that does not bind to a target/subject nucleic acid in the member.

In an embodiment, the subject interval comprises a subgenomic interval.

In an embodiment, the subject interval comprises an expressed subgenomic interval.

In an embodiment, the method comprises evaluating the clonal profile of a subgenomic interval and of an expressed subgenomic interval.

In an embodiment, the method comprises comparing the sequence of a first allele or signature (e.g., a first V segment) at the subject interval with a comparison value, e.g., a preselected value, e.g., a value that is a function of the sequence of a second allele or signature (e.g., a second V segment).

In an embodiment, the method further comprises:
(e) acquiring:
  (i) a value for the distribution, expression (the occurrence or level of transcribed copies of a subgenomic signature), abundance, or identity, of a sequence, signature or allele at the subject interval, e.g., the relative abundance, of a sequence, a signature, or an allele, or the relative abundance of each of a plurality of sequences, signatures, or alleles, at the subject interval; or
  (ii) a value for variability, e.g., sequence variability arising from a somatic hypermutation, sequence variability arising from a VD, DJ, or VJ junction, e.g., by the formation of an indel at the junction, or a CDR, e.g., heavy chain CDR3, sequence variability, within a signature or subject interval, e.g., wherein a value for variability is a function of the number of different variants present for the subject interval in a subject or sample.

In an embodiment, (i) comprises acquiring a value for the relative abundance of a first sequence, allele, or signature at the subject interval relative to the abundance of a first sequence, allele, or signature at the subject interval. In an embodiment, (i) comprises acquiring a value for the relative abundance of a first sequence, allele, or signature at the subject interval relative to the abundance of a second sequence, allele, or signature at a second subject interval.

In an embodiment, (i) comprises acquiring a value for the relative abundance of a first sequence, allele, or signature at the subject interval relative to the abundance of a plurality of sequences, alleles, or signatures at the subject interval.

In an embodiment, (i) comprises acquiring a value for the occurrence or level of a sequence, allele, or signature, e.g., a rearrangement, e.g., a translocation, at an expressed subgenomic interval.

In an embodiment, the method further comprises acquiring a value for the occurrence or level of the sequence, allele, or signature, e.g., a rearrangement, e.g., a translocation, at the corresponding subgenomic interval.

In an embodiment, (ii) comprises acquiring a value for the number of different sequences, alleles, or signatures, occurring at a subject interval.

In an embodiment, the method comprises acquiring (e)(i).
In an embodiment, the method comprises acquiring (e)(i) for a signature.
In an embodiment, the method comprises acquiring (e)(i) for an allele.
In an embodiment, the method comprises acquiring (e)(ii).
In an embodiment, the method comprises providing the clonal profile of a sequence, allele or signature, e.g., a V segment, or VDJ or VJ rearrangement, at a first subject interval; and i) a phenotype, e.g., disease state, of the subject; or
ii) the genotype at a second subject interval, e.g., the genotype of a gene selected from Tables 1-9 or an MHC gene, e.g., a MHC class I or MHC class II gene.

In an embodiment, the phenotype comprises:
an infection with an infectious agent, e.g., a bacterium, virus, protozoan, or fungus;
stage of disease;
a change in the genotype of a disorder, e.g., a cancer;
a change in the manifestation of a disorder, e.g., in the case of cancer, a change in aggressiveness or resistance to treatment, e.g., in the case of cancer, development of metastases;
responsiveness to a treatment develops;
progression, relapse, recurrence, or persistence of a disease or disorder;
prior exposure to an agent associated with a disease;
prior exposure or response to an antigen or vaccine;
proteomic data from the subject;
age;
gender;
weight;
medical history, e.g., prior incidence of disease or prior treatment; or
an environmental or occupational factor.

In an embodiment, the genotype at the second subject interval comprises a somatic mutation, e.g., rearrangement, e.g., translocation, e.g., in a gene from Tables 1-9.

In an embodiment, step (d):
(i) comprises acquiring the sequence of each of a plurality of occurrences of the subject interval, e.g., acquiring the sequence of first occurrence of a subject interval comprising a V segment and of a second occurrence of the interval comprising the V segment, wherein the first and second occurrences differ by the diversity at a VD, DJ, or VJ junction; or
(ii) comprises acquiring the sequence of a first subject interval and of a second different subject interval, e.g., wherein the first subject interval comprises a sequence from a first gene and the second subject interval comprises sequence from a second gene.

In an embodiment, step (d) comprises acquiring the sequence of each of a plurality of occurrences of the subject interval, e.g., a plurality of occurrences of a subject interval comprising a VDJ sequence, e.g., a plurality of occurrences of a subject interval comprising a VDJ sequence comprising a specific V segment, a specific D segment, and a specific J segment.

In an embodiment, the first occurrence of the plurality of occurrences of the subject interval comprises a subgenomic interval.

In an embodiment, the second occurrence of the plurality of occurrences of the subject interval comprises a subgenomic interval.

In an embodiment, the first occurrence of the plurality of occurrence s of the subject interval comprises an expressed subgenomic interval.

In an embodiment, the second occurrence of the plurality of occurrences of the subject interval comprises an expressed subgenomic interval.

In an embodiment, the first occurrence of the plurality of occurrence s of the subject interval comprises a subgenomic interval, e.g., a rearrangement, e.g., a translocation; and the second occurrence of the plurality of occurrences of the subject interval comprises an expressed subgenomic interval, e.g., an expressed subgenomic interval that corresponds to the subgenomic interval, which, e.g., allows for evaluation of the expression of genomic, e.g., somatic genomic, rearrangements, e.g., allows for evaluation of the relative abundance of a genomic rearrangement and its expression.

In an embodiment, the method comprises evaluating the occurrence or level of expression of a signature present in a subgenomic interval.

In an embodiment, step (d) comprises acquiring the sequence of a first subject interval and of a second different subject interval, e.g., where the first and second intervals correspond to different genomic sequences from the subject interval, e.g., a sequence from a first gene and sequence from a second gene.

In an embodiment, the first subject interval comprises a first combination of VDJ segments and the second subject interval comprises a second combination of VDJ segments, e.g., the first subject interval comprises a first V segment and the second subject interval comprises a second V segment.

In an embodiment, the first subject interval comprises a first subgenomic interval and the second subject interval comprises a second subgenomic interval.

In an embodiment, the first subject interval comprises a first express subgenomic interval and the second subject interval comprises a second expressed subgenomic interval.

In an embodiment, the first subject interval comprises a subgenomic interval and the second subject interval comprises an expressed subgenomic interval.

In an embodiment, evaluating comprises providing the clonal profile for a first clone of a cancer.

In an embodiment, evaluating comprises providing the clonal profile for a second clone of a cancer.

In an embodiment, evaluating comprises providing a value for the abundance of the first clone of the cancer, e.g., relative to a reference, e.g., relative to the abundance of the second clone of a cancer.

In an embodiment, the method comprises providing the relative abundance of a first clone of a cancer comprising a genotype and a second clone comprising a second genotype.

In an embodiment, the method comprises providing the relative abundance of a first clone of a cancer comprising a first mutation, e.g., rearrangement, and a second clone not comprising the mutation.

In an embodiment, the method comprises providing the relative abundance of a first clone of a cancer comprising a first mutation, e.g., a rearrangement, e.g., a translocation, and a second clone not comprising a second comprising a second mutation, e.g., a rearrangement, e.g., a translocation.

In an embodiment, evaluating comprises providing the clonal profile for a first V segment.

In an embodiment, evaluating comprises providing the clonal profile for a second V segment.

In an embodiment, evaluating comprises providing a value for the relative abundance of the first V segment and the second V segment.

In an embodiment, evaluating comprises providing the clonal profile for a first D segment.

In an embodiment, evaluating comprises providing the clonal profile for a second D segment.

In an embodiment, evaluating comprises providing a value for the relative abundance of the first D segment and the second D segment.

In an embodiment, evaluating comprises providing the clonal profile for a first J segment.

In an embodiment, evaluating comprises providing the clonal profile for a second J segment.

In an embodiment, evaluating comprises providing a value for the relative abundance of the first J segment and the second J segment.

In an embodiment, evaluating comprises providing the clonal profile for a first VDJ or VJ combination.

In an embodiment, evaluating comprises providing the clonal profile for a second VDJ or VJ combination.

In an embodiment, evaluating comprises providing a value for the relative abundance of the first VDJ or VJ combination and the second VDJ or VJ combination.

In an embodiment, evaluating comprises providing the clonal profile for an antibody light chain.

In an embodiment, evaluating comprises providing the clonal profile for an antibody heavy chain.

In an embodiment, evaluating comprises providing a value for the relative abundance of an antibody light chain and an antibody heavy chain.

In an embodiment, evaluating comprises providing the clonal profile for a sequence, allele or signature in a subgenomic interval.

In an embodiment, evaluating comprises providing the clonal profile for a sequence, allele or signature in an expressed subgenomic interval.

In an embodiment, evaluating comprises providing a value for the relative abundance for a sequence, allele or signature in a subgenomic interval and for a sequence, allele or signature in an expressed subgenomic interval.

In an embodiment, evaluating comprises providing the variability for hypermutation in a locus, e.g., in a V, D, or J segment, in a subject interval.

In an embodiment, evaluating comprises providing the variability arising from a VD, DJ, or VJ junction, e.g., by the formation of an indel at the junction, in a subject interval.

In an embodiment, evaluating comprises providing the variability in a CDR, e.g., heavy chain CDR3, in a subject interval.

In an embodiment, evaluating comprises providing the clonal profile for a sequence from Table 10 (or a cell that comprises the sequence):

TABLE 10 sequence encoding an antibody;
sequence encoding an antibody light chain;
sequence encoding an antibody heavy chain;
sequence encoding a variable region, e.g., a heavy chain or light chain variable region;
sequence encoding a constant region, e.g., a heavy chain or light chain constant region;
sequence diagnostic for light chain type, e.g., kappa or lambda specific sequence;
constant region sequence, e.g., a constant region sequence which can distinguish one or more of Ig classes and subclasses, e.g., IgG, e.g., IgG1, IgG2, IgG3, or IgG4, IgM, IgD, IgA, e.g., IgA1, IgA2, or IgE.
sequence from a CDR, e.g., a light chain CDR1, CDR2, or CDR3, or a heavy chain CDR1, CDR2, or CDR3, e.g., a heavy chain CDR3;
sequence encoding a T cell receptor, e.g., sequence encoding an alpha, beta, delta, or gamma chain
sequence encoding an antibody, B cell receptor, or T cell receptor, variable region;
sequence encoding an antibody, B cell receptor, or T cell receptor, diversity region;
sequence encoding an antibody, B cell receptor, or T cell receptor, joining region;
sequence encoding an antibody, B cell receptor, or T cell receptor, switch region;
sequence encoding an antibody, B cell receptor, or T cell receptor, constant region.
sequence encoding a V segment (prior to or after rearrangement) of an antibody or Ig superfamily-receptor, e.g., an immunoglobulin gene, a T cell receptor or B cell receptor;
sequence encoding a D segment (prior to or after rearrangement) of an antibody or Ig superfamily-receptor, e.g., an immunoglobulin gene, a T cell receptor or B cell receptor;
sequence encoding a J segment (prior to or after rearrangement) of an antibody or Ig superfamily-receptor, e.g., an immunoglobulin gene, a TABLE 10-continued T cell receptor or B cell receptor;
sequence encoding V, D, and J segments (prior to or after rearrangement) of an antibody or Ig superfamily-receptor, e.g., an immunoglobulin gene, a T cell receptor or B cell receptor;
sequence encoding V and J segments (prior to or after rearrangement) of an antibody or Ig superfamily-receptor, e.g., an immunoglobulin gene, a T cell receptor or B cell receptor;
sequence comprising a VD junction of an Ig superfamily-receptor, e.g., an immunoglobulin gene, a T cell receptor or B cell receptor;
sequence comprising a DJ junction of an antibody or Ig superfamily-receptor, e.g., an immunoglobulin gene, a T cell receptor or B cell receptor;
sequence comprising a VJ junction of an antibody or Ig superfamily-receptor, e.g., an immunoglobulin gene, a T cell receptor or B cell receptor;

In an embodiment, the method comprises acquiring a value for e(i).

In an embodiment, the value of (e)(i) comprises a value for the abundance of a sequence, signature, or allele (e.g., a first V segment) in a subject interval relative to a comparison value, e.g., a preselected value, e.g., a value that is a function of the abundance of a second sequence, signature, or allele (e.g., a second V segment).

In an embodiment, the value of (e)(i) comprises a value for the abundance of an event, e.g., a sequence, allele, or signature, e.g., a mutation or rearrangement, in a subject interval, relative to a comparison value, e.g., a preselected value, e.g., a value that is a function of the abundance of a sequence lacking the event, e.g., an unmutated or unrearranged sequence in the subject interval.

In an embodiment, the value of (e)(i) comprises a value of relative abundance for each of X unique (i.e., different from one another) sequences, signatures, or alleles, at a subject interval.

In an embodiment, X is equal to or greater than 3, 4, 5, 6, 7, 8, 9, 10, 20, 30, 40, 50, 100, or 200.

In an embodiment, X is equal to or greater than 1,000, 10,000, 100,000, 1,000,000, 10,000,000, or 50,000,000.

In an embodiment, the method further comprises displaying the value of (e)(i), e.g., as function of abundance, e.g., relative abundance, e.g., as a histogram.

In an embodiment, the subject interval comprises: a sequence from an Ig superfamily-receptor, e.g., a T cell receptor or B cell receptor.

In an embodiment, the subject interval comprises: a sequence from a V segment, a D segment or a J segment.

In an embodiment, the subject interval comprises a sequence from Table 10.

In an embodiment, the method comprises providing the relative abundance for a V segment sequence, signature, or allele.

In an embodiment, the method comprises providing the relative abundance for a plurality of V segment sequences, signatures, or alleles.

In an embodiment, the method comprises providing the relative abundance for a J segment sequence, signature, or allele.

In an embodiment, the method comprises providing the relative abundance for a plurality of J segment sequences, signatures, or alleles.

In an embodiment, the method comprises providing the relative abundance for a D segment sequence, signature, or allele.

In an embodiment, the method comprises providing the relative abundance for a plurality of D segment sequences, signatures, or alleles.

In an embodiment, the method comprises providing the relative abundance for a class switch region sequence, signature, or allele.

In an embodiment, the method comprises providing the relative abundance for a plurality of class switch region sequences, signatures, or alleles.

In an embodiment, the method comprises acquiring (e)(i) and (e)(ii).

In an embodiment, the method comprises acquiring a value for e(ii).

In an embodiment, the method comprises acquiring a value for variability from somatic hypermutation.

In an embodiment, the method comprises acquiring a value for variability arising from a VD, DJ, or VT junction, e.g., by the formation of an indel at the junction.

In an embodiment, the method comprises acquiring a value for variability arising from a CDR, e.g., heavy chain CDR3, variability.

In an embodiment, the subject interval comprises a sequence from Table 10.

In an embodiment, the method comprises acquiring the sequence of a plurality of unique copies of the subject interval, e.g., a plurality of unique signatures at the subject interval.

In an embodiment, the value in (e)(ii) comprises a value for the sequence diversity in a plurality of, e.g., X, signatures for the subject interval.

In an embodiment, the value comprises the number of unique signatures at the subject interval.

In an embodiment, the value comprises a display, record or listing of the unique signatures at the subject interval.

In an embodiment, the value comprises a measure of the number of unique copies, e.g., as a function of the total copies of the subject interval.

In an embodiment, X is equal to or greater than 3, 4, 5, 6, 7, 8, 9, 10, 20, 30, 40, 50, 100, 200, 300, 400, or 500.

In an embodiment, X is equal to or greater than 1,000, 10,000, 100,000, 1,000,000, 10,000,000, or 50,000,000.

In an embodiment, the plurality of signatures are all for a single VDJ or VJ combination, and, e.g., provide a value for sequence diversity in a selected VDJ or VJ combination.

In an embodiment, the variability comprises variability from segment joining, e.g., diversity at a VD, DJ, or VJ junction, e.g., an insertion or deletion at the junction.

In an embodiment, the variability comprises variability from a somatic hypermutation.

In an embodiment, each of the plurality of signatures is for a different VDJ or VJ combination.

In an embodiment, the variability comprises variability from a segment joining, e.g., a diversity at a VD, DJ, or VJ junction, e.g., an insertion or deletion at the junction.

In an embodiment, the library is made from B cells, e.g., from a subject comprising a B cell malignancy, e.g., a subject comprising Mantle cell cancer.

In an embodiment, the subject interval comprises a sequence that encodes a V, D, or J segment, or a VD or DJ junction, from a B cell receptor.

In an embodiment, the method further comprises comparing the amount of variability, e.g., a somatic hypermutation, with a comparison value, wherein a preselected relationship with the comparison value, e.g., greater than the comparison value, is indicative of outcome, prognosis, or stage of disease.

In an embodiment, the method comprises contacting the library with a single bait set.

In an embodiment, the method comprises contacting the library with a plurality of bait sets.

In an embodiment, the method comprises contacting the library with a bait set which, captures, specifically captures, captures with a preselected efficiency, is optimized to capture, or hybridizes with:
- a sequence at the subject interval;
- a signature at the subject interval; or
- an allele at the subject interval.

In an embodiment, the method comprises contacting the library with a second bait set which, captures, specifically captures, captures with a preselected efficiency, is optimized to capture, or hybridizes with:
- a second sequence at the subject interval;
- a second signature at the subject interval; or
- a second allele at the subject interval.

In an embodiment, the method comprises contacting with a plurality, e.g., at least X, unique bait sets, wherein each bait set of the plurality, captures, specifically captures, captures with a preselected efficiency, is optimized to capture, or hybridizes with:
- a different sequence from the subject interval;
- a different signature at the subject interval; or
- a different allele at the subject interval, wherein X is equal to 2, 3, 4, 5, 6, 7, 8, 9, 10, 50, 100, or 200.

In an embodiment, the method comprises contacting with a bait set which, captures, specifically captures, captures with a preselected efficiency, is optimized to capture, or hybridizes with:
- a first sequence and a second sequence at the subject interval;
- a first signature and a second signature at the subject interval; or
- a first allele and a second allele at the subject interval.

In an embodiment, the method comprises contacting with a bait set which, captures, specifically captures, captures with a preselected efficiency, is optimized to capture, or hybridizes with:
- at least X sequences from the subject interval;
- at least X signatures at the subject interval; or
- at least X alleles at the subject interval, wherein, X, independently is equal to 2, 3, 4, 5, 6, 7, 8, 9, 10, 50, 100, or 200.

In an embodiment, the method comprises contacting with a bait set which, captures, specifically captures, captures with a preselected efficiency, is optimized to capture, or hybridizes with, a first sequence, allele, or signature which is not present at the subject interval in the subject or sample.

In an embodiment, the subject interval comprises a sequence from Table 10.

In an embodiment, the method comprises contacting with a bait set which, captures, specifically captures, captures with a preselected efficiency, is optimized to capture, or hybridizes with, a sequence from a first V, D or J segment and a sequence from a second V, D or J segment.

In an embodiment, the subject interval comprises sequence of a V, D or J segment.

In an embodiment, the method comprises contacting the library with a bait set that is optimized to capture, or hybridizes with, a V segment (and not a D or J segment).

In an embodiment, the method comprises contacting the library with a bait set that is optimized to capture, or hybridizes with, a D segment (and not a V or J segment).

In an embodiment, the method comprises contacting the library with a bait set that is optimized to capture, or hybridizes with, a J segment (and not a V or D segment).

In an embodiment, the method comprises contacting the library with a bait set that is optimized to capture, or hybridizes with, a V segment.

In an embodiment, the method comprises contacting the library with a bait set that is optimized to capture, or hybridizes with, a D segment.

In an embodiment, the method comprises contacting the library with a bait set that is optimized to capture, or hybridizes with, a J segment.

In an embodiment, the method comprises contacting the library with a bait set that comprises bait(s) that span a VD, DJ, or VJ junction.

In an embodiment, the method comprises contacting the library with a bait set that comprises bait(s) that span a rearranged VDJ or VJ sequence.

In an embodiment, the method comprises contacting the library with a bait set that comprises bait(s) comprising a nucleic acid analog, e.g., locked nucleic acid (LNA), peptide nucleic acid (PNA), or bicyclic nucleic acid (BNA).

In an embodiment, the method comprises contacting the library with a bait set that comprises bait(s) that are long enough to be functional but short enough to optimized affinity.

In an embodiment, the subject interval comprises a subgenomic interval.

In an embodiment, the subject interval comprises an expressed subgenomic interval.

In an embodiment, the method comprises acquiring the sequence of a subgenomic interval and acquiring the sequence of an expressed subgenomic interval.

In an embodiment, the method comprises evaluating the clonal profile of a subgenomic interval.

In an embodiment, the method comprises evaluating the clonal profile of an expressed subgenomic interval.

In an embodiment, the method comprises evaluating the clonal profile of a subgenomic interval and evaluating the clonal profile of an expressed subgenomic interval.

In an embodiment, the method comprises evaluating the occurrence or level of expression of a signature present in a subgenomic interval, e.g., where the signature, e.g., a rearrangement, e.g., a translocation, is present in the corresponding subgenomic interval.

In an embodiment, the method comprises evaluating the occurrence or level of expression of a signature present in a subgenomic interval, e.g., where the signature, e.g., a rearrangement, e.g., a translocation, as a function of the abundance in the corresponding subgenomic interval.

In an embodiment, the method comprises evaluating comprises providing a value for the relative abundance for a sequence, allele or signature in a subgenomic interval and for a sequence, allele or signature in an expressed subgenomic interval.

In an embodiment, the method comprises acquiring the sequence of each of a plurality of occurrences of the subject interval;
  wherein one of steps (a), (b) and (c) are performed separately for a first occurrence of the subject interval and for a second occurrence of the subject interval, e.g., wherein one of steps (a), (b) and (c) is performed in a first reaction mixture for the first occurrence and in a second reaction mixture for the second occurrence.

In an embodiment, step(s) (a); (b); (c); (a) and (b); (a) and (c); (b) and (c); or (a), (b), and (c), are performed separately.

In an embodiment, the first copy of the plurality of unique copies of the subject interval comprises a subgenomic interval.

In an embodiment, the second copy of the plurality of unique copies of the subject interval comprises a subgenomic interval, e.g., an expressed subgenomic interval that corresponds to the subgenomic interval.

In an embodiment,
the first occurrence of the plurality comprises a subgenomic interval, e.g., wherein the subgenomic interval comprises a VDJ sequence, e.g., a VDJ sequence comprising a specific V segment, a specific D segment, and a specific J segment; and
the second occurrence of the plurality comprises an expressed subgenomic interval, e.g., wherein the expressed subgenomic interval comprises a VDJ sequence, e.g., a VDJ sequence comprising a specific V segment, a specific D segment, and a specific J segment.

In an embodiment, the first occurrence of the subject interval comprises an expressed subgenomic interval.

In an embodiment, the second occurrence of the subject interval comprises an expressed subgenomic interval.

In an embodiment, the method comprises acquiring the sequence of each of a plurality of occurrences of the subject interval;
wherein at least one of steps (a), (b) and (c) is performed in the same reaction mixture for a first occurrence of the subject interval and for a second occurrence of the subject interval.

In an embodiment, step(s) (a); (b); (c); (a) and (b); (a) and (c); (b) and (c); or all of steps (a), (b), and (c), are performed in the same reaction mixture.

In an embodiment, wherein:
in step (b) the first copy of the plurality of occurrences of the subject interval is contacted with a first bait set; and
in step (b) the second occurrence of the subject interval is contacted with a second bait set, e.g., a second bait set that comprises a bait comprising a different sequence from any bait in the first bait set.

In an embodiment, in step (b) the first copy of the plurality of unique copies of the subject interval is contacted with a bait set; and in step (b) the second copy of the plurality of unique copies of the subject interval is contacted with the same bait set, e.g., wherein both bait sets comprise the same bait(s).

In an embodiment, the method comprises acquiring the sequence of the subject interval and of a second different subject interval (wherein different means from different chromosomal locations), wherein one of steps (a), (b) and (c) is performed in a first reaction mixture for the first subject interval and in a second reaction mixture for the second subject interval.

In an embodiment, step(s) (a); (b); (c); (a) and (b); (a) and (c); (b) and (c); or all of steps (a), (b), and (c), are performed separately.

In an embodiment, the subject interval comprises a subgenomic interval.

In an embodiment, the second different subject interval comprises a subgenomic interval.

In an embodiment, the first subject interval comprises an expressed subgenomic interval.

In an embodiment, the second different subject interval comprises an expressed subgenomic interval.

In an embodiment, the first subject interval comprises a subgenomic interval and the second different subject interval comprises an expressed subgenomic interval.

In an embodiment, the method comprises acquiring the sequence of the subject interval and of a second different subject interval (wherein different means from different chromosomal locations), wherein at least one of steps (a), (b) and (c) is performed in the same reaction mixture for the first subject interval and for a second subject interval.

In an embodiment, step(s) (a); (b); (c); (a) and (b); (a) and (c); (b) and (c); or all of steps (a), (b), and (c), are performed in the same reaction mixture.

In an embodiment, in step (b) a first subject interval is contacted with a first bait set; and in step (b) a second subject interval is contacted with a second bait set, e.g., a second bait set that comprises a bait comprising a different sequence from any bait in the first bait set.

In an embodiment, in step (b) a first subject interval is contacted with a bait set; and in step (b) a second subject interval is contacted with the same bait set, e.g., wherein both bait sets comprise the same bait(s).

In an embodiment, the method comprises repeating steps (a) to (d).

In an embodiment, the method comprises repeating steps (a) to (d) after one or more of:
the passage of a preselected period of time;
a change in the genotype of a disorder, e.g., a cancer;
a change in the manifestation of a disorder, e.g., in the case of cancer, a change in aggressiveness or resistance to treatment, e.g., in the case of cancer, development of metastases;
lack of responsiveness to a treatment develops; or
progression, relapse, recurrence, or persistence of a disease or disorder.

In an embodiment, the library is made from chromosomal DNA.

In an embodiment, the library is made from RNA, e.g., mRNA.

In an embodiment, the method comprises:
(a) evaluating the clonal profile of a subgenomic interval from a library made from chromosomal DNA;
(b) evaluating the clonal profile of an expressed subgenomic interval from a library made from RNA, e.g., mRNA; and
optionally, comparing the evaluations provided in steps (a) and (b), e.g., to determine if a selected sequence, allele or signature of an subject interval is expressed.

In an embodiment, steps (a) and or (b) comprises acquiring:
(i) a value for the distribution, expression (the occurrence or level of transcribed copies of a subgenomic signature) abundance, or identity, of an allele at the subject interval, e.g., the relative abundance, an allele, or the relative abundance of each of a plurality of alleles, at the subject interval; or
(ii) a value for the distribution, expression (the occurrence or level of transcribed copies of a subgenomic signature) abundance, or identity, of a signature at the subject interval, e.g., the relative abundance, a signature, or the relative abundance of each of a plurality of signatures, at the subject interval; or
(iii) a value for variability, e.g., somatic hypermutation, within a signature or subject interval.

In an embodiment,
step (a) comprises (i) and step (b) comprises (i);
step (a) comprises (i) and step (b) comprises (ii);
step (a) comprises (i) and step (b) comprises (iii);
step (a) comprises (ii) and step (b) comprises (i);
step (a) comprises (ii) and step (b) comprises (ii);
step (a) comprises (ii) and step (b) comprises (iii);
step (a) comprises (iii) and step (b) comprises (i);
step (a) comprises (iii) and step (b) comprises (ii); or
step (a) comprises (iii) and step (b) comprises (iii).

In an embodiment, the library is made from disease state tissue, e.g., from cancer cells.

In an embodiment, the library is made from cells from a solid tumor, e.g., a solid tumor described herein.

In an embodiment, the library is made from cells, e.g., B cells or T cells, that have infiltrated solid tumor, e.g., a solid tumor described herein.

In an embodiment, the library is made from cells from a hematologic malignancy (or premalignancy), e.g., a hematologic malignancy (or premalignancy) described herein.

In an embodiment, the library is made from cell free DNA.

In an embodiment, the library is made from non-disease state tissue.

In an embodiment, the library is made from peripheral blood, bone marrow, tumor tissue, tumor infiltrating cells, lymphocytes, B cells, pre-B cells, mature B cells, T cells, or cell free DNA.

In an embodiment, the library is made from tumor infiltrating cells, e.g., tumor infiltrating B cells, pre-B cells, mature B cells, or T cells.

In an embodiment, the library is made from peripheral B cells, pre-B cells, mature B cells, or T cells, e.g., CD4+ or CD8+, T cells.

In an embodiment, the method comprises evaluating a clonal profile for non-disease-state tissue, e.g., for a cell not associated with a tumor, e.g., a non-tumor cell, or peripheral blood lymphocyte.

In an embodiment, the method comprises evaluating a clonal profile for a disease-state tissue, e.g., for a tumor cell or a tumor infiltrating cell, or for a non-cancerous disorder.

In an embodiment, the library is made from T cells and the subgenomic interval comprises sequence that encodes a T cell receptor, e.g., an alpha/beta or delta/gamma, TCR chain.

In an embodiment, the method comprises:
(a) evaluating the clonal profile of a subject interval from a first cell type, e.g., from a library made from the first cell type, e.g., made from chromosomal DNA, or RNA, e.g., mRNA, from the first cell type;
(b) evaluating the clonal profile of a subject interval from a second cell type, e.g., from a library made from the second cell type, e.g., made from chromosomal DNA, or RNA, e.g., mRNA, from the second cell type; and
optionally, comparing the evaluations provided in (a) and (b), e.g., to determine if an allele or signature of an subject interval is expressed.

In an embodiment, the method comprises:
(a) evaluating the clonal profile of a subject interval from a first cell type;
(b) evaluating the clonal profile of a subject interval from a second cell type; and
optionally, comparing the evaluations provided in steps (a) and (b), e.g., to determine if an allele or signature of an subject interval is expressed.

In an embodiment, the method comprises:
(a) evaluating the clonal profile of a subject interval from a library made from chromosomal DNA;
(b) evaluating the clonal profile of a subject interval from a library made from RNA, e.g., mRNA, e.g., cDNA; and
optionally, comparing the evaluations provided in steps (a) and (b), e.g., to determine if an allele or signature of an subject interval is expressed.

In an embodiment, the method comprises:
(a) evaluating the clonal profile of a subject interval at a first time period;
(b) evaluating the clonal profile of a subject interval at a second time period; and
optionally, comparing the evaluations provided in steps (a) and (b), e.g., to determine if an allele or signature of an subject interval is expressed.

In an embodiment, said first time period is prior to a preselected event and the second time period is after a preselected event, wherein the preselected event can comprise infection, a medical or surgical procedure, e.g., receiving a transplant, a diagnosis, or administration of a treatment, e.g., a first line treatment or a second line treatment, a reoccurrence or relapse or disease.

In an embodiment, the method comprises:
evaluating the clonal profile of a sequence, allele, or signature, from a subject interval from a disease state cell; and
evaluating the clonal profile of a sequence, allele, or signature, from a the subject interval from a disease state cell.

In an embodiment, the method comprises:
evaluating the clonal profile of a sequence, allele, or signature, from a first subject interval from a disease state cell; and
evaluating the clonal profile of a sequence, allele, or signature, from a second different subject interval from a disease state cell.

In an embodiment, the subject has cancer. In another embodiment, the subject has a hematologic malignancy (or premalignancy). In yet another embodiment, the subject has a solid tumor.

In an embodiment, the library is made from B cells and the subject has a B cell malignancy, e.g., mantle cell cancer.

In an embodiment, the subject has a disorder other than cancer.

In an embodiment, the subject has an immune disorder, e.g., an autoimmune disorder, an immune deficiency, e.g., an inherited or an acquired immune deficiency, e.g., AIDs or HIV infection.

In an embodiment, the subject is a graft recipient, e.g., a bone marrow recipient, a solid organ recipient, or a skin graft recipient.

In an embodiment, the subject has an infection or infectious disease, e.g., a viral, bacterial, protozoan, or fungal infection or disease.

In an embodiment, the subject interval comprises a nucleotide position, or a junction, or a sequence, representative of a clonal event.

In an embodiment, the subject interval comprises a nucleotide position, or a junction, or a sequence, representative of a T cell clone or B cell clone.

In an embodiment, step (c), or the method, does not comprise, amplifying each member, or any member of the plurality, by a method that relies on a sequence specific interaction with target/subject nucleic acid in the member, e.g., by amplifying each member of the plurality with a primer that binds to target/subject nucleic acid in the member.

In an embodiment, step (d) comprises;
acquiring a read for a subject interval from a member from said library (or library catch); and
assigning a nucleotide value from the read for a nucleotide position within the subject interval for each of a plurality of members.

In an embodiment, the method comprises attaching, e.g., ligating, an adaptor sequence to the 5' or 3' end of the nucleic acid from the subject in each member of the plurality of members.

In an embodiment, the method comprises, attaching, e.g., ligating, an adaptor sequence to the 5' and 3' ends of the nucleic acid from the subject in each member of the plurality of members.

In an embodiment, each member of said plurality of members comprises, in the 5' to 3' direction, a 5' adaptor sequence, subject sequence (e.g., genomic or transcribed sequence), and a 3' adaptor.

In an embodiment, each member of said plurality of members comprises, in the 5' to 3' direction, a 5' adaptor sequence, subject sequence (e.g., genomic or transcribed sequence), and a 3' adaptor, and one of the adaptors comprises an identifier, e.g., a sequence that can function as a bar code.

In an embodiment, each member of the plurality is amplified with a primer specific for the adaptor sequence.

In an embodiment, each member of the plurality is amplified with a primer set comprising a primer that binds to the 5' adaptor or a primer that binds to the 3' adaptor.

In an embodiment, each member of the plurality is amplified with a primer set comprising a primer that binds to the 5' adaptor.

In an embodiment, each member of the plurality is amplified with a primer set comprising a primer that binds to the 3' adaptor.

In an embodiment, each member of the plurality is amplified with a primer specific for the adaptor sequence and a primer specific for the target/subject nucleic acid in the member.

In an embodiment, step (d) comprises:
acquiring a read for a subgenomic interval from a member, e.g., a tumor member from said library or library catch, e.g., by a method comprising sequencing, e.g., with a next generation sequencing method;
aligning said read by an alignment method, e.g., an alignment method described herein; and
assigning a nucleotide value (e.g., calling a mutation, e.g., with a Bayesian method or a method described herein) from said read for the preselected nucleotide position.

Methods described herein for providing a clonal profile for a subject interval can be augmented with methods that provide other information. In an embodiment the methods can provide the sequence of subject intervals for genes other than those for which a clonal profile is provided, e.g., for genes that do not undergo somatic rearrangement or somatic hypermutation, e.g., genes other than immunoglobulin genes and other than T cell receptor genes. These sequences can be provided with the use of solution hybridization and baits to retrieve the nucleic acids of interest.

In an embodiment, the method further comprises providing the sequence of a second, e.g., second subject interval, e.g., a subject interval comprising sequence from a gene described herein, e.g., selected from Tables 1-9.

In an embodiment, the method further comprises providing the sequence of a second, e.g., second subject interval, e.g., a subject interval comprising sequence encoding an miRNA, a promoter, or other element.

In an embodiment, the method further comprises providing the sequence of a second subject interval which is from a gene other than an immunoglobulin or T cell or B cell receptor gene. In an embodiment, the method comprises providing the sequence of a third, or of at least X additional subject intervals, e.g., selected from Tables 1-9, wherein X is equal to 4, 5, 6, 7, 8, 9, 10, 50, 100, 150, 200, 250, 300, 350, 400, 450 or 500.

In an embodiment, the third, or of X additional subject intervals, is from a gene other than an immunoglobulin, B cell receptor, or T cell receptor gene.

In an embodiment, X is equal to or greater than, 5, 10, 20, 30, 40, 50, 100, 150, 200, 250, 300, 350, 400, 450, or 500.

In an embodiment, the method comprises:
(a) evaluating the clonal profile of a first subject interval, e.g., selected from Table 10, from a first cell type, e.g., from a library made from the first cell type, e.g., a non-cancer cell or a non-malignant cell (e.g., a tumor-infiltrating lymphocyte); and
(b) providing the sequence of a second subject interval, e.g., selected from Tables 1-9, from a second cell type, e.g., from a library made from the second cell type, e.g., a cancer cell or a malignant cell.

In an embodiment, the method comprises:
(a) evaluating the clonal profile of a first subject interval, e.g., selected from Table 10, from a first cell type, e.g., from a library made from the first cell type, e.g., a non-cancer cell or a non-malignant cell (e.g., a tumor-infiltrating lymphocyte); and
(b) providing the sequence of a second, a third, or at least X additional subject intervals, e.g., selected from Tables 1-9, wherein X is equal to 4, 5, 6, 7, 8, 9, 10, 50, 100, 150, 200, 250, 300, 350, 400, 450 or 500, from a second cell type, e.g., from a library made from the second cell type, e.g., a cancer cell or a malignant cell.

In an embodiment, the method comprises:
(a) evaluating the clonal profile of a first, a second, or at least X additional subject intervals, e.g., selected from Table 10, wherein X is equal to 3, 4, 5, 6, 7, 8, 9, 10, 50, 100, 150, 200, 250, 300, 350, 400, 450 or 500, from a first cell type, e.g., from a library made from the first cell type, e.g., a non-cancer cell or a non-malignant cell (e.g., a tumor-infiltrating lymphocyte); and
(b) providing the sequence of a (X+1)th subject interval, e.g., selected from Tables 1-9, from a second cell type, e.g., from a library made from the second cell type, e.g., a cancer cell or a malignant cell.

In an embodiment, the method comprises:
(a) evaluating the clonal profile of one or more (e.g., 2, 3, 4, 5, 6, 7, 8, 9, 10, 50, 100, 150, 200, 250, 300, 350, 400, 450, 500, or more) subject intervals, e.g., selected from Table 10, from a first cell type, e.g., from a library made from the first cell type, e.g., a non-cancer cell or a non-malignant cell (e.g., a tumor-infiltrating lymphocyte); and
(b) providing the sequence of one or more (e.g., 2, 3, 4, 5, 6, 7, 8, 9, 10, 50, 100, 150, 200, 250, 300, 350, 400, 450, 500, or more) subject intervals, e.g., selected from Tables 1-9, from a second cell type, e.g., from a library made from the second cell type, e.g., a cancer cell or a malignant cell.

In an embodiment, the first cell type, or the library made from the first cell type, is obtained from the same sample as the sample from which the second cell type, or the library made from the second cell type, is obtained. For example, the sample can contain both a non-cancer cell (or a non-malignant cell, e.g., a tumor-infiltrating lymphocyte) and a cancer cell (or a malignant cell).

In an embodiment, the first cell type, or the library made from the first cell type, is obtained from a different sample than the sample from which the second cell type, or the library made from the second cell type, is obtained. For example, the sample from which the first cell type, or the library made from the first cell type, is obtained, can contain a non-cancer cell (or a non-malignant cell, e.g., a tumor-infiltrating lymphocyte) and is essentially free of a cancer cell (or a malignant cell); and the sample from which the second cell type, or the library made from the second cell type, is obtained can contain a cancer cell (or a malignant cell) and is essentially free of a non-cancer cell (or a non-malignant cell, e.g., a tumor-infiltrating lymphocyte).

In an embodiment, the first cell type and the second cell type are obtained at the same time. In another embodiment, the first cell type is obtained before, e.g., at least 1 day, 2 days, 3 days, 1 week, 2 weeks, 3 weeks, 1 month, 2 months, 3 months, 4 months, 5 months, or 6 months before, the second cell type is obtained. In yet another embodiment, the first cell type is obtained after, e.g., at least 1 day, 2 days, 3 days, 1 week, 2 weeks, 3 weeks, 1 month, 2 months, 3 months, 4 months, 5 months, or 6 months after, the second cell type is obtained.

In an embodiment, the method further comprises isolating the first cell type, e.g., a non-cancer cell or a non-malignant cell (e.g., a tumor-infiltrating lymphocyte) from the sample, e.g., a tumor sample. In another embodiment, the method further comprises isolating the second cell type, e.g., a cancer cell or a malignant cell from the sample, e.g., a tumor sample. In yet another embodiment, the method further comprises isolating the first cell type, e.g., a non-cancer cell or a non-malignant cell (e.g., a tumor-infiltrating lymphocyte); and the second cell type, e.g., a cancer cell or a malignant cell, from the sample, e.g., a tumor sample.

In an embodiment, the method is performed, e.g., the library is made, without isolation of the first cell type (e.g., a non-cancer cell or a non-malignant cell, e.g., a tumor-infiltrating lymphocyte), the second cell type (e.g., a cancer cell or a malignant cell), or both, from the sample, e.g., tumor sample.

In an embodiment, the method comprises providing the sequence of the second (or subsequent) subject interval by:
(a) acquiring a nucleic acid library comprising a plurality of members, each member of the plurality comprising nucleic acid from the subject e.g., the library described herein;
(b) contacting the library with a bait set, e.g., under conditions of solution or surface hybridization, to provide a plurality of selected members, each of which comprises the second (or subsequent) subject interval, or a portion thereof (sometimes referred to herein as a library catch);
(c) amplifying each member of the plurality, e.g., by a method that does not rely on a sequence specific interaction with target/subject nucleic acid in the member, e.g., by amplifying each member of the plurality with a primer that does not bind to target/subject nucleic acid in the member; and
(d) acquiring the sequence of each of the subject interval.

In an embodiment, step (d) comprises:
(d)(i) acquiring a read for a subgenomic interval from a member, e.g., a tumor member from said library or library catch, e.g., by a method comprising sequencing, e.g., with a next generation sequencing method;
(d)(ii) aligning said read by an alignment method, e.g., an alignment method described herein; and
(d)(iii) assigning a nucleotide value (e.g., calling a mutation, e.g., with a Bayesian method or a method described herein) from said read for the preselected nucleotide position.

In another aspect, the invention features a method of evaluating a subject for the occurrence of a whole arm or large rearrangement, e.g., a rearrangement, e.g., a translocation, duplication, insertion, or deletion, comprising, e.g., at least 5%, 10%, 20%, 30%, 40%, 50%, 60%, 70%, 80%, or 90%, or all of a chromosome arm, comprising:
(a) acquiring a nucleic acid library comprising a plurality of members, each member of the plurality comprising nucleic acid from the subject;
(b) contacting the library with a bait set, e.g., under conditions of solution hybridization, to provide a plurality of selected members, each of which comprises a subject interval, or a portion thereof (sometimes referred to herein as a library catch);
(c) amplifying each member of the plurality, e.g., by a method that does not rely on a sequence specific interaction with target/subject nucleic acid in the member, e.g., by amplifying each member of the plurality with a primer that does not bind to target/subject nucleic acid in the member; and
(d) acquiring the sequence of a plurality of subject intervals, wherein said plurality of subject intervals is disposed on a chromosome such as to allow determination of a whole arm or large rearrangement.

As used herein, a "large rearrangement" refers to an rearrangement that affects, e.g., at least about 10%, 20%, 30%, 40%, 50%, 60%, or 70% of a chromosome, or at least about 10%, 20%, 30%, 40%, 50%, 60%, 70%, 80%, 90%, or 100% of an arm (e.g., a long arm or short arm) of a chromosome.

In yet another aspect, the invention features a method of evaluating a subject, comprising:
(a) acquiring a nucleic acid library comprising a plurality of members, each member of the plurality comprising nucleic acid from the subject, e.g., a plurality of tumor members from a hematological-cancer sample;
(b) contacting the library with a bait set, e.g., under conditions of solution hybridization, to provide a plurality of selected members, each of which comprises the subject interval, or a portion thereof (sometimes referred to herein as a library catch);
(c) amplifying each member of the plurality of selected members, e.g., by a method that does not rely on a sequence specific interaction with target/subject nucleic acid in the member, e.g., by amplifying each member of the plurality of selected members with a primer that does not bind to target/subject nucleic acid in the member;
(d) acquiring the sequence of a subgenomic interval and an expressed subgenomic interval;
thereby evaluating the subject,
wherein:
(i) the method comprises contacting the library with a bait set that provides both a subgenomic interval and an expressed subgenomic interval;
(ii) the method comprises contacting the library with a first bait set that provides a subgenomic interval and a second bait set that provides an expressed subgenomic interval;
(iii) wherein the library comprises genomic DNA and is contacted with a bait set that provides a subgenomic interval and the method further comprises a second library which comprises cDNA which is contacted with the bait set to provide an expressed subgenomic interval;
(iv) wherein the library comprises genomic DNA and is contacted with a bait set that provides a subgenomic interval and the method further comprises a second library which comprises cDNA which is contacted with a second bait set to provide an expressed subgenomic interval; or (v) the method comprises performing one of steps (a), (b) and (c) in a first reaction mix to provide a first subject interval, e.g., a subgenomic interval, and on a second reaction mix to provide a second subject interval, e.g., an expressed subgenomic interval, e.g., that corresponds to the subgenomic interval.

In an embodiment, step(s) (a); (b); (c); (a) and (b); (a) and (c); (b) and (c); or all of steps (a), (b), and (c), are performed separately.

In an embodiment, the subgenomic interval and expressed subgenomic interval are, independently, selected from Tables 1-4.

In an embodiment, the method comprises providing the sequence of at least X subject intervals, wherein X is equal to 2, 3, 4, 5, 10, 20, 30, 40, 50, 100, 150, 200, 250, 300, 350, 400, 450, 500, or greater.

In an embodiment, the subgenomic interval and the expressed subgenomic interval correspond to the same subject interval, e.g., comprise sequence(s) from the same gene.

In one aspect, the invention features a method of analyzing a tumor sample from a hematologic malignancy (or premalignancy), e.g., a hematologic malignancy (or premalignancy) described herein. The method comprises:

(a) acquiring one or a plurality of libraries comprising a plurality of target members, e.g., tumor members, from a sample, e.g., a tumor sample;
(b) optionally, contacting the one or a plurality of libraries with a bait set (or plurality of bait sets) to provide selected members (sometimes referred to herein as "library catch");
(c) acquiring a read for a subject interval (e.g., a subgenomic interval or an expressed subgenomic interval) from a tumor member from a library or library catch, e.g., by sequencing, e.g., with a next generation sequencing method;
(d) aligning said read; and
(e) assigning a nucleotide value (e.g., calling a mutation, e.g., with a Bayesian method) from said read for a preselected nucleotide position, e.g., for a preselected nucleotide position in each of a plurality of subject intervals (e.g., subgenomic intervals, expressed subgenomic intervals, or both), e.g., each of a plurality genes, thereby analyzing said sample, optionally wherein:
(i) each of X nucleotide positions is analyzed under a unique set of conditions for one or a combination of steps (b), (c), (d), or (e) (wherein unique means different from the other X−1 sets of conditions and wherein X is at least 2, 5, 10, 20, 30, 40, 50, 100, 200, 300, 400, 500, 600, 700, 800, 900, or 1000). E.g., a first set of conditions, e.g., a set of conditions described herein, is used for a first nucleotide position, e.g., in a first subgenomic interval or gene, and a second set of conditions, e.g., a second set of conditions described herein, is used for a second nucleotide position, e.g., in a second subgenomic interval or gene;
(ii) for each of X nucleotide positions, responsive to a characteristic, e.g., a characteristic described herein, of a preselected alteration, e.g., mutation, that can occur at the nucleotide position, the nucleotide position is analyzed under a unique set of conditions (wherein unique means different from the other X−1 sets of conditions and wherein X is at least 2, 5, 10, 20, 30, 40, 50, 100, 200, 300, 400, 500, 600, 700, 800, 900, or 1,000). E.g., responsive to a characteristic, e.g., a characteristic described herein, of a preselected alteration, e.g., mutation, that can occur at a nucleotide position in a first subject interval (a subgenomic interval or an expressed subgenomic interval), the nucleotide position is analyzed under a first set of conditions, and responsive to a characteristic, e.g., a characteristic described herein, of a preselected alteration, e.g., mutation, that can occur at a nucleotide position in a second subject interval (e.g., a subgenomic interval or an expressed subgenomic interval), the nucleotide position is analyzed under second set of conditions;
(iii) wherein said method is performed on a sample, e.g., a preserved tumor sample, under conditions that allow for 95, 98, or 99% sensitivity or specificity for nucleotide positions in at least 2, 5, 10, 20, 50, 100, 200, 300, 400, 500, 600, 700, 800, 900, or 1,000 subject intervals (e.g., subgenomic intervals, expressed subgenomic intervals, or both), e.g., genes; or
(iv) wherein the method comprises one or more or all of:
a) sequencing a first subject interval (e.g., a subgenomic interval or an expressed subgenomic interval) to provide for about 500× or higher sequencing depth, e.g., to sequence a mutation present in no more than 5% of the cells from the sample;
b) sequencing a second subject interval (e.g., a subgenomic interval or an expressed subgenomic interval) to provide for about 200× or higher, e.g., about 200×-about 500×, sequencing depth, e.g., to sequence a mutation present in no more than 10% of the cells from the sample;
c) sequencing a third subject interval (e.g., a subgenomic interval or an expressed subgenomic interval) to provide for about 10-100× sequencing depth, e.g., to sequence one or more subject intervals (e.g., subgenomic intervals, expressed subgenomic intervals, or both, e.g., exons) that are chosen from: a) a pharmacogenomic (PGx) single nucleotide polymorphism (SNP) that may explain the ability of patient to metabolize different drugs, or b) a genomic SNPs that may be used to uniquely identify (e.g., fingerprint) a patient;
d) sequencing a fourth subject interval (e.g., a subgenomic interval or an expressed subgenomic interval) to provide for about 5-50× sequencing depth, e.g., to detect a structural breakpoint, such as a genomic translocation or an indel. For example, detection of an intronic breakpoint requires 5-50× sequence-pair spanning depth to ensure high detection reliability. Such bait sets can be used to detect, for example, translocation/indel-prone cancer genes; or
e) sequencing a fifth subject interval (e.g., a subgenomic interval or an expressed subgenomic interval) to provide for about 0.1-300× sequencing depth, e.g., to detect copy number changes. In one embodiment, the sequencing depth ranges from about 0.1-10× sequencing depth to detect copy number changes. In other embodiments, the sequencing depth ranges from about 100-300× to detect a genomic SNPs/loci that is used to assess copy number gains/losses of genomic DNA or loss-of-heterozygosity (LOH).

In an embodiment, the method comprises acquiring a library from which a member corresponding to a subgenomic interval and a member corresponding to an expressed subgenomic interval, is obtained.

In an embodiment, the method comprises acquiring a first library from which a member corresponding to a subgenomic interval is obtained and acquiring a second library from which a member corresponding to an expressed subgenomic interval is obtained.

In an embodiment a bait set is used to provide members or a library catch comprising both a subgenomic interval and an expressed interval.

In an embodiment a first bait set is used to provide members or a library catch comprising a subgenomic interval and a second bait set is used to provide members or a library catch comprising an expressed subgenomic interval.

Exemplary first and second sets of conditions include those wherein:
- a first bait set is used for the first subject interval (e.g., a subgenomic interval or an expressed interval), and a second bait set is used for the second subject interval (e.g., a subgenomic interval or an expressed subgenomic interval);
- a first alignment method is applied to a read for the first subject interval (e.g., a subgenomic interval or an expressed subgenomic interval), and a second alignment method is applied to a read for second subject interval (e.g., a subgenomic interval or an expressed subgenomic interval);
- a first mutation calling method is applied to a nucleotide position of the first subject interval (e.g., a subgenomic interval or an expressed subgenomic interval), and a second mutation calling method is applied to a nucleotide position of the second subject interval (e.g., a subgenomic interval or an expressed subgenomic interval).

In an embodiment:
- a first nucleotide position is analyzed with a first set of bait conditions, a first alignment method, and a first mutation calling method;
- a second nucleotide position is analyzed with said first set of bait conditions, a second alignment method, and said first mutation calling method;
- a third nucleotide position is analyzed with said first set of bait conditions, said first alignment method, and a second mutation calling method,
to provide three nucleotide positions each analyzed under unique, as compared to the other two, conditions.

In an embodiment, the conditions comprise those wherein:
- a first bait set is used for the first subject interval (e.g., a subgenomic interval or an expressed subgenomic interval), and a second bait set is used for the second subject interval (e.g., a subgenomic interval or an expressed subgenomic interval);
- a first alignment method is applied to a read for the first subject interval (e.g., a subgenomic interval or an expressed subgenomic interval), and a second alignment method is applied to a read for second subject interval (e.g., a subgenomic interval or an expressed subgenomic interval); or
- a first mutation calling method is applied to a nucleotide position of the first subject interval (e.g., a subgenomic interval or an expressed subgenomic interval), and a second mutation calling method is applied to a nucleotide position of the second subject interval (e.g., a subgenomic interval or an expressed subgenomic interval).

Exemplary characteristics include:
(i) the gene, or type of gene, in which the alteration is located, e.g., an oncogene or tumor suppressor, a gene or type of gene characterized by a preselected or variant or type of variant, e.g., a mutation, or by a mutation of a preselected frequency, or other gene or type of gene described herein;
(ii) the type of alteration, e.g., a substitution, insertion, deletion, or translocation;
(iii) the type of sample, e.g., an FFPE sample, a blood sample, or a bone marrow aspirate sample, being analyzed for the alteration;
(iv) sequence in or near said the nucleotide position of the alteration being evaluated, e.g., sequence which can affect the expected propensity for misalignment for the subject interval (e.g., a subgenomic interval or an expressed subgenomic interval), e.g., the presence of repeated sequences in or near the nucleotide position;
(v) a prior (e.g., literature) expectation of observing a read showing the alteration, e.g., mutation, e.g., in a tumor of preselected type;
(vi) the probability of observing a read showing the alteration due to base-calling error alone); or
(vii) a preselected depth of sequencing desired for detecting the alteration.

In an embodiment, the characteristic is other than the identity of the nucleotide being sequenced, e.g, the characteristic is not whether the sequence is A or T.

In an embodiment, step (b) is present. In an embodiment, step (b) is absent.

In an embodiment, subgenomic intervals from at least X genes, e.g. at least X genes from Tables 1-4, are analyzed under different conditions, and X is equal to 2, 3, 4, 5, 10, 15, 20, 30, 40, 50, 60, 70, 80, 90, 100, 200, 300, 400, 500, or greater.

In an embodiment, the method comprises one or more of the following:
(i) the method, e.g., step (b) of the method above, comprises the use of a bait set described herein, e.g., a bait set as described under the heading "Bait";
(ii) the method, e.g., step (c) of the method above, comprises acquiring reads for a set or group of subject intervals (e.g., subgenomic intervals, expressed subgenomic intervals, or both) or from a set or group of genes described herein;
(iii) the method, e.g., step (d) of the method above, comprises the use of a plurality of alignment methods described herein, e.g., methods described under the heading "Alignment";
(iv) the method, e.g., step (e) of the method above, comprises the use of a plurality of methods for assigning a nucleotide value to a preselected nucleotide position, described herein, e.g., methods described under the heading "Mutation Calling" or in the section entitled "A Bayesian Approach for Sensitive Detection of Somatic Genomic Alterations from Next-generation Sequencing of Clinical Cancer Specimens"; or
(v) the method comprises assigning a nucleotide value to a set of subject intervals described herein, e.g., subgenomic intervals, expressed subgenomic intervals, or both, as described herein, e.g., in the sections entitled "Gene Selection."

In an embodiment, the method includes: (i) and one, two, three, or all of (ii)-(v).

In an embodiment, the method includes: (ii) and one, two, three, or all of (i) and (iii)-(v).

In an embodiment, the method includes: (iii) and one, two, three, or all of (i), (ii), (iv) and (v).

In an embodiment, the method includes: (iv) and one, two, three, or all of (i)-(iii) and (v).

In an embodiment, the method includes: (v) and one, two, three, or all of (i)-(iv).

Alignment

Methods disclosed herein can integrate the use of multiple, individually tuned, alignment methods or algorithms to optimize performance in sequencing methods, particularly in methods that rely on massively parallel sequencing of a large number of diverse genetic events in a large number of diverse genes, e.g., methods of analyzing tumor samples, e.g., from a cancer described herein. In embodiments, multiple alignment methods that are individually customized or tuned to each of a number of variants in different genes are used to analyze reads. In embodiments, tuning can be a function of (one or more of) the gene (or other subgenomic interval) being sequenced, the tumor type in the sample, the variant being sequenced, or a characteristic of the sample or the subject. The selection or use of alignment conditions that are individually tuned to a number of subject intervals (e.g., subgenomic intervals, expressed subgenomic intervals, or both) to be sequenced allows optimization of speed, sensitivity and specificity. The method is particularly effective when the alignments of reads for a relatively large number of diverse subject intervals (e.g., subgenomic intervals, expressed subgenomic intervals, or both) are optimized.

Accordingly, in one aspect, the invention features, a method of analyzing a sample, e.g., a tumor sample from a hematologic malignancy (or premalignancy), e.g., a hematologic malignancy (or premalignancy) described herein. The method comprises:
  (a) acquiring one or a plurality of libraries comprising a plurality members from a sample, e.g., a plurality of tumor members from a tumor sample;
  (b) optionally, enriching the one or a plurality of libraries for preselected sequences, e.g., by contacting the one or a plurality of libraries with a bait set (or plurality of bait sets) to provide selected members (sometimes referred to herein as library catch);
  (c) acquiring a read for a subject interval, e.g., a subgenomic interval or an expressed subgenomic interal, from a member, e.g., a tumor member from a library or library catch, e.g., by a method comprising sequencing, e.g., with a next generation sequencing method;
  (d) aligning said read by an alignment method, e.g., an alignment method described herein; and
  (e) assigning a nucleotide value (e.g., calling a mutation, e.g., with a Bayesian method) from said read for the preselected nucleotide position,
thereby analyzing said tumor sample,
  optionally wherein:
  a read from each of X unique subject intervals (e.g., subgenomic intervals, expressed subgenomic intervals, or both) is aligned with a unique alignment method, wherein unique subject interval (e.g., subgenomic interval or expressed subgenomic interval) means different from the other X−1 subject intervals (e.g., subgenomic intervals, expressed subgenomic intervals, or both), and wherein unique alignment method means different from the other X−1 alignment methods, and X is at least 2.

In an embodiment, the method comprises acquiring a library from which a member corresponding to a subgenomic interval and a member corresponding to an expressed subgenomic interval, is obtained.

In an embodiment, the method comprises acquiring a first library from which a member corresponding to a subgenomic interval is obtained and acquiring a second library from which a member corresponding to an expressed subgenomic interval is obtained.

In an embodiment a bait set is used to provide members or a library catch comprising both a subgenomic interval and an expressed interval.

In an embodiment a first bait set is used to provide members or a library catch comprising a subgenomic interval and a second bait set is used to provide members or a library catch comprising an expressed subgenomic interval.

In an embodiment, step (b) is present. In an embodiment step (b) is absent.

In an embodiment, X is at least 3, 4, 5, 10, 15, 20, 30, 50, 100, 200, 300, 400, 500, 600, 700, 800, 900, or 1,000.

In an embodiment, subject intervals (e.g., subgenomic intervals, expressed subgenomic intervals, or both) from at least X genes, e.g. at least X genes from Tables 1-4, are aligned with unique alignment methods, and X is equal to 2, 3, 4, 5, 10, 15, 20, 30, 40, 50, 60, 70, 80, 90, 100, 200, 300, 400, 500, or greater.

In an embodiment, a method (e.g., element (d) of the method recited above) comprises selecting or using an alignment method for analyzing, e.g., aligning, a read,
  wherein said alignment method is a function of, is selected responsive to, or is optimized for, one or more or all of:
  (i) tumor type, e.g., the tumor type in said sample;
  (ii) the gene, or type of gene, in which said subject interval (e.g., subgenomic interval or expressed subgenomic interval) being sequenced is located, e.g., a gene or type of gene characterized by a preselected or variant or type of variant, e.g., a mutation, or by a mutation of a preselected frequency;
  (iii) the site (e.g., nucleotide position) being analyzed;
  (iv) the type of variant, e.g., a substitution, within the subject interval (e.g., subgenomic interval or expressed subgenomic interval) being evaluated;
  (v) the type of sample, e.g., an FFPE sample, a blood sample, or a bone marrow aspirate sample; and
  (vi) sequence in or near said subgenomic interval being evaluated, e.g., the expected propensity for misalignment for said subject interval (e.g., subgenomic interval or expressed subgenomic interval), e.g., the presence of repeated sequences in or near said subject interval (e.g., subgenomic interval or expressed subgenomic interval).

As referred to elsewhere herein, a method is particularly effective when the alignment of reads for a relatively large number of subject intervals (e.g., subgenomic intervals, expressed subgenomic intervals, or both) is optimized. Thus, in an embodiment, at least X unique alignment methods are used to analyze reads for at least X unique subgenomic intervals, wherein unique means different from the other X−1, and X is equal to 2, 3, 4, 5, 10, 15, 20, 30, 50, 100, 200, 300, 400, 500, 600, 700, 800, 900, 1,000, or greater.

In an embodiment, subject intervals (e.g., subgenomic intervals, expressed subgenomic intervals, or both) from at least X genes from Tables 1-4, are analyzed, and X is equal to 2, 3, 4, 5, 10, 15, 20, 30, 40, 50, 60, 70, 80, 90, 100, 200, 300, 400, 500, or greater.

In an embodiment, a unique alignment method is applied to subject intervals (e.g., subgenomic intervals, expressed subgenomic intervals, or both) in each of at least 3, 5, 10, 20, 40, 50, 60, 70, 80, 90, 100, 200, 300, 400, or 500 different genes.

In an embodiment, a nucleotide position in at least 20, 40, 60, 80, 100, 120, 140, 160 or 180, 200, 300, 400, or 500 genes, e.g., genes from Tables 1-4, is assigned a nucleotide value. In an embodiment a unique alignment method is applied to subject intervals (e.g., subgenomic intervals or expressed subgenomic intervals) in each of at least 10, 20, 30, 40, or 50% of said genes analyzed.

Methods disclosed herein allow for the rapid and efficient alignment of troublesome reads, e.g., a read having a rearrangement. Thus, in embodiment where a read for a subject interval (e.g., a subgenomic interval or an expressed subgenomic interval) comprises a nucleotide position with a rearrangement, e.g., an indel, the method can comprise using an alignment method that is appropriately tuned and that includes:

- selecting a rearrangement reference sequence for alignment with a read, wherein said rearrangement reference sequence is preselected to align with a preselected rearrangement (in embodiments the reference sequence is not identical to the genomic rearrangement);
- comparing, e.g., aligning, a read with said preselected rearrangement reference sequence.

In embodiments, other methods are used to align troublesome reads. These methods are particularly effective when the alignment of reads for a relatively large number of diverse subgenomic intervals is optimized. By way of example, a method of analyzing a tumor sample can comprise:

- performing a comparison, e.g., an alignment comparison, of a read under a first set of parameters (e.g., a first mapping algorithm or with a first reference sequence), and determining if said read meets a first predetermined alignment criterion (e.g., the read can be aligned with said first reference sequence, e.g., with less than a preselected number of mismatches);
- if said read fails to meet the first predetermined alignment criterion, performing a second alignment comparison under a second set of parameters, (e.g., a second mapping algorithm or with a second reference sequence); and,
- optionally, determining if said read meets said second predetermined criterion (e.g., the read can be aligned with said second reference sequence with less than a preselected number of mismatches),
- wherein said second set of parameters comprises use of a set of parameters, e.g., said second reference sequence, which, compared with said first set of parameters, is more likely to result in an alignment with a read for a preselected variant, e.g., a rearrangement, e.g., an insertion, deletion, or translocation.

These and other alignment methods are discussed in more detail elsewhere herein, e.g., in the section entitled "Alignment." Elements of that module can be included in methods of analyzing a tumor. In embodiments, alignment methods from the section entitled "Alignment" are combined with mutation calling methods from the section entitled "Mutation Calling" and/or a bait set from the section entitled "Bait." The method can be applied to set of subject intervals (e.g., subgenomic intervals, expressed subgenomic intervals, or both) from the section entitled "Gene Selection."

Mutation Calling

Methods disclosed herein can integrate the use of customized or tuned mutation calling parameters to optimize performance in sequencing methods, particularly in methods that rely on massively parallel sequencing of a large number of diverse genetic events in a large number of diverse genes, e.g., from tumor samples, e.g., from a cancer described herein. In embodiments of the method mutation calling for each of a number of preselected subject intervals (e.g., subgenomic intervals, expressed subgenomic intervals, or both) is, individually, customized or fine tuned. The customization or tuning can be based on one or more of the factors described herein, e.g., the type of cancer in a sample, the gene in which subject interval (e.g., subgenomic interval or expressed subgenomic interval) to be sequenced is located, or the variant to be sequenced. This selection or use of alignment conditions finely tuned to a number of subject intervals (e.g., subgenomic intervals, expressed subgenomic intervals, or both) to be sequenced allows optimization of speed, sensitivity and specificity. The method is particularly effective when the alignment of reads for a relatively large number of diverse subject intervals (e.g., subgenomic intervals, expressed subgenomic intervals, or both) is optimized.

Accordingly, in one aspect, the invention features, a method of analyzing a sample, e.g., a tumor sample from a hematologic malignancy (or premalignancy), e.g., a hematologic malignancy (or premalignancy) described herein. The method comprises:

(a) acquiring one or a plurality of libraries comprising a plurality members from a sample, e.g., a plurality of tumor members from the sample, e.g., the tumor sample;

(b) optionally, enriching the one or a plurality of libraries for preselected sequences, e.g., by contacting the library with a bait set (or plurality of bait sets) to provide selected members, e.g., a library catch;

(c) acquiring a read for a subject interval (e.g., a subgenomic interval or an expressed subgenomic interval) from a member, e.g., a tumor member from said library or library catch, e.g., by a method comprising sequencing, e.g., with a next generation sequencing method;

(d) aligning said read by an alignment method, e.g., an alignment method described herein; and (e) assigning a nucleotide value (e.g., calling a mutation, e.g., with a Bayesian method or a calling method described herein) from said read for the preselected nucleotide position, thereby analyzing said tumor sample.

optionally wherein a nucleotide value is assigned for a nucleotide position in each of X unique subject intervals (subgenomic intervals, expressed subgenomic intervals, or both) is assigned by a unique calling method, wherein unique subject interval (e.g., subgenomic interval or expressed subgenomic interval) means different from the other X−1 subject intervals (e.g., subgenomic intervals, expressed subgenomic intervals, or both), and wherein unique calling method means different from the other X−1 calling methods, and X is at least 2. The calling methods can differ, and thereby be unique, e.g., by relying on different Bayesian prior values.

In an embodiment, the method comprises acquiring a library from which a member corresponding to a subgenomic interval and a member corresponding to an expressed subgenomic interval, is obtained.

In an embodiment, the method comprises acquiring a first library from which a member corresponding to a subgenomic interval is obtained and acquiring a second library from which a member corresponding to an expressed subgenomic interval is obtained.

In an embodiment a bait set is used to provide members or a library catch comprising both a subgenomic interval and an expressed interval.

In an embodiment a first bait set is used to provide members or a library catch comprising a subgenomic interval and a second bait set is used to provide members or a library catch comprising an expressed subgenomic interval.

In an embodiment, step (b) is present. In an embodiment, step (b) is absent.

In an embodiment, assigning said nucleotide value is a function of a value which is or represents the prior (e.g., literature) expectation of observing a read showing a preselected variant, e.g., a mutation, at said preselected nucleotide position in a tumor of type.

In an embodiment, them method comprises assigning a nucleotide value (e.g., calling a mutation) for at least 10, 20, 40, 50, 60, 70, 80, 90, 100, 200, 300, 400, 500, 600, 700, 800, 900, or 1,000 preselected nucleotide positions, wherein each assignment is a function of a unique (as opposed to the value for the other assignments) value which is or represents the prior (e.g., literature) expectation of observing a read showing a preselected variant, e.g., a mutation, at said preselected nucleotide position in a tumor of type.

In an embodiment, assigning said nucleotide value is a function of a set of values which represent the probabilities of observing a read showing said preselected variant at said preselected nucleotide position if the variant is present in the sample at a frequency (e.g., 1%, 5%, 10%, etc.) and/or if the variant is absent (e.g., observed in the reads due to base-calling error alone).

In an embodiment, a method (e.g., step (e) of the method recited above) comprises a mutation calling method. The mutation calling methods described herein can include the following:

acquiring, for a preselected nucleotide position in each of said X subject intervals (e.g., subgenomic intervals, expressed subgenomic intervals, or both):
(i) a first value which is or represents the prior (e.g., literature) expectation of observing a read showing a preselected variant, e.g., a mutation, at said preselected nucleotide position in a tumor of type X; and
(ii) a second set of values which represent the probabilities of observing a read showing said preselected variant at said preselected nucleotide position if the variant is present in the sample at a frequency (e.g., 1%, 5%, 10%, etc.) and/or if the variant is absent (e.g., observed in the reads due to base-calling error alone);
responsive to said values, assigning a nucleotide value (e.g., calling a mutation) from said reads for each of said preselected nucleotide positions by weighing, e.g., by a Bayesian method described herein, the comparison among the values in the second set using the first value (e.g., computing the posterior probability of the presence of a mutation), thereby analyzing said sample.

In an embodiment, the method comprises one or more or all of:
(i) assigning a nucleotide value (e.g., calling a mutation) for at least 10, 20, 40, 50, 60, 70, 80, 90, 100, 200, 300, 400, 500, 600, 700, 800, 900, or 1,000 preselected nucleotide positions, wherein each assignment is based on a unique (as opposed to the other assignments) first and/or second values;
(ii) the assignment of method of (i), wherein at least 10, 20, 30, 40, 50, 60, 70, 80, 90, 100, 200, 300, 400, or 500 of the assignments are made with first values which are a function of a probability of a preselected variant being present of less than 5, 10, or 20%, e.g., of the cells in a preselected tumor type;
(iii) assigning a nucleotide value (e.g., calling a mutation) for at least X preselected nucleotide positions, each of which of which being associated with a preselected variant having a unique (as opposed to the other X−1 assignments) probability of being present in a tumor of preselected type, e.g., the tumor type of said sample, wherein, optionally, each said of X assignments is based on a unique (as opposed to the other X−1 assignments) first and/or second value (wherein X=2, 3, 5, 10, 20, 40, 50, 60, 70, 80, 90, 100, 200, 300, 400, or 500);
(iv) assigning a nucleotide value (e.g., calling a mutation) at a first and a second nucleotide position, wherein the likelihood of a first preselected variant at said first nucleotide position being present in a tumor of preselected type (e.g., the tumor type of said sample) is at least 2, 5, 10, 20, 30, or 40 times greater than the likelihood of a second preselected variant at said second nucleotide position being present, wherein, optionally, each assignment is based on a unique (as opposed to the other assignments) first and/or second value;
(v) assigning a nucleotide value to a plurality of preselected nucleotide positions (e.g., calling mutations), wherein said plurality comprises an assignment for variants falling into one or more, e.g., at least 3, 4, 5, 6, 7, or all, of the following probability ranges:
less than or equal to 0.01;
greater than 0.01 and less than or equal to 0.02;
greater than 0.02 and less than or equal to 0.03;
greater than 0.03 and less than or equal to 0.04;
greater than 0.04 and less than or equal to 0.05;
greater than 0.05 and less than or equal to 0.1;
greater than 0.1 and less than or equal to 0.2;
greater than 0.2 and less than or equal to 0.5;
greater than 0.5 and less than or equal to 1.0;
greater than 1.0 and less than or equal to 2.0;
greater than 2.0 and less than or equal to 5.0;
greater than 5.0 and less than or equal to 10.0;
greater than 10.0 and less than or equal to 20.0;
greater than 20.0 and less than or equal to 50.0; and
greater than 50 and less than or equal to 100.0%;
wherein, a probability range is the range of probabilities that a preselected variant at a preselected nucleotide position will be present in a tumor of preselected type (e.g., the tumor type of said sample) or the probability that a preselected variant at a preselected nucleotide position will be present in the recited % of the cells in a tumor sample, a library from the tumor sample, or library catch from that library, for a preselected type (e.g., the tumor type of said sample), and wherein, optionally, each assignment is based on a unique first and/or second value (e.g., unique as opposed to the other assignments in a recited probability range or unique as opposed to the first and/or second values for one or more or all of the other listed probability ranges).
(vi) assigning a nucleotide value (e.g., calling a mutation) for at least 1, 2, 3, 5, 10, 20, 40, 50, 60, 70, 80, 90, 100, 200, 300, 400, 500, 600, 700, 800, 900, or 1,000 preselected nucleotide positions each, independently, having a preselected variant present in less than 50, 40, 25, 20, 15, 10, 5, 4, 3, 2, 1, 0.5, 0.4, 0.3, 0.2, or 0.1% of the DNA in said sample, wherein, optionally, each assignment is based on a unique (as opposed to the other assignments) first and/or second value;
(vii) assigning a nucleotide value (e.g., calling a mutation) at a first and a second nucleotide position, wherein the likelihood of a preselected variant at the first position in the DNA of said sample is at least 2, 5, 10, 20, 30, or 40 times greater than a the likelihood of a preselected variant at said second nucleotide position in the DNA of said sample, wherein, optionally, each assignment is based on a unique (as opposed to the other assignments) first and/or second value;
(viii) assigning a nucleotide value (e.g., calling a mutation) in one or more or all of the following:

(1) at least 1, 2, 3, 4 or 5 preselected nucleotide positions having a preselected variant present in less than 1% of the cells in said sample, of the nucleic acid in a library from said sample, or the nucleic acid in a library catch from that library;
(2) at least 1, 2, 3, 4 or 5 preselected nucleotide positions having a preselected variant present in 1-2% of the cells in said sample, of the nucleic acid in a library from said sample, or the nucleic acid in a library catch from that library;
(3) at least 1, 2, 3, 4 or 5 preselected nucleotide positions having a preselected variant present in greater than 2% and less than or equal to 3% of the cells in said sample, of the nucleic acid in a library from said sample, or the nucleic acid in a library catch from that library
(4) at least 1, 2, 3, 4 or 5 preselected nucleotide positions having a preselected variant present in greater than 3% and less than or equal to 4% of the cells in said sample, of the nucleic acid in a library from said sample, or the nucleic acid in a library catch from that library;
(5) at least 1, 2, 3, 4 or 5 preselected nucleotide positions having a preselected variant present in greater than 4% and less than or equal to 5% of the cells in said sample, of the nucleic acid in a library from said sample, or the nucleic acid in a library catch from that library;
(6) at least 1, 2, 3, 4 or 5 preselected nucleotide positions having a preselected variant present in greater than 5% and less than or equal to 10% of the cells in said sample, of the nucleic acid in a library from said sample, or the nucleic acid in a library catch from that library;
(7) at least 1, 2, 3, 4 or 5 preselected nucleotide positions having a preselected variant present in greater than 10% and less than or equal to 20% of the cells in said sample, of the nucleic acid in a library from said sample, or the nucleic acid in a library catch from that library;
(8) at least 1, 2 3, 4 or 5 preselected nucleotide positions having a preselected variant present in greater than 20% and less than or equal to 40% of the cells in said sample, of the nucleic acid in a library from said sample, or the nucleic acid in a library catch from that library;
(9) at least 1, 2 3, 4 or 5 preselected nucleotide positions having a preselected variant present at greater than 40% and less than or equal to 50% of the cells in said sample, of the nucleic acid in a library from said sample, or the nucleic acid in a library catch from that library; or
(10) at least 1, 2 3, 4 or 5 preselected nucleotide positions having a preselected variant present in greater than 50% and less than or equal to 100% of the cells in said sample, of the nucleic acid in a library from said sample, or the nucleic acid in a library catch from that library;
wherein, optionally, each assignment is based on a unique first and/or second value (e.g., unique as opposed to the other assignments in the recited range (e.g., the range in (i) of less than 1%) or unique as opposed to a first and/or second values for a determination in one or more or all of the other listed ranges); or
(ix) assigning a nucleotide value (e.g., calling a mutation) at each of X nucleotide positions, each nucleotide position, independently, having a likelihood (of a preselected variant being present in the DNA of said sample) that is unique as compared with the likelihood for a preselected variant at the other X−1 nucleotide positions, wherein X is equal to or greater than 1, 2, 3, 5, 10, 20, 40, 50, 60, 70, 80, 90, 100, 200, 300, 400, 500, 600, 700, 800, 900, or 1,000, and wherein each assignment is based on a unique (as opposed to the other assignments) first and/or second value.

In embodiments of the method, a "threshold value" is used to evaluate reads, and select from the reads a value for a nucleotide position, e.g., calling a mutation at a specific position in a gene. In embodiments of the method, a threshold value for each of a number of preselected subject intervals (e.g., subgenomic intervals, expressed subgenomic intervals, or both) is customized or fine tuned. The customization or tuning can be based on one or more of the factors described herein, e.g., the type of cancer in a sample, the gene in which subject interval (subgenomic interval or expressed subgenomic interval) to be sequenced is located, or the variant to be sequenced. This provides for calling that is finely tuned to each of a number of subject intervals (e.g., subgenomic intervals, expressed subgenomic intervals, or both) to be sequenced. The method is particularly effective when a relatively large number of diverse subgenomic intervals are analyzed.

Thus, in another embodiment the method of analyzing a tumor comprises the following mutation calling method:
 acquiring, for each of said X subject intervals (e.g., subgenomic intervals, expressed subgenomic intervals, or both), a threshold value, wherein each of said acquired X threshold values is unique as compared with the other X−1 threshold values, thereby providing X unique threshold values;
 for each of said X subject intervals (e.g., subgenomic intervals, expressed subgenomic intervals, or both), comparing an observed value which is a function of the number of reads having a preselected nucleotide value at a preselected nucleotide position with its unique threshold value, thereby applying to each of said X subject intervals (e.g., subgenomic intervals, expressed subgenomic intervals, or both), its unique threshold value; and
 optionally, responsive to the result of said comparison, assigning a nucleotide value to a preselected nucleotide position,
 wherein X is equal to or greater than 2.

In an embodiment, the method includes assigning a nucleotide value at at least 2, 3, 5, 10, 20, 40, 50, 60, 70, 80, 90, 100, 200, 300, 400, 500, 600, 700, 800, 900, or 1,000 preselected nucleotide positions, each having, independently, a first value that is a function of a probability that is less than 0.5, 0.4, 0.25, 0.15, 0.10, 0.05, 0.04, 0.03, 0.02, or 0.01.

In an embodiment, the method includes assigning a nucleotide value at at each of at least X nucleotide positions, each independently having a first value that is unique as compared with the other X−1 first values, and wherein each of said X first values is a function of a probability that is less than 0.5, 0.4, 0.25, 0.15, 0.10, 0.05, 0.04, 0.03, 0.02, or 0.01, wherein X is equal to or greater than 1, 2, 3, 5, 10, 20, 40, 50, 60, 70, 80, 90, 100, 200, 300, 400, 500, 600, 700, 800, 900, or 1,000.

In an embodiment, a nucleotide position in at least 20, 40, 60, 80, 100, 120, 140, 160 or 180, 200, 300, 400, or 500 genes, e.g., genes from Tables 1-4, is assigned a nucleotide value. In an embodiment unique first and/or second values are applied to subject intervals (e.g., subgenomic intervals, expressed subgenomic intervals, or both) in each of at least 10, 20, 30, 40, or 50% of said genes analyzed.

Embodiments of the method can be applied where threshold values for a relatively large number of subject intervals (e.g., subgenomic intervals, expressed subgenomic intervals, or both), are optimized, as is seen, e.g., from the following embodiments.

In an embodiment, a unique threshold value is applied to subject intervals, e.g., subgenomic intervals or expressed subgenomic intervals, in each of at least 3, 5, 10, 20, 40, 50, 60, 70, 80, 90, 100, 200, 300, 400, 500, 600, 700, 800, 900, or 1,000 different genes.

In an embodiment, a nucleotide position in at least 20, 40, 60, 80, 100, 120, 140, 160 or 180, 200, 300, 400, or 500 genes, e.g., genes from Tables 1-4, is assigned a nucleotide value. In an embodiment a unique threshold value is applied to a subgenomic interval in each of at least 10, 20, 30, 40, or 50% of said genes analyzed.

In an embodiment, a nucleotide position in at least 5, 10, 20, 30, or 40 genes from Tables 1-4 is assigned a nucleotide value. In an embodiment a unique threshold value is applied to a subject interval (e.g., a subgenomic interval or an expressed subgenomic interval) in each of at least 10, 20, 30, 40, or 50% of said genes analyzed.

These and other mutation calling methods are discussed in more detail elsewhere herein, e.g., in the section entitled "Mutation." Elements of that module can be included in methods of analyzing a tumor. In embodiments, alignment methods from the section entitled "Mutation Calling" are combined with alignment methods from the section entitled "Alignment" and/or a bait set from the section entitled "Bait." The method can be applied to set of subject intervals (e.g., subgenomic intervals, expressed subgenomic intervals, or both) from the section entitled "Gene Selection."

Bait

Methods described herein provide for optimized sequencing of a large number of genes and gene products from samples, e.g., tumor samples, e.g., from a cancer described herein, from one or more subjects by the appropriate selection of baits, e.g., baits for use in solution hybridization, for the selection of target nucleic acids to be sequenced. The efficiency of selection for various subject intervals (e.g., subgenomic intervals, expressed subgenomic intervals, or both), or classes thereof, are matched according to bait sets having preselected efficiency of selection. As used in this section, "efficiency of selection" refers to the level or depth of sequence coverage as it is adjusted according to a target subject interval(s) (e.g., subgenomic interval(s), expressed subgenomic interval(s), or both).

Thus a method (e.g., step (b) of the method recited above) comprises contacting the library with a plurality of baits to provide selected members (e.g., a library catch).

Accordingly, in one aspect, the invention features, a method of analyzing a sample, e.g., a tumor sample from a hematologic malignancy (or premalignancy), e.g., a hematologic malignancy (or premalignancy) described herein. The method comprises:

(a) acquiring one or a plurality of libraries comprising a plurality of members (e.g., target members) from a sample, e.g., a plurality of tumor members from a tumor sample;

(b) contacting the one or a plurality of libraries with a bait set (or a plurality of bait sets) to provide selected members (e.g., a library catch);

(c) acquiring a read for a subject interval, e.g., a subgenomic interval, an expressed subgenomic interval, or both, from a member, e.g., a tumor member from said library or library catch, e.g., by a method comprising sequencing, e.g., with a next generation sequencing method;

(d) aligning said read by an alignment method, e.g., an alignment method described herein; and (e) assigning a nucleotide value (e.g., calling a mutation, e.g., with a Bayesian method or a method described herein) from said read for the preselected nucleotide position, thereby analyzing said tumor sample, optionally wherein the method comprises contacting the library with a plurality, e.g., at least two, three, four, or five, of baits or bait sets, wherein each bait or bait set of said plurality has a unique (as opposed to the other bait sets in the plurality), preselected efficiency for selection. E.g., each unique bait or bait set provides for a unique depth of sequencing. The term "bait set", as used herein, collectively refers to one bait or a plurality of bait molecules.

In an embodiment, the method comprises acquiring a library from which a member corresponding to a subgenomic interval and a member corresponding to an expressed genomic interval, is obtained.

In an embodiment, the method comprises acquiring a first library from which a member corresponding to a subgenomic interval is obtained and acquiring a second library from which a member corresponding to an expressed subgenomic interval is obtained.

In an embodiment a bait set is used to provide members or a library catch comprising both a subgenomic interval and an expressed interval.

In an embodiment a first bait set is used to provide members or a library catch comprising a subgenomic interval and a second bait set is used to provide members or a library catch comprising an expressed subgenomic interval.

In an embodiment, the efficiency of selection of a first bait set in the plurality differs from the efficiency of a second bait set in the plurality by at least 2 fold. In an embodiment, the first and second bait sets provide for a depth of sequencing that differs by at least 2 fold.

In an embodiment, the method comprises contacting one, or a plurality of the following bait sets with the library:

a) a bait set that selects sufficient members comprising a subgenomic interval to provide for about 500× or higher sequencing depth, e.g., to sequence a mutation present in no more than 5% of the cells from the sample;

b) a bait set that selects sufficient members comprising a subgenomic interval to provide for about 200× or higher, e.g., about 200×-about 500×, sequencing depth, e.g., to sequence a mutation present in no more than 10% of the cells from the sample;

c) a bait set that selects sufficient members comprising a subgenomic interval to provide for about 10-100× sequencing depth, e.g., to sequence one or more subgenomic intervals (e.g., exons) that are chosen from: a) a pharmacogenomic (PGx) single nucleotide polymorphism (SNP) that may explain the ability of patient to metabolize different drugs, or b) a genomic SNPs that may be used to uniquely identify (e.g., fingerprint) a patient;

d) a bait set that selects sufficient members comprising a subject interval (e.g., a subgenomic interval or an expressed subgenomic interval) to provide for about 5-50× sequencing depth, e.g., to detect a structural breakpoint, such as a genomic translocation or an indel. For example, detection of an intronic breakpoint requires 5-50× sequence-pair spanning depth to ensure high detection reliability. Such bait sets can be used to detect, for example, translocation/indel-prone cancer genes; or e) a bait set that selects sufficient members comprising a subject interval (e.g., a subgenomic interval or an expressed subgenomic interval) to provide for about 0.1-300× sequencing depth, e.g., to detect copy number changes. In one embodiment, the sequencing depth ranges from about 0.1-10× sequencing depth to detect copy number changes. In other embodiments, the sequencing depth ranges from about 100-300× to detect a genomic SNPs/loci that is used to assess copy number gains/losses of genomic DNA or loss-of-heterozygosity (LOH). Such bait sets can be used to detect, for example, amplification/deletion-prone cancer genes.

The level of sequencing depth as used herein (e.g., X-fold level of sequencing depth) refers to the level of coverage of reads (e.g., unique reads), after detection and removal of duplicate reads, e.g., PCR duplicate reads.

In one embodiment, the bait set selects a subject interval (e.g., a subgenomic interval or an expressed subgenomic interval) containing one or more rearrangements, e.g., an intron containing a genomic rearrangement. In such embodiments, the bait set is designed such that repetitive sequences are masked to increase the selection efficiency. In those embodiments where the rearrangement has a known juncture sequence, complementary bait sets can be designed to the juncture sequence to increase the selection efficiency.

In embodiments, the method comprises the use of baits designed to capture two or more different target categories, each category having a different bait design strategies. In embodiments, the hybrid capture methods and compositions disclosed herein capture a defined subset of target sequences (e.g., target members) and provide homogenous coverage of the target sequence, while minimizing coverage outside of that subset. In one embodiment, the target sequences include the entire exome out of genomic DNA, or a selected subset thereof. In another embodiment, the target sequences include a large chromosomal region, e.g., a whole chromosome arm. The methods and compositions disclosed herein provide different bait sets for achieving different depths and patterns of coverage for complex target nucleic acid sequences (e.g., nucleic acid libraries).

In an embodiment, the method comprises providing selected members of one or a plurality of nucleic acid libraries (e.g., a library catch). The method includes:

providing one or a plurality of libraries (e.g., one or a plurality of nucleic acid libraries) comprising a plurality of members, e.g., target nucleic acid members (e.g., including a plurality of tumor members, reference members, and/or PGx members);

contacting the one or a plurality of libraries, e.g., in a solution-based reaction, with a plurality of baits (e.g., oligonucleotide baits) to form a hybridization mixture comprising a plurality of bait/member hybrids;

separating the plurality of bait/member hybrids from said hybridization mixture, e.g., by contacting said hybridization mixture with a binding entity that allows for separation of said plurality of bait/member hybrid, thereby providing a library-catch (e.g., a selected or enriched subgroup of nucleic acid molecules from the one or a plurality of libraries), optionally wherein the plurality of baits includes two or more of the following:

a) a first bait set that selects a high-level target (e.g., one or more tumor members that include a subject interval (e.g., a subgenomic interval or an expressed subgenomic interval), such a gene, an exon, or a base) for which the deepest coverage is required to enable a high level of sensitivity for an alteration (e.g., one or more mutations) that appears at a low frequency, e.g., about 5% or less (i.e., 5% of the cells from the sample harbor the alteration in their genome). In one embodiment; the first bait set selects (e.g., is complementary to) a tumor member that includes an alteration (e.g., a point mutation) that requires about 500× or higher sequencing depth;

b) a second bait set that selects a mid-level target (e.g., one or more tumor members that include a subject interval (e.g., a subgenomic interval or an expressed subgenomic interval) such as a gene, an exon, or a base) for which high coverage is required to enable high level of sensitivity for an alteration (e.g., one or more mutations) that appears at a higher frequency than the high-level target in a), e.g., a frequency of about 10% (i.e., 10% of the cells from the sample harbor the alteration in their genome). In one embodiment; the second bait set selects (e.g., is complementary to) a tumor member that includes an alteration (e.g., a point mutation) that requires about 200× or higher sequencing depth;

c) a third bait set that selects a low-level target (e.g., one or more PGx members that includes a subject interval (e.g., a subgenomic interval or an expressed subgenomic interval), such as a gene, an exon, or a base) for which low-medium coverage is required to enable high level of sensitivity, e.g., to detect heterozygous alleles. For example, detection of heterozygous alleles requires 10-100× sequencing depth to ensure high detection reliability. In one embodiment, the third bait set selects one or more subject intervals (e.g., subgenomic intervals, expressed subgenomic intervals, or both, e.g., exons) that are chosen from: a) a pharmacogenomic (PGx) single nucleotide polymorphism (SNP) that may explain the ability of patient to metabolize different drugs, or b) a genomic SNPs that may be used to uniquely identify (e.g., fingerprint) a patient;

d) a fourth bait set that selects a first intron target (e.g., a member that includes an intron sequence) for which low-medium coverage is required, e.g., to detect a structural breakpoint, such as a genomic translocation or an indel. For example, detection of an intronic breakpoint requires 5-50× sequence-pair spanning depth to ensure high detection reliability. Said fourth bait sets can be used to detect, for example, translocation/indel-prone cancer genes; or e) a fifth bait set that selects a second intron target (e.g., an intron member) for which sparse coverage is required to improve the ability to detect copy number changes. For example, detection of a one-copy deletion of several terminal exons requires 0.1-300× coverage to ensure high detection reliability. In one embodiment, the coverage depth ranges from about 0.1-10× to detect copy number changes. In other embodiments, the coverage depth ranges from about 100-300× to detect a genomic SNPs/loci that is used to assess copy number gains/losses of genomic DNA or loss-of-heterozygosity (LOH). Said fifth bait sets can be used to detect, for example, amplification/deletion-prone cancer genes.

Any combination of two, three, four or more of the aforesaid bait sets can be used, for example, a combination of the first and the second bait sets; first and third bait sets; first and fourth bait sets; first and fifth bait sets; second and third bait sets; second and fourth bait sets; second and fifth bait sets; third and fourth bait sets; third and fifth bait sets; fourth and fifth bait sets; first, second and third bait sets; first, second and fourth bait sets; first, second and fifth bait sets; first, second, third, fourth bait sets; first, second, third, fourth and fifth bait sets, and so on.

In one embodiment, each of the first, second, third, fourth, or fifth bait set has a preselected efficiency for selection (e.g., capture). In one embodiment, the value for efficiency of selection is the same for at least two, three, four of all five baits according to a)-e). In other embodiments, the value for efficiency of selection is different for at least two, three, four of all five baits according to a)-e).

In some embodiments, at least two, three, four, or all five bait sets have a preselected efficiency value that differ. For example, a value for efficiency of selection chosen from one of more of:
- (i) the first preselected efficiency has a value for first efficiency of selection that is at least about 500× or higher sequencing depth (e.g., has a value for efficiency of selection that is greater than the second, third, fourth or fifth preselected efficiency of selection (e.g., about 2-3 fold greater than the value for the second efficiency of selection; about 5-6 fold greater than the value for the third efficiency of selection; about 10 fold greater than the value for the fourth efficiency of selection; about 50 to 5,000-fold greater than the value for the fifth efficiency of selection);
- (ii) the second preselected efficiency has a value for second efficiency of selection that is at least about 200× or higher sequencing depth, e.g., has a value for efficiency of selection that is greater than the third, fourth or fifth preselected efficiency of selection (e.g., about 2 fold greater than the value for the third efficiency of selection; about 4 fold greater than the value for the fourth efficiency of selection; about 20 to 2,000-fold greater than the value for the fifth efficiency of selection);
- (iii) the third preselected efficiency has a value for third efficiency of selection that is at least about 100× or higher sequencing depth, e.g., has a value for efficiency of selection that is greater than the fourth or fifth preselected efficiency of selection (e.g., about 2 fold greater than the value for the fourth efficiency of selection; about 10 to 1000-fold greater than the value for the fifth efficiency of selection);
- (iv) the fourth preselected efficiency has a value for fourth efficiency of selection that is at least about 50× or higher sequencing depth, e.g., has a value for efficiency of selection that is greater than the fifth preselected efficiency of selection (e.g., about 50 to 500-fold greater than the value for the fifth efficiency of selection); or
- (v) the fifth preselected efficiency has a value for fifth efficiency of selection that is at least about 10× to 0.1× sequencing depth.

In certain embodiments, the value for efficiency of selection is modified by one or more of: differential representation of different bait sets, differential overlap of bait subsets, differential bait parameters, mixing of different bait sets, and/or using different types of bait sets. For example, a variation in efficiency of selection (e.g., relative sequence coverage of each bait set/target category) can be adjusted by altering one or more of:
- (i) Differential representation of different bait sets—The bait set design to capture a given target (e.g., a target member) can be included in more/fewer number of copies to enhance/reduce relative target coverage depths;
- (ii) Differential overlap of bait subsets—The bait set design to capture a given target (e.g., a target member) can include a longer or shorter overlap between neighboring baits to enhance/reduce relative target coverage depths;
- (iii) Differential bait parameters—The bait set design to capture a given target (e.g., a target member) can include sequence modifications/shorter length to reduce capture efficiency and lower the relative target coverage depths;
- (iv) Mixing of different bait sets—Bait sets that are designed to capture different target sets can be mixed at different molar ratios to enhance/reduce relative target coverage depths;
- (v) Using different types of oligonucleotide bait sets—In certain embodiments, the bait set can include:
  - (a) one or more chemically (e.g., non-enzymatically) synthesized (e.g., individually synthesized) baits,
  - (b) one or more baits synthesized in an array,
  - (c) one or more enzymatically prepared, e.g., in vitro transcribed, baits;
  - (d) any combination of (a), (b) and/or (c),
  - (e) one or more DNA oligonucleotides (e.g., a naturally or non-naturally occurring DNA oligonucleotide),
  - (f) one or more RNA oligonucleotides (e.g., a naturally or non-naturally occurring RNA oligonucleotide),
  - (g) a combination of (e) and (f), or
  - (h) a combination of any of the above.

The different oligonucleotide combinations can be mixed at different ratios, e.g., a ratio chosen from 1:1, 1:2, 1:3, 1:4, 1:5, 1:10, 1:20, 1:50; 1:100, 1:1000, or the like. In one embodiment, the ratio of chemically-synthesized bait to array-generated bait is chosen from 1:5, 1:10, or 1:20. The DNA or RNA oligonucleotides can be naturally- or non-naturally-occurring. In certain embodiments, the baits include one or more non-naturally-occurring nucleotide to, e.g., increase melting temperature. Exemplary non-naturally occurring oligonucleotides include modified DNA or RNA nucleotides. Exemplary modified nucleotides (e.g., modified RNA or DNA nucleotides) include, but are not limited to, a locked nucleic acid (LNA), wherein the ribose moiety of an LNA nucleotide is modified with an extra bridge connecting the 2' oxygen and 4' carbon; peptide nucleic acid (PNA), e.g., a PNA composed of repeating N-(2-aminoethyl)-glycine units linked by peptide bonds; a DNA or RNA oligonucleotide modified to capture low GC regions; a bicyclic nucleic acid (BNA); a crosslinked oligonucleotide; a modified 5-methyl deoxycytidine; and 2,6-diaminopurine. Other modified DNA and RNA nucleotides are known in the art.

In certain embodiments, a substantially uniform or homogeneous coverage of a target sequence (e.g., a target member) is obtained. For example, within each bait set/target category, uniformity of coverage can be optimized by modifying bait parameters, for example, by one or more of:
- (i) Increasing/decreasing bait representation or overlap can be used to enhance/reduce coverage of targets (e.g., target members), which are under/over-covered relative to other targets in the same category;
- (ii) For low coverage, hard to capture target sequences (e.g., high GC content sequences), expand the region being targeted with the bait sets to cover, e.g., adjacent sequences (e.g., less GC-rich adjacent sequences);

(i) Differential representation of different bait sets—The bait set design to capture a given target (e.g., a target (iii) Modifying a bait sequence can be made to reduce secondary structure of the bait and enhance its efficiency of selection;

(iv) Modifying a bait length can be used to equalize melting hybridization kinetics of different baits within the same category. Bait length can be modified directly (by producing baits with varying lengths) or indirectly (by producing baits of consistent length, and replacing the bait ends with arbitrary sequence);

(v) Modifying baits of different orientation for the same target region (i.e. forward and reverse strand) may have different binding efficiencies. The bait set with either orientation providing optimal coverage for each target may be selected;

(vi) Modifying the amount of a binding entity, e.g., a capture tag (e.g. biotin), present on each bait may affect its binding efficiency. Increasing/decreasing the tag level of baits targeting a specific target may be used to enhance/reduce the relative target coverage;

(vii) Modifying the type of nucleotide used for different baits can be altered to affect binding affinity to the target, and enhance/reduce the relative target coverage; or (viii) Using modified oligonucleotide baits, e.g., having more stable base pairing, can be used to equalize melting hybridization kinetics between areas of low or normal GC content relative to high GC content.

For example, different types of oligonucleotide bait sets can be used.

In one embodiment, the value for efficiency of selection is modified by using different types of bait oligonucleotides to encompass pre-selected target regions. For example, a first bait set (e.g., an array-based bait set comprising 10,000-50,000 RNA or DNA baits) can be used to cover a large target area (e.g., 1-2 MB total target area). The first bait set can be spiked with a second bait set (e.g., individually synthesized RNA or DNA bait set comprising less than 5,000 baits) to cover a pre-selected target region (e.g., selected subgenomic intervals of interest spanning, e.g., 250 kb or less, of a target area) and/or regions of higher secondary structure, e.g., higher GC content. Selected subject intervals (e.g., subgenomic intervals, expressed subgenomic intervals, or both) of interest may correspond to one or more of the genes or gene products described herein, or a fragment thereof. The second bait set may include about 1-5,000, 2-5,000, 3-5,000, 10-5,000, 100-5,000, 500-5,000, 100-5,000, 1,000-5,000, 2,000-5,000 baits depending on the bait overlap desired. In other embodiments, the second bait set can include selected oligo baits (e.g., less than 400, 200, 100, 50, 40, 30, 20, 10, 5, 4, 3, 2 or 1 baits) spiked into the first bait set. The second bait set can be mixed at any ratio of individual oligo baits. For example, the second bait set can include individual baits present as a 1:1 equimolar ratio. Alternatively, the second bait set can include individual baits present at different ratio (e.g., 1:5, 1:10, 1:20), for example, to optimize capture of certain targets (e.g., certain targets can have a 5-10× of the second bait compared to other targets).

In other embodiments, the efficiency of selection is adjusted by leveling the efficiency of individual baits within a group (e.g., a first, second or third plurality of baits) by adjusting the relative abundance of the baits, or the density of the binding entity (e.g., the hapten or affinity tag density) in reference to differential sequence capture efficiency observed when using an equimolar mix of baits, and then introducing a differential excess of internally-leveled group 1 to the overall bait mix relative to internally-leveled group 2.

In an embodiment, the method comprises the use of a plurality of bait sets that includes a bait set that selects a tumor member, e.g., a nucleic acid molecule comprising a subject interval (e.g., a subgenomic interval or an expressed subgenomic interval) from a tumor cell (also referred to herein as "a tumor bait set"). The tumor member can be any nucleotide sequence present in a tumor cell, e.g., a mutated, a wild-type, a PGx, a reference or an intron nucleotide sequence, as described herein, that is present in a tumor or cancer cell. In one embodiment, the tumor member includes an alteration (e.g., one or more mutations) that appears at a low frequency, e.g., about 5% or less of the cells from the tumor sample harbor the alteration in their genome. In other embodiments, the tumor member includes an alteration (e.g., one or more mutations) that appears at a frequency of about 10% of the cells from the tumor sample. In other embodiments, the tumor member includes a subgenomic interval from a PGx gene or gene product, an intron sequence, e.g., an intron sequence as described herein, a reference sequence that is present in a tumor cell.

In another aspect, the invention features, a bait set described herein, combinations of individual bait sets described herein, e.g., combinations described herein. The bait set(s) can be part of a kit which can optionally comprise instructions, standards, buffers or enzymes or other reagents.

Gene Selection

Preselected subject intervals, e.g., subgenomic intervals, expressed subgenomic intervals, or both, for analysis, e.g., a group or set of subgenomic intervals for sets or groups of genes and other regions, are described herein.

Thus, in embodiments a method comprises sequencing, e.g., by a next generation sequencing method, a subject interval (e.g., a subgenomic interval or an expressed subgenomic interval) from at least 5, 6, 7, 8, 9, 10, 15, 20, 25, 30, 40, 50, 60, 70, 80, 90, 100, 200, 300, 400, 500, or more genes or gene products from the acquired nucleic acid sample, wherein the genes or gene products are chosen from Tables 1-4, thereby analyzing the tumor sample, e.g., from a cancer described herein.

Accordingly, in one aspect, the invention features, a method of analyzing a sample, e.g., a tumor sample from a hematologic malignancy (or premalignancy), e.g., a hematologic malignancy (or premalignancy) described herein. The method comprises:

(a) acquiring one or a plurality of libraries comprising a plurality members from a sample, e.g., a plurality of tumor members from a tumor sample from a hematologic malignancy (or premalignancy), e.g., a hematologic malignancy (or premalignancy) described herein;

(b) optionally, enriching the one or a plurality of libraries for preselected sequences, e.g., by contacting the one or a plurality of libraries with a bait set (or plurality of bait sets) to provide selected members (e.g., a library catch);

(c) acquiring a read for a subject interval (e.g., a subgenomic interval or an expressed subgenomic interval) from a member, e.g., a tumor member from said library or library catch, e.g., by a method comprising sequencing, e.g., with a next generation sequencing method;

(d) aligning said read by an alignment method, e.g., an alignment method described herein; and (e) assigning a nucleotide value (e.g., calling a mutation, e.g., with a Bayesian method or a method described herein) from said read for the preselected nucleotide position, thereby analyzing said tumor sample, optionally wherein the method comprises sequencing, e.g., by a next generation sequencing method, a subject interval (e.g., a subgenomic interval or an expressed subgenomic interval) from at least 5, 6, 7, 8, 9, 10, 15, 20, 25, 30, 40, 50, 60, 70, 80, 90, 100, 200, 300, 400, 500, or more genes or gene products from the sample, wherein the genes or gene products are chosen from Tables 1-4.

In an embodiment, step (b) is present. In an embodiment, step (b) is absent.

In another embodiment, subject intervals (e.g., subgenomic intervals, expressed subgenomic intervals, or both) of one of the following sets or groups are analyzed. E.g., subject intervals (e.g., subgenomic intervals, expressed subgenomic intervals, or both) associated with a tumor or cancer gene or gene product, a reference (e.g., a wild type) gene or gene product, and a PGx gene or gene product, can provide a group or set of subgenomic intervals from the tumor sample.

In an embodiment, the method acquires a read, e.g., sequences, a set of subject intervals (e.g., subgenomic intervals, expressed subgenomic intervals, or both) from the tumor sample, wherein the subject intervals (e.g., subgenomic intervals, expressed subgenomic intervals, or both) are chosen from at least 1, 2, 3, 4, 5, 6, 7 or all of the following:
- A) at least 5, 6, 7, 8, 9, 10, 15, 20, 25, 30, 40, 50, 60, 70, 80, 90, 100, 200, 300, 400, 500, or more subject intervals, e.g., subgenomic intervals, or expressed subgenomic intervals, or both, from a mutated or wild-type gene or gene product according to Tables 1-4;
- B) at least 5, 6, 7, 8, 9, 10, 15, 20, 25, 30, 40, 50, 60, 70, 80, 90, 100, 200, 300, 400, 500, or more subject intervals (e.g., subgenomic intervals, expressed subgenomic intervals, or both) from a gene or gene product that is associated with a tumor or cancer (e.g., is a positive or negative treatment response predictor, is a positive or negative prognostic factor for, or enables differential diagnosis of a tumor or cancer, e.g., a gene or gene product according to Tables 1-4;
- C) at least 5, 6, 7, 8, 9, 10, 15, 20, 25, 30, 40, 50, 60, 70, 80, 90, 100, 200, 300, 400, 500, or more of subject intervals (e.g., subgenomic intervals, expressed subgenomic intervals, or both) from a mutated or wild type gene or gene product (e.g., single nucleotide polymorphism (SNP)) of a subgenomic interval that is present in a gene or gene product associated with one or more of drug metabolism, drug responsiveness, or toxicity (also referred to therein as "PGx" genes) chosen from Tables 1-4;
- D) at least 5, 6, 7, 8, 9, 10, 15, 20, 25, 30, 40, 50, 60, 70, 80, 90, 100, 200, 300, 400, 500, or more of subject intervals (e.g., subgenomic intervals, expressed subgenomic intervals, or both) from a mutated or wild type PGx gene or gene product (e.g., single nucleotide polymorphism (SNP)) of a subject interval (e.g., a subgenomic interval or an expressed subgenomic interval) that is present in a gene or gene product associated with one or more of: (i) better survival of a cancer patient treated with a drug (e.g., better survival of a breast cancer patient treated with paclitaxel); (ii) paclitaxel metabolism; (iii) toxicity to a drug; or (iv) a side effect to a drug, chosen from Tables 1-4;
- E) a translocation alteration of at least 5, 6, 7, 8, 9, 10, 15, 20, 25, 30, 40, 50, 60, 70, 80, 90, 100, 200, 300, 400, 500, or more genes or gene products according to Tables 1-4;
- F) at least five genes or gene products selected from Tables 1-4, wherein an allelic variation, e.g., at the preselected position, is associated with a preselected type of tumor and wherein said allelic variation is present in less than 5% of the cells in said tumor type;
- G) at least five genes or gene products selected from Tables 1-4, which are embedded in a GC-rich region; or
- H) at least five genes or gene products indicative of a genetic (e.g., a germline risk) factor for developing cancer (e.g., the gene or gene product is chosen from Tables 1-4).

In yet another embodiment, the method acquires a read, e.g., sequences, a set of subject intervals (e.g., subgenomic intervals, expressed subgenomic intervals, or both) from the tumor sample, wherein the subject intervals (e.g., subgenomic intervals, expressed subgenomic intervals, or both) are chosen from 5, 6, 7, 8, 9, 10, 15, 20, 25, 30, 40, 50, 60, 70, 80, 90, 100, 200, 300, 400, or all of the genes or gene products described in Table 1.

In yet another embodiment, the method acquires a read, e.g., sequences, a set of subject intervals (e.g., subgenomic intervals, expressed subgenomic intervals, or both) from the tumor sample, wherein the subject intervals (e.g., subgenomic intervals, expressed subgenomic intervals, or both) are chosen from 5, 6, 7, 8, 9, 10, 15, 20, 25, 30, or all of the genes or gene products described in Table 2.

In yet another embodiment, the method acquires a read, e.g., sequences, a set of subject intervals (e.g., subgenomic intervals, expressed subgenomic intervals, or both) from the tumor sample, wherein the subject intervals (e.g., subgenomic intervals, expressed subgenomic intervals, or both) are chosen from 5, 6, 7, 8, 9, 10, 15, 20, 25, 30, 40, 50, 60, 70, 80, 90, 100, 200, 300, or all of the genes or gene products described in Table 3.

In yet another embodiment, the method acquires a read, e.g., sequences, a set of subject intervals (e.g., subgenomic intervals, expressed subgenomic intervals, or both) from the tumor sample, wherein the subject intervals (e.g., subgenomic intervals, expressed subgenomic intervals, or both) are chosen from 5, 6, 7, 8, 9, 10, 15, 20, 25, 30, 40, 50, 60, 70, 80, or all of the genes or gene products described in Table 4.

These and other sets and groups of subgenomic intervals are discussed in more detail elsewhere herein, e.g., in the section entitled "Gene Selection."

Any of the methods described herein can be combined with one or more of the embodiments below.

In other embodiments, the sample is a tumor sample, e.g., includes one or more premalignant or malignant cells. In certain embodiments, the sample, e.g., the tumor sample, is acquired from a hematologic malignancy (or premalignancy), e.g., a hematologic malignancy (or premalignancy) described herein. In certain embodiments, the sample, e.g., the tumor sample, is acquired from a solid tumor, a soft tissue tumor or a metastatic lesion. In other embodiments, the sample, e.g., the tumor sample, includes tissue or cells from a surgical margin. In certain embodiments, the sample, e.g., the tumor sample, includes tumor-infiltrating lymphocytes. The sample can be histologically normal tissue. In another embodiment, the sample, e.g., tumor sample, includes one or more circulating tumor cells (CTC) (e.g., a CTC acquired from a blood sample). In an embodiment, the sample, e.g., the tumor sample, includes one or more non-malignant cells. In an embodiment, the sample, e.g., the tumor sample, includes one or more tumor-infiltrating lymphocytes.

In one embodiment, the method further includes acquiring a sample, e.g., a tumor sample as described herein. The sample can be acquired directly or indirectly. In an embodiment, the sample is acquired, e.g., by isolation or purification, from a sample that contains both a malignant cell and a non-malignant cell (e.g., tumor-infiltrating lymphocyte).

In other embodiments, the method includes evaluating a sample, e.g., a histologically normal sample, e.g., from a surgical margin, using the methods described herein. Applicants have discovered that samples obtained from histologically normal tissues (e.g., otherwise histologically normal tissue margins) may still have an alteration as described herein. The methods may thus further include re-classifying a tissue sample based on the presence of the detected alteration.

In another embodiment, at least 10, 20, 30, 40, 50, 60, 70, 80, or 90% of the reads acquired or analyzed are for subject intervals (e.g., subgenomic intervals, expressed subgenomic intervals, or both) from genes described herein, e.g., genes from Table 1-4.

In an embodiment, at least 10, 20, 30, 40, 50, 60, 70, 80, or 90% of the mutation calls made in the method are for subject intervals (e.g., subgenomic intervals, expressed subgenomic intervals, or both) from genes or gene products described herein, e.g., genes or gene products from Table 1-4.

In an embodiment, at least 10, 20, 30, 40, 50, 60, 70, 80, or 90% of the unique threshold values used the method are for subject intervals (e.g., subgenomic intervals, expressed subgenomic intervals, or both) from genes or gene products described herein, e.g., genes or gene products from Table 1-4.

In an embodiment, at least 10, 20, 30, 40, 50, 60, 70, 80, or 90% of the mutation calls annotated, or reported to a third party, are for subject intervals (e.g., subgenomic intervals, expressed subgenomic intervals, or both) from genes or gene products described herein, e.g., genes or gene products from Table 1-4.

In an embodiment, the method comprises acquiring a nucleotide sequence read obtained from a tumor and/or control nucleic acid sample (e.g., an FFPE-derived nucleic acid sample).

In an embodiment, the reads are provided by a NGS sequencing method.

In an embodiment, the method includes providing one or a plurality of libraries of nucleic acid members and sequencing preselected subgenomic intervals from a plurality of members of said one or a plurality of libraries. In embodiments the method can include a step of selecting a subset of said one or a plurality of libraries for sequencing, e.g., a solution-based selection or a solid support- (e.g., array-) based selection.

In an embodiment, the method includes the step of contacting one or a plurality of libraries with a plurality of baits to provide a selected subgroup of nucleic acids, e.g., a library catch. In one embodiment, the contacting step is effected in solution hybridization. In another embodiment, the contacting step is effected in a solid support, e.g., an array. In certain embodiments, the method includes repeating the hybridization step by one or more additional rounds of hybridization. In some embodiments, the methods further include subjecting the library catch to one or more additional rounds of hybridization with the same or different collection of baits.

In yet other embodiments, the methods further include analyzing the library catch. In one embodiment, the library catch is analyzed by a sequencing method, e.g., a next-generation sequencing method as described herein. The methods include isolating a library catch by, e.g., solution hybridization, and subjecting the library catch by nucleic acid sequencing. In certain embodiments, the library catch can be re-sequenced. Next generation sequencing methods are known in the art, and are described, e.g., in Metzker, M. (2010) *Nature Biotechnology Reviews* 11:31-46.

In an embodiment, the assigned value for a nucleotide position is transmitted to a third party, optionally, with explanatory annotation.

In an embodiment, the assigned value for a nucleotide position is not transmitted to a third party.

In an embodiment, the assigned value for a plurality of nucleotide position is transmitted to a third party, optionally, with explanatory annotations, and the assigned value for a second plurality of nucleotide position is not transmitted to a third party.

In an embodiment, at least 0.01, 0.02, 0.03, 0.05, 0.1, 0.2, 0.3, 0.4, 0.5, 0.6, 0.7, 0.8, 0.9, 1.0, 15, or 30 megabases bases, e.g., genomic bases, are sequenced.

In an embodiment, the method comprises evaluating a plurality of reads that include at least one SNP.

In an embodiment, the method comprises determining an SNP allele ratio in the sample and/or control read.

In an embodiment, the method comprises assigning one or more reads to a subject, e.g., by barcode deconvolution.

In an embodiment, the method comprises assigning one or more reads as a tumor read or a control read, e.g., by barcode deconvolution.

In an embodiment, the method comprises mapping, e.g., by alignment with a reference sequence, each of said one or more reads.

In an embodiment, the method comprises memorializing a called mutation.

In an embodiment, the method comprises annotating a called mutation, e.g., annotating a called mutation with an indication of mutation structure, e.g., a mis-sense mutation, or function, e.g., a disease phenotype.

In an embodiment, the method comprises acquiring nucleotide sequence reads for tumor and control nucleic acid.

In an embodiment, the method comprises calling a nucleotide value, e.g., a variant, e.g., a mutation, for each of the subject intervals (e.g., subgenomic intervals, expressed subgenomic intervals, or both), e.g., with a Bayesian calling method or a non-Bayesian calling method.

In an embodiment, multiple samples, e.g., from different subjects, are processed simultaneously.

The methods disclosed herein can be used to detect alterations present in the genome or transcriptome of a subject, and can be applied to DNA and RNA sequencing, e.g., targeted RNA and/or DNA sequencing. Thus, another aspect featured in the invention includes methods for targeted RNA sequencing, e.g., sequencing of a cDNA derived from an RNA acquired from a sample, e.g., an FFPE-sample, a blood sample, or a bone marrow aspirate sample, to detect an alteration described herein. The alteration can be rearrangement, e.g., a rearrangement encoding a gene fusion. In other embodiments, the method includes detection of a change (e.g., an increase or decrease) in the level of a gene or gene product, e.g., a change in expression of a gene or gene product described herein. The methods can, optionally, include a step of enriching a sample for a target RNA. In other embodiments, the methods include the step of depleting the sample of certain high abundance RNAs, e.g., ribosomal or globin RNAs. The RNA sequencing methods can be used, alone or in combination with the DNA sequencing methods described herein. In one embodiment, the method includes performing a DNA sequencing step and an RNA sequencing step. The methods can be performed in any order. For example, the method can include confirming by RNA sequencing the expression of an alteration described herein, e.g., confirming expression of mutation or a fusion detected by the DNA sequencing methods of the invention. In other embodiments, the method includes performing an RNA sequencing step, followed by a DNA sequencing step.

In another aspect, the invention features a method comprising building a database of sequencing/alignment artifacts for the targeted subgenomic regions. In embodiment the database can be used to filter out spurious mutation calls and improve specificity. In an embodiment the database is built by sequencing unrelated non-tumor (e.g., FFPE, blood, or bone marrow aspirate) samples or cell-lines and recording non-reference allele events that appear more frequently than expected due to random sequencing error alone in 1 or more of these normal samples. This approach may classify germline variation as artifact, but that is acceptable in method concerned with somatic mutations. This mis-classification of germ-line variation as artifact may be ameliorated if desired by filtering this database for known germ-line variation (removing common variants) and for artifacts that appear in only 1 individual (removing rarer variation).

Methods disclosed herein allow integration of a number of optimized elements including optimized bait-based selection, optimized alignment, and optimized mutation calling, as applied, e.g., to cancer related segments of the genome. Methods described herein provide for NGS-based analysis of tumors that can be optimized on a cancer-by-cancer, gene-by-gene and site-by-site basis. This can be applied e.g., to the genes/sites and tumor types described herein. The methods optimize levels of sensitivity and specificity for mutation detection with a given sequencing technology. Cancer by cancer, gene by gene, and site by site optimization provides very high levels sensitivity/specificity (e.g., >99% for both) that are essential for a clinical product.

Methods described herein provide for clinical and regulatory grade comprehensive analysis and interpretation of genomic aberrations for a comprehensive set of plausibly actionable genes (which may typically range from 50 to 500 genes) using next generation sequencing technologies from routine, real-world samples in order to inform optimal treatment and disease management decisions.

Methods described herein provide one-stop-shopping for oncologists/pathologists to send a tumor sample and receive a comprehensive analysis and description of the genomic and other molecular changes for that tumor, in order to inform optimal treatment and disease management decisions.

Methods described herein provide a robust, real-world clinical oncology diagnostic tool that takes standard available tumor samples and in one test provides a comprehensive genomic and other molecular aberration analysis to provide the oncologist with a comprehensive description of what aberrations may be driving the tumor and could be useful for informing the oncologists treatment decisions.

Methods described herein provide for a comprehensive analysis of a patient's cancer genome, with clinical grade quality. Methods include the most relevant genes and potential alterations and include one or more of the analysis of mutations, copy number, rearrangements, e.g., translocations, expression, and epigenetic markers. The out put of the genetic analysis can be contextualized with descriptive reporting of actionable results. Methods connect the use with an up to date set of relevant scientific and medical knowledge.

Methods described herein provide for increasing both the quality and efficiency of care. This includes applications where a tumor is of a rare or poorly studied type such that there is no standard of care or the patient is refractory to established lines of therapy and a rational basis for selection of further therapy or for clinical trial participation could be useful. E.g., methods allow, at any point of therapy, selection where the oncologist would benefit by having the full "molecular image" and/or "molecular sub-diagnosis" available to inform decision making.

Methods described herein can comprise providing a report, e.g., in electronic, web-based, or paper form, to the patient or to another person or entity, e.g., a caregiver, e.g., a physician, e.g., an oncologist, a hospital, clinic, third-party payor, insurance company or government office. The report can comprise output from the method, e.g., the identification of nucleotide values, the indication of presence or absence of an alteration, mutation, or wildtype sequence, e.g., for subject intervals (e.g., subgenomic intervals, expressed subgenomic intervals, or both) associated with a tumor of the type of the sample. The report can also comprise information on the role of a sequence, e.g., an alteration, mutation, or wildtype sequence, in disease. Such information can include information on prognosis, resistance, or potential or suggested therapeutic options. The report can comprise information on the likely effectiveness of a therapeutic option, the acceptability of a therapeutic option, or the advisability of applying the therapeutic option to a patient, e.g., a patient having a sequence, alteration or mutation identified in the test, and in embodiments, identified in the report. E.g., the report can include information, or a recommendation on, the administration of a drug, e.g., the administration at a preselected dosage or in a preselected treatment regimen, e.g., in combination with other drugs, to the patient. In an embodiment, not all mutations identified in the method are identified in the report. E.g., the report can be limited to mutations in genes having a preselected level of correlation with the occurrence, prognosis, stage, or susceptibility of the cancer to treatment, e.g., with a preselected therapeutic option. Methods featured herein allow for delivery of the report, e.g., to an entity described herein, within 7, 14, or 21 days from receipt of the sample by the entity practicing the method.

Thus, methods featured in the invention allow a quick turn around time, e.g., within 7, 14 or 21 days of receipt of sample.

Methods described herein can also be used to evaluate a histologically normal sample, e.g., samples from surgical margins. If one or more alterations as described herein is detected, the tissue can be re-classified, e.g., as malignant or pre-malignant, and/or the course of treatment can be modified.

In certain aspects, the sequencing methods described herein are useful in non-cancer applications, e.g., in forensic applications (e.g., identification as alternative to, or in addition to, use of dental records), paternity testing, and disease diagnosis and prognosis, e.g., for an infectious disease, an autoimmune disorder, cystic fibrosis, Huntington's Disease, Alzheimer's Disease, among others. For example, identification of genetic alterations by the methods described herein can indicate the presence or risk of an individual for developing a particular disorder.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, drawings, and from the claims.

DETAILED DESCRIPTION

Figure 1A:
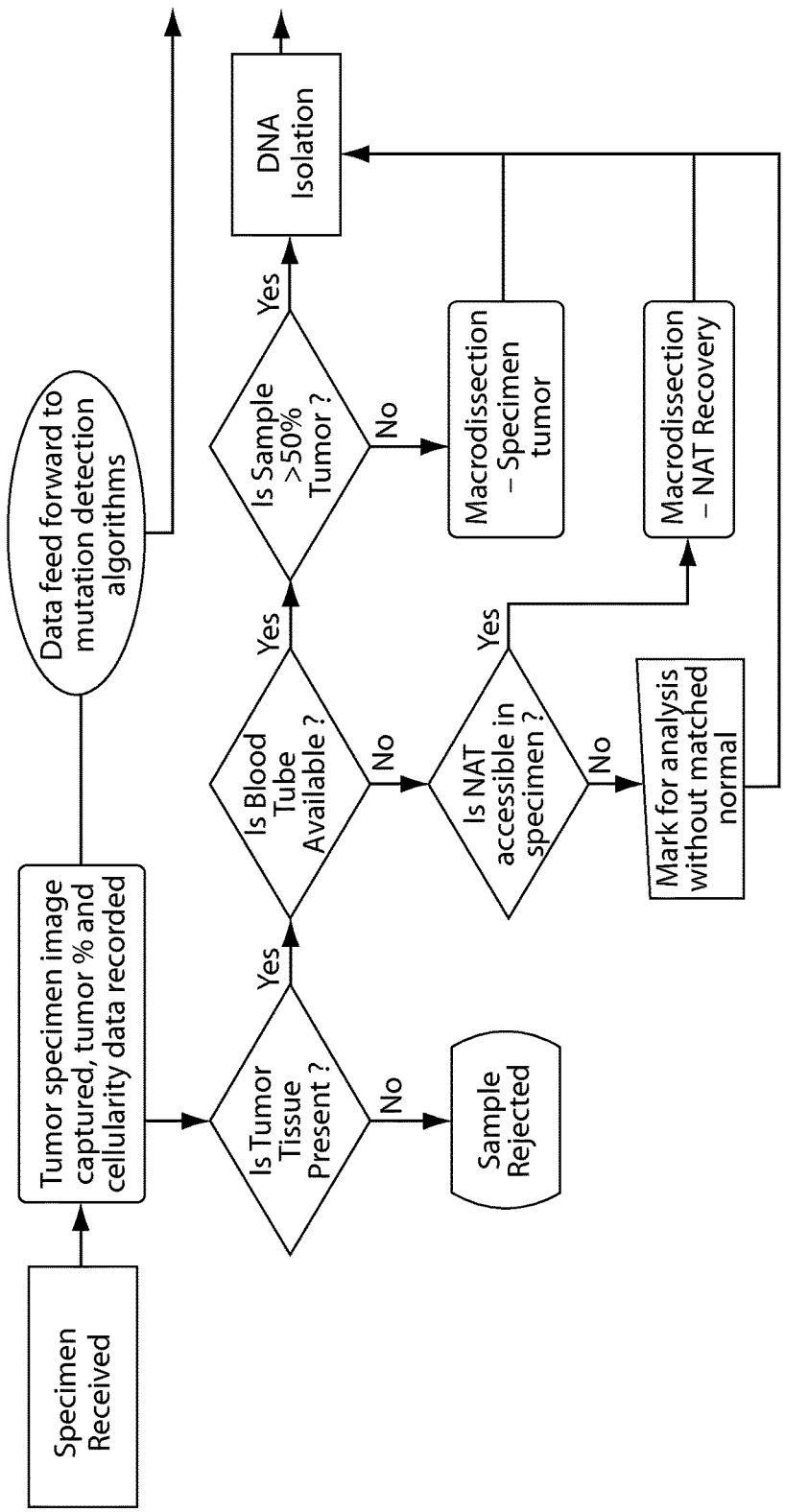
FIGS. 1A-1F show a flowchart depiction of an embodiment of a method for multigene analysis of a tumor sample.
Figure 1B:
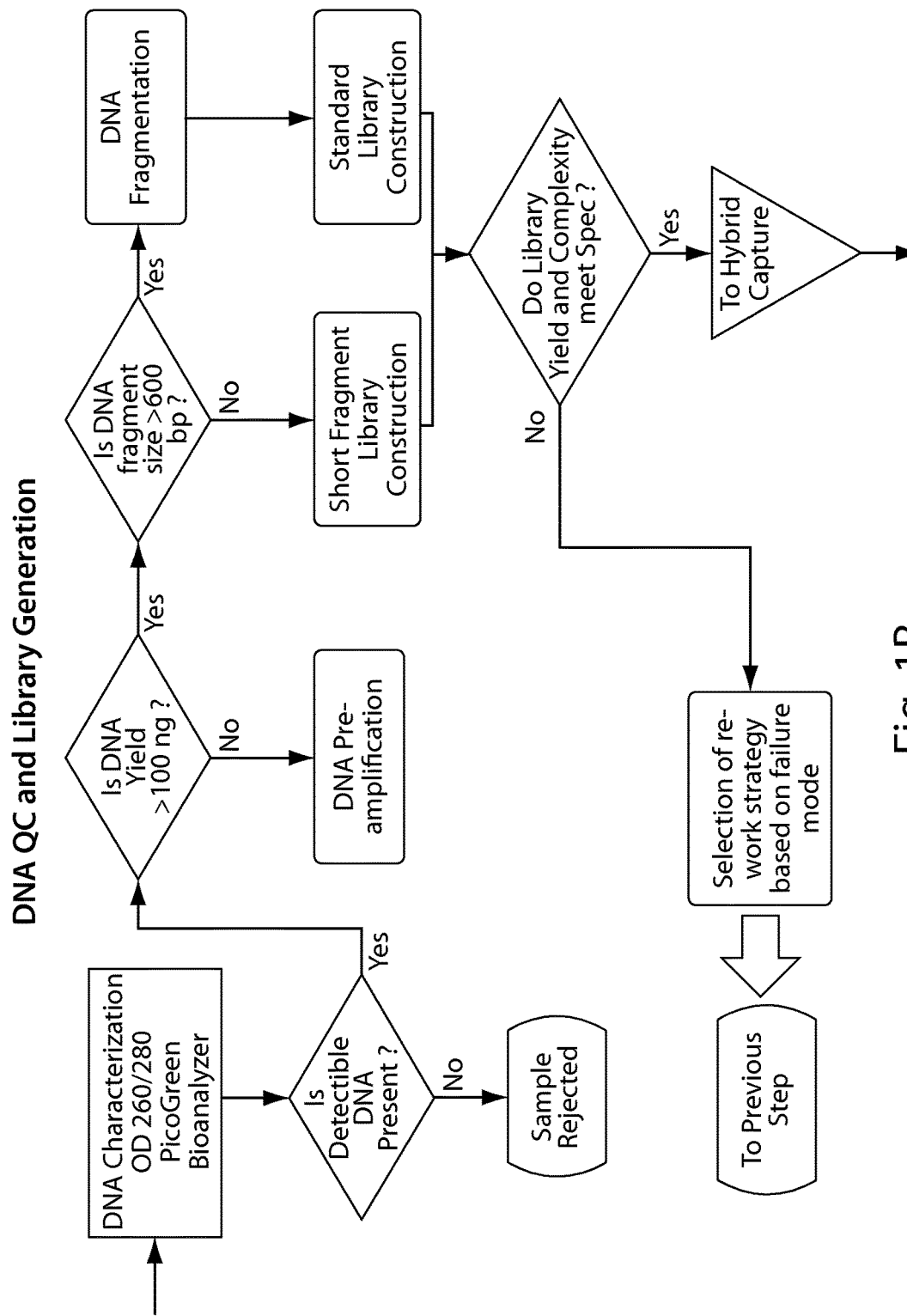
Figure 1C:
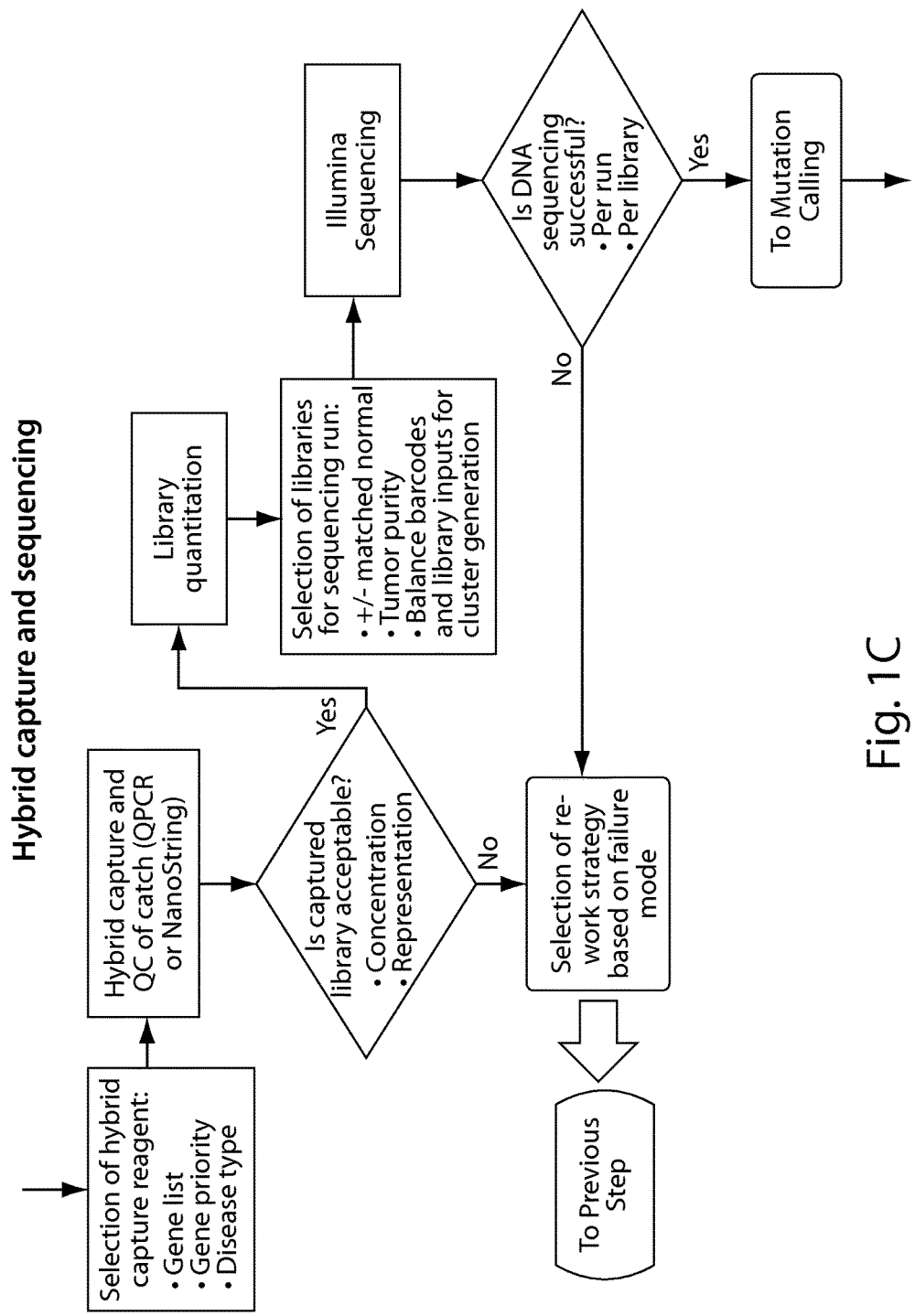
Figure 1D:
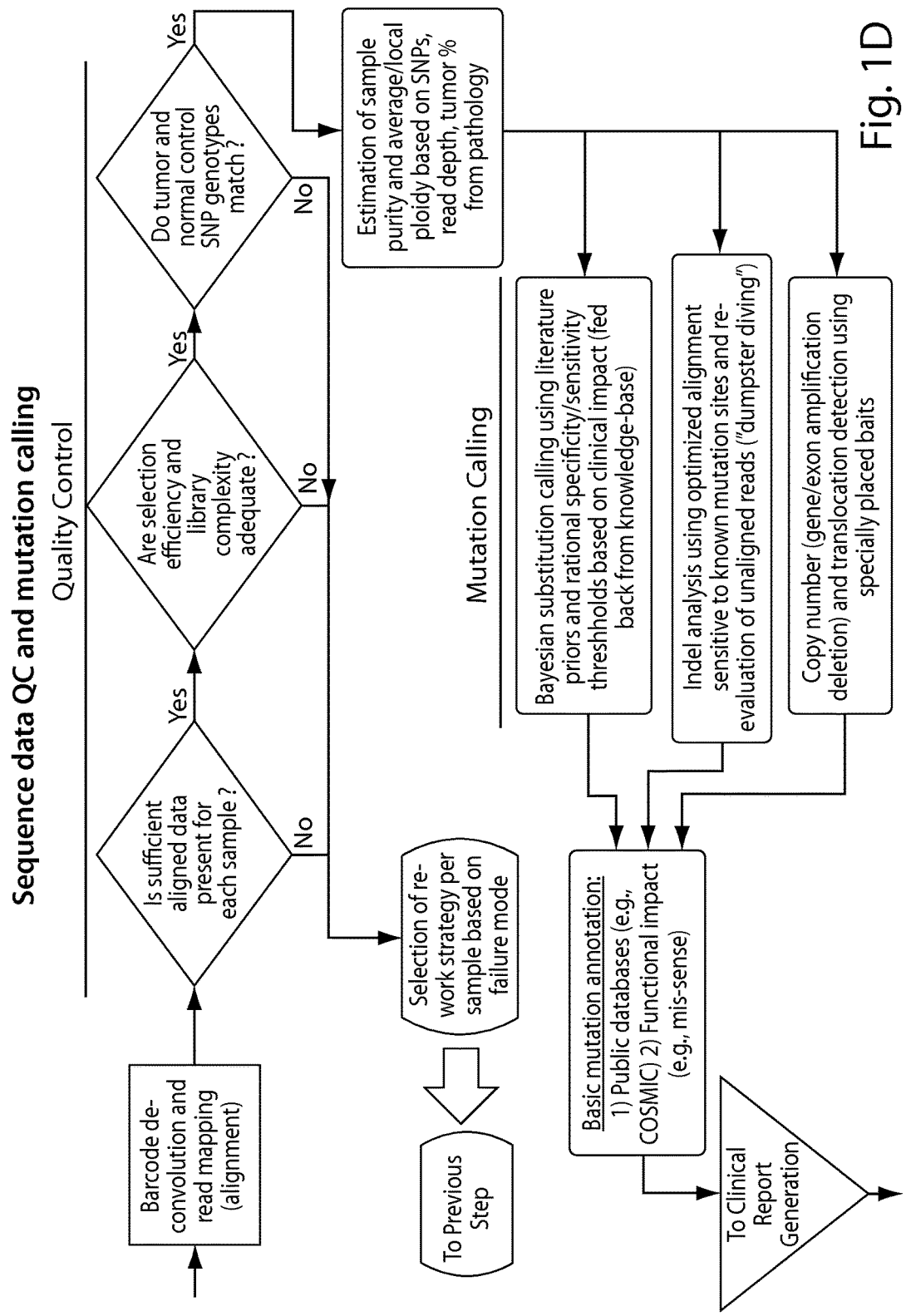
Figure 1E:
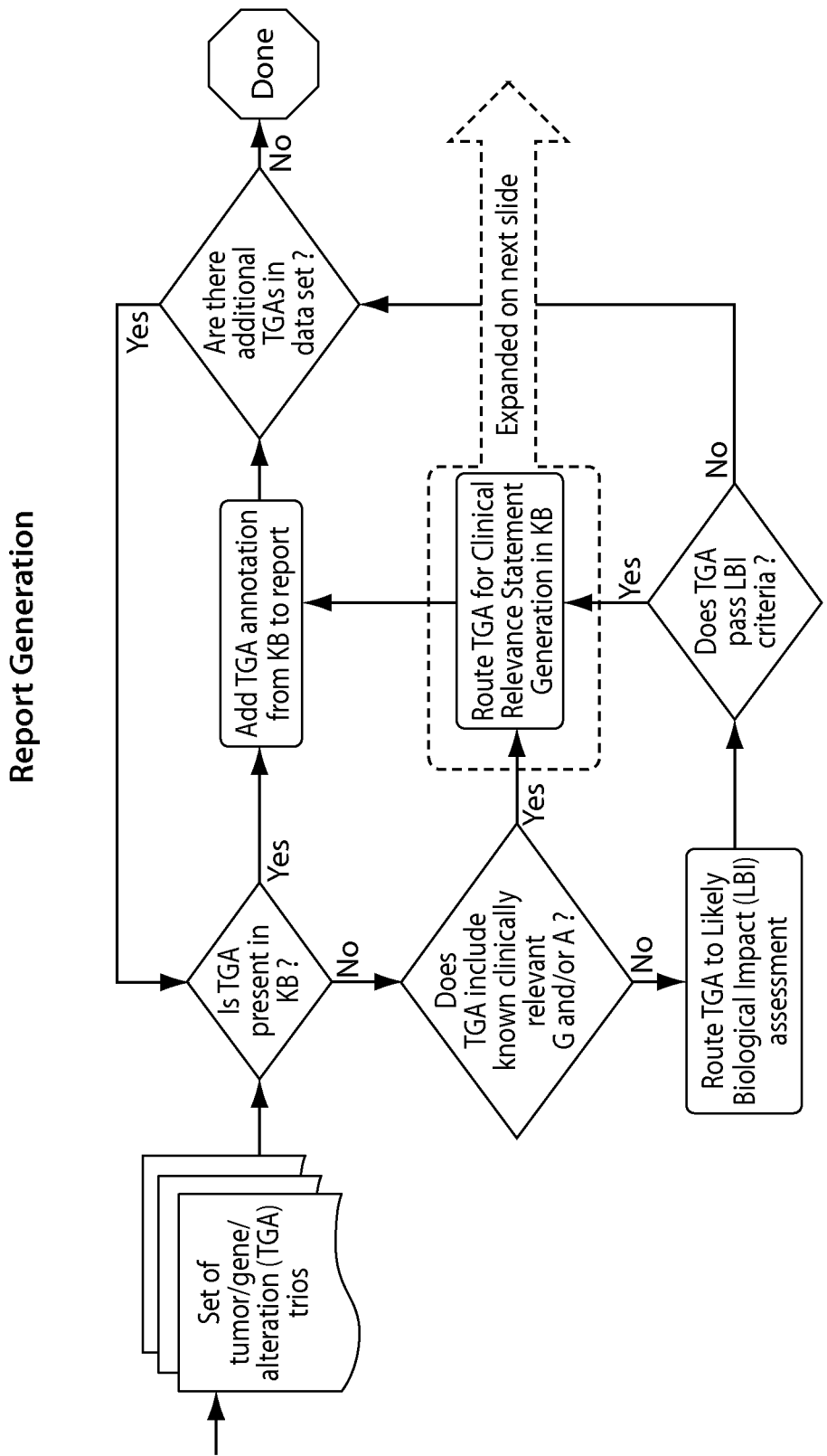
Figure 1F:
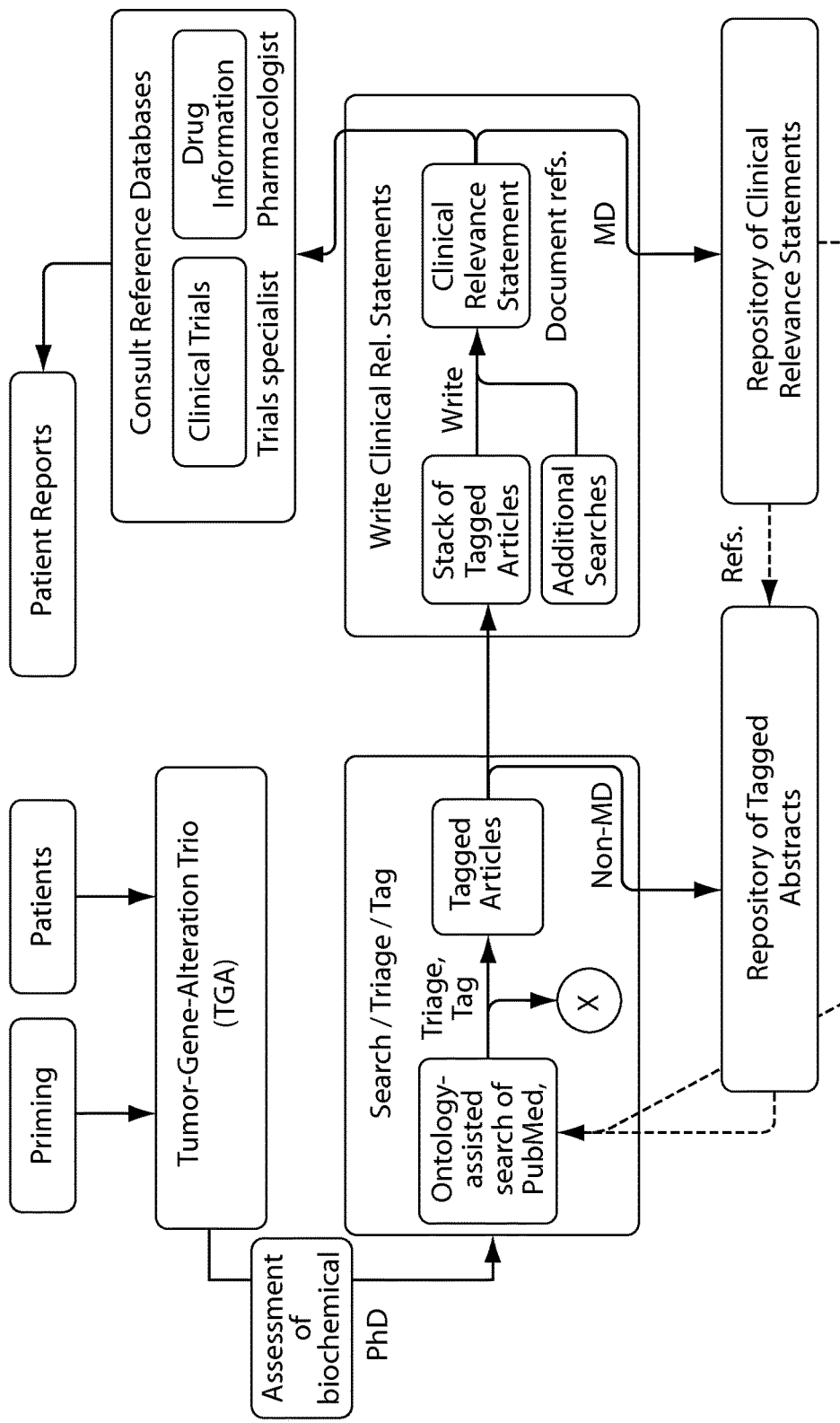

Optimized methods and assays for sequencing large numbers of genes and gene products, e.g., antibodies or immunoglobulin superfamily receptors (e.g., T cell receptors or B cell receptors), from samples, e.g., disease-state tissues or non-disease-state tissues, from one or more subjects by evaluating a selected group of genes and gene products are disclosed. In one embodiment, the methods and assays featured in the invention are used in a multiplex assay format, e.g., assays incorporated multiple signals from a large number of diverse genetic events in a large number of genes. Disclosed herein are methods and assays that are based, at least in part, on a selected group of genes or gene products that are associated (e.g., positively or negatively) with a cancerous phenotype (e.g., one or more of cancer risk, cancer progression, cancer treatment or resistance to treatment). Such pre-selected genes or gene products enable the application of sequencing methods, particularly methods that rely on massively parallel sequencing of a large number of diverse genes, e.g., from tumor or control samples.

Methods disclosed herein provide for clonal analysis of subject intervals, e.g., at one or both of the DNA and RNA levels. E.g., methods disclosed herein allow for providing the relative abundance of an event at a subject interval, e.g., the relative abundance of a particular V segment, or VD, VJ, or DJ junction, e.g., in an immunoglobulin, B-cell receptor, or T-cell receptor. Other methods allow for the evaluation of the levels of diversity, e.g., from somatic hypermutation, at a subject interval. Other methods allow for the analysis of large chromosomal, e.g., whole arm, rearrangements. Other methods, allow for evaluation, e.g., at one or both the DNA or RNA levels, of subject intervals implicated in hematologic malignancies (or premalignancy).

Certain terms are first defined. Additional terms are defined throughout the specification.

As used herein, the articles "a" and "an" refer to one or to more than one (e.g., to at least one) of the grammatical object of the article.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

"Acquire" or "acquiring" as the terms are used herein, refer to obtaining possession of a physical entity, or a value, e.g., a numerical value, by "directly acquiring" or "indirectly acquiring" the physical entity or value. "Directly acquiring" means performing a process (e.g., performing a synthetic or analytical method) to obtain the physical entity or value. "Indirectly acquiring" refers to receiving the physical entity or value from another party or source (e.g., a third party laboratory that directly acquired the physical entity or value). Directly acquiring a physical entity includes performing a process that includes a physical change in a physical substance, e.g., a starting material. Exemplary changes include making a physical entity from two or ore starting materials, shearing or fragmenting a substance, separating or purifying a substance, combining two or more separate entities into a mixture, performing a chemical reaction that includes breaking or forming a covalent or non covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non covalent bond, between a first and a second atom of the analyte; or by changing the structure of a reagent, or a fragment or other derivative thereof, e.g., by breaking or forming a covalent or non covalent bond, between a first and a second atom of the reagent.

"Acquiring a sequence" or "acquiring a read" as the term is used herein, refers to obtaining possession of a nucleotide sequence or amino acid sequence, by "directly acquiring" or "indirectly acquiring" the sequence or read. "Directly acquiring" a sequence or read means performing a process (e.g., performing a synthetic or analytical method) to obtain the sequence, such as performing a sequencing method (e.g., a Next Generation Sequencing (NGS) method). "Indirectly acquiring" a sequence or read refers to receiving information or knowledge of, or receiving, the sequence from another party or source (e.g., a third party laboratory that directly acquired the sequence). The sequence or read acquired need not be a full sequence, e.g., sequencing of at least one nucleotide, or obtaining information or knowledge, that identifies one or more of the alterations disclosed herein as being present in a subject constitutes acquiring a sequence.

Directly acquiring a sequence or read includes performing a process that includes a physical change in a physical substance, e.g., a starting material, such as a tissue or cellular sample, e.g., a biopsy, or an isolated nucleic acid (e.g., DNA or RNA) sample. Exemplary changes include making a physical entity from two or more starting materials, shearing or fragmenting a substance, such as a genomic DNA fragment; separating or purifying a substance (e.g., isolating a nucleic acid sample from a tissue); combining two or more separate entities into a mixture, performing a chemical reaction that includes breaking or forming a covalent or non-covalent bond. Directly acquiring a value includes performing a process that includes a physical change in a sample or another substance as described above.

"Acquiring a sample" as the term is used herein, refers to obtaining possession of a sample, e.g., a tissue sample or nucleic acid sample, by "directly acquiring" or "indirectly acquiring" the sample. "Directly acquiring a sample" means performing a process (e.g., performing a physical method such as a surgery or extraction) to obtain the sample. "Indirectly acquiring a sample" refers to receiving the sample from another party or source (e.g., a third party laboratory that directly acquired the sample). Directly acquiring a sample includes performing a process that includes a physical change in a physical substance, e.g., a starting material, such as a tissue, e.g., a tissue in a human patient or a tissue that has was previously isolated from a patient. Exemplary changes include making a physical entity from a starting material, dissecting or scraping a tissue; separating or purifying a substance (e.g., a sample tissue or a nucleic acid sample); combining two or more separate entities into a mixture; performing a chemical reaction that includes breaking or forming a covalent or non-covalent bond. Directly acquiring a sample includes performing a process that includes a physical change in a sample or another substance, e.g., as described above.

"Alignment selector," as used herein, refers to a parameter that allows or directs the selection of an alignment method, e.g., an alignment algorithm or parameter, that can optimize the sequencing of a preselected subgenomic interval. An alignment selector can be specific to, or selected as a function, e.g., of one or more of the following:

1. The sequence context, e.g., sequence context, of a subgenomic interval (e.g., the preselected nucleotide position to be evaluated) that is associated with a propensity for misalignment of reads for said subgenomic interval. E.g., the existence of a sequence element in or near the subgenomic interval to be evaluated that is repeated elsewhere in the genome can cause misalignment and thereby reduce performance. Performance can be enhanced by selecting an algorithm or an algorithm parameter that minimizes misalignment. In this case the value for the alignment selector can be a function of the sequence context, e.g., the presence or absence of a sequence of preselected length that is repeated at least a preselected number of times in the genome (or in the portion of the genome being analyzed).
2. The tumor type being analyzed. E.g., a specific tumor type can be characterized by increased rate of deletions. Thus, performance can be enhanced by selecting an algorithm or algorithm parameter that is more sensitive to indels. In this case the value for the alignment selector can be a function of the tumor type, e.g., an identifier for the tumor type. In an embodiment the value is the identity of the tumor type, e.g., a hematologic malignancy (or premalignancy).
3. The gene, or type of gene, being analyzed, e.g., a gene, or type of gene, can be analyzed. Oncogenes, by way of example, are often characterized by substitutions or in-frame indels. Thus, performance can be enhanced by selecting an algorithm or algorithm parameter that is particularly sensitive to these variants and specific against others. Tumor suppressors are often characterized by frame-shift indels. Thus, performance can be enhanced by selecting an algorithm or algorithm parameter that is particularly sensitive to these variants. Thus, performance can be enhanced by selecting an algorithm or algorithm parameter matched with the subgenomic interval. In this case the value for the alignment selector can be a function of the gene or gene type, e.g., an identifier for gene or gene type. In an embodiment the value is the identity of the gene.
4. The site (e.g., nucleotide position) being analyzed. In this case the value for the alignment selector can be a function of the site or the type of site, e.g., an identifier for the site or site type. In an embodiment the value is the identity of the site. (E.g., if the gene containing the site is highly homologous with another gene, normal/fast short read alignment algorithms (e.g., BWA) may have difficulty distinguishing between the two genes, potentially necessitating more intensive alignment methods (Smith-Waterman) or even assembly (ARACHNE). Similarly, if the gene sequence contains low-complexity regions (e.g., AAAAAA), more intensive alignment methods may be necessary.
5. The variant, or type of variant, associated with the subgenomic interval being evaluated. E.g., a substitution, insertion, deletion, translocation or other rearrangement. Thus, performance can be enhanced by selecting an algorithm or algorithm parameter that is more sensitive to the specific variant type. In this case the value for the alignment selector can be a function of the type of variant, e.g., an identifier for the type of variant. In an embodiment the value is the identity of the type of variant, e.g., a substitution.
6. The type of sample, a FFPE or other fixed sample. Sample type/quality can affect error (spurious observation of non-reference sequence) rate. Thus, performance can be enhanced by selecting an algorithm or algorithm parameter that accurately models the true error rate in the sample. In this case the value for the alignment selector can be a function of the type of sample, e.g., an identifier for the sample type. In an embodiment, the value is the identity of the sample type, e.g., a fixed sample.

"Alteration" or "altered structure" as used herein, of a gene or gene product (e.g., a marker gene or gene product) refers to the presence of a mutation or mutations within the gene or gene product, e.g., a mutation, which affects amount or activity of the gene or gene product, as compared to the normal or wild-type gene. The alteration can be in amount, structure, and/or activity in a cancer tissue or cancer cell, as compared to its amount, structure, and/or activity, in a normal or healthy tissue or cell (e.g., a control), and is associated with a disease state, such as cancer. For example, an alteration which is associated with cancer, or predictive of responsiveness to anti-cancer therapeutics, can have an altered nucleotide sequence (e.g., a mutation), amino acid sequence, chromosomal translocation, intra-chromosomal inversion, copy number, expression level, protein level, protein activity, or methylation status, in a cancer tissue or cancer cell, as compared to a normal, healthy tissue or cell. Exemplary mutations include, but are not limited to, point mutations (e.g., silent, missense, or nonsense), deletions, insertions, inversions, linking mutations, duplications, translocations, inter- and intra-chromosomal rearrangements. Mutations can be present in the coding or non-coding region of the gene. In certain embodiments, the alteration(s) is detected as a rearrangement, e.g., a genomic rearrangement comprising one or more introns or fragments thereof (e.g., one or more rearrangements in the 5'- and/or 3'-UTR). In certain embodiments, the alterations are associated (or not associated) with a phenotype, e.g., a cancerous phenotype (e.g., one or more of cancer risk, cancer progression, cancer treatment or resistance to cancer treatment). In one embodiment, the alteration is associated with one or more of: a genetic risk factor for cancer, a positive treatment response predictor, a negative treatment response predictor, a positive prognostic factor, a negative prognostic factor, or a diagnostic factor.

"Clonal profile", as that term is used herein, refers to the occurrence, identity, variability, distribution, expression (the occurrence or level of transcribed copies of a subgenomic signature), or abundance, e.g., the relative abundance, of one or more sequences, e.g., an allele or signature, of a subject interval (or of a cell comprising the same). In an embodiment, the clonal profile is a value for the relative abundance for one sequence, allele, or signature, for a subject interval (or of a cell comprising the same) when a plurality of sequences, alleles, or signatures for that subject interval are present in a sample. E.g., in an embodiment, a clonal profile comprises a value for the relative abundance, of one or more of a plurality of VDJ or VJ combinations for a subject interval. In an embodiment, a clonal profile comprises a value for the relative abundance, of a selected V segment, for a subject interval. In an embodiment, a clonal profile comprises a value for the diversity, e.g., as arises from somatic hypermutation, within the sequences of a subject interval. In an embodiment, a clonal profile comprises a value for the occurrence or level of expression of a sequence, allele, or signature, e.g., as evidenced by the occurrence or level of an expressed subgenomic interval comprising the sequence, allele or signature.

"Expressed subgenomic interval", as that term is used herein, refers to the transcribed sequence of a subgenomic interval. In an embodiment, the sequence of the expressed subgenomic interval will differ from the subgenomic interval from which it is transcribed, e.g., as some sequence may not be transcribed.

"Signature", as that term is used herein, refers to a sequence of a subject interval. A signature can be diagnostic of the occurrence of one of a plurality of possibilities at a subject interval, e.g., a signature can be diagnostic of: the occurrence of a selected V segment in a rearranged heavy or light chain variable region gene; the occurrence of a selected VJ junction, e.g., the occurrence of a selected V and a selected J segment in a rearranged heavy chain variable region gene. In an embodiment, a signature comprises a plurality of a specific nucleic acid sequences. Thus, a signature is not limited to a specific nucleic acid sequence, but rather is sufficiently unique that it can distinguish between a first group of sequences or possibilities at a subject interval and a second group of possibilities at a subject interval, e.g., it can distinguish between a first V segment and a second V segment, allowing e.g., evaluation of the usage of various V segments. The term signature comprises the term specific signature, which is a specific nucleic acid sequence. In an embodiment the signature is indicative of, or is the product of, a specific event, e.g., a rearrangement event.

"Subgenomic interval" as that term is used herein, refers to a portion of genomic sequence. In an embodiment, a subgenomic interval can be a single nucleotide position, e.g., a nucleotide position variants of which are associated (positively or negatively) with a tumor phenotype. In an embodiment, a subgenomic interval comprises more than one nucleotide position. Such embodiments include sequences of at least 2, 5, 10, 50, 100, 150, or 250 nucleotide positions in length. Subgenomic intervals can comprise an entire gene, or a preselected portion thereof, e.g., the coding region (or portions thereof), a preselected intron (or portion thereof) or exon (or portion thereof). A subgenomic interval can comprise all or a part of a fragment of a naturally occurring, e.g., genomic, nucleic acid. E.g., a subgenomic interval can correspond to a fragment of genomic DNA which is subjected to a sequencing reaction. In embodiments, a subgenomic interval is continuous sequence from a genomic source. In embodiments, a subgenomic interval includes sequences that are not contiguous in the genome, e.g., it can include junctions formed found at exon-exon junctions in cDNA.

In an embodiment, a subgenomic interval corresponds to a rearranged sequence, e.g., a sequence in a B or T cell that arises as a result of the joining of, a V segment to a D segment, a D segment to a J segment, a V segment to a J segment, or a J segment to a class segment.

In an embodiment, there is no diversity at a subgenomic interval.

In an embodiment, there is diversity at a subgenomic interval, e.g., the subgenomic interval is represented by more than one sequence, e.g., the subgenomic interval that covers a VD sequence can be represented by more than one signature.

In an embodiment, a subgenomic interval comprises or consists of: a single nucleotide position; an intragenic region or an intergenic region; an exon or an intron, or a fragment thereof, typically an exon sequence or a fragment thereof; a coding region or a non-coding region, e.g., a promoter, an enhancer, a 5' untranslated region (5' UTR), or a 3' untranslated region (3' UTR), or a fragment thereof; a cDNA or a fragment thereof; an SNP; a somatic mutation, a germ line mutation or both; an alteration, e.g., a point or a single mutation; a deletion mutation (e.g., an in-frame deletion, an intragenic deletion, a full gene deletion); an insertion mutation (e.g., intragenic insertion); an inversion mutation (e.g., an intra-chromosomal inversion); a linking mutation; a linked insertion mutation; an inverted duplication mutation; a tandem duplication (e.g., an intrachromosomal tandem duplication); a translocation (e.g., a chromosomal translocation, a non-reciprocal translocation); a rearrangement (e.g., a genomic rearrangement (e.g., a rearrangement of one or more introns, or a fragment thereof; a rearranged intron can include a 5'- and/or 3'-UTR); a change in gene copy number; a change in gene expression; a change in RNA levels, or a combination thereof. The "copy number of a gene" refers to the number of DNA sequences in a cell encoding a particular gene product. Generally, for a given gene, a mammal has two copies of each gene. The copy number can be increased, e.g., by gene amplification or duplication, or reduced by deletion.

"Subject interval", as that term is used herein, refers to a subgenomic interval or an expressed subgenomic interval. In an embodiment, a subgenomic interval and an expressed subgenomic interval correspond, meaning that the expressed subgenomic interval comprises sequence expressed from the corresponding subgenomic interval. In an embodiment, a subgenomic interval and an expressed subgenomic interval are non-corresponding, meaning that the expressed subgenomic interval does not comprise sequence expressed from the non-corresponding subgenomic interval, but rather corresponds to a different subgenomic interval. In an embodiment, a subgenomic interval and an expressed subgenomic interval partially correspond, meaning that the expressed subgenomic interval comprises sequence expressed from the corresponding subgenomic interval and sequence expressed from a different corresponding subgenomic interval.

As used herein, the term "library" refers to a collection of members. In one embodiment, the library includes a collection of nucleic acid members, e.g., a collection of whole genomic, subgenomic fragments, cDNA, cDNA fragments, RNA, e.g., mRNA, RNA fragments, or a combination thereof. In one embodiment, a portion or all of the library members comprises an adapter sequence. The adapter sequence can be located at one or both ends. The adapter sequence can be useful, e.g., for a sequencing method (e.g., an NGS method), for amplification, for reverse transcription, or for cloning into a vector.

The library can comprise a collection of members, e.g., a target member (e.g., a tumor member, a reference member, a PGx member, or a combination thereof). The members of the library can be from a single individual. In embodiments, a library can comprise members from more than one subject (e.g., 2, 3, 4, 5, 6, 7, 8, 9, 10, 20, 30 or more subjects), e.g., two or more libraries from different subjects can be combined to from a library comprising members from more than one subject. In one embodiment, the subject is human having, or at risk of having, a cancer or tumor.

"Library-catch" refers to a subset of a library, e.g., a subset enriched for preselected subgenomic intervals, e.g., product captured by hybridization with preselected baits.

"Member" or "library member" or other similar term, as used herein, refers to a nucleic acid molecule, e.g., a DNA, RNA, or a combination thereof, that is the member of a library. Typically, a member is a DNA molecule, e.g., genomic DNA or cDNA. A member can be fragmented, e.g., sheared or enzymatically prepared, genomic DNA. Members comprise sequence from a subject and can also comprise sequence not derived from the subject, e.g., adapters sequence, a primer sequence, or other sequences that allow for identification, e.g., "barcode" sequences.

"Bait," as used herein, is type of hybrid capture reagent. A bait can be a nucleic acid molecule, e.g., a DNA or RNA molecule, which can hybridize to (e.g., be complementary to), and thereby allow capture of a target nucleic acid. In one embodiment, a bait is an RNA molecule (e.g., a naturally-occurring or modified RNA molecule); a DNA molecule (e.g., a naturally-occurring or modified DNA molecule), or a combination thereof. In other embodiments, a bait includes a binding entity, e.g., an affinity tag, that allows capture and separation, e.g., by binding to a binding entity, of a hybrid formed by a bait and a nucleic acid hybridized to the bait. In one embodiment, a bait is suitable for solution phase hybridization. In one embodiment, a bait is a bicyclic nuclei acid (BNA) molecule.

"Bait set," as used herein, refers to one or a plurality of bait molecules.

"Binding entity" means any molecule to which molecular tags can be directly or indirectly attached that is capable of specifically binding to an analyte. The binding entity can be an affinity tag on each bait sequence. In certain embodiments, the binding entity allows for separation of the bait/member hybrids from the hybridization mixture by binding to a partner, such as an avidin molecule, or an antibody that binds to the hapten or an antigen-binding fragment thereof. Exemplary binding entities include, but are not limited to, a biotin molecule, a hapten, an antibody, an antibody binding fragment, a peptide, and a protein.

"Complementary" refers to sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In certain embodiments, the first region comprises a first portion and the second region comprises a second portion, whereby, when the first and second portions are arranged in an antiparallel fashion, at least about 50%, at least about 75%, at least about 90%, or at least about 95% of the nucleotide residues of the first portion are capable of base pairing with nucleotide residues in the second portion. In other embodiments, all nucleotide residues of the first portion are capable of base pairing with nucleotide residues in the second portion.

The term "cancer" or "tumor" is used interchangeably herein. These terms refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell, such as a leukemia cell. These terms include a solid tumor, a soft tissue tumor, or a metastatic lesion. As used herein, the term "cancer" includes premalignant, as well as malignant cancers.

"Likely to" or "increased likelihood," as used herein, refers to an increased probability that an item, object, thing or person will occur. Thus, in one example, a subject that is likely to respond to treatment has an increased probability of responding to treatment relative to a reference subject or group of subjects.

"Unlikely to" refers to a decreased probability that an event, item, object, thing or person will occur with respect to a reference. Thus, a subject that is unlikely to respond to treatment has a decreased probability of responding to treatment relative to a reference subject or group of subjects.

"Control member" refers to a member having sequence from a non-tumor cell.

"Indel alignment sequence selector," as used herein, refers to a parameter that allows or directs the selection of a sequence to which a read is to be aligned with in the case of a preselected indel. Use of such a sequence can optimize the sequencing of a preselected subgenomic interval comprising an indel. The value for an indel alignment sequence selector is a function of a preselected indel, e.g., an identifier for the indel. In an embodiment the value is the identity of the indel.

"Next-generation sequencing or NGS or NG sequencing" as used herein, refers to any sequencing method that determines the nucleotide sequence of either individual nucleic acid molecules (e.g., in single molecule sequencing) or clonally expanded proxies for individual nucleic acid molecules in a high through-putfashion (e.g., greater than $10^3$, $10^4$, $10^5$ or more molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. (2010) *Nature Biotechnology Reviews* 11:31-46, incorporated herein by reference. Next generation sequencing can detect a variant present in less than 5% of the nucleic acids in a sample.

"Nucleotide value" as referred herein, represents the identity of the nucleotide(s) occupying or assigned to a preselected nucleotide position. Typical nucleotide values include: missing (e.g., deleted); additional (e.g., an insertion of one or more nucleotides, the identity of which may or may not be included); or present (occupied); A; T; C; or G. Other values can be, e.g., not Y, wherein Y is A, T, G, or C; A or X, wherein X is one or two of T, G, or C; T or X, wherein X is one or two of A, G, or C; G or X, wherein X is one or two of T, A, or C; C or X, wherein X is one or two of T, G, or A; a pyrimidine nucleotide; or a purine nucleotide. A nucleotide value can be a frequency for 1 or more, e.g., 2, 3, or 4, bases (or other value described herein, e.g., missing or additional) at a nucleotide position. E.g., a nucleotide value can comprise a frequency for A, and a frequency for G, at a nucleotide position.

"Or" is used herein to mean, and is used interchangeably with, the term "and/or", unless context clearly indicates otherwise. The use of the term "and/or" in some places herein does not mean that uses of the term "or" are not interchangeable with the term "and/or" unless the context clearly indicates otherwise.

"Primary control" refers to a non tumor tissue other than NAT tissue in a tumor sample. Blood is a typical primary control.

"Rearrangement alignment sequence selector," as used herein, refers to a parameter that allows or directs the selection of a sequence to which a read is to be aligned with in the case of a preselected rearrangement. Use of such a sequence can optimize the sequencing of a preselected subgenomic interval comprising a rearrangement. The value for a rearrangement alignment sequence selector is a function of a preselected rearrangement, e.g., an identifier for the rearrangement. In an embodiment the value is the identity of the rearrangement. An "indel alignment sequence selector" (also defined elsewhere herein) is an example of a rearrangement alignment sequence selector.

"Sample," "tissue sample," "patient sample," "patient cell or tissue sample" or "specimen" each refers to a collection of similar cells obtained from a tissue, or circulating cells, of a subject or patient. The source of the tissue sample can be solid tissue as from a fresh, frozen and/or preserved organ, tissue sample, biopsy, or aspirate; blood or any blood constituents; bodily fluids such as cerebral spinal fluid, amniotic fluid, peritoneal fluid or interstitial fluid; or cells from any time in gestation or development of the subject. The tissue sample can contain compounds that are not naturally intermixed with the tissue in nature such as preservatives, anticoagulants, buffers, fixatives, nutrients, antibiotics or the like. In one embodiment, the sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample. In another embodiment, the sample is a blood sample. In yet another embodiment, the sample is a bone marrow aspirate sample.

In an embodiment, the sample is a cell associated with a tumor, e.g., a tumor cell or a tumor-infiltrating lymphocyte (TIL). In one embodiment, the sample is a tumor sample, e.g., includes one or more premalignant or malignant cells. In an embodiment, the sample is acquired from a hematologic malignancy (or premalignancy), e.g., a hematologic malignancy (or premalignancy) described herein. In certain embodiments, the sample, e.g., the tumor sample, is acquired from a solid tumor, a soft tissue tumor or a metastatic lesion. In other embodiments, the sample, e.g., the tumor sample, includes tissue or cells from a surgical margin. In another embodiment, the sample, e.g., tumor sample, includes one or more circulating tumor cells (CTC) (e.g., a CTC acquired from a blood sample). In an embodiment, the sample is a cell not associated with a tumor, e.g., a non-tumor cell or a peripheral blood lymphocyte.

"Sensitivity," as used herein, is a measure of the ability of a method to detect a preselected sequence variant in a heterogeneous population of sequences. A method has a sensitivity of S % for variants of F % if, given a sample in which the preselected sequence variant is present as at least F % of the sequences in the sample, the method can detect the preselected sequence at a preselected confidence of C %, S % of the time. By way of example, a method has a sensitivity of 90% for variants of 5% if, given a sample in which the preselected variant sequence is present as at least 5% of the sequences in the sample, the method can detect the preselected sequence at a preselected confidence of 99%, 9 out of 10 times (F=5%; C=99%; S=90%). Exemplary sensitivities include those of S=90%, 95%, 99% for sequence variants at F=1%, 5%, 10%, 20%, 50%, 100% at confidence levels of C=90%, 95%, 99%, and 99.9%.

"Specificity," as used herein, is a measure of the ability of a method to distinguish a truly occurring preselected sequence variant from sequencing artifacts or other closely related sequences. It is the ability to avoid false positive detections. False positive detections can arise from errors introduced into the sequence of interest during sample preparation, sequencing error, or inadvertent sequencing of closely related sequences like pseudo-genes or members of a gene family. A method has a specificity of X % if, when applied to a sample set of $N_{Total}$ sequences, in which $X_{True}$ sequences are truly variant and $X_{Not\ true}$ are not truly variant, the method selects at least X % of the not truly variant as not variant. E.g., a method has a specificity of 90% if, when applied to a sample set of 1,000 sequences, in which 500 sequences are truly variant and 500 are not truly variant, the method selects 90% of the 500 not truly variant sequences as not variant. Exemplary specificities include 90, 95, 98, and 99%.

A "tumor nucleic acid sample" as used herein, refers to nucleic acid molecules from a tumor or cancer sample. Typically, it is DNA, e.g., genomic DNA, or cDNA derived from RNA, from a tumor or cancer sample. In certain embodiments, the tumor nucleic acid sample is purified or isolated (e.g., it is removed from its natural state).

A "control" or "reference" "nucleic acid sample" as used herein, refers to nucleic acid molecules from a control or reference sample. Typically, it is DNA, e.g., genomic DNA, or cDNA derived from RNA, not containing the alteration or variation in the gene or gene product. In certain embodiments, the reference or control nucleic acid sample is a wild type or a non-mutated sequence. In certain embodiments, the reference nucleic acid sample is purified or isolated (e.g., it is removed from its natural state). In other embodiments, the reference nucleic acid sample is from a non-tumor sample, e.g., a blood control, a normal adjacent tissue (NAT), or any other non-cancerous sample from the same or a different subject.

"Sequencing" a nucleic acid molecule requires determining the identity of at least 1 nucleotide in the molecule (e.g., a DNA molecule, an RNA molecule, or a cDNA molecule derived from an RNA molecule). In embodiments the identity of less than all of the nucleotides in a molecule are determined. In other embodiments, the identity of a majority or all of the nucleotides in the molecule is determined.

"Threshold value," as used herein, is a value that is a function of the number of reads required to be present to assign a nucleotide value to a subject interval (e.g., a subgenomic interval or an expressed subgenomic interval). E.g., it is a function of the number of reads having a specific nucleotide value, e.g., A, at a nucleotide position, required to assign that nucleotide value to that nucleotide position in the subgenomic interval. The threshold value can, e.g., be expressed as (or as a function of) a number of reads, e.g., an integer, or as a proportion of reads having the preselected value. By way of example, if the threshold value is X, and X+1 reads having the nucleotide value of "A" are present, then the value of "A" is assigned to the preselected position in the subject interval (e.g., subgenomic interval or expressed subgenomic interval). The threshold value can also be expressed as a function of a mutation or variant expectation, mutation frequency, or of Bayesian prior. In an embodiment, a preselected mutation frequency would require a preselected number or proportion of reads having a nucleotide value, e.g., A or G, at a preselected position, to call that that nucleotide value. In embodiments the threshold value can be a function of mutation expectation, e.g., mutation frequency, and tumor type. E.g., a preselected variant at a preselected nucleotide position could have a first threshold value if the patient has a first tumor type and a second threshold value if the patient has a second tumor type.

As used herein, "target member" refers to a nucleic acid molecule that one desires to isolate from the nucleic acid library. In one embodiment, the target members can be a tumor member, a reference member, a control member, or a PGx member as described herein.

"Tumor member," or other similar term (e.g., a "tumor or cancer-associated member"), as used herein refers to a member having sequence from a tumor cell. In one embodiment, the tumor member includes a subject interval (e.g., a subgenomic interval or an expressed subgenomic interval) having a sequence (e.g., a nucleotide sequence) that has an alteration (e.g., a mutation) associated with a cancerous phenotype. In other embodiments, the tumor member includes a subject interval (e.g., a subgenomic interval or an expressed subgenomic interval) having a wild type sequence (e.g., a wild type nucleotide sequence). For example, a subject interval (e.g., a subgenomic interval or an expressed subgenomic interval) from a heterozygous or homozygous wild type allele present in a cancer cell. A tumor member can include a reference member or a PGx member.

"Reference member," or other similar term (e.g., a "control member"), as used herein, refers to a member that comprises a subject interval (e.g., a subgenomic interval or an expressed subgenomic interval) having a sequence (e.g., a nucleotide sequence) that is not associated with the cancerous phenotype. In one embodiment, the reference member includes a wild-type or a non-mutated nucleotide sequence of a gene or gene product that when mutated is associated with the cancerous phenotype. The reference member can be present in a cancer cell or non-cancer cell.

"PGx member" or other similar term, as used herein, refers to a member that comprises a subject interval (e.g., a subgenomic interval or an expressed subgenomic interval) that is associated with the pharmacogenetic or pharmacogenomic profile of a gene. In one embodiment, the PGx member includes an SNP (e.g., an SNP as described herein). In other embodiments, the PGx member includes a subject interval (e.g., a subgenomic interval or an expressed subgenomic interval) according to Tables 1-4.

"Variant," as used herein, refers to a structure that can be present at a subgenomic interval that can have more than one structure, e.g., an allele at a polymorphic locus.

Headings, e.g., (a), (b), (i) etc, are presented merely for ease of reading the specification and claims. The use of headings in the specification or claims does not require the steps or elements be performed in alphabetical or numerical order or the order in which they are presented.

Selection of Gene or Gene Products

The selected genes or gene products (also referred to herein as the "target genes or gene products") can include subject intervals (e.g., subgenomic intervals, expressed subgenomic intervals, or both) comprising intragenic regions or intergenic regions. For example, the subject intervals (e.g., subgenomic interval or expressed subgenomic interval) can include an exon or an intron, or a fragment thereof, typically an exon sequence or a fragment thereof. The subject interval (e.g., subgenomic interval or expressed subgenomic interval) can include a coding region or a non-coding region, e.g., a promoter, an enhancer, a 5' untranslated region (5' UTR), or a 3' untranslated region (3' UTR), or a fragment thereof. In other embodiments, the subject interval includes a cDNA or a fragment thereof. In other embodiments, the subject interval includes an SNP, e.g., as described herein.

In other embodiments, the subject intervals (e.g., subgenomic intervals, expressed subgenomic intervals, or both) include substantially all exons in a genome, e.g., one or more of the subject intervals (e.g., subgenomic intervals, expressed subgenomic intervals, or both) as described herein (e.g., exons from selected genes or gene products of interest (e.g., genes or gene products associated with a cancerous phenotype as described herein)). In one embodiment, the subject interval (e.g., subgenomic interval or expressed subgenomic interval) includes a somatic mutation, a germ line mutation or both. In one embodiment, the subject interval (e.g., subgenomic interval or expressed subgenomic interval) includes an alteration, e.g., a point or a single mutation, a deletion mutation (e.g., an in-frame deletion, an intragenic deletion, a full gene deletion), an insertion mutation (e.g., intragenic insertion), an inversion mutation (e.g., an intra-chromosomal inversion), a linking mutation, a linked insertion mutation, an inverted duplication mutation, a tandem duplication (e.g., an intrachromosomal tandem duplication), a translocation (e.g., a chromosomal translocation, a non-reciprocal translocation), a rearrangement, a change in gene copy number, or a combination thereof. In certain embodiments, the subject interval (e.g., subgenomic interval or expressed subgenomic interval) constitutes less than 5, 1, 0.5, 0.1%, 0.01%, 0.001% of the coding region of the genome of the tumor cells in a sample. In other embodiments, the subject intervals (e.g., subgenomic intervals, expressed subgenomic intervals, or both) are not involved in a disease, e.g., are not associated with a cancerous phenotype as described herein.

In one embodiment, the target gene or gene product is a biomarker. As used herein, a "biomarker" or "marker" is a gene, mRNA, or protein which can be altered, wherein said alteration is associated with cancer. The alteration can be in amount, structure, and/or activity in a cancer tissue or cancer cell, as compared to its amount, structure, and/or activity, in a normal or healthy tissue or cell (e.g., a control), and is associated with a disease state, such as cancer. For example, a marker associated with cancer, or predictive of responsiveness to anti-cancer therapeutics, can have an altered nucleotide sequence, amino acid sequence, chromosomal translocation, intra-chromosomal inversion, copy number, expression level, protein level, protein activity, or methylation status, in a cancer tissue or cancer cell as compared to a normal, healthy tissue or cell. Furthermore, a "marker" includes a molecule whose structure is altered, e.g., mutated (contains an mutation), e.g., differs from the wild type sequence at the nucleotide or amino acid level, e.g., by substitution, deletion, or insertion, when present in a tissue or cell associated with a disease state, such as cancer.

In one embodiment, the target gene or gene product includes a single-nucleotide polymorphism (SNP). In another embodiment, the gene or gene product has a small deletion, e.g., a small intragenic deletion (e.g., an in-frame or frame-shift deletion). In yet another embodiment, the target sequence results from the deletion of an entire gene. In still another embodiment, the target sequence has a small insertion, e.g., a small intragenic insertion. In one embodiment, the target sequence results from an inversion, e.g., an intrachromosal inversion. In another embodiment, the target sequence results from an interchromosal translocation. In yet another embodiment, the target sequence has a tandem duplication. In one embodiment, the target sequence has an undesirable feature (e.g., high GC content or repeat element). In another embodiment, the target sequence has a portion of nucleotide sequence that cannot itself be successfully targeted, e.g., because of its repetitive nature. In one embodiment, the target sequence results from alternative splicing. In another embodiment, the target sequence is chosen from a gene or gene product, or a fragment thereof according to Tables 1-4.

In an embodiment, the target gene or gene product, or a fragment thereof, is an antibody gene or gene product, an immunoglobulin superfamily receptor (e.g., B-cell receptor (BCR) or T-cell receptor (TCR)) gene or gene product, or a fragment thereof.

Human antibody molecules (and B cell receptors) are composed of heavy and light chains with both constant (C) and variable (V) regions that are encoded by genes on at least the following three loci.
1. Immunoglobulin heavy locus (IGH@) on chromosome 14, containing gene segments for the immunoglobulin heavy chain;
2. Immunoglobulin kappa (κ) locus (IGK@) on chromosome 2, containing gene segments for the immunoglobulin light chain;
3. Immunoglobulin lambda (λ) locus (IGL@) on chromosome 22, containing gene segments for the immunoglobulin light chain.

Each heavy chain and light chain gene contains multiple copies of three different types of gene segments for the variable regions of the antibody proteins. For example, the immunoglobulin heavy chain region can contain one of five different classes γ, δ, α, μ and ε, 44 Variable (V) gene segments, 27 Diversity (D) gene segments, and 6 Joining (J) gene segments. The light chains can also possess numerous V and J gene segments, but do not have D gene segments. The lambda light chain has 7 possible C regions and the kappa light chain has 1.

Immunoglobulin heavy locus (IGH@) is a region on human chromosome 14 that contains genes for the heavy chains of human antibodies (or immunoglobulins). For example, the IGH locus includes IGHV (variable), IGHD (diversity), IGHJ (joining), and IGHC (constant) genes. Exemplary genes encoding the immunoglobulin heavy chains include, but are not limited to IGHV1-2, IGHV1-3, IGHV1-8, IGHV1-12, IGHV1-14, IGHV1-17, IGHV1-18, IGHV1-24, IGHV1-45, IGHV1-46, IGHV1-58, IGHV1-67, IGHV1-68, IGHV1-69, IGHV1-38-4, IGHV1-69-2, IGHV2-5, IGHV2-10, IGHV2-26, IGHV2-70, IGHV3-6, IGHV3-7, IGHV3-9, IGHV3-11, IGHV3-13, IGHV3-15, IGHV3-16, IGHV3-19, IGHV3-20, IGHV3-21, IGHV3-22, IGHV3-23, IGHV3-25, IGHV3-29, IGHV3-30, IGHV3-30-2, IGHV3-30-3, IGHV3-30-5, IGHV3-32, IGHV3-33, IGHV3-33-2, IGHV3-35, IGHV3-36, IGHV3-37, IGHV3-38, IGHV3-41, IGHV3-42, IGHV3-43, IGHV3-47, IGHV3-48, IGHV3-49, IGHV3-50, IGHV3-52, IGHV3-53, IGHV3-54, IGHV3-57, IGHV3-60, IGHV3-62, IGHV3-63, IGHV3-64, IGHV3-65, IGHV3-66, IGHV3-71, IGHV3-72, IGHV3-73, IGHV3-74, IGHV3-75, IGHV3-76, IGHV3-79, IGHV3-38-3, IGHV3-69-1, IGHV4-4, IGHV4-28, IGHV4-30-1, IGHV4-30-2, IGHV4-30-4, IGHV4-31, IGHV4-34, IGHV4-39, IGHV4-55, IGHV4-59, IGHV4-61, IGHV4-80, IGHV4-38-2, IGHV5-51, IGHV5-78, IGHV5-10-1, IGHV6-1, IGHV7-4-1, IGHV7-27, IGHV7-34-1, IGHV7-40, IGHV7-56, IGHV7-81, IGHVII-1-1, IGHVII-15-1, IGHVII-20-1, IGHVII-22-1, IGHVII-26-2, IGHVII-28-1, IGHVII-30-1, IGHVII-31-1, IGHVII-33-1, IGHVII-40-1, IGHVII-43-1, IGHVII-44-2, IGHVII-46-1, IGHVII-49-1, IGHVII-51-2, IGHVII-53-1, IGHVII-60-1, IGHVII-62-1, IGHVII-65-1, IGHVII-67-1, IGHVII-74-1, IGHVII-78-1, IGHVIII-2-1, IGHVIII-5-1, IGHVIII-5-2, IGHVIII-11-1, IGHVIII-13-1, IGHVIII-16-1, IGHVIII-22-2, IGHVIII-25-1, IGHVIII-26-1, IGHVIII-38-1, IGHVIII-44, IGHVIII-47-1, IGHVIII-51-1, IGHVIII-67-2, IGHVIII-67-3, IGHVIII-67-4, IGHVIII-76-1, IGHVIII-82, IGHVIV-44-1, IGHD1-1, IGHD1-7, IGHD1-14, IGHD1-20, IGHD1-26, IGHD2-2, IGHD2-8, IGHD2-15, IGHD2-21, IGHD3-3, IGHD3-9, IGHD3-10, IGHD3-16, IGHD3-22, IGHD4-4, IGHD4-11, IGHD4-17, IGHD4-23, IGHD5-5, IGHD5-12, IGHD5-18, IGHD5-24, IGHD6-6, IGHD6-13, IGHD6-19, IGHD6-25, IGHD7-27, IGHJ1, IGHJ1P, IGHJ2, IGHJ2P, IGHJ3, IGHJ3P, IGHJ4, IGHJ5, IGHJ6, IGHA1, IGHA2, IGHG1, IGHG2, IGHG3, IGHG4, IGHGP, IGHD, IGHE, IGHEP1, IGHM, and IGHV1-69D.

Immunoglobulin kappa locus (IGK@) is a region on human chromosome 2 that contains genes for the kappa (κ) light chains of antibodies (or immunoglobulins). For example, the IGK locus includes IGKV (variable), IGKJ (joining), and IGKC (constant) genes. Exemplary genes encoding the immunoglobulin kappa light chains include, but are not limited to, IGKV1-5, IGKV1-6, IGKV1-8, IGKV1-9, IGKV1-12, IGKV1-13, IGKV1-16, IGKV1-17, IGKV1-22, IGKV1-27, IGKV1-32, IGKV1-33, IGKV1-35, IGKV1-37, IGKV1-39, IGKV1D-8, IGKV1D-12, IGKV1D-13, IGKV1D-16, IGKV1D-17, IGKV1D-22, IGKV1D-27, IGKV1D-32, IGKV1D-33, IGKV1D-35, IGKV1D-37, IGKV1D-39, IGKV1D-42, IGKV1D-43, IGKV2-4, IGKV2-10, IGKV2-14, IGKV2-18, IGKV2-19, IGKV2-23, IGKV2-24, IGKV2-26, IGKV2-28, IGKV2-29, IGKV2-30, IGKV2-36, IGKV2-38, IGKV2-40, IGKV2D-10, IGKV2D-14, IGKV2D-18, IGKV2D-19, IGKV2D-23, IGKV2D-24, IGKV2D-26, IGKV2D-28, IGKV2D-29, IGKV2D-30, IGKV2D-36, IGKV2D-38, IGKV2D-40, IGKV3-7, IGKV3-11, IGKV3-15, IGKV3-20, IGKV3-25, IGKV3-31, IGKV3-34, IGKV3D-7, IGKV3D-11, IGKV3D-15, IGKV3D-20, IGKV3D-25, IGKV3D-31, IGKV3D-34, IGKV4-1, IGKV5-2, IGKV6-21, IGKV6D-21, IGKV6D-41, IGKV7-3, IGKJ1, IGKJ2, IGKJ3, IGKJ4, IGKJ5, and IGKC.

Immunoglobulin lambda locus (IGL@) is a region on human chromosome 22 that contains genes for the lambda light chains of antibody (or immunoglobulins). For example, the IGL locus includes IGLV (variable), IGLJ (joining), and IGLC (constant) genes. Exemplary genes encoding the immunoglobulin lambda light chains include, but are not limited to, IGLV1-36, IGLV1-40, IGLV1-41, IGLV1-44, IGLV1-47, IGLV1-50, IGLV1-51, IGLV1-62, IGLV2-5, IGLV2-8, IGLV2-11, IGLV2-14, IGLV2-18, IGLV2-23, IGLV2-28, IGLV2-33, IGLV2-34, IGLV3-1, IGLV3-2, IGLV3-4, IGLV3-6, IGLV3-7, IGLV3-9, IGLV3-10, IGLV3-12, IGLV3-13, IGLV3-15, IGLV3-16, IGLV3-17, IGLV3-19, IGLV3-21, IGLV3-22, IGLV3-24, IGLV3-25, IGLV3-26, IGLV3-27, IGLV3-29, IGLV3-30, IGLV3-31, IGLV3-32, IGLV4-3, IGLV4-60, IGLV4-69, IGLV5-37, IGLV5-39, IGLV5-45, IGLV5-48, IGLV5-52, IGLV6-57, IGLV7-35, IGLV7-43, IGLV7-46, IGLV8-61, IGLV9-49, IGLV10-54, IGLV10-67, IGLV11-55, IGLVI-20, IGLVI-38, IGLVI-42, IGLVI-56, IGLVI-63, IGLVI-68, IGLVI-70, IGLVIV-53, IGLVIV-59, IGLVIV-64, IGLVIV-65, IGLVIV-66-1, IGLVV-58, IGLVV-66, IGLVVI-22-1, IGLVVI-25-1, IGLVVII-41-1, IGLJ1, IGLJ2, IGLJ3, IGLJ4, IGLJ5, IGLJ6, IGLJ7, IGLC1, IGLC2, IGLC3, IGLC4, IGLC5, IGLC6, and IGLC7.

The B-cell receptor (BCR) is composed of two parts: i) A membrane-bound immunoglobulin molecule of one isotype (e.g., IgD or IgM). With the exception of the presence of an integral membrane domain, these can be identical to their secreted forms. ii) Signal transduction moiety: A heterodimer called Ig-α/Ig-β (CD79), bound together by disulfide bridges. Each member of the dimer spans the plasma membrane and has a cytoplasmic tail bearing an immunoreceptor tyrosine-based activation motif (ITAM).

The T-cell receptor (TCR) is composed of two different protein chains (i.e., a heterodimer). In 95% of T cells, this consists of an alpha (α) and beta (β) chain, whereas in 5% of T cells this consists of gamma and delta (γ/δ) chains. This ratio can change during ontogeny and in diseased states. The T cell receptor genes are similar to immunoglobulin genes in that they too contain multiple V, D and J gene segments in their beta and delta chains (and V and J gene segments in their alpha and gamma chains) that are rearranged during the development of the lymphocyte to provide that cell with a unique antigen receptor.

T-cell receptor alpha locus (TRA) is a region on human chromosome 14 that contains genes for the TCR alpha chains. For example, the TRA locus includes, e.g., TRAY (variable), TRAJ (joining), and TRAC (constant) genes. Exemplary genes encoding the T-cell receptor alpha chains include, but are not limited to, TRAV1-1, TRAV1-2, TRAV2, TRAV3, TRAV4, TRAV5, TRAV6, TRAV7, TRAV8-1, TRAV8-2, TRAV8-3, TRAV8-4, TRAV8-5, TRAV8-6, TRAV8-7, TRAV9-1, TRAV9-2, TRAV10, TRAV11, TRAV12-1, TRAV12-2, TRAV12-3, TRAV13-1, TRAV13-2, TRAV14DV4, TRAV15, TRAV16, TRAV17, TRAV18, TRAV19, TRAV20, TRAV21, TRAV22, TRAV23DV6, TRAV24, TRAV25, TRAV26-1, TRAV26-2, TRAV27, TRAV28, TRAV29DV5, TRAV30, TRAV31, TRAV32, TRAV33, TRAV34, TRAV35, TRAV36DV7, TRAV37, TRAV38-1, TRAV38-2DV8, TRAV39, TRAV40, TRAV41, TRAJ1, TRAJ2, TRAJ3, TRAJ4, TRAJ5, TRAJ6, TRAJ7, TRAJ8, TRAJ9, TRAJ10, TRAJ11, TRAJ12, TRAJ13, TRAJ14, TRAJ15, TRAJ16, TRAJ17, TRAJ18, TRAJ19, TRAJ20, TRAJ21, TRAJ22, TRAJ23, TRAJ24, TRAJ25, TRAJ26, TRAJ27, TRAJ28, TRAJ29, TRAJ30, TRAJ31, TRAJ32, TRAJ33, TRAJ34, TRAJ35, TRAJ36, TRAJ37, TRAJ38, TRAJ39, TRAJ40, TRAJ41, TRAJ42, TRAJ43, TRAJ44, TRAJ45, TRAJ46, TRAJ47, TRAJ48, TRAJ49, TRAJ50, TRAJ51, TRAJ52, TRAJ53, TRAJ54, TRAJ55, TRAJ56, TRAJ57, TRAJ58, TRAJ59, TRAJ60, TRAJ61, and TRAC.

T-cell receptor beta locus (TRB) is a region on human chromosome 7 that contains genes for the TCR beta chains. For example, the TRB locus includes, e.g., TRBV (variable), TRBD (diversity), TRBJ (joining), and TRBC (constant) genes. Exemplary genes encoding the T-cell receptor beta chains include, but are not limited to, TRBV1, TRBV2, TRBV3-1, TRBV3-2, TRBV4-1, TRBV4-2, TRBV4-3, TRBV5-1, TRBV5-2, TRBV5-3, TRBV5-4, TRBV5-5, TRBV5-6, TRBV5-7, TRBV6-2, TRBV6-3, TRBV6-4, TRBV6-5, TRBV6-6, TRBV6-7, TRBV6-8, TRBV6-9, TRBV7-1, TRBV7-2, TRBV7-3, TRBV7-4, TRBV7-5, TRBV7-6, TRBV7-7, TRBV7-8, TRBV7-9, TRBV8-1, TRBV8-2, TRBV9, TRBV10-1, TRBV10-2, TRBV10-3, TRBV11-1, TRBV11-2, TRBV11-3, TRBV12-1, TRBV12-2, TRBV12-3, TRBV12-4, TRBV12-5, TRBV13, TRBV14, TRBV15, TRBV16, TRBV17, TRBV18, TRBV19, TRBV20-1, TRBV21-1, TRBV22-1, TRBV23-1, TRBV24-1, TRBV25-1, TRBV26, TRBV27, TRBV28, TRBV29-1, TRBV30, TRBVA, TRBVB, TRBV5-8, TRBV6-1, TRBD1, TRBD2, TRBJ1-1, TRBJ1-2, TRBJ1-3, TRBJ1-4, TRBJ1-5, TRBJ1-6, TRBD2-1, TRBD2-2, TRBD2-2P, TRBD2-3, TRBD2-4, TRBD2-5, TRBD2-6, TRBJ2-7, TRBC1, and TRBC2.

T-cell receptor delta locus (TRD) is a region on human chromosome 14 that contains genes for the TCR delta chains. For example, the TRD locus includes, e.g., TRDV (variable), TRDJ (joining), and TRDC (constant) genes. Exemplary genes encoding the T-cell receptor delta chains include, but are not limited to, TRDV1, TRDV2, TRDV3, TRDD1, TRDD2, TRDD3, TRDJ1, TRDJ2, TRDJ3, TRDJ4, and TRDC.

T-cell receptor gamma locus (TRG) is a region on human chromosome 7 that contains genes for the TCR gamma chains. For example, the TRG locus includes, e.g., TRGV (variable), TRGJ (joining), and TRGC (constant) genes. Exemplary genes encoding the T-cell receptor gamma chains include, but are not limited to, TRGV1, TRGV2, TRGV3, TRGV4, TRGV5, TRGV5P, TRGV6, TRGV7, TRGV8, TRGV9, TRGV10, TRGV11, TRGVA, TRGVB, TRGJ1, TRGJ2, TRGJP, TRGJP1, TRGJP2, TRGC1, and TRGC2.

Exemplary cancers include, but are not limited to, B cell cancer, e.g., multiple myeloma, melanomas, breast cancer, lung cancer (such as non-small cell lung carcinoma or NSCLC), bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, adenocarcinomas, inflammatory myofibroblastic tumors, gastrointestinal stromal tumor (GIST), colon cancer, multiple myeloma (MM), myelodysplastic syndrome (MDS), myeloproliferative disorder (MPD), acute lymphocytic leukemia (ALL), acute myelocytic leukemia (AML), chronic myelocytic leukemia (CML), chronic lymphocytic leukemia (CLL), polycythemia Vera, Hodgkin lymphoma, non-Hodgkin lymphoma (NHL), soft-tissue sarcoma, fibrosarcoma, myxosarcoma, liposarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, seminoma, embryonal carcinoma, Wilms' tumor, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, retinoblastoma, follicular lymphoma, diffuse large B-cell lymphoma, mantle cell lymphoma, hepatocellular carcinoma, thyroid cancer, gastric cancer, head and neck cancer, small cell cancers, essential thrombocythemia, agnogenic myeloid metaplasia, hypereosinophilic syndrome, systemic mastocytosis, familiar hypereosinophilia, chronic eosinophilic leukemia, neuroendocrine cancers, carcinoid tumors, and the like.

In an embodiment, the cancer is a hematologic malignancy (or premalignancy). As used herein, a hematologic malignancy refers to a tumor of the hematopoietic or lymphoid tissues, e.g., a tumor that affects blood, bone marrow, or lymph nodes. Exemplary hematologic malignancies include, but are not limited to, leukemia (e.g., acute lymphoblastic leukemia (ALL), acute myeloid leukemia (AML), chronic lymphocytic leukemia (CLL), chronic myelogenous leukemia (CML), hairy cell leukemia, acute monocytic leukemia (AMoL), chronic myelomonocytic leukemia (CMML), juvenile myelomonocytic leukemia (JMML), or large granular lymphocytic leukemia), lymphoma (e.g., AIDS-related lymphoma, cutaneous T-cell lymphoma, Hodgkin lymphoma (e.g., classical Hodgkin lymphoma or nodular lymphocyte-predominant Hodgkin lymphoma), mycosis fungoides, non-Hodgkin lymphoma (e.g., B-cell non-Hodgkin lymphoma (e.g., Burkitt lymphoma, small lymphocytic lymphoma (CLL/SLL), diffuse large B-cell lymphoma, follicular lymphoma, immunoblastic large cell lymphoma, precursor B-lymphoblastic lymphoma, or mantle cell lymphoma) or T-cell non-Hodgkin lymphoma (mycosis fungoides, anaplastic large cell lymphoma, or precursor T-lymphoblastic lymphoma)), primary central nervous system lymphoma, Sézary syndrome, Waldenström macroglobulinemia), chronic myeloproliferative neoplasm, Langerhans cell histiocytosis, multiple myeloma/plasma cell neoplasm, myelodysplastic syndrome, or myelodysplastic/myeloproliferative neoplasm. Premalignancy, as used herein, refers to a tissue that is not yet malignant but is poised to become malignant.

In one embodiment, the target gene or gene product, or a fragment thereof, is selected from any of the genes or gene products described in Tables 1-4.

TABLE 1

Exemplary genes with complete exonic coverage in an exemplary DNA-seq baitset

| | | | | | | | | | |
|---|---|---|---|---|---|---|---|---|---|
| ABL1 | BTK | CTNNB1 | FAS (TNFRSF6) | HIST1H1C | KDR | MYCN | PDK1 | RPL13 | SUFU |
| ACTB | BTLA | CUL4A | FAT3 | HIST1H1D | KEAP1 | MYD88 | PHF6 | RPL15 | SUZ12 |
| AKT1 | c11orf30 (EMSY) | CUL4B | FBXO11 | HIST1H1E | KIT | MYO18A | PIK3C2G | RPL35A | SYK |
| AKT2 | CAD | CUX1 | FBXO31 | HIST1H2AC | KLHL6 | NBN | PIK3C3 | RPS14 | TAF1 |
| AKT3 | CARD11 | CXCR4 | FBXW7 | HIST1H2AG | KMT2A (MLL) | NCOR1 | PIK3CA | RPS19 | TBL1XR1 |
| ALK | CASP8 | CYP17A1 | FGF10 | HIST1H2AL | KMT2B (MLL2) | NCOR2 | PIK3CG | RPS26 | TBX3 |
| ALOX12B | CBFB | DAXX | FGF12 | HIST1H2AM | KMT2C (MLL3) | NCSTN | PIK3R1 | RPTOR | TCF3 |
| AMER1 (FAM123B or WTX) | CBL | DDR2 | FGF14 | HIST1H2BC | KRAS | NF1 | PIK3R2 | RUNX1 | TCL1A |
| APC | CCND1 | DDX3X | FGF19 | HIST1H2BJ | LEF1 | NF2 | PIM1 | RUNX1T1 | TET2 |
| APCDD1 | CCND2 | DIS3 | FGF23 | HIST1H2BK | LMO1 | NFE2L2 | PLCG2 | S1PR2 | TGFBR2 |
| APH1A | CCND3 | DKC1 | FGF3 | HIST1H2BO | LRP1B | NFKBIA | PMS2 | SBDS | TIPARP |
| AR | CCNE1 | DNM2 | FGF4 | HIST1H3B | LRRK2 | NKX2-1 | PNRC1 | SDHA | TLL2 |
| ARAF | CCT6B | DNMT3A | FGF6 | HLA-A | MAF | NOD1 | POT1 | SDHB | TMEM30A |
| ARFRP1 | CD22 | DOT1L | FGF7 | HNF1A | MAFB | NOTCH1 | PPP2R1A | SDHC | TMSB4XP8 (TMSL3) |
| ARHGAP26 (GRAF) | CD274 (PDL1) | DTX1 | FGFR1 | HRAS | MAGED1 | NOTCH2 | PRDM1 | SDHD | TNFAIP3 |
| ARID1A | CD36 | DUSP2 | FGFR2 | HSP90AA1 | MALT1 | NOTCH3 | PRKAR1A | SERP2 | TNFRSF11A |
| ARID2 | CD58 | DUSP9 | FGFR3 | ICK | MAP2K1 | NOTCH4 | PRKDC | SETBP1 | TNFRSF14 |
| ASMTL | CD70 | EBF1 | FGFR4 | ID3 | MAP2K2 | NPM1 | PRSS8 | SETD2 | TNFRSF17 |
| ASXL1 | CD79A | ECT2L | FHIT | IDH1 | MAP2K4 | NRAS | PTCH1 | SF3B1 | TOP1 |
| ATM | CD79B | EED | FLCN | IDH2 | MAP3K1 | NSD1 | PTEN | SGK1 | TP53 |
| ATR | CDC73 | EGFR | FLT1 | IGF1 | MAP3K13 | NT5C2 | PTPN11 | SH2B3 | TP63 |
| ATRX | CDH1 | ELP2 | FLT3 | IGF1R | MAP3K14 | NTRK1 | PTPN2 | SMAD2 | TRAF2 |
| AURKA | CDK12 | EP300 | FLT4 | IGF2 | MAP3K6 | NTRK2 | PTPN6 (SHP-1) | SMAD4 | TRAF3 |
| AURKB | CDK4 | EPHA3 | FLYWCH1 | IKBKE | MAP3K7 | NTRK3 | PTPRO | SMARCA1 | TRAF5 |
| AXIN1 | CDK6 | EPHA5 | FOXL2 | IKZF1 | MAPK1 | NUP93 | RAD21 | SMARCA4 | TRRAP |
| AXL | CDK8 | EPHA7 | FOXO1 | IKZF2 | MCL1 | NUP98 | RAD50 | SMARCB1 | TSC1 |
| B2M | CDKN1B | EPHB1 | FOXO3 | IKZF3 | MDM2 | P2RY8 | RAD51 | SMARCD1 | TSC2 |
| BAP1 | CDKN2A | ERBB2 | FOXP1 | IL7R | MDM4 | PAG1 | RAD51B | SMC1A | TSHR |
| BARD1 | CDKN2B | ERBB3 | FRS2 | INHBA | MED12 | PAK3 | RAD51C | SMC3 | TUSC3 |
| BCL10 | CDKN2C | ERBB4 | GADD45B | INPP4B | MEF2B | PAK7 | RAD51D | SMO | TYK2 |
| BCL11B | CEBPA | ERG | GATA1 | INPP5D (SHIP) | MEF2C | PALB2 | RAD52 | SOCS1 | U2AF1 |
| BCL2 | CHD2 | ESR1 | GATA2 | IRF1 | MEN1 | PARP1 | RAD54L | SOCS2 | U2AF2 |
| BCL2L2 | CHEK1 | ETS1 | GATA3 | IRF4 | MET | PARP2 | RAF1 | SOCS3 | VHL |
| BCL6 | CHEK2 | ETV6 | GID4 (c17orf39) | IRF8 | MIB1 | PARP3 | RARA | SOX10 | WDR90 |
| BCL7A | CHUK | EXOSC6 | GNA11 | IRS2 | MITF | PARP4 | RASGEF1A | SOX2 | WHSC1 (MMSET or NSD2) |
| BCOR | CIC | EZH2 | GNA12 | JAK1 | MKI67 | PASK | RB1 | SPEN | WISP3 |
| BCORL1 | CIITA | FAF1 | GNA13 | JAK2 | MLH1 | PAX5 | REL | SPOP | WT1 |
| BIRC3 | CKS1B | FAM46C | GNAQ | JAK3 | MPL | PBRM1 | RELN | SRC | XBP1 |
| BLM | CPS1 | FANCA | GNAS | JARID2 | MRE11A | PC | RET | SRSF2 | XPO1 |
| BRAF | CRBN | FANCC | GPR124 | JUN | MSH2 | PCBP1 | RHOA | STAG2 | XRCC3 |
| BRCA1 | CREBBP | FANCD2 | GRIN2A | KAT6A (MYST3) | MSH3 | PCLO | RICTOR | STAT3 | YY1AP1 |

TABLE 1-continued

Exemplary genes with complete exonic coverage in an exemplary DNA-seq baitset

| | | | | | | | | | |
|---|---|---|---|---|---|---|---|---|---|
| BRCA2 | CRKL | FANCE | GSK3B | KDM2B | MSH6 | PDCD1 | RMRP | STAT4 | ZMYM3 |
| BRD4 | CRLF2 | FANCF | GTSE1 | KDM4C | MTOR | PDCD11 | RNF43 | STAT5A | ZNF217 |
| BRIP1 (BACH1) | CSF1R | FANCG | HDAC1 | KDM5A | MUTYH | PDCD1LG2 (PDL2) | ROS1 | STAT5B | ZNF24 (ZSCAN3) |
| BRSK1 | CSF3R | FANCI | HDAC4 | KDM5C | MYC | PDGFRA | RPA1 | STAT6 | ZNF703 |
| BTG1 | CTCF | FANCL | HDAC7 | KDM6A | MYCL (MYCL1) | PDGFRB | RPL11 | STK11 | ZRSR2 |
| BTG2 | CTNNA1 | FANCM | HGF | | | | | | |

TABLE 2

Exemplary genes with select introns covered in an exemplary DNA-seq baitset

| | | | | | | | | | |
|---|---|---|---|---|---|---|---|---|---|
| ALK | BRAF | EGFR | ETV4 | EWSR1 | IGK | JAK2 | NTRK1 | RAF1 | ROS1 |
| BCL2 | CCND1 | EPOR | ETV5 | FGFR2 | IGL | KMT2A (MLL) | PDGFRA | RARA | TMPRSS2 |
| BCL6 | CRLF2 | ETV1 | ETV6 | IGH | JAK1 | MYC | PDGFRB | RET | TRG |
| BCR | | | | | | | | | |

TABLE 3

Exemplary genes targeted in an exemplary RNA-seq baitset

| | | | | | | | | | |
|---|---|---|---|---|---|---|---|---|---|
| ABI1 | BRCA2 | CTNNB1 | FGFR3 | IGH | MDS2 | NKX2-1 | PIK3R1 | RPS14 | TET1 |
| ABL1 | BTG1 | DDIT3 | FLI1 | IGK | MECOM | NOTCH1 | PIK3R2 | RPS15 | TFE3 |
| ABL2 | CAMTA1 | DDR1 | FNBP1 | IGL | MEF2C | NPM1 | PIM1 | RPS19 | TFG |
| ACSL6 | CARS | DDX10 | FOXO1 | IKZF1 | MKL1 | NR4A3 | PLAG1 | RPS26 | TFPT |
| AFF1 | CBFA2T3 | DDX6 | FOXO3 | IKZF3 | MKL2 | NSD1 | PML | RUNX1 | TFRC |
| AFF4 | CBFB | DEK | FOXO4 | IL21R | MLF1 | NTRK1 | POU2AF1 | RUNX1T1 (ETO) | TLX1 |
| ALK | CBL | DLEU2 | FOXP1 | IL3 | MLLT1 (ENL) | NTRK2 | PPP1CB | RUNX2 | TLX3 |
| ARHGAP26 | CCND1 | DNMT3A | FSTL3 | INSR | MLLT10 (AF10) | NTRK3 | PRDM1 | SEC31A | TMPRSS2 |
| ARHGEF12 | CCND2 | DUSP22 | FUS | IRF4 | MLLT3 | NUMA1 | PRDM16 | SEPT5 | TNFRSF11A |
| ARID1A | CCND3 | EGFR | GAS7 | ITK | MLLT4 (AF6) | NUP214 | PRRX1 | SEPT6 | TNFSF9 |
| ARID1B | CD247 | EIF4A2 | GLI1 | JAK1 | MLLT6 | NUP98 | PSIP1 | SEPT9 | TOP1 |
| ARNT | CD274 (PDL1) | ELF4 | GLIS2 | JAK2 | MN1 | NUTM2A | PTCH1 | SET | TP53 |
| ASXL1 | CD70 | ELL | GMPS | JAK3 | MNX1 | OLIG2 | PTEN | SH3GL1 | TP63 |
| ATF1 | CDC73 | ELN | GPHN | JAZF1 | MSH2 | OMD | PTK7 | SLC1A2 | TPM3 |
| ATG5 | CDK6 | EML4 | HDAC4 | KAT6A (MYST3) | MSH6 | P2RY8 | RABEP1 | SMARCB1 | TPM4 |
| ATIC | CDKN2A | EP300 | HERPUD1 | KDM4C | MSI2 | PAFAH1B2 | RAF1 | SNX29 (RUNDC2A) | TRAF2 |
| ATM | CDX2 | EPHA7 | HEY1 | KDSR | MSN | PALB2 | RALGDS | SRSF3 | TRAF3 |
| ATR | CEBPA | EPOR | HIP1 | KIF5B | MTAP | PAX3 | RANBP17 | SS18 | TRAF5 |
| ATXN1 | CHIC2 | EPS15 | HIST1H1A | KMT2A (MLL) | MTCP1 | PAX5 | RAP1GDS1 | SSX1 | TRG |
| AXL | CHN1 | ERBB2 | HIST1H4I | LASP1 | MUC1 | PAX7 | RARA | SSX2 | TRIM24 |
| BAP1 | CHTOP (C1orf77) | ERG | HLF | LCK | MYB | PBX1 | RB1 | SSX4 | TRIP11 |
| BCL10 | CIC | ETS1 | HMGA1 | LCP1 | MYC | PCM1 | RBM15 | STAT6 | TSC1 |
| BCL11A | CIITA | ETV1 | HMGA2 | LEF1 | MYH11 | PCSK7 | RCOR1 | STK11 | TSC2 |
| BCL11B | CKS1B | ETV4 | HOXA11 | LMO1 | MYH9 | PDCD1LG2 (PDL2) | RET | STL | TTL |
| BCL2 | CLP1 | ETV5 | HOXA13 | LMO2 | NACA | PDE4DIP | RHOH | SYK | TYK2 |
| BCL3 | CLTC | ETV6 | HOXA3 | LPP | NBEAP1 (BCL8) | PDGFB | RNF213 | TAF15 | USP6 |
| BCL6 | CLTCL1 | EWSR1 | HOXA9 | LTK | NCOA2 | PDGFRA | ROS1 | TAL1 | WHSC1 |
| BCL7A | CNTRL (CEP110) | FBXW7 | HOXC11 | LYL1 | NDRG1 | PDGFRB | RPA1 | TAL2 | WHSC1L1 |
| BCL9 | COL1A1 | FCGR2B | HOXC13 | MAF | NF1 | PDK1 | RPL13 | TBL1XR1 | YPEL5 |
| BCOR | CREB3L1 | FCRL4 | HOXD11 | MAFB | NF2 | PER1 | RPL15 | TCF3 (E2A) | ZBTB16 |
| BCR | CREB3L2 | FEV | HOXD13 | MAGEA5 | NFKB2 | PGAM5 | RPL22 | TCL1A (TCL1) | ZMYM2 |
| BIRC3 | CREBBP | FGFR1 | HSP90AA1 | MALT1 | NFKBIE | PHF1 | RPL35A | TCL6 | ZNF384 |
| BRAF | CRLF2 | FGFR1OP | HSP90AB1 | MAP3K7 | NIN | PICALM | RPN1 | TEC | ZNF521 |
| BRCA1 | CSF1 | FGFR2 | | | | | | | |

TABLE 4

Additional exemplary genes with complete exonic coverage in an exemplary DNA-seq baitset

| | | | | | | | | | |
|---|---|---|---|---|---|---|---|---|---|
| ASMTL | CKS1B | EXOSC6 | GNA12 | IKZF2 | MIB1 | PDCD1 | RPL15 | SDHC | TCL1A |
| AXIN1 | CPS1 | FAF1 | GTSE1 | IKZF3 | MKI67 | PDCD11 | RPL35A | SDHD | TLL2 |
| BRD4 | CSF3R | FBXO11 | HDAC1 | INPP4B | MSH3 | PLCG2 | RPS14 | SERP2 | TMEM30A |
| BRSK1 | CXCR4 | FBXO31 | HIST1H1D | KMT2C (MLL3) | MYO18A | POT1 | RPS19 | SOCS2 | TP63 |
| BTLA | DDX3X | FHIT | HIST1H2AC | MAF | NCOR2 | RASGEF1A | RPS26 | SOCS3 | TUSC3 |
| CAD | DKC1 | FLYWCH1 | HIST1H2AM | MAFB | NOD1 | RHOA | S1PR2 | STAT5A | WDR90 |
| CCT6B | EBF1 | FOXP1 | HIST1H2BJ | MALT1 | PASK | RMRP | SBDS | STAT5B | WHSC1 (MMSET or NSD2) |
| CD36 | ELP2 | FRS2 | HNF1A | MAP3K6 | PC | RPL11 | SDHA | TAF1 | YY1AP1 |
| CHD2 | ETS1 | GADD45B | ICK | MAPK1 | PCBP1 | RPL13 | SDHB | TBL1XR1 | ZNF24 (ZSCAN3) |
| CALR | | | | | | | | | |

In one embodiment, the target gene or gene product, or a fragment thereof, has one or more of substitutions, indels, or copy number alterations that are associated with cancer, e.g., a hematologic malignancy (or premalignancy). Exemplary genes or gene products include, but are not limited to, ABL1, ACTB, AKT1, AKT2, AKT3, ALK, AMER1 (FAM123B or WTX), APC, APH1A, AR, ARAF, ARFRP1, ARHGAP26 (GRAF) ARID1A, ARID2, ASMTL, ASXL1, ATM, ATR, ATRX, AURKA, AURKB, AXIN1, AXL, B2M, BAP1, BARD1, BCL10, BCL11B, BCL2, BCL2L2, BCL6, BCL7A, BCOR, BCORL1, BIRC3, BLM, BRAF, BRCA1, BRCA2, BRD4, BRIP1 (BACH1), BRSK1, BTG2, BTK, BTLA, c11 or, f30 (EMSY), CAD, CARD11, CBFB, CBL, CCND1, CCND2, CCND3, CCNE1, CCT6B, CD22, CD274, (PDL 1), CD36, CD58, CD70, CD79A, CD79B, CDC73, CDH1, CDK12, CDK4, CDK6, CDK8, CDKN1B, CDKN2A, CDKN2B, CDKN2C, CEBPA, CHD2, CHEK1, CHEK2, CIC, CIITA, CKS1B, CPS1, CREBBP, CRKL, CRLF2, CSF1R, CSF3R, CTCF, CTNNA1, CTNNB1, CUX1, CXCR4, DAXX, DDR2, DDX3X, DNM2, DNMT3A, DOT1L, DTX1, DUSP2, DUSP9, EBF1, ECT2L, EED, EGFR, ELP2, EP300, EPHA3, EPHA5, EPHA7, EPHB1, ERBB2, ERBB3, ERBB4, ERG, ESR1, ETS1, ETV6, EXOSC6, EZH2, FAF1, FAM46C, FANCA, FANCC, FANCD2, FANCE, FANCF, FANCG, FANCL, FAS (TNFRSF6), FBXO11, FBXO31, FBXW7, FGF10, FGF14, FGF19, FGF23, FGF3, FGF4, FGF6, FGFR1, FGFR2, FGFR3, FGFR4, FHIT, FLCN, FLT1, FLT3, FLT4, FLYWCH1, FOXL2, FOXO1, FOXO3, FOXP1, FRS2, GADD45B, GATA1, GATA2, GATA3, GID4 (C17orf39), GNA11, GNA12, GNA13, GNAQ, GNAS, GPR124, GRIN2A, GSK3B, GTSE1, HDAC1, HDAC4, HDAC7, HGF, HIST1H1C, HIST1H1D, HIST1H1E, HIST1H2AC, HIST1H2AG, HIST1H2AL, HIST1H2AM, HIST1H2BC, HIST1H2BJ, HIST1H2BK, HIST1H2BO, HIST1H3B, HNF1A, HRAS, HSP90AA1, ICK, ID3, IDH1, IDH2, IGF1R, IKBKE, IKZF1, IKZF2, IKZF3, IL7R, INHBA, INPP4B, INPP5D (SHIP), IRF1, IRF4, IRF8, IRS2, JAK1, JAK2, JAK3, JARID2, JUN, KAT6A (MYST3), KDM2B, KDM4C, KDM5A, KDM5C, KDM6A, KDR, KEAP1, KIT, KLHL6, KMT2A (MLL), KMT2B (MLL2), KMT2C (MLL3), KRAS, LEF1, LRP1B, LRRK2, MAF, MAFB, MAGED1, MALT1, MAP2K1, MAP2K2, MAP2K4, MAP3K1, MAP3K14, MAP3K6, MAP3K7, MAPK1, MCL1, MDM2, MDM4, MED12, MEF2B, MEF2C, MEN1, MET, MIB1, MITF, MKI67, MLH1, MPL, MRE11A, MSH2, MSH3, MSH6, MTOR, MUTYH, MYC, MYCL (MYCL1), MYCN, MYD88, MYO18A, NCOR2, NCSTN, NF1, NF2, NFE2L2, NFKBIA, NKX2-1, NOD1, NOTCH1, NOTCH2, NPM1, NRAS, NT5C2, NTRK1, NTRK2, NTRK3, NUP93, NUP98, P2RY8, PAG1, PAK3, PALB2, PASK, PAX5, PBRM1, PC, PCBP1, PCLO, PDCD1, PDCD11, PDCD1LG2 (PDL2), PDGFRA, PDGFRB, PDK1, PHF6, PIK3CA, PIK3CG, PIK3R1, PIK3R2, PIM1, PLCG2, POT1, PPP2R1A, PRDM1, PRKAR1A, PRKDC, PRSS8, PTCH1, PTEN, PTPN11, PTPN2, PTPN6 (SHP-1), PTPRO, RAD21, RAD50, RAD51, RAF1, RARA, RASGEF1A, RB1, RELN, RET, RHOA, RICTOR, RNF43, ROS1, RPTOR, RUNX1, S1PR2, SDHA, SDHB, SDHC, SDHD, SERP2, SETBP1, SETD2, SF3B1, SGK1, SMAD2, SMAD4, SMARCA1, SMARCA4, SMARCB1, SMC1A, SMC3, SMO, SOCS1, SOCS2, SOCS3, SOX10, SOX2, SPEN, SPOP, SRC, SRSF2, STAG2, STAT3, STAT4, STAT5A, STAT5B, STAT6, STK11, SUFU, SUZ12, TAF1, TBL1XR1, TCF3, TCL1A, TET2, TGFBR2, TLL2, TMEM30A, TMSB4XP8 (TMSL3), TNFAIP3, TNFRSF11A, TNFRSF14, TNFRSF17, TOP1, TP53, TP63, TRAF2, TRAF3, TRAF5, TSC1, TSC2, TSHR, TUSC3, TYK2, U2AF1, U2AF2, VHL, WDR90, WHSC1 (MMSET, or, NSD2), WISP3, WT1, XBP1, XPO1, YY1AP1, ZMYM3, ZNF217, ZNF24 (ZSCAN3), ZNF703, or ZRSR2.

In one embodiment, the target gene or gene product, or a fragment thereof, has one or more rearrangements that are associated with cancer, e.g., a hematologic malignancy (or premalignancy). Exemplary genes or gene products include, but are not limited to, ALK, BCL6, BRAF, CRLF2, EPOR, ETV4, ETV6, FGFR2, IGK, BCL2, BCR, CCND1, EGFR, ETV1, ETV5, EWSR1, IGH, IGL, JAK1, KMT2A, (MLL), NTRK1, PDGFRB, RARA, ROS1, TRG, JAK2, MYC, PDGFRA, RAF1, RET, or TMPRSS2.

In another embodiment, the target gene or gene product, or a fragment thereof, has one or more fusions that are associated with cancer. Exemplary genes or gene products include, but are not limited to, ABI1, CBFA2T3, EIF4A2, FUS, JAK1, MUC1, PBX1, RNF213, TET1, ABL1, CBFB, ELF4, GAS7, JAK2, MYB, PCM1, ROS1, TFE3, ABL2, CBL, ELL, GLI1, JAK3, MYC, PCSK7, RPL22, TFG, ACSL6, CCND1, ELN, GMPS, JAZF1, MYH11, PDCD1LG2 (PDL2), RPN1, TFPT, AFF1, CCND2, EML4, GPHN, KAT6A (MYST3), MYH9, PDE4DIP, RUNX1, TFRC, AFF4, CCND3, EP300, HERPUD1, KDSR, NACA, PDGFB, RUNX1T1 (ETO), TLX1, ALK, CD274 (PDL1), EPOR, HEY1, KIF5B, NBEAP1 (BCL8), PDGFRA, RUNX2, TLX3, ARHGAP26 (GRAF), CDK6, EPS15, HIP1, KMT2A (MLL), NCOA2, PDGFRB, SEC31A, TMPRSS2, ARHGEF12, CDX2, ERBB2, HIST1H4I, LASP1, NDRG1, PER1, SEPT5, TNFRSF11A, ARID1A, CHIC2, ERG, HLF, LCP1, NF1, PHF1, SEPT6, TOP1, ARNT, CHN1, ETS1, HMGA1, LMO1, NF2, PICALM, SEPT9, TP63, ASXL1, CIC, ETV1, HMGA2, LMO2, NFKB2, PIM1, SET, TPM3, ATF1, CIITA, ETV4, HOXA11, LPP, NIN, PLAG1, SH3GL1, TPM4, ATG5, CLP1, ETV5, HOXA13, LYL1, NOTCH1, PML, SLC1A2, TRIM24, ATIC, CLTC, ETV6, HOXA3, MAF, NPM1, POU2AF1, SNX29 (RUNDC2A), TRIP11, BCL10, CLTCL1, EWSR1, HOXA9, MAFB, NR4A3, PPP1CB, SRSF3, TTL, BCL11A, CNTRL (CEP110), FCGR2B, HOXC11, MALT1, NSD1, PRDM1, SS18, TYK2, BCL11B, COL1A1, FCRL4, HOXC13, MDS2, NTRK1, PRDM16, SSX1, USP6, BCL2, CREB3L1, FEV, HOXD11, MECOM, NTRK2, PRRX1, SSX2, WHSC1 (MMSET, or, NSD2), BCL3, CREB3L2, FGFR1, HOXD13, MKL1, NTRK3, PSIP1, SSX4, WHSC1L1, BCL6, CREBBP, FGFR1OP, HSP90AA1, MLF1, NUMA1, PTCH1, STAT5, YPEL5, BCL7A, CRLF2, FGFR2, HSP90AB1, MLLT1 (ENL), NUP214, PTK7, STL, ZBTB16, BCL9, CSF1, FGFR3, IGH, MLLT10 (AF10), NUP98, RABEP1, SYK, ZMYM2, BCOR, CTNNB1, FLI1, IGK, MLLT3, NUTM2A, RAF1, TAF15, ZNF384, BCR, DDIT3, FNBP1, IGL, MLLT4, (AF6), OMD, RALGDS, TAL1, ZNF521, BIRC3, DDX10, FOXO1, IKZF1, MLLT6, P2RY8, RAP1GDS1, TAL2, BRAF, DDX6, FOXO3, IL21R, MN1, PAFAH1B2, RARA, TBL1XR1, BTG1, DEK, FOXO4, IL3, MNX1, PAX3, RBM15, TCF3 (E2A), CAMTA1, DUSP22, FOXP1, IRF4, MSI2, PAX5, RET, TCL1A (TCL1), CARS, EGFR, FSTL3, ITK, MSN, PAX7, RHOH, or TEC.

In one embodiment, the target gene or gene product, or a fragment thereof, is selected from any of the genes or gene products described in Tables 5A-9.

TABLE 5A

List of exemplary selected genes and variants, associated cancer types, and priority codons for multiplex analysis

| Hugo Gene | Gene Category | Cancer Types | Priority Codons |
|---|---|---|---|
| ABL1 | Priority 1 | Leukemia (e.g., chronic myeloid leukemia (CML), acute myeloid leukemia (AML), acute lymphoblastic leukemia (ALL)) | 315 |
| AKT1 | Priority 1 | breast cancer, colorectal cancer, ovarian cancer | |
| ALK | Priority 1 | Lymphoma (e.g., non-Hodgkin lymphoma, anaplastic large-cell lymphoma (ALCL)), inflammatory myofibroblastic tumor | |
| APC | Priority 1 | Colorectal cancer, medulloblastoma, mismatch repair cancer syndrome | 1114, 1338, 1450, 1556 |
| AR | Priority 1 | Prostate cancer | |
| BRAF | Priority 1 | Lung cancer, non-Hodgkin lymphoma, colorectal cancer, thyroid cancer, melanoma | 600 |
| CDKN2A | Priority 1 | melanoma, pancreatic cancer, Li-Fraumeni syndrome, lung cancer (e.g., non-small cell lung cancer (NSCLC)), squamous cell carcinoma, retinoblastoma, astrocytoma | |
| CEBPA | Priority 1 | Leukemia (e.g., acute myeloid leukemia (AML), acute myeloid leukemia (AML), monoblastic leukemia), retinoblastoma | |
| CTNNB1 | Priority 1 | Colorectal cancer, ovarian cancer, prostate cancer, liver cancer (e.g., hepatoblastoma (HB), hepatocellular carcinoma (HCC)), pilomatrixoma, medulloblastoma, salivary gland pleiomorphic adenomas | 32, 33, 34, 37, 41, 45 |
| EGFR | Priority 1 | Lung cancer, squamous cell carcinoma, glioblastoma, glioma, colorectal cancer | 719, 746-750, 768, 790, 858, 861 |
| ERBB2 | Priority 1 | Gastric cancer, glioma, ovarian cancer, lung cancer | |
| ESR1 | Priority 1 | Breast cancer, endometrial cancer, endometrial adenocarcinoma, leiomyoma, mammary ductal carcinoma | |
| FGFR1 | Priority 1 | Leukemia, lymphoma | |
| FGFR2 | Priority 1 | Breast cancer, prostate cancer | |
| FGFR3 | Priority 1 | Bladder cancer, cervical cancer, multiple myeloma, | |
| FLT3 | Priority 1 | Leukemia (e.g., acute myeloid leukemia (AML), acute promyelocytic leukemia, acute lymphoblastic leukemia) | 835 |
| HRAS | Priority 1 | Hurthle cell thyroid carcinoma, bladder cancer, melanoma, colorectal cancer | 12, 13, 61 |
| JAK2 | Priority 1 | Leukemia (e.g., chronic lymphoblastic leukemia (CLL), acute lymphoblastic leukemia (ALL), chronic myelogenous leukemia | 617 |

TABLE 5A-continued

List of exemplary selected genes and variants, associated cancer types, and priority codons for multiplex analysis

| Hugo Gene | Gene Category | Cancer Types | Priority Codons |
|---|---|---|---|
| KIT | Priority 1 | (CML), acute myelogenous leukemia (AML)) Gastrointestinal stromal tumor (GIST), testicular tumor, leukemia (e.g., acute myeloid leukemia (AML)), mast cell tumor, mesenchymal tumor, adenoid cystic carcinoma, lung cancer (e.g., small cell lung cancer), lymphoma (e.g., Burkitt lymphoma) | 816 |
| KRAS | Priority 1 | Leukemia (e.g., acute myelogenous leukemia (AML), juvenile myelomonocytic leukemia (JMML)), colorectal cancer, lung cancer | 12, 13, 61 |
| MET | Priority 1 | Gastric cancer, hepatocellular carcinoma (HCC), hereditary papillary renal carcinoma (HPRC), lung cancer (e.g., non-small cell lung cancer), papillary thyroid carcinoma, glioma, esophageal adenocarcinoma, osteosarcoma, endometrial cancer, squamous cell carcinoma, melanoma, breast cancer | |
| MLL | Priority 1 | Leukemia (e.g., acute lymphoblastic leukemia (ALL), acute myeloid leukemia (AML) | |
| MYC | Priority 1 | chronic lymphocytic leukemia (CLL), Burkitt lymphoma, plasmacytoma, | |
| NF1 | Priority 1 | Leukemia (e.g., juvenile myelomonocytic leukemia (JMML)), neurofibroma, | |
| NOTCH1 | Priority 1 | Squamous cell carcinoma, leukemia (e.g., acute lymphoblastic leukemia (ALL)), medullary thyroid carcinoma, lymphoma (e.g., thymic lymphoma, T-cell lymphoma) | 1575, 1601 |
| NPM1 | Priority 1 | Lymphoma (e.g., non-Hodgkin lymphoma, anaplastic large cell lymphoma, anaplastic lymphoma), leukemia (e.g., acute promyelocytic leukemia, acute myelogenous leukemia (AML)) | |
| NRAS | Priority 1 | Leukemia (e.g., juvenile myelomonocytic leukemia (JMML), acute myeloid leukemia (AML), acute lymphoblastic leukemia), melanoma, | 12, 13, 61 |
| PDGFRA | Priority 1 | Gastrointestinal stromal tumor (GIST), leukemia (e.g., chronic eosinophilic leukemia (CEL), acute lymphocytic leukemia (ALL)), mesenchymal tumor | |
| PIK3CA | Priority 1 | Colorectal cancer, breast cancer, ovarian cancer, hepatocellular carcinoma, head and neck squamous cell carcinoma (HNSCC), anaplastic thyroid carcinoma, endometrial cancer, gallbladder adenocarcinoma, glioblastoma | 88, 542, 545, 546, 1047, 1049 |
| PTEN | Priority 1 | Head and neck squamous cell carcinomas (HNSCC), endometrial cancer, glioma, prostate cancer, glioblastoma | 130, 173, 233, 267 |
| RB1 | Priority 1 | Retinoblastoma, bladder cancer, osteosarcoma, lung cancer (e.g., small cell lung cancer, non-small cell lung cancer), leukemia (e.g., acute lymphoblastic leukemia (ALL)) | |
| RET | Priority 1 | Colorectal cancer, medullary thyroid carcinoma, multiple neoplasia type 2B, pheochromocytoma, multiple neoplasia type 2A, thyroid papillary | 918 |

TABLE 5A-continued

List of exemplary selected genes and variants, associated cancer types, and priority codons for multiplex analysis

| Hugo Gene | Gene Category | Cancer Types | Priority Codons |
|---|---|---|---|
| | | carcinoma, thryoid cancer, retinoblastoma | |
| TP53 | Priority 1 | TP53 is frequently mutated or inactivated in about 60% of cancers, e.g., esophageal squamous cell carcinoma, Li-Fraumeni syndrome, head and neck squamous cell carcinomas (HNSCC), lung cancer, hereditary adrenocortical carcinoma, astrocytoma, squamous cell carcinoma, bladder cancer, colorectal cancer, glioblastoma, retinoblastoma | 175, 245, 248, 273, 306 |
| ABL2 | Cancer Gene | Acute myeloid leukemia (AML) | |
| AKT2 | Cancer Gene | Ovarian cancer, pancreatic cancer | |
| AKT3 | Cancer Gene | Melanoma, glioma, uternine cancer, prostate cancer, oral cancer, ovarian cancer | |
| ARAF | Cancer Gene | Angioimmunoblastic T-cell lymphoma, ehrlich ascites tumor | |
| ARFRP1 | Cancer Gene | Breast cancer | |
| ARID1A | Cancer Gene | Neuroblastoma, acute lymphoblastic leukemia (ALL), neuroendocrine tumor | |
| ATM | Cancer Gene | Leukemia (e.g., T-cell prolymphocytic leukemia (T-PLL)), lymphoma, medulloblastoma, glioma | |
| ATR | Cancer Gene | Pyothorax-associated lymphoma, T-cell lymphoma | |
| AURKA | Cancer Gene | Laryngeal squamous cell carcinoma, ovarian cancer, bladder cancer, head and neck squamous cell carcinoma (HNSCC), laryngeal carcinoma, esophageal squamous cell carcinoma (ESCC), pancreatic cancer | |
| AURKB | Cancer Gene | Colorectal cancer, astrocytoma, ependymal tumor, glioma, esophageal squamous cell carcinoma (ESCC), acute myeloid leukemia (AML) | |
| BCL2 | Cancer Gene | Lymphoma, colorectal adenocarcinoma, esophageal squamous cell carcinoma (ESCC), synovial sarcoma, leukemia | |
| BCL2A1 | Cancer Gene | Pulmonary granuloma, gastric adenoma, burkitt lymphoma, parotid adenoma, kaposi sarcoma, gastric cancer, colon cancer | |
| BCL2L1 | Cancer Gene | Head and neck squamous cell carcinoma, glioblastoma, mesothelioma, pancreatic cancer, adenocarcinoma lung | |
| BCL2L2 | Cancer Gene | Brain cancer, leukemia, lymphoma, colorectal adenocarcinoma, colorectal cancer, adenoma, cervical squamous cell carcinoma | |
| BCL6 | Cancer Gene | Lymphoma, leukemia | |
| BRCA1 | Cancer Gene | Breast cancer, ovarian cancer | |
| BRCA2 | Cancer Gene | Breast cancer, ovarian cancer, pancreatic cancer | |
| CARD11 | Cancer Gene | Lymphoma | |
| CBL | Cancer Gene | Lymphoma, leukemia | |
| CCND1 | Cancer Gene | Chronic lymphoblastic leukemia (CLL), B-cell acute lymphoblastic leukemia (B-ALL), breast cancer | |
| CCND2 | Cancer Gene | Retinoblastoma, mantle cell lymphoma, T-cell acute lymphoblastic leukemia (T-ALL), Burkitt lymphoma, testicular germ cell tumor, ovarian granulosa cell tumor, multiple myeloma | |
| CCND3 | Cancer Gene | Retinoblastoma, mantle cell lymphoma, anaplastic large cell lymphoma, lymphoma (non-hodgkins), B-cell lymphoma, | |

TABLE 5A-continued

List of exemplary selected genes and variants, associated cancer types, and priority codons for multiplex analysis

| Hugo Gene | Gene Category | Cancer Types | Priority Codons |
|---|---|---|---|
| | | laryngeal squamous cell carcinoma, indolent lymphoma, null cell adenoma | |
| CCNE1 | Cancer Gene | Breast cancer, ovarian cancer, bladder cancer, retinoblastoma | |
| CDH1 | Cancer Gene | Gastric cancer, lobular carcinoma, squamous cell carcinoma, invasive ductal carcinoma, invasive lobular carcinoma | |
| CDH2 | Cancer Gene | Melanoma, malignant mesothelioma, pleural mesothelioma, desmoplastic melanoma, lung adenocarcinoma, endometrioid tumor, mesothelioma, bladder cancer, esophageal squamous cell carcinoma (ESCC) | |
| CDH20 | Cancer Gene | Breast cancer | |
| CDH5 | Cancer Gene | Granuloma, epithelioid sarcoma | |
| CDK4 | Cancer Gene | Melanoma | |
| CDK6 | Cancer Gene | Acute lymphoblastic leukemia (ALL) | |
| CDK8 | Cancer Gene | Colon cancer, lung cancer, rectal cancer, acute lymphoblastic leukemia (ALL) | |
| CDKN2B | Cancer Gene | Leukemia, retinoblastoma, laryngeal squamous cell carcinoma | |
| CDKN2C | Cancer Gene | Thyroid carcinoma, pituitary adenoma, oligodendroglioma, pancreatic endocrine tumor, multiple myeloma, hepatoblastoma, lymphoid tumor, multiple endocrine neoplasia type 1, anaplastic oligodendroglioma | |
| CHEK1 | Cancer Gene | Leukemia, colon cancer | |
| CHEK2 | Cancer Gene | Breast cancer | |
| CRKL | Cancer Gene | Leukemia, lymphoma | |
| CRLF2 | Cancer Gene | Leukemia | |
| DNMT3A | Cancer Gene | Testicular germ cell tumor, lymphosarcoma, hepatocellular carcinoma, salivary gland tumor | |
| DOT1L | Cancer Gene | Leukemia | |
| EPHA3 | Cancer Gene | Rhabdomyosarcoma, lymphoma, prostate cancer, hepatocellular carcinoma, leukemia, melanoma | |
| EPHA5 | Cancer Gene | Glioblastoma, breast cancer, astrocytoma, Wilms' tumor, glioma | |
| EPHA6 | Cancer Gene | Breast cancer | |
| EPHA7 | Cancer Gene | Glioblastoma multiforme (GBM), colon cancer, duodenal cancer, parathyroid tumor, prostate cancer | |
| EPHB1 | Cancer Gene | Colorectal cancer, embryonal carcinoma, gastric cancer, teratocarcinoma, mucinous carcinoma | |
| EPHB4 | Cancer Gene | Head and neck squamous cell carcinoma (HNSCC), brain cancer, endometrial cancer, ovarian cancer | |
| EPHB6 | Cancer Gene | Neuroblastoma, melanoma, non-small cell lung cancer (NSCLL) | |
| ERBB3 | Cancer Gene | Breast cancer, non-small cell lung cancer (NSCLC), pancreatic cancer, invasive ductal carcinoma, lung adenocarcinoma, endometrioid carcinoma, pilocytic astrocytoma | |
| ERBB4 | Cancer Gene | Breast cancer, medulloblastoma, cervical squamous cell carcinoma, prostate cancer, leukemia | |
| ERG | Cancer Gene | Prostate cancer, Ewing's sarcoma, leukemia, prostate cancer | |
| ETV1 | Cancer Gene | Prostate cancer, breast cancer, Ewing's sarcoma, desmoplastic small round cell tumor, myxoid liposarcoma, clear cell sarcoma | |
| ETV4 | Cancer Gene | Breast cancer, ovarian cancer, squamous cell carcinoma tongue, Ewing's sarcoma | |

TABLE 5A-continued

List of exemplary selected genes and variants, associated cancer types, and priority codons for multiplex analysis

| Hugo Gene | Gene Category | Cancer Types | Priority Codons |
|---|---|---|---|
| ETV5 | Cancer Gene | Ganglioglioma, brain tumor | |
| ETV6 | Cancer Gene | Leukemia, congenital fibrosarcoma, secretory carcinoma, myelodysplastic syndrome | |
| EWSR1 | Cancer Gene | Ewing's sarcoma, clear cell sarcoma, desmoplastic small round cell tumor, extraskeletal myxoid chondrosarcoma, myxoid liposarcoma, angiomatoid fibrous histiocytoma | |
| EZH2 | Cancer Gene | Prostate cancer, gallbladder adenocarcinoma, breast cancer, bladder cancer, gastric cancer, Ewing's sarcoma | |
| FANCA | Cancer Gene | Leukemia | |
| FBXW7 | Cancer Gene | Colorectal cancer, endometrial cancer, T-cell acute lymphoblastic leukemia (T-ALL) | |
| FGFR4 | Cancer Gene | Pituitary tumor, prostate cancer, lung cancer, astrocytoma, rhabdomyosarcoma, pituitary adenoma, fibroadenoma | |
| FLT1 | Cancer Gene | Breast cancer, prostate cancer | |
| FLT4 | Cancer Gene | Lung cancer, Kaposi's sarcoma, gastric cancer, lymphangioma, squamous cell carcinoma | |
| FOXP4 | Cancer Gene | Lymphoma, brain tumor | |
| GATA1 | Cancer Gene | Megakaryoblastic leukemia of Downs Syndrome | |
| GNA11 | Cancer Gene | Breast cancer | |
| GNAQ | Cancer Gene | Uveal melanoma | |
| GNAS | Cancer Gene | Pituitary adenoma | |
| GPR124 | Cancer Gene | Colon cancer | |
| GUCY1A2 | Cancer Gene | Breast cancer | |
| HOXA3 | Cancer Gene | Breast cancer | |
| HSP90AA1 | Cancer Gene | Lymphoma, myeloma | |
| IDH1 | Cancer Gene | Glioblastoma multiforme (GBM) | |
| IDH2 | Cancer Gene | Glioblastoma multiforme (GBM) | |
| IGF1R | Cancer Gene | Ewing's sarcoma, breast cancer, uveal melanoma, adrenocortical carcinoma, pancreatic cancer | |
| IGF2R | Cancer Gene | Gastrointestinal tumor, liver cancer | |
| IKBKE | Cancer Gene | Breast cancer | |
| IKZF1 | Cancer Gene | Lymphoma, leukemia | |
| INHBA | Cancer Gene | Erythroleukemia, barrett metaplasia, esophageal adenocarcinoma, granulosa cell tumor, sex cord-stromal tumor, lung adenocarcinoma, pheochromocytoma, krukenberg tumor, ovarian cancer | |
| IRS2 | Cancer Gene | Hyperinsulinemia, uterine leiomyosarcoma | |
| JAK1 | Cancer Gene | Leukemia, ovarian cancer, breast cancer | |
| JAK3 | Cancer Gene | Acute lymphoblastic leukemia (ALL) | |
| JUN | Cancer Gene | Skin cancer, leukemia | |
| KDR | Cancer Gene | Non-small cell lung cancer (NSCLC), angiosarcoma | |
| LRP1B | Cancer Gene | Lung cancer, gastric cancer, esophageal cancer | |
| LTK | Cancer Gene | Lymphoma, breast cancer | |
| MAP2K1 | Cancer Gene | Prostate cancer, gastric cancer | |
| MAP2K2 | Cancer Gene | Pancreatic cancer, intestinal tumor | |
| MAP2K4 | Cancer Gene | Pancreatic cancer, breast cancer, colorectal cancer | |
| MCL1 | Cancer Gene | Multiple myeloma, leukemia, lymphoma | |
| MDM2 | Cancer Gene | Sarcoma, glioma, colorectal cancer | |
| MDM4 | Cancer Gene | Glioblastoma multiforme (GBM), bladder cancer, retinoblastoma | |
| MEN1 | Cancer Gene | Parathyroid tumor | |
| MITF | Cancer Gene | Melanoma | |
| MLH1 | Cancer Gene | Colorectal cancer, endometrial cancer, ovarian cancer, CNS cancer | |

TABLE 5A-continued

List of exemplary selected genes and variants, associated cancer types, and priority codons for multiplex analysis

| Hugo Gene | Gene Category | Cancer Types | Priority Codons |
|---|---|---|---|
| MPL | Cancer Gene | Myeloproliferative disorder (MPD) | |
| MRE11A | Cancer Gene | Breast cancer, lymphoma | |
| MSH2 | Cancer Gene | Colorectal cancer, endometrial cancer, ovarian cancer | |
| MSH6 | Cancer Gene | Colorectal cancer | |
| MTOR | Cancer Gene | Lymphoma lung cancer, renal cancer, clear cell carcinoma, glioma | |
| MUTYH | Cancer Gene | Colorectal cancer | |
| MYCL1 | Cancer Gene | Small cell lung cancer (SCLC) | |
| MYCN | Cancer Gene | Neuroblastoma | |
| NF2 | Cancer Gene | Meningioma, acoustic neuroma, renal cancer | |
| NKX2-1 | Cancer Gene | Lung cancer, thyroid cancer, adenocarcinoma | |
| NTRK1 | Cancer Gene | Papillary thyroid cancer | |
| NTRK3 | Cancer Gene | Congenital fibrosarcoma, secretory breast cancer | |
| PAK3 | Cancer Gene | Lung cancer | |
| PAX5 | Cancer Gene | Non-Hodgkin Lymphoma (NHL), acute lymphoblastic leukemia (ALL, e.g., B-cell ALL) | |
| PDGFRB | Cancer Gene | Myeloproliferative disorder (MPD), acute myeloid leukemia (AML), chronic myeloid leukemia (CML), chronic myelomonocytic leukemia (CMML) | |
| PIK3R1 | Cancer Gene | Glioblastoma, ovarian cancer, colorectal cancer | |
| PKHD1 | Cancer Gene | Pancreatic cancer | |
| PLCG1 | Cancer Gene | Head and neck cancer, leukemia | |
| PRKDC | Cancer Gene | Glioma, glioblastoma, gastric cancer, ovarian cancer | |
| PTCH1 | Cancer Gene | Skin basal cell, medulloblastoma | |
| PTPN11 | Cancer Gene | Juvenile myelomonocytic leukemia (JMML), acute myeloid leukemia (AML), myelodysplastic syndromes (MDS) | |
| PTPRD | Cancer Gene | Lung cancer, cutaneous squamous cell carcinoma, glioblastoma, neuroblastoma | |
| RAF1 | Cancer Gene | Pilocytic astrocytoma | |
| RARA | Cancer Gene | Leukemia | |
| RICTOR | Cancer Gene | Colon cancer, lymphoma, glioma, breast cancer | |
| RPTOR | Cancer Gene | Breast cancer, prostate cancer | |
| RUNX1 | Cancer Gene | Acute myeloid leukemia (AML), pre-B-cell acute lymphoblastic leukemia (preB-ALL), T-cell acute lymphoblastic leukemia (T-ALL) | |
| SMAD2 | Cancer Gene | esophageal squamous cell carcinoma (ESCC) | |
| SMAD3 | Cancer Gene | Skin cancer, choriocarcinoma | |
| SMAD4 | Cancer Gene | Pancreatic cancer, colon cancer | |
| SMARCA4 | Cancer Gene | Non-small cell lung cancer (NSCLC) | |
| SMARCB1 | Cancer Gene | Malignant rhabdoid | |
| SMO | Cancer Gene | Skin basal cell cancer | |
| SOX10 | Cancer Gene | Oligodendroglioma | |
| SOX2 | Cancer Gene | Embryonal carcinoma, germ cell tumor | |
| SRC | Cancer Gene | Sarcoma, colon cancer, breast cancer | |
| STK11 | Cancer Gene | Non-small cell lung cancer (NSCLC), pancreatic cancer | |
| TBX22 | Cancer Gene | Breast cancer | |
| TET2 | Cancer Gene | Myelodysplastic syndromes (MDS) | |
| TGFBR2 | Cancer Gene | Lung cancer, gastric cancer, colon cancer | |
| TMPRSS2 | Cancer Gene | Prostate cancer | |
| TOP1 | Cancer Gene | Acute myeloid leukemia (AML) | |
| TSC1 | Cancer Gene | Hamartoma, renal cell cancer | |
| TSC2 | Cancer Gene | Hamartoma, renal cell cancer | |
| USP9X | Cancer Gene | Leukemia | |
| VHL | Cancer Gene | Renal cancer, hemangioma, pheochromocytoma | |

TABLE 5A-continued

List of exemplary selected genes and variants, associated cancer types, and priority codons for multiplex analysis

| Hugo Gene | Gene Category | Cancer Types | Priority Codons |
|---|---|---|---|
| WT1 | Cancer Gene | Wilms' tumor, desmoplastic small round cell tumor | |
| ABCB1 | PGx Gene | | |
| ABCC2 | PGx Gene | | |
| ABCC4 | PGx Gene | | |
| ABCG2 | PGx Gene | | |
| C1orf144 | PGx Gene | | |
| CYP1B1 | PGx Gene | | |
| CYP2C19 | PGx Gene | | |
| CYP2C8 | PGx Gene | | |
| CYP2D6 | PGx Gene | | |
| CYP3A4 | PGx Gene | | |
| CYP3A5 | PGx Gene | | |
| DPYD | PGx Gene | | |
| ERCC2 | PGx Gene | | |
| ESR2 | PGx Gene | | |
| FCGR3A | PGx Gene | | |
| GSTP1 | PGx Gene | | |
| ITPA | PGx Gene | | |
| LRP2 | PGx Gene | | |
| MAN1B1 | PGx Gene | | |
| MTHFR | PGx Gene | | |
| NQO1 | PGx Gene | | |
| NRP2 | PGx Gene | | |
| SLC19A1 | PGx Gene | | |
| SLC22A2 | PGx Gene | | |
| SLCO1B3 | PGx Gene | | |
| SOD2 | PGx Gene | | |
| SULT1A1 | PGx Gene | | |
| TPMT | PGx Gene | | |
| TYMS | PGx Gene | | |
| UGT1A1 | PGx Gene | | |
| UMPS | PGx Gene | | |

"Priority 1" refers to the highest priority of selected genes or gene products.

"Cancer Genes" refer to cancer-associated genes or gene products of less priority relative to Priority 1.

"PGx Genes" refers to genes that are important for pharmacogenetics and pharmacogenomics (PGx).

TABLE 5B

Additional exemplary selected genes and variants, associated cancer types, priority codons, actionability category, and potential therapies

| Hugo Gene | Gene Category | Cancer Types | Priority Codons | Actionability Category | Reason |
|---|---|---|---|---|---|
| ASXL1 | Priority 1 | Mutiple myeloma (MM) | | D | Prognostic (neg MDS) |
| BACH1 | Priority 1 | Breast | | C | PARP Inhibitors |
| BAP1 | Priority 1 | Uveal melanoma, breast, NSCLC | | C | PARP Inhibitors |
| BARD1 | Priority 1 | Breast | | C | PARP Inhibitors |
| BLM | Priority 1 | Leukemia, lymphoma, skin squamous cell, other cancers | | C | |
| BRIP1 | Priority 1 | Acute myeloid leukemia (AML), leukemia, breast | | C | PARP Inhibitors |
| CDKN1B | Priority 1 | Breast | | D | |
| CREBBP | Priority 1 | Acute lymphoblastic leukemia (ALL), AML, DLBCL, B-cell non-Hodgkin's lymphoma (B-NHL) | | D | |
| DDR2 | Priority 1 | NSCLC | | C | Dasatinib |
| EMSY | Priority 1 | Breast | | C | PARP Inhibitors |
| FANCC | Priority 1 | AML, leukemia | | C | PARP inhibitor |
| FANCD2 | Priority 1 | AML, leukemia | | C | PARP inhibitor |
| FANCE | Priority 1 | AML, leukemia | | C | PARP inhibitor |
| FANCF | Priority 1 | AML, leukemia | | C | PARP inhibitor |
| FANCG | Priority 1 | AML, leukemia | | C | PARP inhibitor |
| FANCL | Priority 1 | AML, leukemia | | C | PARP inhibitor |
| HGF | Priority 1 | MM | | C | Resistance |

TABLE 5B-continued

Additional exemplary selected genes and variants, associated cancer types, priority codons, actionability category, and potential therapies

| Hugo Gene | Gene Category | Cancer Types | Priority Codons | Actionability Category | Reason |
|---|---|---|---|---|---|
| NFKB1 | Priority 1 | Breast | | D | Possible POOR PROGNOSIS |
| NOTCH2 | Priority 1 | Marginal zone lymphoma, DLBCL | | D | — |
| PALB2 | Priority 1 | Wilms tumor, medulloblastoma, AML, breast | | C | PARP Inhibitors |
| PBRM1 | Priority 1 | Clear cell renal carcinoma, breast | | E | HDAC inhibitors? |
| PDK1 | Priority 1 | NSCLC | | C | PDK1 inhibitors |
| PIK3R2 | Priority 1 | NSCLC | | C | PI3K-PATHWAY INHIBITORS |
| RAD50 | Priority 1 | Breast | | C | PARP Inhibitors |
| RAD51 | Priority 1 | Breast | | C | PARP Inhibitors |
| ROS1 | Priority 1 | Glioblastoma, NSCLC | | C | |
| SF3B1 | Priority 1 | MDS, CML, ALL, pancreatic, breast | | E | |
| SPOP | Priority 1 | Malignant melanoma | | E | |
| ACVR1B | Cancer Gene | Pancreas, breast | | E | |
| ALOX12B | Cancer Gene | Mutiple myeloma (MM) | | E | |
| ATRX | Cancer Gene | Pancreatic neuroendocrine tumors | | E | |
| AXL | Cancer Gene | Non small cell lung cancer (NSCLC), MM | | E | |
| BCOR | Cancer Gene | Breast | | E | |
| BCORL1 | Cancer Gene | Breast | | E | |
| C17orf39 | Cancer Gene | Breast | | E | |
| CASP8 | Cancer Gene | Breast | | E | |
| CBFB | Cancer Gene | AML | | E | |
| CD22 | Cancer Gene | NSCLC, breast | | E | |
| CD79A | Cancer Gene | Diffuse large B-cell lymphoma (DLBCL) | | E | |
| CD79B | Cancer Gene | DLBCL | | E | |
| CDC73 | Cancer Gene | Parathyroid | | E | |
| CDK12 | Cancer Gene | Ovarian | | E | |
| CHUK | Cancer Gene | Colorectal | | E | |
| CRBN | Cancer Gene | Upper aerodigestive tract | | E | |
| CSF1R | Cancer Gene | NSCLC | | E | |
| CTCF | Cancer Gene | Breast | | E | |
| CTNNA1 | Cancer Gene | Breast | | E | |
| CUL4A | Cancer Gene | Leukemia | | E | |
| CUL4B | Cancer Gene | Leukemia | | E | |
| CYP17A1 | Cancer Gene | Breast | | E | |
| DAXX | Cancer Gene | Pancreatic neuroendocrine tumors | | E | |
| DIS3 | Cancer Gene | MM | | E | |
| EP300 | Cancer Gene | Colorectal, breast, pancreatic, AML, ALL, DLBCL | | E | |
| ERCC2 | Cancer Gene | Skin basal cell, skin squamous cell, melanoma | | E | |
| FAM46C | Cancer Gene | MM | | E | |
| FGF1 | Cancer Gene | Breast | | E | |
| FGF10 | Cancer Gene | Breast | | E | |
| FGF12 | Cancer Gene | Breast | | E | |
| FGF14 | Cancer Gene | Breast | | E | |
| FGF19 | Cancer Gene | Breast | | E | |
| FGF23 | Cancer Gene | Breast | | E | |
| FGF3 | Cancer Gene | Breast | | E | |
| FGF4 | Cancer Gene | Breast | | E | |
| FGF6 | Cancer Gene | Breast | | E | |
| FGF7 | Cancer Gene | Breast | | E | |
| FOXL2 | Cancer Gene | Granulosa-cell tumour of the ovary | 134 | E | |
| GATA2 | Cancer Gene | AML, Chronic Myeloid Leukemia (CML, blast transformation) | | E | |
| GATA3 | Cancer Gene | Breast | | E | |
| GRAF | Cancer Gene | AML, myelodysplastic syndrome (MDS) | | E | |
| GRIN2A | Cancer Gene | Malignant melanoma | | E | |
| GSK3B | Cancer Gene | NSCLC | | E | |
| HLA-A | Cancer Gene | MM | | E | |
| IGF1 | Cancer Gene | Breast | | E | |
| IGF2 | Cancer Gene | Breast | | E | |
| IL7R | Cancer Gene | T-cell acute lymphoblastic leukemia (T-ALL) | | E | |
| INSR | Cancer Gene | NSCLC, glioblastoma, gastric | | E | |
| IRF4 | Cancer Gene | Multiple myeloma (MM) | | E | |

TABLE 5B-continued

Additional exemplary selected genes and variants, associated cancer types, priority codons, actionability category, and potential therapies

| Hugo Gene | Gene Category | Cancer Types | Priority Codons | Actionability Category | Reason |
|---|---|---|---|---|---|
| KDM4C | Cancer Gene | Ovarian, breast | | E | |
| KDM5A | Cancer Gene | AML | | E | |
| KDM6A | Cancer Gene | Renal, oesophageal squamous cell carcinoma (SCC), MM | | E | |
| KEAP1 | Cancer Gene | NSCLC | | E | |
| KLHL6 | Cancer Gene | Chronic lymphocytic leukaemia (CLL) | | E | |
| LMO1 | Cancer Gene | T-cell acute lymphoblastic leukemia (T-ALL), neuroblastoma | | E | |
| LRP6 | Cancer Gene | NSCLC, malignant melanoma | | E | |
| LRRK2 | Cancer Gene | Ovarian, NSCLC | | E | |
| MAGED1 | Cancer Gene | MM | | E | |
| MAP3K1 | Cancer Gene | Breast | | E | |
| MAP3K13 | Cancer Gene | Breast | | E | |
| MLL2 | Cancer Gene | Medulloblastoma, renal | | E | |
| MLST8 | Cancer Gene | Breast | | E | |
| MYD88 | Cancer Gene | Activated B cell-like-DLBCL (ABC-DLBCL) | | E | |
| MYST3 | Cancer Gene | Breast | | E | |
| NCOR1 | Cancer Gene | Breast | | E | |
| NFE2L2 | Cancer Gene | NSCLC, head and neck squamous cell carcinoma (HNSCC) | | E | |
| NFKBIA | Cancer Gene | Breast | | E | |
| NOTCH3 | Cancer Gene | NSCLC, breast | | E | |
| NOTCH4 | Cancer Gene | NSCLC, breast | | E | |
| NSD1 | Cancer Gene | AML | | E | |
| NTRK2 | Cancer Gene | Renal, NSCLC | | E | |
| NUP93 | Cancer Gene | Breast | | E | |
| PAK7 | Cancer Gene | NSCLC, malignant melanoma | | E | |
| PHLPP2 | Cancer Gene | Ovarian, glioblastoma, NSCLC | | E | |
| PHOX2B | Cancer Gene | Neuroblastoma | | E | |
| PIK3C2G | Cancer Gene | NSCLC | | E | |
| PIK3C3 | Cancer Gene | NSCLC | | E | |
| PIK3CG | Cancer Gene | NSCLC | | E | |
| PNRC1 | Cancer Gene | MM | | E | |
| PRDM1 | Cancer Gene | DLBCL | | E | |
| PRKAR1A | Cancer Gene | Adrenal gland, thyroid | | E | |
| PRSS8 | Cancer Gene | Breast | | E | |
| PTCH2 | Cancer Gene | Malignant melanoma | | E | |
| PTK2 | Cancer Gene | NSCLC, glioblastoma | | E | |
| PTK2B | Cancer Gene | NSCLC, breast | | E | |
| REL | Cancer Gene | Hodgkin Lymphoma | | E | |
| RHEB | Cancer Gene | NSCLC, colorectal | | E | |
| ROCK1 | Cancer Gene | Breast | | E | |
| RUNXT1 | Cancer Gene | NSCLC, colorectal | | E | |
| SETD2 | Cancer Gene | Clear cell renal carcinoma | | E | |
| SH2B3 | Cancer Gene | Myelodysplastic syndrome (MDS) | | E | |
| SOCS1 | Cancer Gene | DLBCL | | E | |
| SPEN | Cancer Gene | Adenoid cystic carcinoma | | E | |
| STAG2 | Cancer Gene | Glioblastoma | | E | |
| STAT3 | Cancer Gene | Breast | | E | |
| STAT4 | Cancer Gene | Breast | | E | |
| STK12 | Cancer Gene | PNET, NSCLC | | E | |
| SUFU | Cancer Gene | Medulloblastoma | | E | |
| TBX23 | Cancer Gene | Breast | | E | |
| TBX3 | Cancer Gene | Breast | | E | |
| TNFAIP3 | Cancer Gene | Marginal zone B-cell lymphomas, Hodgkin's lymphoma, primary mediastinal B cell lymphoma | | E | |
| TNFRSF14 | Cancer Gene | Follicular lymphoma | | E | |
| TNFRSF17 | Cancer Gene | Intestinal T-cell lymphoma | | E | |
| TNKS | Cancer Gene | NSCLC | | E | |
| TNKS2 | Cancer Gene | Melanoma, breast | | E | |
| TRRAP | Cancer Gene | Colorectal, glioblastoma | | E | |
| TYK2 | Cancer Gene | NSCLC, breast | | E | |
| XBP1 | Cancer Gene | MM | | E | |
| XPO1 | Cancer Gene | Chronic lymphocytic leukaemia (CLL) | | E | |
| ZNF217 | Cancer Gene | Breast | | E | |
| ZNF703 | Cancer Gene | Breast | | E | |

The actionability categories are classified as described below. Table 6 provides a summary of the application of the different categories to exemplary alterations in different cancer types.

Category A: Approved/standard alterations that predict sensitivity or resistance to approved/standard therapies
  KRAS G13D in metastatic colon cancer
  ERBB2 amplification in breast cancer
  EGFR L858R in non small cell lung cancer Category B: Alterations that are inclusion or exclusion criteria for specific experimental therapies
  KRAS G13D in colon cancer, lung cancer, or breast cancer
  BRAF V600E in melanoma, colon cancer, or lung cancer
  NRAS Q61K in melanoma
  PIK3CA H1047R in breast cancer
  FGFR1 amplification in breast cancer
  PTEN biallelic inactivation in breast cancer
  BRCA1 biallelic inactivation in breast cancer or pancreatic cancer Category C: Alterations with limited evidence (early clinical data, conflicting clinical data, pre-clinical data, theoretical) that predict sensitivity or resistance to standard or experimental therapies
  KRAS Q61H in colon cancer (early clinical)
  PIK3CA H1047R in breast cancer (conflicting clinical)
  BRAF V600E in colon cancer (conflicting clinical)
  ERBB2 mutation or amplification in lung cancer (case reports)
  BRAF D594G in lung cancer (pre-clinical)
  FGFR1 amplification in breast cancer (pre-clinical)
  ATM biallelic inactivation in breast cancer (pre-clinical)
  TSC1 biallelic inactivation in colon cancer (pre-clinical)
  ATR biallelic inactivation in breast cancer (theoretical)
  BRAF V600E mutation in sarcoma (theoretical)

Category D: Alterations with prognostic or diagnostic utility in a particular subtype of cancer
  MSH2 biallelic inactivation in colon cancer (strong clinical evidence)
  BRAF V600E in colon cancer (strong clinical evidence)
  KRAS G13D in lung cancer (strong clinical evidence)
  BRCA1 inactivation in breast cancer (strong clinical evidence)

Category E: Alterations with clear biological significance in cancer (i.e. driver mutations) without clear clinical implications
  APC biallelic inactivation in colon cancer
  TP53 biallelic inactivation in breast cancer
  MITF amplification in melanoma
  ARID1A in ovarian cancer Category F: Alterations without known biological significance in cancer
  Novel alterations in known cancer genes
  Targets of therapy
  Orthologues of known cancer genes

TABLE 6

Exemplary Classification of Alterations in Different Cancer Types

|  |  | A | B | C | D | E |
|---|---|---|---|---|---|---|
| KRAS G13D | Colon Cancer | x | x |  | x | x |
| KRAS G13D | Lung Cancer |  | x |  | x | x |
| KRAS G13D | Breast Cancer |  | x |  |  | x |
| NRAS Q61K | Melanoma |  | x | x |  | x |
| KRAS Q61H | Colon Cancer |  |  | x | x |  |
| BRAF V600E | Melanoma |  | x |  |  | x |
| BRAF V600E | Colon Cancer |  | x | x | x | x |
| BRAF V600E | Lung Cancer |  | x |  |  | x |
| BRAF D594G | Lung Cancer |  |  | x |  | x |
| PIK3CA H1047R | Breast Cancer |  | x | x |  | x |
| PIK3CA H1047R | Colon Cancer |  | x | x |  | x |
| EGFR L858R | Lung Cancer | x |  |  |  | x |
| EGFR T790M | Lung Cancer | x | x |  |  | x |
| ERBBA Amplification | Breast Cancer | x |  |  |  | x |
| BRCA1 biallelic inactivation | Breast Cancer |  | x | x | x | x |
| BRCA2 biallelic inactivation | Pancreatic Cancer |  | x | x | x | x |
| ATM biallelic inactivation | Breast Cancer |  |  | x |  | x |
| TSC biallelec inactivation | Colon Cancer |  |  | x |  | x |
| PTEN biallelic inactivation | Colon Cancer |  |  | x |  | x |
| PTEN biallelic inactivation | Breast Cancer |  | x | x |  | x |
| VHL biallelic inactivation | Kidney Cancer |  |  |  | x | x |
| MSH2 biallelic inactivation | Colon Cancer |  |  |  | x | x |
| ATR bialleic inactiation | Breast Cancer |  |  | x |  | x |
| MYC amplification | Breast Cancer |  |  | x |  | x |

TABLE 7

Exemplary selected genes associated with pharmacogenetics and pharmacogenomics (PGx).

| Gene | Locus | Mutation | Effect |
|---|---|---|---|
| ABCB1 | chr7: 86976581 | 3853C > T | Better survival in Asian AML treated with Ida/AraC; Survival in breast cancer patients treated with paclitaxel |
| ABCB1 | chr7: 86998554 | 2677G > T/A | Response to taxanes, platinums and GI toxicity; Better survival in Asian AML treated with Ida/AraC |
| ABCC2 | chr10: 101610761 |  | Doxcetaxel induced leukopenia |
| ABCC4 | chr13: 94613416 |  | 6MP Toxicity |
| ABCG2 | chr4: 89252551 |  | MTX |
| ABCG2 | chr4: 89271347 | q141K | Diarrhea after gefitinib |
| ABCG2 | chr4: 89274403 |  | MTX |
| C1orf144 | chr1: 16578662 |  | Toxicity from daunorubicin |
| CYP1B1 | chr2: 38151707 | CYP1B1*3 | Toxicity from daunorubicin; Survival in breast cancer patients treated with paclitaxel |

TABLE 7-continued

Exemplary selected genes associated with pharmacogenetics and pharmacogenomics (PGx).

| Gene | Locus | Mutation | Effect |
|---|---|---|---|
| CYP2C19 | chr10: 96509051 | CYP2C19*17 | Improved benefit from tamoxifen |
| CYP2C19 | chr10: 96511647 | CYP2C19*17 | Improved benefit from tamoxifen |
| CYP2C8 | chr10: 96786964 | 461delV | Paclitexel metabolism |
| CYP2C8 | chr10: 96788739 | K399R | Paclitexel metabolism |
| CYP2C8 | chr10: 96808096 | | Paclitexel metabolism |
| CYP2C8 | chr10: 96808109 | | Paclitexel metabolism |
| CYP2C8 | chr10: 96817020 | | Paclitexel metabolism |
| CYP2D6 | chr22: 40853554 | CYP2D6: 3183 G > A | CYP2D6*29, present in Tanzanians |
| CYP2D6 | chr22: 40853749 | CYP2D6: 2988 G > A | CYP2D6*41 (IM) |
| CYP2D6 | chr22: 40853887 | CYP2D6: 2850 C > T | CYP2D6*2 (EM) |
| CYP2D6 | chr22: 40854122 | CYP2D6: 2613-2615 del AGA | CYP2D6*9 (unclear function?) |
| CYP2D6 | chr22: 40854188 | CYP2D6: 2549 del A | CYP2D6*3 |
| CYP2D6 | chr22: 40854891 | CYP2D6: 1846 G > A | CYP2D6*4 |
| CYP2D6 | chr22: 40855030 | CYP2D6: 1707 del T | CYP2D6*6 |
| CYP2D6 | chr22: 40855078 | CYP2D6: 1659G > A | CYP2D6*29, present in Tanzanians |
| CYP2D6 | chr22: 40855716 | CYP2D6: 1023 C > T | Present in CYP2D6*17 |
| CYP2D6 | chr22: 40856638 | CYP2D6: 100C > T | Present in CYP2D6*10 (casuative) and *4 (associated) |
| CYP3A4 | chr7: 99196395 | | |
| CYP3A4 | chr7: 99196460 | | |
| CYP3A4 | chr7: 99197606 | | |
| CYP3A4 | chr7: 99204017 | | |
| CYP3A4 | chr7: 99204029 | CYP3A4*16B | Paclitaxel metabolism in Japanse |
| CYP3A4 | chr7: 99205328 | | |
| CYP3A4 | chr7: 99205363 | | |
| CYP3A4 | chr7: 99219597 | | |
| CYP3A4 | chr7: 99220032 | CYP3A4*1B | Greater clearance of docetaxel |
| CYP3A5 | chr7: 99088330 | | |
| CYP3A5 | chr7: 99100771 | | |
| CYP3A5 | chr7: 99108475 | | |
| DPYD | chr1: 97688202 | DPYD*2A | Toxicity to 5FU |
| DPYD | chr1: 97753983 | DPYD*5 | Toxicity to 5FU |
| DPYD | chr1: 97937679 | 496A > G | 5FU, Xeloda toxicity |
| DPYD | chr1: 98121473 | DPYD*9A | Toxicity to 5FU |
| ERCC2 | chr19: 50546759 | 2251A > C | Relapse after 5FU in Asians |
| ESR1 | chr6: 152205074 | | Tamoxifen induced hypercholesterolemia |
| ESR2 | chr14: 63769569 | | Tamoxifen induced hypercholesterolemia |
| FCGR3A | chr1: 159781166 | V158F | Response to cetuximab |
| FGFR4 | chr5: 176452849 | GLY388ARG | |
| GSTP1 | chr11: 67109265 | I105V | Resistance to multiple chemotherapies |
| GSTP1 | chr11: 67110155 | A114V | Unclear, linkage disequlibrium with I105V |
| ITPA | chr20: 3141842 | | 6MP Toxicity |
| LRP2 | chr2: 169719231 | | Associated with ototoxicity from cisplatin |
| MAN1B1 | chr9: 139102689 | | Toxicity from daunorubicin |
| MTHFR | chr1: 11777044 | | MTX |
| MTHFR | chr1: 11777063 | | MTX |
| MTHFR | chr1: 11778965 | 677C > T | MTX |
| NQO1 | chr16: 68302646 | NQO1*2 | Rapid degradation (cisplatin, doxorubicin); poor survival in breast cancer treated with anthracyclines |
| NRP2 | chr2: 206360545 | | Toxicity from daunorubicin |
| SLC19A1 | chr21: 45782222 | | MTX |
| SLC22A2 | chr6: 160590272 | Ala270Ser | Reduced cisplatin nephrotoxicity |
| SLCO1B3 | chr12: 20936961 | | Doxcetaxel induced leukopenia |
| SOD2 | chr6: 160033862 | V16A | Inferior survival in breast cancer treated with cyclophosphamide |
| SULT1A1 | chr16: 28524986 | | |
| SULT1A1 | chr16: 28525015 | | |
| SULT1A1 | chr16: 28528073 | | |
| SULT1A1 | chr16: 28528301 | | |
| TMPT | chr6: 18247207 | TPMT*3B | Purine toxicity |
| TPMT | chr6: 18238897 | | 6MP Toxicity |
| TPMT | chr6: 18238991 | | 6MP Toxicity |
| TPMT | chr6: 18251934 | | 6MP Toxicity |
| TYMS | chr18: 647646 | 28bp tandem repeat | Toxicity to 5FU |

TABLE 7-continued

Exemplary selected genes associated with pharmacogenetics and pharmacogenomics (PGx).

| Gene | Locus | Mutation | Effect |
| --- | --- | --- | --- |
| TYMS | chr18: 663451 | 6bp deletion | Toxicity to 5FU |
| UGT1A1 | chr2: 234255266 | | Anemia from irinotecan |
| UGT1A1 | chr2: 234255709 | | thrombocytopenia from irinotecan |
| UGT1A1 | chr2: 234330398 | | UGT1A1*60 |
| UGT1A1 | chr2: 234330521 | | UGT1A1*93 |
| UGT1A1 | chr2: 234333620 | | UGT1A1*28 |
| UGT1A1 | chr2: 234333883 | | UGT1A1*6 |
| UGT1A1 | chr2: 234334358 | | UGT1A1*27 |
| UMPS | chr3: 125939432 | Gly213Ala | Toxicity to 5FU |

TABLE 8

Exemplary selected genes associated with translocation mutations in solid tumors

| Hugo Gene | Gene Category | Translocation Partner | Cancer Types |
| --- | --- | --- | --- |
| ACSL3 | Priority 1 | ETV1 | prostate |
| ALK | Priority 1 | NPM1, TPM3, TFG, TPM4, ATIC, CLTC, MSN, ALO17, CARS, EML4 | ALCL, NSCLC, Neuroblastoma |
| BRAF | Priority 1 | AKAP9, KIAA1549 | melanoma, colorectal, papillary thyroid, borderline ov, Non small-cell lung cancer (NSCLC), cholangiocarcinoma, pilocytic astrocytoma |
| C15orf21 | Priority 1 | ETV1 | prostate |
| CANT1 | Priority 1 | ETV4 | prostate |
| CCND1 | Priority 1 | IGH, FSTL3 | CLL, B-ALL, breast |
| DDX5 | Priority 1 | ETV4 | prostate |
| ELK4 | Priority 1 | SLC45A3 | prostate |
| EML4 | Priority 1 | ALK | NSCLC |
| EP300 | Priority 1 | MLL, RUNXBP2 | colorectal, breast, pancreatic, AML |
| ERG | Priority 1 | EWSR1, TMPRSS2, ELF4, FUS, HERPUD1 | Ewing sarcoma, prostate, AML |
| ETV1 | Priority 1 | EWSR1, TMPRSS2, SLC45A3, C15orf21, HNRNPA2B1. ACSL3 | Ewing sarcoma, prostate |
| ETV4 | Priority 1 | EWSR1, TMPRSS2, DDX5, KLK2, CANT1 | Ewing sarcoma, Prostate carcinoma |
| ETV5 | Priority 1 | TMPRSS2, SCL45A3 | Prostate |
| FGFR3 | Priority 1 | IGH@, ETV6 | bladder, MM, T-cell lymphoma |
| HERPUD1 | Priority 1 | ERG | prostate |
| HNRNPA2B1 | Priority 1 | ETV1 | prostate |
| KLK2 | Priority 1 | ETV4 | prostate |
| RET | Priority 1 | H4, PRKAR1A, NCOA4, PCM1, GOLGA5, TRIM33, KTN1, TRIM27, HOOK3 | medullary thyroid, papillary thyroid, pheochromocytoma |
| ROS1 | Priority 1 | GOPC, ROS1 | glioblastoma, NSCLC |
| SLC45A3 | Priority 1 | ETV1, ETV5, ELK4, ERG | prostate |
| TMPRSS2 | Priority 1 | ERG, ETV1, ETV4, ETV5 | prostate |
| AKAP9 | | BRAF | papillary thyroid |
| ASPSCR1 | | TFE3 | alveolar soft part sarcoma |
| ATF1 | | EWSR1, FUS | malignant melanoma of soft parts, angiomatoid fibrous histiocytoma |
| BRD3 | | NUT | lethal midline carcinoma of young people |
| BRD4 | | NUT | lethal midline carcinoma of young people |
| C12orf9 | | LPP | lipoma |
| CD74 | | ROS1 | NSCLC |
| CDH11 | | USP6 | aneurysmal bone cysts |
| CHCHD7 | | PLAG1 | salivary adenoma |
| CHN1 | | TAF15 | extraskeletal myxoid chondrosarcoma |
| CIC | | DUX4 | soft tissue sarcoma |
| CMKOR1 | | HMGA2 | lipoma |
| COL1A1 | | PDGFB, USP6 | dermatofibrosarcoma protuberans, aneurysmal bone cyst |
| COX6C | | HMGA2 | uterine leiomyoma |
| CREB1 | | EWSR1 | clear cell sarcoma, angiomatoid fibrous histiocytoma |
| CREB3L2 | | FUS | fibromyxoid sarcoma |
| CRTC3 | | MAML2 | salivary gland mucoepidermoid |

TABLE 8-continued

Exemplary selected genes associated with translocation mutations in solid tumors

| Hugo Gene | Gene Category | Translocation Partner | Cancer Types |
|---|---|---|---|
| CTNNB1 | | PLAG1 | colorectal, ovarian, hepatoblastoma, others, pleomorphic salivary adenoma |
| D10S170 | | RET, PDGFRB | papillary thyroid, CML |
| DDIT3 | | FUS | liposarcoma |
| DUX4 | | CIC | soft tissue sarcoma |
| ELKS | | RET | papillary thyroid |
| ETV6 | | NTRK3, RUNX1, PDGFRB, ABL1, MN1, ABL2, FACL6, CHIC2, ARNT, JAK2, EVI1, CDX2, STL, HLXB9, MDS2, PER1, SYK, TTL, FGFR3, PAX5 | congenital fibrosarcoma, multiple leukemia and lymphoma, secretory breast, MDS, ALL |
| EWSR1 | | FLI1, ERG, ZNF278, NR4A3, FEV, ATF1, ETV1, ETV4, WT1, ZNF384, CREB1, POU5F1, PBX1 | Ewing sarcoma, desmoplastic small round cell tumor, ALL, clear cell sarcoma, sarcoma, myoepithelioma |
| FEV | | EWSR1, FUS | Ewing sarcoma |
| FLI1 | | EWSR1 | Ewing sarcoma |
| FOXO1A | | PAX3 | alveolar rhabdomyosarcomas |
| FUS | | DDIT3, ERG, FEV, ATF1, CREB3L2 | liposarcoma, AML, Ewing sarcoma, angiomatoid fibrous histiocytoma, fibromyxoid sarcoma |
| GOLGA5 | | RET | papillary thyroid |
| HEI10 | | HMGA2 | uterine leiomyoma |
| HMGA1 | | ? | microfollicular thyroid adenoma, various benign mesenchymal tumors |
| HMGA2 | | LHFP, RAD51L1, LPP, HEI10, COX6C, CMKOR1, NFIB | lipoma |
| HOOK3 | | RET | papillary thyroid |
| JAZF1 | | SUZ12 | endometrial stromal tumours |
| KTN1 | | RET | papillary thyroid |
| LHFP | | HMGA2 | lipoma |
| LIFR | | PLAG1 | salivary adenoma |
| LPP | | HMGA2, MLL, C12orf9 | lipoma, leukemia |
| MAML2 | | MECT1, CRTC3 | salivary gland mucoepidermoid |
| MECT1 | | MAML2 | salivary gland mucoepidermoid |
| MN1 | | ETV6 | AML, meningioma |
| MYB | | NFIB | adenoid cystic carcinoma |
| MYC | | IGK, BCL5, BCL7A, BTG1, TRA, IGH | Burkitt lymphoma, amplified in other cancers, B-CLL |
| NCOA1 | | PAX3 | alveolar rhadomyosarcoma |
| NCOA4 | | RET | papillary thyroid |
| NFIB | | MYB, HGMA2 | adenoid cystic carcinoma, lipoma |
| NONO | | TFE3 | papillary renal cancer |
| NR4A3 | | EWSR1 | extraskeletal myxoid chondrosarcoma |
| NTRK1 | | TPM3, TPR, TFG | papillary thyroid |
| NTRK3 | | ETV6 | congenital fibrosarcoma, Secretory breast |
| NUT | | BRD4, BRD3 | lethal midline carcinoma of young people |
| OMD | | USP6 | aneurysmal bone cysts |
| PAX3 | | FOXO1A, NCOA1 | alveolar rhabdomyosarcoma |
| PAX7 | | FOXO1A | alveolar rhabdomyosarcoma |
| PAX8 | | PPARG | follicular thyroid |
| PBX1 | | TCF3, EWSR1 | pre B-ALL, myoepithelioma |
| PCM1 | | RET, JAK2 | papillary thyroid, CML, MPD |
| PDGFB | | COL1A1 | DFSP |
| PDGFRA | | FIP1L1 | GIST, idiopathic hypereosinophilic syndrome |
| PLAG1 | | TCEA1, LIFR, CTNNB1, CHCHD7 | salivary adenoma |
| POU5F1 | | EWSR1 | sarcoma |
| PPARG | | PAX8 | follicular thyroid |
| PRCC | | TFE3 | papillary renal |
| PRKAR1A | | RET | papillary thyroid |
| PRO1073 | | TFEB | renal cell carcinoma (childhood epithelioid) |
| RAD51L1 | | HMGA2 | lipoma, uterine leiomyoma |
| RAF1 | | SRGAP3 | pilocytic astrocytoma |
| SFPQ | | TFE3 | papillary renal cell |
| SRGAP3 | | RAF1 | pilocytic astrocytoma |
| SS18 | | SSX1, SSX2 | synovial sarcoma |
| SS18L1 | | SSX1 | synovial sarcoma |
| SSX1 | | SS18 | synovial sarcoma |
| SSX2 | | SS18 | synovial sarcoma |
| SSX4 | | SS18 | synovial sarcoma |

TABLE 8-continued

Exemplary selected genes associated with translocation mutations in solid tumors

| Hugo Gene | Gene Category | Translocation Partner | Cancer Types |
|---|---|---|---|
| SUZ12 | | JAZF1 | endometrial stromal tumours |
| TAF15 | | TEC, CHN1, ZNF384 | extraskeletal myxoid chondrosarcomas, ALL |
| TCEA1 | | PLAG1 | salivary adenoma |
| TCF12 | | TEC | extraskeletal myxoid chondrosarcoma |
| TFE3 | | SFPQ, ASPSCR1, PRCC, NONO, CLTC | papillary renal, alveolar soft part sarcoma, renal |
| TFEB | | ALPHA | renal (childhood epithelioid) |
| TFG | | NTRK1, ALK | papillary thyroid, ALCL, NSCLC |
| THRAP3 | | USP6 | aneurysmal bone cysts |
| TPM3 | | NTRK1, ALK | papillary thyroid, ALCL |
| TPR | | NTRK1 | papillary thyroid |
| TRIM27 | | RET | papillary thyroid |
| TRIM33 | | RET | papillary thyroid |
| USP6 | | COL1A1, CDH11, ZNF9, OMD | aneurysmal bone cysts |
| ZNF278 | | EWSR1 | Ewing sarcoma |
| ZNF331 | | ? | follicular thyroid adenoma |
| ZNF9 | | USP6 | aneurysmal bone cysts |

TABLE 9

Exemplary selected genes associated with translocation mutations in hematologic malignancies

| Hugo Gene | Gene Category | Translocation Partner | Cancer Types |
|---|---|---|---|
| ABL1 | Priority 1 | BCR, ETV6, NUP214 | CML, ALL, T-ALL |
| ALK | Priority 1 | NPM1, TPM3, TFG, TPM4, ATIC, CLTC, MSN, ALO17, CARS, EML4 | ALCL, NSCLC, Neuroblastoma |
| BCL2 | Priority 1 | IGH | NHL, CLL |
| BCL6 | Priority 1 | IG loci, ZNFN1A1, LCP1, PIM1, TFRC, MHC2TA, NACA, HSPCB, HSPCA, HIST1H4I, IL21R, POU2AF1, ARHH, EIF4A2, SFRS3 | NHL, CLL |
| CCND1 | Priority 1 | IGH, FSTL3 | CLL, B-ALL, breast |
| CREBBP | Priority 1 | MLL, MORF, RUNXBP2 | AL, AML |
| FGFR1 | Priority 1 | BCR, FOP, ZNF198, CEP1 | MPD, NHL |
| FGFR3 | Priority 1 | IGH, ETV6 | bladder, MM, T-cell lymphoma |
| JAK2 | Priority 1 | ETV6, PCM1, BCR | ALL, AML, MPD, CML |
| MLL | Priority 1 | MLL, MLLT1, MLLT2, MLLT3, MLLT4, MLLT7, MLLT10, MLLT6, ELL, EPS15, AF1Q, CREBBP, SH3GL1, FNBP1, PNUTL1, MSF, GPHN, GMPS, SSH3BP1, ARHGEF12, GAS7, FOXO3A, LAF4, LCX, SEPT6, LPP, CBFA2T1, GRAF, EP300, PICALM, HEAB | AML, ALL |
| PDGFRA | Priority 1 | FIP1L1 | GIST, idiopathic hypereosinophilic syndrome |
| RARA | Priority 1 | PML, ZNF145, TIF1, NUMA1, NPM1 | APL |
| SEPT6 | | MLL | AML |
| ABL2 | | ETV6 | AML |
| AF15Q14 | | MLL | AML |
| AF1Q | | MLL | ALL |
| AF3p21 | | MLL | ALL |
| AF5q31 | | MLL | ALL |
| ALO17 | | ALK | ALCL |
| ARHGEF12 | | MLL | AML |
| ARHH | | BCL6 | NHL |
| ARNT | | ETV6 | AML |
| ATIC | | ALK | ALCL |
| BCL10 | | IGH | MALT |
| BCL11A | | IGH | B-CLL |
| BCL11B | | TLX3 | T-ALL |
| BCL3 | | IGH | CLL |
| BCL5 | | MYC | CLL |
| BCL7A | | MYC | BNHL |
| BCL9 | | IGH, IGL | B-ALL |
| BCR | | ABL1, FGFR1, JAK2 | CML, ALL, AML |

TABLE 9-continued

Exemplary selected genes associated with translocation mutations in hematologic malignancies

| Hugo Gene | Gene Category | Translocation Partner | Cancer Types |
|---|---|---|---|
| BIRC3 | | MALT1 | MALT |
| BTG1 | | MYC | BCLL |
| CARS | | ALK | ALCL |
| CBFA2T1 | | MLL, RUNX1 | AML |
| CBFA2T3 | | RUNX1 | AML |
| CBFB | | MYH11 | AML |
| CBL | | MLL | AML, JMML, MDS |
| CCND2 | | IGL | NHL, CLL |
| CCND3 | | IGH | MM |
| CDK6 | | MLLT10 | ALL |
| CDX2 | | ETV6 | AML |
| CEP1 | | FGFR1 | MPD, NHL |
| CHIC2 | | ETV6 | AML |
| CLTC | | ALK, TFE3 | ALCL, renal |
| CLTCL1 | | ? | ALCL |
| DDX10 | | NUP98 | AML* |
| DDX6 | | IGH | B-NHL |
| DEK | | NUP214 | AML |
| EIF4A2 | | BCL6 | NHL |
| ELF4 | | ERG | AML |
| ELL | | MLL | AL |
| ELN | | PAX5 | B-ALL |
| EP300 | | MLL, RUNXBP2 | colorectal, breast, pancreatic, AML |
| EPS15 | | MLL | ALL |
| ERG | | EWSR1, TMPRSS2, ELF4, FUS, HERPUD1 | Ewing sarcoma, prostate, AML |
| ETV6 | | NTRK3, RUNX1, PDGFRB, ABL1, MN1, ABL2, FACL6, CHIC2, ARNT, JAK2, EVI1, CDX2, STL, HLXB9, MDS2, PER1, SYK, TTL, FGFR3, PAX5 | congenital fibrosarcoma, multiple leukemia and lymphoma, secretory breast, MDS, ALL |
| EVI1 | | RUNX1, ETV6, PRDM16, RPN1 | AML, CML |
| EWSR1 | | FLI1, ERG, ZNF278, NR4A3, FEV, ATF1, ETV1, ETV4, WT1, ZNF384, CREB1, POU5F1, PBX1 | Ewing sarcoma, desmoplastic small round cell tumor, ALL, clear cell sarcoma, sarcoma, myoepithelioma |
| FACL6 | | ETV6 | AML, AEL |
| FCGR2B | | ? | ALL |
| FGFR1OP | | FGFR1 | MPD, NHL |
| FIP1L1 | | PDGFRA | idiopathic hypereosinophilic syndrome |
| FNBP1 | | MLL | AML |
| FOXO3A | | MLL | AL |
| FOXP1 | | PAX5 | ALL |
| FSTL3 | | CCND1 | B-CLL |
| FUS | | DDIT3, ERG, FEV, ATF1, CREB3L2 | liposarcoma, AML, Ewing sarcoma, angiomatoid fibrous histiocytoma, fibromyxoid sarcoma |
| FVT1 | | IGK | B-NHL |
| GAS7 | | MLL | AML* |
| GMPS | | MLL | AML |
| GPHN | | MLL | AL |
| GRAF | | MLL | AML, MDS |
| HCMOGT-1 | | PDGFRB | JMML |
| HEAB | | MLL | AML |
| HIP1 | | PDGFRB | CMML |
| HIST1H4I | | BCL6 | NHL |
| HLF | | TCF3 | ALL |
| HLXB9 | | ETV6 | AML |
| HOXA11 | | NUP98 | CML |
| HOXA13 | | NUP98 | AML |
| HOXA9 | | NUP98, MSI2 | AML* |
| HOXC11 | | NUP98 | AML |
| HOXC13 | | NUP98 | AML |
| HOXD11 | | NUP98 | AML |
| HOXD13 | | NUP98 | AML* |
| HSPCA | | BCL6 | NHL |
| HSPCB | | BCL6 | NHL |
| IGH | | MYC, FGFR3, PAX5, IRTA1, IRF4, CCND1, BCL9, BCL8, BCL6, BCL2, BCL3, BCL10, BCL11A. LHX4, DDX6, NFKB2, PAFAH1B2, PCSK7 | MM, Burkitt lymphoma, NHL, CLL, B-ALL, MALT, MLCLS |
| IGK | | MYC, FVT1 | Burkitt lymphoma, B-NHL |
| IGL | | BCL9, MYC, CCND2 | Burkitt lymphoma |
| IL2 | | TNFRSF17 | intestinal T-cell lymphoma |

TABLE 9-continued

Exemplary selected genes associated with translocation mutations in hematologic malignancies

| Hugo Gene | Gene Category | Translocation Partner | Cancer Types |
|---|---|---|---|
| IL21R | | BCL6 | NHL |
| IRF4 | | IGH | MM |
| IRTA1 | | IGH | B-NHL |
| ITK | | SYK | peripheral T-cell lymphoma |
| KDM5A | | NUP98 | AML |
| LAF4 | | MLL, RUNX1 | ALL, T-ALL |
| LASP1 | | MLL | AML |
| LCK | | TRB | T-ALL |
| LCP1 | | BCL6 | NHL |
| LCX | | MLL | AML |
| LMO1 | | TRD | T-ALL |
| LMO2 | | TRD | T-ALL |
| LPP | | HMGA2, MLL, C12orf9 | lipoma, leukemia |
| LYL1 | | TRB | T-ALL |
| MAF | | IGH | MM |
| MAFB | | IGH | MM |
| MALT1 | | BIRC3 | MALT |
| MDS1 | | RUNX1 | MDS, AML |
| MDS2 | | ETV6 | MDS |
| MHC2TA | | BCL6 | NHL |
| MKL1 | | RBM15 | acute megakaryocytic leukemia |
| MLF1 | | NPM1 | AML |
| MLLT1 | | MLL | AL |
| MLLT10 | | MLL, PICALM, CDK6 | AL |
| MLLT2 | | MLL | AL |
| MLLT3 | | MLL | ALL |
| MLLT4 | | MLL | AL |
| MLLT6 | | MLL | AL |
| MLLT7 | | MLL | AL |
| MN1 | | ETV6 | AML, meningioma |
| MSF | | MLL | AML* |
| MSI2 | | HOXA9 | CML |
| MSN | | ALK | ALCL |
| MTCP1 | | TRA | T cell prolymphocytic leukemia |
| MUC1 | | IGH | B-NHL |
| MYC | | IGK, BCL5, BCL7A, BTG1, TRA, IGH | Burkitt lymphoma, amplified in other cancers, B-CLL |
| MYH11 | | CBFB | AML |
| MYH9 | | ALK | ALCL |
| MYST4 | | CREBBP | AML |
| NACA | | BCL6 | NHL |
| NCOA2 | | RUNXBP2 | AML |
| NFKB2 | | IGH | B-NHL |
| NIN | | PDGFRB | MPD |
| NOTCH1 | | TRB | T-ALL |
| NPM1 | | ALK, RARA, MLF1 | NHL, APL, AML |
| NSD1 | | NUP98 | AML |
| NUMA1 | | RARA | APL |
| NUP214 | | DEK, SET, ABL1 | AML, T-ALL |
| NUP98 | | HOXA9, NSD1, WHSC1L1, DDX10, TOP1, HOXD13, PMX1, HOXA13, HOXD11, HOXA11, RAP1GDS1, HOXC11 | AML |
| OLIG2 | | TRA | T-ALL |
| PAFAH1B2 | | IGH | MLCLS |
| PAX5 | | IGH, ETV6, PML, FOXP1, ZNF521, ELN | NHL, ALL, B-ALL |
| PBX1 | | TCF3, EWSR1 | pre B-ALL, myoepithelioma |
| PCM1 | | RET, JAK2 | papillary thyroid, CML, MPD |
| PCSK7 | | IGH | MLCLS |
| PDE4DIP | | PDGFRB | MPD |
| PDGFRB | | ETV6, TRIP11, HIP1, RAB5EP, H4, NIN, HCMOGT-1, PDE4DIP | MPD, AML, CMML, CML |
| PER1 | | ETV6 | AML, CMML |
| PICALM | | MLLT10, MLL | TALL, AML, |
| PIM1 | | BCL6 | NHL |
| PML | | RARA, PAX5 | APL, ALL |
| PMX1 | | NUP98 | AML |
| PNUTL1 | | MLL | AML |
| POU2AF1 | | BCL6 | NHL |
| PRDM16 | | EVI1 | MDS, AML |
| PSIP2 | | NUP98 | AML |
| RAB5EP | | PDGFRB | CMML |
| RANBP17 | | TRD | ALL |
| RAP1GDS1 | | NUP98 | T-ALL |

TABLE 9-continued

Exemplary selected genes associated with translocation mutations in hematologic malignancies

| Hugo Gene | Gene Category | Translocation Partner | Cancer Types |
|---|---|---|---|
| RBM15 | | MKL1 | acute megakaryocytic leukemia |
| RPL22 | | RUNX1 | AML, CML |
| RPN1 | | EVI1 | AML |
| RUNX1 | | RPL22, MDS1, EVI1, CBFA2T3, CBFA2T1, ETV6, LAF4 | AML, preB-ALL, T-ALL |
| RUNXBP2 | | CREBBP, NCOA2, EP300 | AML |
| SET | | NUP214 | AML |
| SFRS3 | | BCL6 | follicular lymphoma |
| SH3GL1 | | MLL | AL |
| SIL | | TAL1 | T-ALL |
| SSH3BP1 | | MLL | AML |
| STL | | ETV6 | B-ALL |
| SYK | | ETV6, ITK | MDS, peripheral T-cell lymphoma |
| TAF15 | | TEC, CHN1, ZNF384 | extraskeletal myxoid chondrosarcomas, ALL |
| TAL1 | | TRD, SIL | lymphoblastic leukemia/biphasic |
| TAL2 | | TRB | T-ALL |
| TCF3 | | PBX1, HLF, TFPT | pre B-ALL |
| TCL1A | | TRA | T-CLL |
| TCL6 | | TRA | T-ALL |
| TFG | | NTRK1, ALK | papillary thyroid, ALCL, NSCLC |
| TFPT | | TCF3 | pre-B ALL |
| TFRC | | BCL6 | NHL |
| TIF1 | | RARA | APL |
| TLX1 | | TRB, TRD | T-ALL |
| TLX3 | | BCL11B | T-ALL |
| TNFRSF17 | | IL2 | intestinal T-cell lymphoma |
| TOP1 | | NUP98 | AML* |
| TPM3 | | NTRK1, ALK | papillary thyroid, ALCL |
| TPM4 | | ALK | ALCL |
| TRA | | ATL, OLIG2, MYC, TCL1A, TCL6, MTCP1, TCL6 | T-ALL |
| TRB | | HOX11, LCK, NOTCH1, TAL2, LYL1 | T-ALL |
| TRD | | TAL1, HOX11, TLX1, LMO1, LMO2, RANBP17 | T-cell leukemia |
| TRIP11 | | PDGFRB | AML |
| TTL | | ETV6 | ALL |
| WHSC1 | | IGH | MM |
| WHSC1L1 | | NUP98 | AML |
| ZNF145 | | RARA | APL |
| ZNF198 | | FGFR1 | MPD, NHL |
| ZNF384 | | EWSR1, TAF15 | ALL |
| ZNF521 | | PAX5 | ALL |
| ZNFN1A1 | | BCL6 | ALL, DLBL |

Applications of the foregoing methods include using a library of oligonucleotides containing all known sequence variants (or a subset thereof) of a particular gene or genes for sequencing in medical specimens.

In certain embodiments, the method or assay further includes one or more of:
(i) fingerprinting the nucleic acid sample;
(ii) quantifying the abundance of a gene or gene product (e.g., a gene or gene product as described herein) in the nucleic acid sample;
(iii) quantifying the relative abundance of a transcript in the sample;
(iv) identifying the nucleic acid sample as belonging to a particular subject (e.g., a normal control or a cancer patient);
(v) identifying a genetic trait in the nucleic acid sample (e.g., one or more subject's genetic make-up (e.g., ethnicity, race, familial traits));
(vi) determining the ploidy in the nucleic acid sample; determining a loss of heterozygosity in the nucleic acid sample;
(vii) determining the presence or absence of a gene duplication event in the nucleic acid sample;
(viii) determining the presence or absence of a gene amplification event in the nucleic acid sample; or
(ix) determining the level of tumor/normal cellular admixture in the nucleic acid sample.

Nucleic Acid Samples

A variety of tissue samples can be the source of the nucleic acid samples used in the present methods. Genomic or subgenomic nucleic acid (e.g., DNA or RNA) can be isolated from a subject's sample (e.g., a tumor sample, a normal adjacent tissue (NAT), a blood sample, a sample containing circulating tumor cells (CTC) or any normal control)). In certain embodiments, the tissue sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample. In certain embodiments, the tissue sample is a blood sample. In other embodiments, the tissue sample is a bone marrow aspirate (BMA) sample. The isolating step can include flow-sorting of individual chromosomes; and/or micro-dissecting a subject's sample (e.g., a tumor sample, a NAT, a blood sample).

An "isolated" nucleic acid molecule is one which is separated from other nucleic acid molecules which are present in the natural source of the nucleic acid molecule. In certain embodiments, an "isolated" nucleic acid molecule is free of sequences (such as protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, less than about 4 kB, less than about 3 kB, less than about 2 kB, less than about 1 kB, less than about 0.5 kB or less than about 0.1 kB of nucleotide sequences which naturally flank the nucleic acid molecule in genomic DNA of the cell from which the nucleic acid is derived. Moreover, an "isolated" nucleic acid molecule, such as an RNA molecule or a cDNA molecule, can be substantially free of other cellular material or culture medium, e.g., when produced by recombinant techniques, or substantially free of chemical precursors or other chemicals, e.g., when chemically synthesized.

The language "substantially free of other cellular material or culture medium" includes preparations of nucleic acid molecule in which the molecule is separated from cellular components of the cells from which it is isolated or recombinantly produced. Thus, nucleic acid molecule that is substantially free of cellular material includes preparations of nucleic acid molecule having less than about 30%, less than about 20%, less than about 10%, or less than about 5% (by dry weight) of other cellular material or culture medium.

In certain embodiments, the nucleic acid is isolated from an aged sample, e.g., an aged FFPE sample. The aged sample, can be, for example, years old, e.g., 1 year, 2 years, 3 years, 4 years, 5 years, 10 years, 15 years, 20 years, 25 years, 50 years, 75 years, or 100 years old or older.

A nucleic acid sample can be obtained from tissue samples (e.g., a biopsy, a FFPE sample, a blood sample, or a bone marrow aspirate sample) of various sizes. For example, the nucleic acid can be isolated from a tissue sample from 5 to 200 µm, or larger. For example, the tissue sample can measure 5 µm, 10 µm, 20 µm, 30 µm, 40 µm, 50 µm, 70 µm, 100 µm, 110 µm, 120 µm, 150 µm or 200 µm or larger.

Protocols for DNA isolation from a tissue sample are provided in Example 1. Additional methods to isolate nucleic acids (e.g., DNA) from formaldehyde- or paraformaldehyde-fixed, paraffin-embedded (FFPE) tissues are disclosed, e.g., in Cronin M. et al., (2004) *Am J Pathol.* 164(1):35-42; Masuda N. et al., (1999) *Nucleic Acids Res.* 27(22):4436-4443; Specht K. et al., (2001) *Am J Pathol.* 158(2):419-429, Ambion RecoverAll™ Total Nucleic Acid Isolation Protocol (Ambion, Cat. No. AM1975, September 2008), Maxwell® 16 FFPE Plus LEV DNA Purification Kit Technical Manual (Promega Literature #TM349, February 2011), E.Z.N.A.® FFPE DNA Kit Handbook (OMEGA bio-tek, Norcross, GA, product numbers D3399-00, D3399-01, and D3399-02; June 2009), and QIAamp® DNA FFPE Tissue Handbook (Qiagen, Cat. No. 37625, October 2007). RecoverAll™ Total Nucleic Acid Isolation Kit uses xylene at elevated temperatures to solubilize paraffin-embedded samples and a glass-fiber filter to capture nucleic acids. Maxwell® 16 FFPE Plus LEV DNA Purification Kit is used with the Maxwell® 16 Instrument for purification of genomic DNA from 1 to 10 µm sections of FFPE tissue. DNA is purified using silica-clad paramagnetic particles (PMPs), and eluted in low elution volume. The E.Z.N.A.® FFPE DNA Kit uses a spin column and buffer system for isolation of genomic DNA. QIAamp® DNA FFPE Tissue Kit uses QIAamp® DNA Micro technology for purification of genomic and mitochondrial DNA. Protocols for DNA isolation from blood are disclosed, e.g., in the Maxwell® 16 LEV Blood DNA Kit and Maxwell 16 Buccal Swab LEV DNA Purification Kit Technical Manual (Promega Literature #TM333, Jan. 1, 2011).

Protocols for RNA isolation are disclosed, e.g., in the Maxwell® 16 Total RNA Purification Kit Technical Bulletin (Promega Literature #TB351, August 2009).

The isolated nucleic acid samples (e.g., genomic DNA samples) can be fragmented or sheared by practicing routine techniques. For example, genomic DNA can be fragmented by physical shearing methods, enzymatic cleavage methods, chemical cleavage methods, and other methods well known to those skilled in the art. The nucleic acid library can contain all or substantially all of the complexity of the genome. The term "substantially all" in this context refers to the possibility that there can in practice be some unwanted loss of genome complexity during the initial steps of the procedure. The methods described herein also are useful in cases where the nucleic acid library is a portion of the genome, i.e., where the complexity of the genome is reduced by design. In some embodiments, any selected portion of the genome can be used with the methods described herein. In certain embodiments, the entire exome or a subset thereof is isolated.

Methods featured in the invention can further include isolating a nucleic acid sample to provide a library (e.g., a nucleic acid library as described herein). In certain embodiments, the nucleic acid sample includes whole genomic, subgenomic fragments, or both. The isolated nucleic acid samples can be used to prepare nucleic acid libraries. Thus, in one embodiment, the methods featured in the invention further include isolating a nucleic acid sample to provide a library (e.g., a nucleic acid library as described herein). Protocols for isolating and preparing libraries from whole genomic or subgenomic fragments are known in the art (e.g., Illumina's genomic DNA sample preparation kit). In certain embodiments, the genomic or subgenomic DNA fragment is isolated from a subject's sample (e.g., a tumor sample, a normal adjacent tissue (NAT), a blood sample or any normal control)). In one embodiment, the sample (e.g., the tumor or NAT sample) is a preserved specimen. For example, the sample is embedded in a matrix, e.g., an FFPE block or a frozen sample. In certain embodiments, the isolating step includes flow-sorting of individual chromosomes; and/or microdissecting a subject's sample (e.g., a tumor sample, a NAT, a blood sample). In certain embodiments, the nucleic acid sample used to generate the nucleic acid library is less than 5 microgram, less than 1 microgram, or less than 500 ng, less than 200 ng, less than 100 ng, less than 50 ng, less than 10 ng, less than 5 ng, or less than 1 ng.

In still other embodiments, the nucleic acid sample used to generate the library includes RNA or cDNA derived from RNA. In some embodiments, the RNA includes total cellular RNA. In other embodiments, certain abundant RNA sequences (e.g., ribosomal RNAs) have been depleted. In some embodiments, the poly(A)-tailed mRNA fraction in the total RNA preparation has been enriched. In some embodiments, the cDNA is produced by random-primed cDNA synthesis methods. In other embodiments, the cDNA synthesis is initiated at the poly(A) tail of mature mRNAs by priming by oligo(dT)-containing oligonucleotides. Methods for depletion, poly(A) enrichment, and cDNA synthesis are well known to those skilled in the art.

The method can further include amplifying the nucleic acid sample by specific or non-specific nucleic acid amplification methods that are well known to those skilled in the art. In some embodiments, certain embodiments, the nucleic acid sample is amplified, e.g., by whole-genome amplification methods such as random-primed strand-displacement amplification.

In other embodiments, the nucleic acid sample is fragmented or sheared by physical or enzymatic methods and ligated to synthetic adapters, size-selected (e.g., by preparative gel electrophoresis) and amplified (e.g., by PCR). In other embodiments, the fragmented and adapter-ligated group of nucleic acids is used without explicit size selection or amplification prior to hybrid selection.

In other embodiments, the isolated DNA (e.g., the genomic DNA) is fragmented or sheared. In some embodiments, the library includes less than 50% of genomic DNA, such as a subfraction of genomic DNA that is a reduced representation or a defined portion of a genome, e.g., that has been subfractionated by other means. In other embodiments, the library includes all or substantially all genomic DNA.

In some embodiments, the library includes less than 50% of genomic DNA, such as a subfraction of genomic DNA that is a reduced representation or a defined portion of a genome, e.g., that has been subfractionated by other means. In other embodiments, the library includes all or substantially all genomic DNA. Protocols for isolating and preparing libraries from whole genomic or subgenomic fragments are known in the art (e.g., Illumina's genomic DNA sample preparation kit), and are described herein in the Examples. Alternative methods for DNA shearing are described herein as Example 4. For example, alternative DNA shearing methods can be more automatable and/or more efficient (e.g., with degraded FFPE samples). Alternatives to DNA shearing methods can also be used to avoid a ligation step during library preparation.

The methods described herein can be performed using a small amount of nucleic acids, e.g., when the amount of source DNA or RNA is limiting (e.g., even after whole-genome amplification). In one embodiment, the nucleic acid comprises less than about 5 µg, 4 µg, 3 µg, 2 µg, 1 µg, 0.8 µg, 0.7 µg, 0.6 µg, 0.5 µg, or 400 ng, 300 ng, 200 ng, 100 ng, 50 ng, 10 ng, 5 ng, 1 ng, or less of nucleic acid sample. For example, one can typically begin with 50-100 ng of genomic DNA. One can start with less, however, if one amplifies the genomic DNA (e.g., using PCR) before the hybridization step, e.g., solution hybridization. Thus it is possible, but not essential, to amplify the genomic DNA before hybridization, e.g., solution hybridization.

The nucleic acid sample used to generate the library can also include RNA or cDNA derived from RNA. In some embodiments, the RNA includes total cellular RNA. In other embodiments, certain abundant RNA sequences (e.g., ribosomal RNAs) have been depleted. In other embodiments, the poly(A)-tailed mRNA fraction in the total RNA preparation has been enriched. In some embodiments, the cDNA is produced by random-primed cDNA synthesis methods. In other embodiments, the cDNA synthesis is initiated at the poly(A) tail of mature mRNAs by priming by oligo(dT)-containing oligonucleotides. Methods for depletion, poly(A) enrichment, and cDNA synthesis are well known to those skilled in the art.

The method can further include amplifying the nucleic acid sample by specific or non-specific nucleic acid amplification methods that are known to those skilled in the art. The nucleic acid sample can be amplified, e.g., by whole-genome amplification methods such as random-primed strand-displacement amplification.

The nucleic acid sample can be fragmented or sheared by physical or enzymatic methods as described herein, and ligated to synthetic adapters, size-selected (e.g., by preparative gel electrophoresis) and amplified (e.g., by PCR). The fragmented and adapter-ligated group of nucleic acids is used without explicit size selection or amplification prior to hybrid selection.

In an embodiment, the nucleic acid sample comprises DNA, RNA (or cDNA derived from RNA), or both, from a non-cancer cell or a non-malignant cell, e.g., a tumor-infiltrating lymphocyte. In an embodiment, the nucleic acid sample comprises DNA, RNA (or cDNA derived from RNA), or both, from a non-cancer cell or a non-malignant cell, e.g., a tumor-infiltrating lymphocyte, and does not comprise, or is essentially free of, DNA, RNA (or cDNA derived from RNA), or both, from a cancer cell or a malignant cell.

In an embodiment, the nucleic acid sample comprises DNA, RNA (or cDNR derived from RNA) from a cancer cell or a malignant cell. In an embodiment, the nucleic acid sample comprises DNA, RNA (or cDNR derived from RNA) from a cancer cell or a malignant cell, and does not comprise, or is essentially free of, DNA, RNA (or cDNA derived from RNA), or both, from a non-cancer cell or a non-malignant cell, e.g., a tumor-infiltrating lymphocyte.

In an embodiment, the nucleic acid sample comprises DNA, RNA (or cDNA derived from RNA), or both, from a non-cancer cell or a non-malignant cell, e.g., a tumor-infiltrating lymphocyte, and DNA, RNA (or cDNA derived from RNA), or both, from a cancer cell or a malignant cell.

Design and Construction of Baits

A bait can be a nucleic acid molecule, e.g., a DNA or RNA molecule, which can hybridize to (e.g., be complementary to), and thereby allow capture of a target nucleic acid. In certain embodiments, the target nucleic acid is a genomic DNA molecule. In other embodiments, the target nucleic acid is an RNA molecule or a cDNA molecule derived from an RNA molecule. In one embodiment, a bait is an RNA molecule. In other embodiments, a bait includes a binding entity, e.g., an affinity tag, that allows capture and separation, e.g., by binding to a binding entity, of a hybrid formed by a bait and a nucleic acid hybridized to the bait. In one embodiment, a bait is suitable for solution phase hybridization.

Typically, RNA molecules are used as bait sequences. A RNA-DNA duplex is more stable than a DNA-DNA duplex, and therefore provides for potentially better capture of nucleic acids.

RNA baits can be made as described elsewhere herein, using methods known in the art including, but not limited to, de novo chemical synthesis and transcription of DNA molecules using a DNA-dependent RNA polymerase. In one embodiment, the bait sequence is produced using known nucleic acid amplification methods, such as PCR, e.g., using human DNA or pooled human DNA samples as the template. The oligonucleotides can then be converted to RNA baits. In one embodiment, in vitro transcription is used, for example, based on adding an RNA polymerase promoter sequence to one end of the oligonucleotide. In one embodiment, the RNA polymerase promoter sequence is added at the end of the bait by amplifying or reamplifying the bait sequence, e.g., using PCR or other nucleic acid amplification methods, e.g., by tailing one primer of each target-specific primer pairs with an RNA promoter sequence. In one embodiment, the RNA polymerase is a T7 polymerase, a SP6 polymerase, or a T3 polymerase. In one embodiment, RNA bait is labeled with a tag, e.g., an affinity tag. In one embodiment, RNA bait is made by in vitro transcription, e.g., using biotinylated UTP. In another embodiment, RNA bait is produced without biotin and then biotin is crosslinked to the RNA molecule using methods well known in the art, such as psoralen crosslinking. In one embodiment, the RNA bait is an RNase-resistant RNA molecule, which can be made, e.g., by using modified nucleotides during transcription to produce RNA molecule that resists RNase degradation. In one embodiment, the RNA bait corresponds to only one strand of the double-stranded DNA target. Typically, such RNA baits are not self-complementary and are more effective as hybridization drivers.

The bait sets can be designed from reference sequences, such that the baits are optimal for selecting targets of the reference sequences. In some embodiments, bait sequences are designed using a mixed base (e.g., degeneracy). For example, the mixed base(s) can be included in the bait sequence at the position(s) of a common SNP or mutation, to optimize the bait sequences to catch both alleles (e.g., SNP and non-SNP; mutant and non-mutant). In some embodiments, all known sequence variations (or a subset thereof) can be targeted with multiple oligonucleotide baits, rather than by using mixed degenerate oligonucleotides.

In certain embodiments, the bait set includes an oligonucleotide (or a plurality of oligonucleotides) between about 100 nucleotides and 300 nucleotides in length. Typically, the bait set includes an oligonucleotide (or a plurality of oligonucleotides) between about 130 nucleotides and 230 nucleotides, or about 150 and 200 nucleotides, in length. In other embodiments, the bait set includes an oligonucleotide (or a plurality of oligonucleotides) between about 300 nucleotides and 1000 nucleotides in length.

In some embodiments, the target member-specific sequences in the oligonucleotide is between about 40 and 1000 nucleotides, about 70 and 300 nucleotides, about 100 and 200 nucleotides in length, typically between about 120 and 170 nucleotides in length.

In some embodiments, the bait set includes a binding entity. The binding entity can be an affinity tag on each bait sequence. In some embodiments, the affinity tag is a biotin molecule or a hapten. In certain embodiments, the binding entity allows for separation of the bait/member hybrids from the hybridization mixture by binding to a partner, such as an avidin molecule, or an antibody that binds to the hapten or an antigen-binding fragment thereof.

In other embodiments, the oligonucleotides in the bait set contains forward and reverse complemented sequences for the same target member sequence whereby the oligonucleotides with reverse-complemented member-specific sequences also carry reverse complemented universal tails. This can lead to RNA transcripts that are the same strand, i.e., not complementary to each other.

In other embodiments, the bait set includes oligonucleotides that contain degenerate or mixed bases at one or more positions. In still other embodiments, the bait set includes multiple or substantially all known sequence variants present in a population of a single species or community of organisms. In one embodiment, the bait set includes multiple or substantially all known sequence variants present in a human population.

In other embodiments, the bait set includes cDNA sequences or is derived from cDNAs sequences. In other embodiments, the bait set includes amplification products (e.g., PCR products) that are amplified from genomic DNA, cDNA or cloned DNA.

In other embodiments, the bait set includes RNA molecules. In some embodiments, the set includes chemically, enzymatically modified, or in vitro transcribed RNA molecules, including but not limited to, those that are more stable and resistant to RNase.

In yet other embodiments, the baits are produced by methods described in US 2010/0029498 and Gnirke, A. et al. (2009) *Nat Biotechnol.* 27(2):182-189, incorporated herein by reference. For example, biotinylated RNA baits can be produced by obtaining a pool of synthetic long oligonucleotides, originally synthesized on a microarray, and amplifying the oligonucleotides to produce the bait sequences. In some embodiments, the baits are produced by adding an RNA polymerase promoter sequence at one end of the bait sequences, and synthesizing RNA sequences using RNA polymerase. In one embodiment, libraries of synthetic oligodeoxynucleotides can be obtained from commercial suppliers, such as Agilent Technologies, Inc., and amplified using known nucleic acid amplification methods.

Accordingly, a method of making the aforesaid bait set is provided. The method includes selecting one or more target specific bait oligonucleotide sequences (e.g., one or more mutation capturing, reference or control oligonucleotide sequences as described herein); obtaining a pool of target specific bait oligonucleotide sequences (e.g., synthesizing the pool of target specific bait oligonucleotide sequences, e.g., by microarray synthesis); and optionally, amplifying the oligonucleotides to produce the bait set.

In other embodiments, the methods further include amplifying (e.g., by PCR) the oligonucleotides using one or more biotinylated primers. In some embodiments, the oligonucleotides include a universal sequence at the end of each oligonucleotide attached to the microarray. The methods can further include removing the universal sequences from the oligonucleotides. Such methods can also include removing the complementary strand of the oligonucleotides, annealing the oligonucleotides, and extending the oligonucleotides. In some of these embodiments, the methods for amplifying (e.g., by PCR) the oligonucleotides use one or more biotinylated primers. In some embodiments, the method further includes size selecting the amplified oligonucleotides.

In one embodiment, an RNA bait set is made. The methods include producing a set of bait sequences according to the methods described herein, adding a RNA polymerase promoter sequence at one end of the bait sequences, and synthesizing RNA sequences using RNA polymerase. The RNA polymerase can be chosen from a T7 RNA polymerase, an SP6 RNA polymerase or a T3 RNA polymerase. In other embodiments, the RNA polymerase promoter sequence is added at the ends of the bait sequences by amplifying (e.g., by PCR) the bait sequences. In embodiments where the bait sequences are amplified by PCR with specific primer pairs out of genomic or cDNA, adding an RNA promoter sequence to the 5' end of one of the two specific primers in each pair will lead to a PCR product that can be transcribed into a RNA bait using standard methods.

In other embodiments, bait sets can be produced using human DNA or pooled human DNA samples as the template. In such embodiments, the oligonucleotides are amplified by polymerase chain reaction (PCR). In other embodiments, the amplified oligonucleotides are reamplified by rolling circle amplification or hyperbranched rolling circle amplification. The same methods also can be used to produce bait sequences using human DNA or pooled human DNA samples as the template. The same methods can also be used to produce bait sequences using subfractions of a genome obtained by other methods, including but not limited to restriction digestion, pulsed-field gel electrophoresis, flow-sorting, CsCl density gradient centrifugation, selective kinetic reassociation, microdissection of chromosome preparations and other fractionation methods known to those skilled in the art.

In certain embodiments, the number of baits in the bait set is less than 1,000. In other embodiments, the number of baits in the bait set is greater than 1,000, greater than 5,000, greater than 10,000, greater than 20,000, greater than 50,000, greater than 100,000, or greater than 500,000.

The length of the bait sequence can be between about 70 nucleotides and 1000 nucleotides. In one embodiment, the bait length is between about 100 and 300 nucleotides, 110 and 200 nucleotides, or 120 and 170 nucleotides, in length. In addition to those mentioned above, intermediate oligonucleotide lengths of about 70, 80, 90, 100, 110, 120, 130, 140, 150, 160, 170, 180, 190, 200, 210, 220, 230, 240, 250, 300, 400, 500, 600, 700, 800, and 900 nucleotides in length can be used in the methods described herein. In some embodiments, oligonucleotides of about 70, 80, 90, 100, 110, 120, 130, 140, 150, 160, 170, 180, 190, 200, 210, 220, or 230 bases can be used.

Each bait sequence can include a target-specific (e.g., a member-specific) bait sequence and universal tails on one or both ends. As used herein, the term "bait sequence" can refer to the target-specific bait sequence or the entire oligonucleotide including the target-specific "bait sequence" and other nucleotides of the oligonucleotide. The target-specific sequences in the baits are between about 40 nucleotides and 1000 nucleotides in length. In one embodiment, the target-specific sequence is between about 70 nucleotides and 300 nucleotides in length. In another embodiment, the target-specific sequence is between about 100 nucleotides and 200 nucleotides in length. In yet another embodiment, the target-specific sequence is between about 120 nucleotides and 170 nucleotides in length, typically 120 nucleotides in length. Intermediate lengths in addition to those mentioned above also can be used in the methods described herein, such as target-specific sequences of about 40, 50, 60, 70, 80, 90, 100, 110, 120, 130, 140, 150, 160, 170, 180, 190, 200, 210, 220, 230, 240, 250, 300, 400, 500, 600, 700, 800, and 900 nucleotides in length, as well as target-specific sequences of lengths between the above-mentioned lengths.

In one embodiment, the bait is an oligomer (e.g., comprised of RNA oligomers, DNA oligomers, or a combination thereof) about 50 to 200 nucleotides in length (e.g., about 50, 60, 80, 90, 100, 110, 120, 130, 140, 150, 160, 170, 190, or 200 nucleotides in length). In one embodiment, each bait oligomer includes about 120 to 170, or typically about 120 nucleotides, which are a target specific bait sequence. The bait can comprise additional non-target specific nucleotide sequences at one or both ends. The additional nucleotide sequences can be used, e.g., for PCT amplification or as a bait identifier. In certain embodiments, the bait additionally comprises a binding entity as described herein (e.g., a capture tag such as a biotin molecule). The binding entity, e.g., biotin molecule, can be attached to the bait, e.g., at the 5'-, 3'-end, or internally (e.g., by incorporating a biotinylated nucleotide), of the bait. In one embodiment, the biotin molecule is attached at the 5'-end of the bait.

In one exemplary embodiment, the bait is an oligonucleotide about 150 nucleotides in length, of which 120 nucleotides are target-specific "bait sequence". The other 30 nucleotides (e.g., 15 nucleotides on each end) are universal arbitrary tails used for PCR amplification. The tails can be any sequence selected by the user. For example, the pool of synthetic oligonucleotides can include oligonucleotides of the sequence of 5'-ATCGCACCAGCGTGTN$_{120}$CACTGCGGCTCCTCA-3' (SEQ ID NO: 1) with N$_{120}$ indicating the target-specific bait sequences.

The bait sequences described herein can be used for selection of exons and short target sequences. In one embodiment, the bait is between about 100 nucleotides and 300 nucleotides in length. In another embodiment, the bait is between about 130 nucleotides and 230 nucleotides in length. In yet another embodiment, the bait is between about 150 nucleotides and 200 nucleotides in length. The target-specific sequences in the baits, e.g., for selection of exons and short target sequences, are between about 40 nucleotides and 1000 nucleotides in length. In one embodiment, the target-specific sequence is between about 70 nucleotides and 300 nucleotides in length. In another embodiment, the target-specific sequence is between about 100 nucleotides and 200 nucleotides in length. In yet another embodiment, the target-specific sequence is between about 120 nucleotides and 170 nucleotides in length.

In some embodiments, long oligonucleotides can minimize the number of oligonucleotides necessary to capture the target sequences. For example, one oligonucleotide can be used per exon. It is known in the art that the mean and median lengths of the protein-coding exons in the human genome are about 164 and 120 base pairs, respective. Longer baits can be more specific and capture better than shorter ones. As a result, the success rate per oligonucleotide bait sequence is higher than with short oligonucleotides. In one embodiment, the minimum bait-covered sequence is the size of one bait (e.g., 120-170 bases), e.g., for capturing exon-sized targets. In determining the length of the bait sequences, one also can take into consideration that unnecessarily long baits catch more unwanted DNA directly adjacent to the target. Longer oligonucleotide baits can also be more tolerant to polymorphisms in the targeted region in the DNA samples than shorter ones. Typically, the bait sequences are derived from a reference genome sequence. If the target sequence in the actual DNA sample deviates from the reference sequence, for example if it contains a single-nucleotide polymorphism (SNP), it can hybridize less efficiently to the bait and may therefore be under-represented or completely absent in the sequences hybridized to the bait sequences. Allelic drop-outs due to SNPs can be less likely with the longer synthetic baits molecules for the reason that a single mispair in, e.g., 120 to 170 bases can have less of an effect on hybrid stability than a single mismatch in, 20 or 70 bases, which are the typical bait or primer lengths in multiplex amplification and microarray capture, respectively.

For selection of targets that are long compared to the length of the capture baits, such as genomic regions, bait sequence lengths are typically in the same size range as the baits for short targets mentioned above, except that there is no need to limit the maximum size of bait sequences for the sole purpose of minimizing targeting of adjacent sequences. Alternatively, oligonucleotides can be titled across a much wider window (typically 600 bases). This method can be used to capture DNA fragments that are much larger (e.g., about 500 bases) than a typical exon. As a result, much more unwanted flanking non-target sequences are selected.

Bait Synthesis

The baits can be any type of oligonucleotide, e.g., DNA or RNA. The DNA or RNA baits ("oligo baits") can be synthesized individually, or can be synthesized in an array, as a DNA or RNA bait set ("array baits"). An oligo bait, whether provided in an array format, or as an isolated oligo, is typically single stranded. The bait can additionally comprise a binding entity as described herein (e.g., a capture tag such as a biotin molecule). The binding entity, e.g., biotin molecule, can be attached to the bait, e.g., at the 5' or 3'-end of the bait, typically, at the 5'-end of the bait. Bait sets can be synthesized by methods described in the art, e.g., as described in International Patent Application Publication No. WO 2012/092426.

Hybridization Conditions

The methods featured in the invention include the step of contacting the library (e.g., the nucleic acid library) with a plurality of baits to provide a selected library catch. The contacting step can be effected in solution hybridization. In certain embodiments, the method includes repeating the hybridization step by one or more additional rounds of solution hybridization. In some embodiments, the methods further include subjecting the library catch to one or more additional rounds of solution hybridization with the same or different collection of baits. Hybridization methods that can be adapted for use in the methods herein are described in the art, e.g., as described in International Patent Application Publication No. WO 2012/092426.

Additional embodiments or features of the present invention are as follows:

In another aspect, the invention features a method of making the aforesaid bait sets. The method includes selecting one or more target specific bait oligonucleotide sequences (e.g., any of the bait sequences corresponding to the subject intervals (e.g., subgenomic intervals, expressed subgenomic intervals, or both) of the gene or gene products as described herein); obtaining a pool of target specific bait oligonucleotide sequences (e.g., synthesizing the pool of target specific bait oligonucleotide sequences, e.g., by microarray synthesis); and optionally, amplifying the oligonucleotides to produce the bait sets.

In yet another aspect, the invention features a method for determining the presence or absence of an alteration associated, e.g., positively or negatively, with a cancerous phenotype (e.g, at least 10, 20, 30, 50 or more of the alterations in the genes or gene products described herein) in a nucleic acid sample. The method includes contacting the nucleic acids in the sample to solution-based selection according to any of the methods and baits described herein to obtain a nucleic acid catch; and sequencing (e.g., by next generation sequencing) all or a subset of the nucleic acid catch, thereby determining the presence or absence of the alteration in the genes or gene products described herein).

In certain embodiments, the bait set includes an oligonucleotide (or a plurality of oligonucleotides) between about 100 nucleotides and 300 nucleotides in length. Typically, the bait set include an oligonucleotide (or a plurality of oligonucleotides) between about 130 nucleotides and 230 nucleotides, or about 150 and 200 nucleotides, in length. In other embodiments, the bait set includes an oligonucleotide (or a plurality of oligonucleotides) between about 300 nucleotides and 1000 nucleotides in length.

In some embodiments, the target member-specific sequences in the oligonucleotide is between about 40 and 1000 nucleotides, about 70 and 300 nucleotides, about 100 and 200 nucleotides in length, typically between about 120 and 170 nucleotides in length.

In some embodiments, the bait set include a binding entity. The binding entity can be an affinity tag on each bait sequence. In some embodiments, the affinity tag is a biotin molecule or a hapten. In certain embodiments, the binding entity allows for separation of the bait/member hybrids from the hybridization mixture by binding to a partner, such as an avidin molecule, or an antibody that binds to the hapten or an antigen-binding fragment thereof.

In other embodiments, the oligonucleotides in the bait set contains forward and reverse complemented sequences for the same target member sequence whereby the oligonucleotides with reverse-complemented member-specific sequences also carry reverse complemented universal tails. This can lead to RNA transcripts that are the same strand, i.e., not complementary to each other.

In other embodiments, the bait set includes oligonucleotides that contain degenerate or mixed bases at one or more positions. In still other embodiments, the bait set includes multiple or substantially all known sequence variants present in a population of a single species or community of organisms. In one embodiment, the bait set includes multiple or substantially all known sequence variants present in a human population.

In other embodiments, the bait set includes cDNA sequences or are derived from cDNAs sequences. In one embodiment, the cDNA is prepared from an RNA sequence, e.g., a tumor- or cancer cell-derived RNA, e.g., an RNA obtained from a tumor-FFPE sample, a blood sample, or a bone marrow aspirate sample. In other embodiments, the bait set includes amplification products (e.g., PCR products) that are amplified from genomic DNA, cDNA or cloned DNA.

In other embodiments, the bait set includes RNA molecules. In some embodiments, the set includes are chemically, enzymatically modified, or in vitro transcribed RNA molecules, including but not limited to, those that are more stable and resistant to RNase.

In yet other embodiments, the baits are produced by methods described in US 2010/0029498 and Gnirke, A. et al. (2009) *Nat Biotechnol.* 27(2):182-189, incorporated herein by reference. For example, biotinylated RNA baits can be produced by obtaining a pool of synthetic long oligonucleotides, originally synthesized on a microarray, and amplifying the oligonucleotides to produce the bait sequences. In some embodiments, the baits are produced by adding an RNA polymerase promoter sequence at one end of the bait sequences, and synthesizing RNA sequences using RNA polymerase. In one embodiment, libraries of synthetic oligodeoxynucleotides can be obtained from commercial suppliers, such as Agilent Technologies, Inc., and amplified using known nucleic acid amplification methods.

Accordingly, a method of making the aforesaid bait set is provided. The method includes selecting one or more target specific bait oligonucleotide sequences (e.g., one or more mutation capturing, reference or control oligonucleotide sequences as described herein); obtaining a pool of target specific bait oligonucleotide sequences (e.g., synthesizing the pool of target specific bait oligonucleotide sequences, e.g., by microarray synthesis); and optionally, amplifying the oligonucleotides to produce the bait set.

In other embodiments, the methods further include amplifying (e.g., by PCR) the oligonucleotides using one or more biotinylated primers. In some embodiments, the oligonucleotides include a universal sequence at the end of each oligonucleotide attached to the microarray. The methods can further include removing the universal sequences from the oligonucleotides. Such methods can also include removing the complementary strand of the oligonucleotides, annealing the oligonucleotides, and extending the oligonucleotides. In some of these embodiments, the methods for amplifying (e.g., by PCR) the oligonucleotides use one or more biotinylated primers. In some embodiments, the method further includes size selecting the amplified oligonucleotides.

In one embodiment, an RNA bait set is made. The methods include producing a set of bait sequences according to the methods described herein, adding a RNA polymerase promoter sequence at one end of the bait sequences, and synthesizing RNA sequences using RNA polymerase. The RNA polymerase can be chosen from a T7 RNA polymerase, an SP6 RNA polymerase or a T3 RNA polymerase. In other embodiments, the RNA polymerase promoter sequence is added at the ends of the bait sequences by amplifying (e.g., by PCR) the bait sequences. In embodiments where the bait sequences are amplified by PCR with specific primer pairs out of genomic or cDNA, adding an RNA promoter sequence to the 5' end of one of the two specific primers in each pair will lead to a PCR product that can be transcribed into a RNA bait using standard methods.

In other embodiments, bait sets can be produced using human DNA or pooled human DNA samples as the template. In such embodiments, the oligonucleotides are amplified by polymerase chain reaction (PCR). In other embodiments, the amplified oligonucleotides are reamplified by rolling circle amplification or hyperbranched rolling circle amplification. The same methods also can be used to produce bait sequences using human DNA or pooled human DNA samples as the template. The same methods can also be used to produce bait sequences using subfractions of a genome obtained by other methods, including but not limited to restriction digestion, pulsed-field gel electrophoresis, flow-sorting, CsCl density gradient centrifugation, selective kinetic reassociation, microdissection of chromosome preparations and other fractionation methods known to those skilled in the art.

In certain embodiments, the number of baits in the bait set is less than 1,000, e.g., 2, 3, 4, 5, 10, 50, 100, 500 baits. In other embodiments, the number of baits in the bait set is greater than 1,000, greater than 5,000, greater than 10,000, greater than 20,000, greater than 50,000, greater than 100,000, or greater than 500,000.

In certain embodiments, a library (e.g., a nucleic acid library) includes a collection of members. As described herein, the library members can include a target member (e.g., a tumor member, a reference member and/or a control member; also referred to herein as a first, second and/or third member, respectively). The members of the library can be from a single individual. In embodiments a library can comprise members from more than one subject (e.g., 2, 3, 4, 5, 6, 7, 8, 9, 10, 20, 30 or more subjects), e.g., two or more libraries from different subjects can be combined to from a library having members from more than one subject. In one embodiment, the subject is human having, or at risk of having, a cancer or tumor.

"Member" or "library member" or other similar term, as used herein, refers to a nucleic acid molecule, e.g., DNA or RNA, that is a member of a library. Typically, a member is a DNA molecule, e.g., genomic DNA or cDNA. A member can be sheared genomic DNA. In other embodiments, the member can be a cDNA. In other embodiments, the member can be an RNA. Members comprise sequence from a subject and can also comprise a sequence not derived from the subject, e.g., primers or sequences that allow for identification, e.g., "barcode" sequences.

In yet another embodiment, the methods featured in the invention further include isolating a nucleic acid sample to provide a library (e.g., a nucleic acid library as described herein). In certain embodiments, the nucleic acid sample includes whole genomic, subgenomic fragments, or both. Protocols for isolating and preparing libraries from whole genomic or subgenomic fragments are known in the art (e.g., Illumina's genomic DNA sample preparation kit). In certain embodiments, the genomic or subgenomic DNA fragment is isolated from a subject's sample (e.g., a tumor sample, a normal adjacent tissue (NAT), a blood sample or any normal control)). In one embodiment, the sample (e.g., the tumor or NAT sample) is a preserved. For example, the sample is embedded in a matrix, e.g., an FFPE block or a frozen sample. In certain embodiments, the isolating step includes flow-sorting of individual chromosomes; and/or microdissecting a subject's sample (e.g., a tumor sample, a NAT, a blood sample). In certain embodiments, the nucleic acid sample used to generate the nucleic acid library is less than 5, less than 1 microgram, or less than 500 ng (e.g., 200 ng or less).

In still other embodiments, the nucleic acid sample used to generate the library includes RNA or cDNA derived from RNA. In some embodiments, the RNA includes total cellular RNA. In other embodiments, certain abundant RNA sequences (e.g., ribosomal RNAs) have been depleted. In some embodiments, the poly(A)-tailed mRNA fraction in the total RNA preparation has been enriched. In some embodiments, the cDNA is produced by random-primed cDNA synthesis methods. In other embodiments, the cDNA synthesis is initiated at the poly(A) tail of mature mRNAs by priming by oligo(dT)-containing oligonucleotides. Methods for depletion, poly(A) enrichment, and cDNA synthesis are well known to those skilled in the art.

The method can further include amplifying the nucleic acid sample by specific or non-specific nucleic acid amplification methods that are well known to those skilled in the art.

In some embodiments, certain embodiments, the nucleic acid sample is amplified, e.g., by whole-genome amplification methods such as random-primed strand-displacement amplification.

In other embodiments, the nucleic acid sample is fragmented or sheared by physical or enzymatic methods and ligated to synthetic adapters, size-selected (e.g., by preparative gel electrophoresis) and amplified (e.g., by PCR). In other embodiments, the fragmented and adapter-ligated group of nucleic acids is used without explicit size selection or amplification prior to hybrid selection.

In other embodiments, the isolated DNA (e.g., the genomic DNA) is fragmented or sheared. In some embodiments, the library includes less than 50% of genomic DNA, such as a subfraction of genomic DNA that is a reduced representation or a defined portion of a genome, e.g., that has been subfractionated by other means. In other embodiments, the library includes all or substantially all genomic DNA.

In certain embodiments, the members of the library include a subgenomic interval that includes an intragenic region or an intergenic region. In another embodiment, the subgenomic interval includes an exon or an intron, or a fragment thereof, typically an exon sequence or a fragment thereof. In one embodiment, the subgenomic interval includes a coding region or a non-coding region, e.g., a promoter, an enhancer, a 5' untranslated region (5' UTR), or a 3' untranslated region (3' UTR), or a fragment thereof. In other embodiments, the subgenomic interval includes a cDNA or a fragment thereof (e.g., cDNA obtained from a tumor RNA (e.g., RNA extracted from a tumor sample, e.g., FFPE-tumor sample). In other embodiments, the subgenomic interval includes an SNP, e.g., as described herein. In other embodiments, the target members include substantially all exons in a genome. In other embodiments, the target members include a subgenomic interval as described herein, e.g., subgenomic intervals, e.g., exons from selected genes or gene products of interest (e.g., genes or gene products associated with a cancerous phenotype as described herein).

In one embodiment, the subgenomic interval includes a somatic mutation, a germ line mutation or both. In one embodiment, the subgenomic interval includes an alteration, e.g., a point or a single mutation, a deletion mutation (e.g., an in-frame deletion, an intragenic deletion, a full gene deletion), an insertion mutation (e.g., intragenic insertion), an inversion mutation (e.g., an intra-chromosomal inversion), a linking mutation, a linked insertion mutation, an inverted duplication mutation, a tandem duplication (e.g., an intrachromosomal tandem duplication), a translocation (e.g., a chromosomal translocation, a non-reciprocal translocation), a rearrangement (e.g., a genomic rearrangement), a change in gene copy number, or a combination thereof. In certain embodiments, the subgenomic interval constitutes less than 5, 1, 0.5, 0.1%, 0.01%, 0.001% of the coding region of the genome of the tumor cells in a sample. In other embodiments, the subgenomic intervals are not involved in a disease, e.g., are not associated with a cancerous phenotype as described herein.

The methods featured in the invention include the step of contacting one or a plurality of libraries (e.g., one or a plurality of nucleic acid libraries) with a plurality of baits to provide a selected subgroup of nucleic acids, e.g., a library catch. In one embodiment, the contacting step is effected in a solid support, e.g., an array. Suitable solid supports for hybridization are described in, e.g., Albert, T. J. et al. (2007) *Nat. Methods* 4(11):903-5; Hodges, E. et al. (2007) *Nat. Genet.* 39(12):1522-7; Okou, D. T. et al. (2007) *Nat. Methods* 4(11):907-9, the contents of which are hereby incorporated by reference. In other embodiments, the contacting step is effected in solution hybridization. In certain embodiments, the method includes repeating the hybridization step by one or more additional rounds of hybridization. In some embodiments, the methods further include subjecting the library catch to one or more additional rounds of hybridization with the same or different collection of baits.

In other embodiments, the methods featured in the invention further include amplifying the library catch (e.g., by PCR). In other embodiments, the library catch is not amplified.

In yet other embodiments, the methods further include analyzing the library catch. In one embodiment, the library catch is analyzed by a sequencing method, e.g., a next-generation sequencing method as described herein. The methods include isolating a library catch by solution hybridization, and subjecting the library catch by nucleic acid sequencing. In certain embodiments, the library catch can be re-sequenced. Next generation sequencing methods are known in the art, and are described, e.g., in Metzker, M. (2010) *Nature Biotechnology Reviews* 11:31-46.

In yet other embodiments, the methods further include the step of subjecting the library catch to genotyping, thereby identifying the genotype of the selected nucleic acids.

In certain embodiments, the method further includes one or more of:
i) fingerprinting the nucleic acid sample;
ii) quantifying the abundance of a gene or gene product (e.g., a gene or gene product as described herein) in the nucleic acid sample (e.g., quantifying the relative abundance of a transcript in the sample);
iii) identifying the nucleic acid sample as belonging to a particular subject (e.g., a normal control or a cancer patient);
iv) identifying a genetic trait in the nucleic acid sample (e.g., one or more subject's genetic make-up (e.g., ethnicity, race, familial traits));
v) determining the ploidy in the nucleic acid sample; determining a loss of heterozygosity in the nucleic acid sample;
vi) determining the presence or absence of a gene duplication event in the nucleic acid sample;
vii) determining the presence or absence of a gene amplification event in the nucleic acid sample; or
viii) determining the level of tumor/normal cellular admixture in the nucleic acid sample.

Any of the methods described herein can be combined with one or more of the embodiments below.

In an embodiment, the method comprises acquiring a nucleotide sequence read obtained from a tumor and/or control nucleic acid sample (e.g., an FFPE-derived nucleic acid sample, or a nucleic acid sample derived from a blood sample or a bone marrow aspirate sample).

In an embodiment, the reads are provided by a next-generation sequencing method.

In an embodiment, the method includes providing a library of nucleic acid members and sequencing a preselected subgenomic interval from a plurality of members of said library. In embodiments, the method can include a step of selecting a subset of said library for sequencing, e.g., a solution-based selection.

In certain embodiments, a method comprises hybrid capture methods which are designed to capture two or more different target categories, each with a different bait design strategies. The hybrid capture methods and compositions are intended to capture a defined subset of target sequences (e.g., target members) and provide homogenous coverage of the target sequence, while minimizing coverage outside of that subset. In one embodiment, the target sequences include the entire exome out of genomic DNA, or a selected subset thereof. The methods and compositions disclosed herein provide different bait sets for achieving different depths and patterns of coverage for complex target nucleic acid sequences (e.g., libraries).

In certain embodiment, the different categories of bait sets and targets are as follows.

A. A first bait set that selects a high-level target (e.g., one or more tumor members and/or reference members, such as genes, exons, or bases) for which the deepest coverage is required to enable a high level of sensitivity for mutations that appear at low frequencies. For example, detection of point mutations that appear at a frequency of about 5% or less (i.e. 5% of the cells from which the sample was prepared harbor this mutation in their genome). The first bait set typically requires about 500× or higher sequencing depth to ensure high detection reliability. In one embodiment, the first bait set selects one or more subgenomic intervals (e.g., exons) that are frequently mutated in certain types of cancer, e.g., a gene or gene product according to Tables 1-4.

B. A second bait set that selects a mid-level target target (e.g., one or more tumor members and/or reference members, such as genes, exons, or bases) for which high coverage is required to enable high level of sensitivity for mutations that appear at a higher frequency than the high level target, e.g., a frequency of about 10%. For example, detection of an alteration (e.g., a point mutation) that appears at a frequency of 10% requires about 200× or higher sequencing depth to ensure high detection reliability. In one embodiment, the second bait set selects one or more subgenomic intervals (e.g., exons) that are chosen from the genes or gene products according to Tables 1-4.

C. A third bait set that selects a low-level target (e.g., one or more PGx members, such as genes, exons, or bases) for which low-medium coverage is required to enable high level of sensitivity, e.g., to detect heterozygous alleles. For example, detection of heterozygous alleles requires 10-100× sequencing depth to ensure high detection reliability. In one embodiment, the third bait set selects one or more subgenomic intervals (e.g., exons) that are chosen from: a) pharmacogenomic SNPs that may explain the ability of patient to metabolize different drugs, b) a genomic SNPs that may be used to uniquely identify (fingerprint) a patient, c) a genomic SNPs/loci that may be used to assess copy number gains/losses of genomic DNA and loss-of-heterozygosity (LOH).

D. A fourth bait set that selects an intron target (e.g., an intron member) for which low-medium coverage is required to detect structural breakpoints such as genomic translocations or indels. For example, detection of an intronic breakpoint requires 5-50× sequence-pair spanning depth to ensure high detection reliability. Said fourth bait sets can be used to detect, for example, translocation/indel-prone cancer genes.

E. A fifth bait set that selects an intron target (e.g., an intron member) for which sparse coverage is required to improve the ability to detect copy number changes. For example, detection of a 1 copy deletion of several terminal exon requires 0.1-10× coverage to ensure high detection reliability. Said fifth bait sets can be used to detect, for example, amplification/deletion-prone cancer genes.

The methods and compositions featured in the invention involve tuning the relative sequence coverage of each bait set/target category. Methods for implementing differences in relative sequence coverage in bait design include one or more of:

(i) Differential representation of different bait sets—The bait set design to capture a given target (e.g., a target member) can be included in more/fewer number of copies to enhance/reduce relative target coverage depths;

(ii) Differential overlap of bait subsets—The bait set design to capture a given target (e.g., a target member) can include a longer or shorter overlap between neighboring baits to enhance/reduce relative target coverage depths;

(iii) Differential bait parameters—The bait set design to capture a given target (e.g., a target member) can include sequence modifications/shorter length to reduce capture efficiency and lower the relative target coverage depths;

(iv) Mixing of different bait sets—Bait sets that are designed to capture different target sets can be mixed at different molar ratios to enhance/reduce relative target coverage depths;

(v) Using different types of oligonucleotide bait sets—In certain embodiments, the bait set can include:

(a) one or more chemically (e.g., non-enzymatically) synthesized (e.g., individually synthesized) baits, (b) one or more baits synthesized in an array, (c) one or more enzymatically prepared, e.g., in vitro transcribed, baits;

(d) any combination of (a), (b) and/or (c), (e) one or more DNA oligonucleotides (e.g., a naturally or non-naturally occurring DNA oligonucleotide), (f) one or more RNA oligonucleotides (e.g., a naturally or non-naturally occurring RNA oligonucleotide), (g) a combination of (e) and (f), or (h) a combination of any of the above.

The different oligonucleotide combinations can be mixed at different ratios, e.g., a ratio chosen from 1:1, 1:2, 1:3, 1:4, 1:5, 1:10, 1:20, 1:50; 1:100, 1:1000, or the like. In one embodiment, the ratio of chemically-synthesized bait to array-generated bait is chosen from 1:5, 1:10, or 1:20. The DNA or RNA oligonucleotides can be naturally- or non-naturally-occurring. In certain embodiments, the baits include one or more non-naturally-occurring nucleotide to, e.g., increase melting temperature. Exemplary non-naturally occurring oligonucleotides include modified DNA or RNA nucleotides. An exemplary modified RNA nucleotide is a locked nucleic acid (LNA), wherein the ribose moiety of an LNA nucleotide is modified with an extra bridge connecting the 2' oxygen and 4' carbon (Kaur, H; Arora, A; Wengel, J; Maiti, S; Arora, A.; Wengel, J.; Maiti, S. (2006). "Thermodynamic, Counterion, and Hydration Effects for the Incorporation of Locked Nucleic Acid Nucleotides into DNA Duplexes". *Biochemistry* 45 (23): 7347-55). Other modified exemplary DNA and RNA nucleotides include, but are not limited to, peptide nucleic acid (PNA) composed of repeating N-(2-aminoethyl)-glycine units linked by peptide bonds (Egholm, M. et al. (1993) *Nature* 365 (6446): 566-8); a DNA or RNA oligonucleotide modified to capture low GC regions; a bicyclic nucleic acid (BNA) or a crosslinked oligonucleotide; a modified 5-methyl deoxycytidine; and 2,6-diaminopurine. Other modified DNA and RNA nucleotides are known in the art.

In certain embodiments, a substantially uniform or homogeneous coverage of a target sequence (e.g., a target member) is obtained. For example, within each bait set/target category, uniformity of coverage can be optimized by modifying bait parameters, for example, by one or more of:

(i) Increasing/decreasing bait representation or overlap can be used to enhance/reduce coverage of targets (e.g., target members), which are under/over-covered relative to other targets in the same category;

(ii) For low coverage, hard to capture target sequences (e.g., high GC content sequences), expand the region being targeted with the bait sets to cover, e.g., adjacent sequences (e.g., less GC-rich adjacent sequences);

(iii) Modifying a bait sequence can be made to reduce secondary structure of the bait and enhance its efficiency of selection;

(iv) Modifying a bait length can be used to equalize melting hybridization kinetics of different baits within the same category. Bait length can be modified directly (by producing baits with varying lengths) or indirectly (by producing baits of consistent length, and replacing the bait ends with arbitrary sequence);

(v) Modifying baits of different orientation for the same target region (i.e. forward and reverse strand) may have different binding efficiencies. The bait set with either orientation providing optimal coverage for each target may be selected;

(vi) Modifying the amount of a binding entity, e.g., a capture tag (e.g. biotin), present on each bait may affect its binding efficiency. Increasing/decreasing the tag level of baits targeting a specific target may be used to enhance/reduce the relative target coverage;

(vii) Modifying the type of nucleotide used for different baits can be altered to affect binding affinity to the target, and enhance/reduce the relative target coverage; or (viii) Using modified oligonucleotide baits, e.g., having more stable base pairing, can be used to equalize melting hybridization kinetics between areas of low or normal GC content relative to high GC content.

For example, different types of oligonucleotide bait sets can be used.

In one embodiment, the value for efficiency of selection is modified by using different types of bait oligonucleotides to encompass pre-selected target regions. For example, a first bait set (e.g., an array-based bait set comprising 10,000-50,000 RNA or DNA baits) can be used to cover a large target area (e.g., 1-2 MB total target area). The first bait set can be spiked with a second bait set (e.g., individually synthesized RNA or DNA bait set comprising less than 5,000 baits) to cover a pre-selected target region (e.g., selected subgenomic intervals of interest spanning, e.g., 250 kb or less, of a target area) and/or regions of higher secondary structure, e.g., higher GC content. Selected subgenomic intervals of interest may correspond to one or more of the genes or gene products described herein, or a fragment thereof. The second bait set may include about 2,000-5,000 baits depending on the bait overlap desired. In yet other embodiments, the second bait set can include selected oligo baits (e.g., less than 400, 200, 100, 50, 40, 30, 20, 10 baits) spiked into the first bait set. The second bait set can be mixed at any ratio of individual oligo baits. For example, the second bait set can include individual baits present as a 1:1 equimolar ratio. Alternatively, the second bait set can include individual baits present at different ratio (e.g., 1:5, 1:10, 1:20), for example, to optimize capture of certain targets (e.g., certain targets can have a 5-10× of the second bait compared to other targets).

Sequencing

The invention also includes methods of sequencing nucleic acids. In these methods, nucleic acid library members are isolated by using the methods described herein, e.g., using solution hybridization, thereby providing a library catch. The library catch or a subgroup thereof can be sequenced. Accordingly, the methods featured in the invention further include analyzing the library catch. In one embodiment, the library catch is analyzed by a sequencing method, e.g., a next-generation sequencing method as described herein. The methods include isolating a library catch by solution hybridization, and subjecting the library catch by nucleic acid sequencing. In certain embodiments, the library catch can be re-sequenced.

Any method of sequencing known in the art can be used. Sequencing of nucleic acids isolated by selection methods are typically carried out using next-generation sequencing (NGS). Sequencing methods suitable for use herein are described in the art, e.g., as described in International Patent Application Publication No. WO 2012/092426.

After NGS reads have been generated, they can be aligned to a known reference sequence or assembled de novo. For example, identifying genetic variations such as single-nucleotide polymorphism and structural variants in a sample (e.g., a tumor sample) can be accomplished by aligning NGS reads to a reference sequence (e.g., a wild-type sequence). Methods of sequence alignment for NGS are described e.g., in Trapnell C. and Salzberg S. L. *Nature Biotech.*, 2009, 27:455-457. Examples of de novo assemblies are described, e.g., in Warren R. et al., *Bioinformatics*, 2007, 23:500-501; Butler J. et al., *Genome Res.*, 2008, 18:810-820; and Zerbino D. R. and Birney E., *Genome Res.*, 2008, 18:821-829. Sequence alignment or assembly can be performed using read data from one or more NGS platforms, e.g., mixing Roche/454 and Illumina/Solexa read data.

Alignment

Alignment is the process of matching a read with a location, e.g., a genomic location. Misalignment (e.g., the placement of base-pairs from a short read on incorrect locations in the genome), e.g., misalignment due to sequence context (e.g., presence of repetitive sequence) of reads around an actual cancer mutation can lead to reduction in sensitivity of mutation detection, as reads of the alternate allele may be shifted off the main pile-up of alternate allele reads. If the problematic sequence context occurs where no actual mutation is present, mis-alignment may introduce artifactual reads of "mutated" alleles by placing actual reads of reference genome bases onto the wrong location. Because mutation-calling algorithms for multiplied multigene analysis should be sensitive to even low-abundance mutations, these misalignments may increase false positive discovery rates/reduce specificity.

As discussed herein, reduced sensitivity for actual mutations may be addressed by evaluating the quality of alignments (manually or in an automated fashion) around expected mutation sites in the genes being analyzed. The sites to be evaluated can be obtained from databases of cancer mutations (e.g. COSMIC). Regions that are identified as problematic can be remedied with the use of an algorithm selected to give better performance in the relevant sequence context, e.g., by alignment optimization (or re-alignment) using slower, but more accurate alignment algorithms such as Smith-Waterman alignment. In cases where general alignment algorithms cannot remedy the problem, customized alignment approaches may be created by, e.g.: adjustment of maximum difference mismatch penalty parameters for genes with a high likelihood of containing substitutions; adjusting specific mismatch penalty parameters based on specific mutation types that are common in certain tumor types (e.g. C→T in melanoma); or adjusting specific mismatch penalty parameters based on specific mutation types that are common in certain sample types (e.g. substitutions that are common in FFPE). Reduced specificity (increased false positive rate) in the evaluated gene regions due to mis-alignment can be assessed by manual or automated examination of all mutation calls in samples sequenced. Those regions found to be prone to spurious mutation calls due to mis-alignment can be subjected to same alignment remedies as above. In cases where no algorithmic remedy is found possible, "mutations" from the problem regions can be classified or screened out from the test panel.

Methods disclosed herein allow the use of multiple, individually tuned, alignment methods or algorithms to optimize performance in the sequencing of subgenomic intervals associated with rearrangements, e.g., indels, particularly in methods that rely on massively parallel sequencing of a large number of diverse genetic events in a large number of diverse genes, e.g., from tumor samples. In embodiments multiple alignment methods that are individually customized or tuned to each of a number of rearrangements in different genes are used to analyze reads. In embodiments tuning can be a function of (one or more of) the gene (or other subgenomic interval) being sequenced, the tumor type in the sample, the variant being sequenced, or a characteristic of the sample or the subject. This selection or use of alignment conditions finely tuned to a number of subgenomic intervals to be sequenced allows optimization of speed, sensitivity and specificity. The method is particularly effective when the alignment of reads for a relatively large number of diverse subgenomic intervals is optimized. In embodiments the method includes the use of alignment methods optimized for rearrangements and others optimized for subgenomic intervals not associated with rearrangements.

Thus, in an embodiment, a method described herein, e.g., a method of analyzing a tumor sample comprises an alignment method for rearrangements described herein.

Generally, the accurate detection of indel mutations is an exercise in alignment, as the spurious indel rate on the sequencing platforms disabled herein is relatively low (thus, even a handful of observations of correctly aligned indels can be strong evidence of mutation). Accurate alignment in the presence of indels can be difficult however (especially as indel length increases). In addition to the general issues associated with alignment, e.g., of substitutions, the indel itself can cause problems with alignment. (For instance, a deletion of 2 bp of a dinucleotide repeat cannot be readily definitively placed.) Both sensitivity and specificity can be reduced by incorrect placement of shorter (<15 bp) apparent indel-containing reads. Larger indels (getting closer in magnitude to the length of individual reads—36 bp in our current process) can cause failure to align the read at all, making detection of the indel impossible in the standard set of aligned reads.

Databases of cancer mutations can be used to address these problems and improve performance. To reduce false positive indel discovery (improve specificity), regions around commonly expected indels can be examined for problematic alignments due to sequence context and addressed similarly to substitutions above. To improve sensitivity of indel detection, several different approaches of using information on the indels expected in cancer can be used. E.g., short-reads contained expected indels can be simulated and alignment attempted. The alignments can be studied and problematic indel regions can have alignment parameters adjusted, for instance by reducing gap open/extend penalties or by aligning partial reads (e.g. the first or second half of a read).

Alternatively, initial alignment can be attempted not just with the normal reference genome, but also with alternate versions of the genome, containing each of the known or likely cancer indel mutations. In this approach, reads of indels that initially failed to align or aligned incorrectly are placed successfully on the alternate (mutated) version of the genome.

In this way, indel alignment (and thus calling) can be optimized for the expected cancer genes/sites. As used herein, a sequence alignment algorithm embodies a computational method or approach used to identify from where in the genome a read sequence (e.g., a short-read sequence, e.g., from next-generation sequencing) most likely originated by assessing the similarity between the read sequence and a reference sequence. A variety of algorithms can be applied to the sequence alignment problem. Some algorithms are relatively slow, but allow relatively high specificity. These include, e.g., dynamic programming-based algorithms. Dynamic programming is a method for solving complex problems by breaking them down into simpler steps. Other approaches are relatively more efficient, but are typically not as thorough. These include, e.g., heuristic algorithms and probabilistic methods designed for large-scale database search.

Alignment parameters are used in alignment algorithms to adjust performance of an algorithm, e.g., to produce an optimal global or local alignment between a read sequence and a reference sequence. Alignment parameters can give weights for match, mismatch, and indels. For example, lower weights allow alignments with more mismatches and indels.

Sequence context, e.g., presence of repetitive sequences (e.g., tandem repeats, interspersed repeats), low-complexity regions, indels, pseudogenes, or paralogs can affect the alignment specificity (e.g., cause misalignment). As used herein, misalignment refers to the placement of base-pairs from the short read on incorrect locations in the genome.

The sensitivity of alignment can be increased when an alignment algorithm is selected or an alignment parameter is adjusted based on tumor type, e.g., a tumor type that tends to have a particular mutation or mutation type.

The sensitivity of alignment can be increased when an alignment algorithm is selected or an alignment parameter is adjusted based on a particular gene type (e.g., oncogene, tumor suppressor gene). Mutations in different types of cancer-associated genes can have different impact on cancer phenotype. For example, mutant oncogene alleles are typically dominant. Mutant tumor suppressor alleles are typically recessive, which means that in most cases both alleles of a tumor suppressor genes must be affected before an effect is manifested.

The sensitivity of alignment can be adjusted (e.g., increased) when an alignment algorithm is selected or an alignment parameter is adjusted based on mutation type (e.g., single-nucleotide polymorphism, indel (insertion or deletion), inversion, translocation, tandem repeat).

The sensitivity of alignment can be adjusted (e.g., increased) when an alignment algorithm is selected or an alignment parameter is adjusted based on mutation site (e.g., a mutation hotspot). A mutation hotspot refers to a site in the genome where mutations occur up to 100 times more frequently than the normal mutation rate.

The sensitivity/specificity of alignment can be adjusted (e.g., increased) when an alignment algorithm is selected or an alignment parameter is adjusted based on sample type (e.g., an FFPE sample).

Alignment algorithms can be selected to adjust (e.g., increase) the alignment sensitivity/specificity, based on sample type (e.g., an FFPE sample, a blood sample, or a bone marrow aspirate sample).

Optimization of alignment is described in the art, e.g., as set out in International Patent Application Publication No. WO 2012/092426.

Mutation Calling

Base calling refers to the raw output of a sequencing device. Mutation calling refers to the process of selecting a nucleotide value, e.g., A, G, T, or C, for a nucleotide position being sequenced. Typically, the sequencing reads (or base calling) for a position will provide more than one value, e.g., some reads will give a T and some will give a G. Mutation calling is the process of assigning a nucleotide value, e.g., one of those values to the sequence. Although it is referred to as "mutation" calling it can be applied to assign a nucleotide value to any nucleotide position, e.g., positions corresponding to mutant alleles, wildtype alleles, alleles that have not been characterized as either mutant or wildtype, or to positions not characterized by variability. Methods for mutation calling can include one or more of the following: making independent calls based on the information at each position in the reference sequence (e.g., examining the sequence reads; examining the base calls and quality scores; calculating the probability of observed bases and quality scores given a potential genotype; and assigning genotypes (e.g., using Bayes rule)); removing false positives (e.g., using depth thresholds to reject SNPs with read depth much lower or higher than expected; local realignment to remove false positives due to small indels); and performing linkage disequilibrium (LD)/imputation based analysis to refine the calls.

Equations to calculate the genotype likelihood associated with a specific genotype and position are described, e.g., in Li H. and Durbin R. *Bioinformatics,* 2010; 26(5): 589-95. The prior expectation for a particular mutation in certain cancer type can be used when evaluating samples from that cancer type. Such likelihood can be derived from public databases of cancer mutations, e.g., Catalogue of Somatic Mutation in Cancer (COSMIC), HGMD (Human Gene Mutation Database), The SNP Consortium, Breast Cancer Mutation Data Base (BIC), and Breast Cancer Gene Database (BCGD).

Examples of LD/imputation based analysis are described, e.g., in Browning B. L. and Yu Z. *Am. J. Hum. Genet.* 2009, 85(6):847-61. Examples of low-coverage SNP calling methods are described, e.g., in Li Y. et al., *Annu. Rev. Genomics Hum. Genet.* 2009, 10:387-406.

After alignment, detection of substitutions can be performed using a calling method, e.g., Bayesian mutation calling method; which is applied to each base in each of the subgenomic intervals, e.g., exons of the gene to be evaluated, where presence of alternate alleles is observed. This method will compare the probability of observing the read data in the presence of a mutation with the probability of observing the read data in the presence of base-calling error alone. Mutations can be called if this comparison is sufficiently strongly supportive of the presence of a mutation.

Methods have been developed that address limited deviations from frequencies of 50% or 100% for the analysis of cancer DNA. (e.g., SNVMix—Bioinformatics. 2010 Mar. 15; 26(6): 730-736.) Method disclosed herein however allow consideration of the possibility of the presence of a mutant allele at anywhere between 1% and 100% of sample DNA, and especially at levels lower than 50% This approach is particularly important for the detection of mutations in low-purity FFPE samples of natural (multi-clonal) tumor DNA.

An advantage of a Bayesian mutation-detection approach is that the comparison of the probability of the presence of a mutation with the probability of base-calling error alone can be weighted by a prior expectation of the presence of a mutation at the site. If some reads of an alternate allele are observed at a frequently mutated site for the given cancer type, then presence of a mutation may be confidently called even if the amount of evidence of mutation does not meet the usual thresholds. This flexibility can then be used to increase detection sensitivity for even rarer mutations/lower purity samples, or to make the test more robust to decreases in read coverage. The likelihood of a random base-pair in the genome being mutated in cancer is ~1e-6. The likelihood of specific mutations at many sites in a typical multigenic cancer genome panel can be orders of magnitude higher. These likelihoods can be derived from public databases of cancer mutations (e.g., COSMIC). Indel calling is a process of finding bases in the sequencing data that differ from the reference sequence by insertion or deletion, typically including an associated confidence score or statistical evidence metric.

Methods of indel calling can include the steps of identifying candidate indel, calculating genotype likelihood through local re-alignment, and performing LD-based genotype inference and calling. Typically, a Bayesian approach is used to obtain potential indel candidates, and then these candidates are tested together with the reference sequence in a Bayesian framework.

Algorithms to generate candidate indels are described, e.g., in McKenna A. et al., *Genome Res.* 2010; 20(9):1297-303; Ye K. et al., *Bioinformatics,* 2009; 25(21):2865-71; Lunter G. and Goodson M. *Genome Res.* 2010, epub ahead of print; Li H. et al., *Bioinformatics* 2009, Bioinformatics 25(16):2078-9.

Methods for generate indel calls and individual-level genotype likelihoods include, e.g., the Dindel algorithm (Albers C. A. et al., *Genome Res.* 2011; 21(6):961-73). For example, the Bayesian EM algorithm can be used to analyze the reads, make initial indel calls, and generate genotype likelihoods for each candidate indel, followed by imputation of genotypes using, e.g., QCALL (Le S. Q. and Durbin R. *Genome Res.* 2011; 21(6):952-60). Parameters, such as prior expectations of observing the indel can be adjusted (e.g., increased or decreased), based on the size or location of the indels.

Optimization of mutation calling is described in the art, e.g., as set out in International Patent Application Publication No. WO 2012/092426.

OTHER EMBODIMENTS

In embodiments of a method described herein a step or parameter in the method is used to modify a downstream step or parameter in the method.

In an embodiment, a characteristic of the tumor sample is used to modify a downstream step or parameter in one or more or all of: isolation of nucleic acid from said sample; library construction; bait design or selection; hybridization conditions; sequencing; read mapping; selection of a mutation calling method; mutation calling, or mutation annotation.

In an embodiment, a characteristic of an isolated tumor, or control, nucleic acid is used to modify a downstream step or parameter in one or more or all of: isolation of nucleic acid from said sample; library construction; bait design or selection; hybridization conditions; sequencing; read mapping; selection of a mutation calling method; mutation calling, or mutation annotation.

In an embodiment, a characteristic of a library is used to modify a downstream step or parameter in one or more or all of: re-isolation of nucleic acid from said sample; subsequent library construction; bait design or selection; hybridization conditions; sequencing; read mapping; selection of a mutation calling method; mutation calling, or mutation annotation.

In an embodiment, a characteristic of a library-catch is used to modify a downstream step or parameter in one or more or all of: re-isolation of nucleic acid from said sample; subsequent library construction; bait design or selection; hybridization conditions; sequencing; read mapping; selection of a mutation calling method; mutation calling, or mutation annotation.

In an embodiment, a characteristic of the sequencing method is used to modify a downstream step or parameter in one or more or all of: re-isolation of nucleic acid from said sample; subsequent library construction; bait design or selection; subsequent determination of hybridization conditions subsequent sequencing; read mapping; selection of a mutation calling method; mutation calling, or mutation annotation.

In an embodiment, characteristic of the collection of mapped reads is used to modify a downstream step or parameter in one or more or all of: re-isolation of nucleic acid from said sample; subsequent library construction; bait design or selection; subsequent determination of hybridization conditions subsequent sequencing; subsequent read mapping; selection of a mutation calling method; mutation calling, or mutation annotation.

In an embodiment, the method comprises acquiring a value for a tumor sample characteristic, e.g., acquiring a value: for the proportion of tumor cells in said sample, for the cellularity of said tumor sample; or from an image of the tumor sample.

In embodiments, the method includes, responsive to said acquired value for a tumor sample characteristic, selecting a parameter for: isolation of nucleic acid from a tumor sample, library construction; bait design or selection; bait/library member hybridization; sequencing; or mutation calling.

In an embodiment, a method further comprising acquiring a value for the amount of tumor tissue present in said tumor sample, comparing said acquired value with a reference criterion, and if said reference criterion is met, accepting said tumor sample, e.g, accepting said tumor sample if said tumor sample contains greater than 30, 40 or 50% tumor cells.

In an embodiment, a method further comprises acquiring a sub-sample enriched for tumor cells, e.g., by macrodissecting tumor tissue from said tumor sample, from a tumor sample that fails to meet the reference criterion.

In an embodiment, a method further comprises determining if a primary control, e.g., a blood sample, is available and if so isolating a control nucleic acid (e.g., DNA) from said primary control.

In an embodiment, a method further comprises determining if NAT is present in said tumor sample (e.g., where no primary control sample is available).

In an embodiment, a method further comprises acquiring a sub-sample enriched for non-tumor cells, e.g., by macrodissecting non-tumor tissue from said NAT in a tumor sample not accompanied by a primary control.

In an embodiment, a method further comprises determining that no primary control and no NAT is available and marking said tumor sample for analysis without matched control.

In an embodiment, a method further comprises isolating nucleic acid from said tumor sample to provide an isolated tumor nucleic acid sample.

In an embodiment, a method further comprises isolating a nucleic acid from a control to provide an isolated control nucleic acid sample.

In an embodiment, a method further comprises rejecting a sample with no detectable nucleic acid.

In an embodiment, a method further comprises acquiring a value for nucleic acid yield in said isolated nucleic acid sample and comparing the acquired value to a reference criterion, e.g., wherein if said acquired value is less than said reference criterion, then amplifying said isolated nucleic acid sample prior to library construction.

In an embodiment, a method further comprises acquiring a value for the size of nucleic acid fragments in said isolated nucleic acid sample and comparing the acquired value to a reference criterion, e.g., a size, e.g., average size, of at least 300, 600, or 900 bp. A parameter described herein can be adjusted or selected in response to this determination.

In an embodiment, a method further comprises acquiring a library wherein the size of said nucleic acid fragments are less than or equal to a reference value said library is made without a fragmentation step between DNA isolation and making the library.

In an embodiment, a method further comprises acquiring nucleic acid fragments and if the size of said nucleic acid fragments are equal to or greater than a reference value and are fragmented and then made into a library.

In an embodiment a method further comprises labeling each of a plurality of library members, e.g., by addition of an identifiable distinct nucleic acid sequence (a barcode), to each of a plurality of members.

In an embodiment, a method further comprises attaching a primer to each of a plurality of library members.

In an embodiment a method further comprises providing a plurality of bait and selecting a plurality of baits, said selection being responsive to: 1) a patient characteristic, e.g., age, stage of tumor, prior treatment, or resistance; 2) tumor type; 3) a characteristic of the tumor sample; 4) a characteristic of a control sample; 5) presence or type of control; 6) a characteristic of the isolated tumor (or control) nucleic acid sample; 7) a library characteristic; 8) a mutation known to be associated with the type of tumor in the tumor sample; 9) a mutation not known to be associated with the type of tumor in the tumor sample; 10) the ability to sequence (or hybridized to or recover) a preselected sequence or identify a preselected mutation, e.g., the difficulty associated with sequence a high gc region or a rearrangement; or 11) the genes being sequenced.

In an embodiment a method further comprises responsive, e.g., to a determination of low number of tumor cells in said tumor sample, selecting a bait, or plurality of baits, giving relatively highly efficient capture of members from a first gene as compared with members of a second gene, e.g., wherein a mutation in the first gene is associated the tumor phenotype for the tumor type of the tumor sample.

In an embodiment a method further comprises acquiring a value for library-catch characteristic, e.g., the nucleic acid concentration or representation, and comparing the acquired value with a reference criterion for nucleic acid concentration, or for representation.

In an embodiment, a method further comprises selecting a library with a value for a library characteristic that does not meet the reference criterion for reworking.

In an embodiment, a method further comprises selecting a library with a value for a library characteristic that meets the reference criterion for library quantitation.

In an embodiment, a method further comprises providing an association of a tumor type, a gene, and a genetic alteration (a TGA) for a subject.

In an embodiment, a method further comprises providing a preselected database having a plurality of elements, wherein each element comprises a TGA.

In an embodiment, a method further comprises characterizing a TGA of a subject comprising:
  determining if said TGA is present in a preselected database, e.g., a database of validated TGAs;
  associating information for the TGA from the predetermined database with said TGA (annotating) from said subject; and
  optionally, determining if a second or subsequent TGA for said subject is present in said preselected database and if so associating information for the second or subsequent TGA from the predetermined database with said second TGA present in said patient.

In an embodiment, a method further comprises memorializing the presence or absence of a TGA, and optionally an associated annotation, of a subject to form a report.

In an embodiment, a method further comprises transmitting said report to a recipient party.

In an embodiment, a method further comprises characterizing a TGA of a subject comprising:
  determining if said TGA is present in a preselected database, e.g., a database of validated TGAs;
  determining if a TGA not in said preselected database has a known clinically relevant G or A and if so providing an entry for said TGA in said preselected database.

In an embodiment, a method further comprises memorializing the presence or absence of a mutation found in the DNA of the tumor sample from a subject to form a report.

In an embodiment, a method further comprises memorializing the presence or absence of a TGA, and optionally an associated annotation, of a subject to form a report.

In an embodiment, a method further comprises transmitting said report to a recipient party.

The present disclosure also includes any of the following numbered paragraphs:

1. A method of evaluating or providing a clonal profile of a subject interval, e.g., a subgenomic interval, or an expressed subgenomic interval (or of a cell containing the same), in a subject, comprising:
   (a) acquiring a nucleic acid library comprising a plurality of members, each member of the plurality comprising a nucleic acid from the subject, e.g., a plurality of tumor members from a solid tumor or hematologic malignancy sample;
   (b) contacting the library with a bait set to provide a plurality of selected members, each of which comprises the subject interval, or a portion thereof (sometimes referred to herein as a library catch);
   optionally, (c) amplifying each member of the plurality of selected members, e.g., to provide an amplified sequence of the subject interval;
   (d) acquiring the sequence of one or more occurrences of the subject interval;
   thereby providing or evaluating the clonal profile of a subject interval.

2. The method of paragraph 1, wherein step (a) comprises fragmenting, e.g., shearing, nucleic acid from the subject.

3. The method of paragraph 1 or 2, wherein step (b) comprises contacting the library with the bait set under conditions of solution hybridization.

4. The method of paragraph 1 or 2, wherein step (b) comprises contacting the library with the bait set under conditions of surface-based hybridization.

5. The method of paragraph 4, wherein step (b) comprises contacting the library with the bait set on a surface, e.g., a bait set disposed on a substrate comprising a plurality of baits.

6. The method of any of paragraphs 1-5, wherein step (c) comprises amplifying each member of the plurality of selected members by a method that relies on or comprises a sequence specific interaction with target/subject nucleic acid in the member, e.g., by amplifying each member of the plurality of selected members with a primer that binds to target/subject nucleic acid in the member.

7. The method of any of paragraphs 1-5, wherein step (c) amplifying each member of the plurality of selected members with a primer pair, wherein at least one member of the primer pair does not bind to target/subject nucleic acid in the member.

8. The method of any of paragraphs 1-5, wherein step (c) comprises amplifying each member of the plurality of selected members by a method that does not rely on or comprise a sequence specific interaction with target/subject nucleic acid in the member.

9. The method of any of paragraphs 1-5, wherein step (c) comprises amplifying each member of the plurality of selected members by amplifying each member of the plurality of selected members with a primer pair that does not bind to target/subject nucleic acid in the member.

10. The method of any of paragraphs 1-9, wherein the subject interval comprises a subgenomic interval.

11. The method of any of paragraphs 1-9, wherein the subject interval comprises an expressed subgenomic interval.

12. The method of any of paragraphs 1-11, comprising evaluating the clonal profile of a subgenomic interval and of an expressed subgenomic interval.

13. The method of any of paragraphs 1-12, comprising comparing the sequence of a first allele or signature (e.g., a first V segment) at the subject interval with a comparison value, e.g., a preselected value, e.g., a value that is a function of the sequence of a second allele or signature (e.g., a second V segment).

14. The method of any of paragraphs 1-13, further comprising:
   (e) acquiring:
      (i) a value for the distribution, expression (the occurrence or level of transcribed copies of a subgenomic signature), abundance, or identity, of a sequence, signature or allele at the subject interval, e.g., the relative abundance, of a sequence, a signature, or an allele, or the relative abundance of each of a plurality of sequences, signatures, or alleles, at the subject interval; or
      (ii) a value for variability, e.g., sequence variability arising from somatic hypermutation, sequence variability arising from at VD, DJ, or VJ, junctions, e.g., by the formation of indels at the junction, or CDR, e.g., heavy chain CDR3, sequence variability, within a signature or subject interval, e.g., wherein a value for variability is a function of number of different variants present for the subject interval in a subject or sample.

15. The method of paragraph 14, wherein (i) comprises acquiring a value for the relative abundance of a first sequence, allele, or signature at the subject interval relative to the abundance of a first sequence, allele, or signature at the subject interval.

16. The method of paragraph 14, wherein (i) comprises acquiring a value for the relative abundance of a first sequence, allele, or signature at the subject interval relative to the abundance of a second sequence, allele, or signature at a second subject interval.

17. The method of paragraph 14, wherein (i) comprises acquiring a value for the occurrence or level of a sequence, allele, or signature, e.g., a rearrangement, e.g., a translocation, at an expressed subgenomic interval.

18. The method of paragraph 17, further comprising acquiring a value for the occurrence or level of the sequence, allele, or signature, e.g., a rearrangement, e.g., a translocation, at the corresponding subgenomic interval.

19. The method of paragraph 14, wherein (ii) comprises acquiring a value for the number of different sequences, alleles, or signatures, occurring at a subject interval.

20. The method of paragraph 14, comprising acquiring (e)(i).

21. The method of paragraph 14, comprising acquiring (e)(i) for a signature.

22. The method of paragraph 14, comprising acquiring (e)(i) for an allele.

23. The method of paragraph 14, comprising acquiring (e)(ii).

24. The method of any of paragraphs 1-23, comprising providing the clonal profile of a sequence, allele or signature, e.g., a V segment, or VDJ or VT rearrangement, at a first subject interval; and
   i) a phenotype, e.g., disease state, of the subject; or
   ii) a genotype at a second subject interval, e.g., the genotype of a gene selected from Tables 1-4 or Tables 5A-9 or an MHC gene, e.g., a MHC class I or MHC class II gene.

25. The method of paragraph 24, wherein the phenotype comprises:
   an infection with an infectious agent, e.g., a bacterium, virus, protozoan, or fungus;
   stage of disease;
   a change in the genotype of a disorder, e.g., a cancer;

a change in the manifestation of a disorder, e.g., in the case of cancer, a change in aggressiveness or resistance to treatment, e.g., in the case of cancer, development of metastases;

responsiveness to a treatment develops;

progression, relapse, recurrence, or persistence of a disease or disorder;

prior exposure to a an agent associated with a disease;

prior exposure or response to an antigen or vaccine;

proteomic data from the subject;

age;

gender;

weight;

medical history, e.g., prior incidence of disease or prior treatment; or an environmental or occupational factor.

26. The method of paragraph 24, wherein the genotype at the second interval comprises a somatic mutation, e.g., rearrangement, e.g., translocation, e.g., in a gene from Tables 1-4 or Tables 5A-9.

27. The method of any of paragraphs 1-26, wherein step (d):
  (i) comprises acquiring the sequence of each of a plurality of occurrences of the subject interval, e.g., acquiring the sequence of first occurrence of a subject interval comprising a V segment and of a second occurrence of the interval comprising the V segment, wherein the first and second occurrence differ by the diversity at a VD, DJ, or VJ junction; or
  (ii) comprises acquiring the sequence of the subject interval and of a second different subject interval, e.g., wherein the first subject interval comprises sequence from a first gene and the second subject interval comprises sequence from a second gene.

28. The method of any of paragraphs 1-27, wherein step (d) comprises acquiring the sequence of each of a plurality of occurrences of the subject interval, e.g., a plurality of occurrences of a subject interval comprising a VDJ sequence, e.g., a plurality of occurrences of a subject interval comprising a VDJ sequence comprising a specific V segment, a specific D segment, and a specific J segment.

29. The method of paragraph 27 or 28, wherein the first occurrence of the plurality of occurrences of the subject interval comprises a subgenomic interval.

30. The method of paragraph 29, wherein the second occurrence of the plurality of occurrences of the subject interval comprises a subgenomic interval.

31. The method of paragraph 27 or 28, wherein the first occurrence of the plurality of occurrences of the subject interval comprises an expressed subgenomic interval.

32. The method of paragraph 31, wherein the second occurrence of the plurality of occurrences of the subject interval comprises an expressed subgenomic interval.

33. The method of paragraph 27 or 28, wherein:
  the first occurrence of the plurality of occurrence s of the subject interval comprises a subgenomic interval, e.g., a rearrangement, e.g., a translocation; and
  the second occurrence of the plurality of occurrence s of the subject interval comprises an expressed subgenomic interval, e.g., an expressed subgenomic interval that corresponds to the subgenomic interval, which, e.g., allows for evaluation of the expression of genomic, e.g., somatic genomic, rearrangements, e.g., allows for evaluation of the relative abundance of a genomic rearrangement and its expression.

34. The method of paragraph 33, comprising evaluating the occurrence or level of expression of a signature present in a subgenomic interval.

35. The method of any of paragraphs 1-34, wherein step (d) comprises acquiring the sequence of a first subject interval and of a second different subject interval, e.g., where the first and second intervals correspond to different genomic sequences from the subject interval, e.g., a sequence from a first gene and sequence from a second gene.

36. The method of paragraph 35, wherein the first subject interval comprises a first combination of VDJ segments and the second subject interval comprises a second combination of VDJ segments, e.g., the first subject interval comprises a first V segment and the second subject interval comprises a second V segment.

37. The method of paragraphs 35, wherein the first subject interval comprises a first subgenomic interval and the second subject interval comprises a second subgenomic interval.

38. The method of paragraphs 35, wherein the first subject interval comprises a first express subgenomic interval and the second subject interval comprises a second expressed subgenomic interval.

39. The method of paragraphs 35, wherein the first subject interval comprises a subgenomic interval and the second subject interval comprises an expressed subgenomic interval.

40. The method of any of paragraphs 1-39, wherein evaluating comprises providing the clonal profile for a clone of a cancer.

41. The method of paragraph 40, wherein evaluating comprises providing the clonal profile for a second clone of a cancer.

42. The method of paragraph 41, wherein evaluating comprises providing a value for the abundance of the first clone of the cancer, e.g., relative to a reference, e.g., relative to the abundance of the second clone of a cancer.

43. The method of paragraph 42, comprising providing the relative abundance of a first clone of a cancer comprising a genotype and a second clone comprising a second genotype.

44. The method of paragraph 42, comprising providing the relative abundance of a first clone of a cancer comprising a first mutation, e.g., rearrangement, and a second clone not comprising the mutation.

45. The method of paragraph 42, comprising providing the relative abundance of a first clone of a cancer comprising a first mutation, e.g., a rearrangement, e.g., a translocation, and a second clone comprising a second mutation, e.g., a rearrangement, e.g., a translocation.

46. The method of any of paragraphs 1-45, wherein evaluating comprises providing the clonal profile for a first V segment.

47. The method of paragraph 46, wherein evaluating comprises providing the clonal profile for a second V segment.

48. The method of paragraph 46, wherein evaluating comprises providing a value for the relative abundance of the first V segment and the second V segment.

49. The method of any of paragraphs 1-48, wherein evaluating comprises providing the clonal profile for a first D segment.

50. The method of paragraph 49, wherein evaluating comprises providing the clonal profile for a second D segment.

51. The method of paragraph 49, wherein evaluating comprises providing a value for the relative abundance of the first D segment and the second D segment.

52. The method of any of paragraphs 1-51, wherein evaluating comprises providing the clonal profile for a first J segment.

53. The method of paragraph 52, wherein evaluating comprises providing the clonal profile for a second J segment.

54. The method of paragraph 52, wherein evaluating comprises providing a value for the relative abundance of the first J segment and the second J segment.

55. The method of any of paragraphs 1-54, wherein evaluating comprises providing the clonal profile for a first VDJ or VJ combination.

56. The method of paragraph 55, wherein evaluating comprises providing the clonal profile for a second VDJ or VJ combination.

57. The method of paragraph 55, wherein evaluating comprises providing a value for the relative abundance of the first VDJ or VJ combination and the second VDJ or VJ combination.

58. The method of any of paragraphs 1-57, wherein evaluating comprises providing the clonal profile for an antibody light chain.

59. The method of paragraph 58, wherein evaluating comprises providing the clonal profile for an antibody heavy chain.

60. The method of paragraph 58, wherein evaluating comprises providing a value for the relative abundance of an antibody light chain and an antibody heavy chain.

61. The method of any of paragraphs 1-60, wherein evaluating comprises providing the clonal profile for a sequence, allele or signature in a subgenomic interval.

62. The method of paragraph 61, wherein evaluating comprises providing the clonal profile for a sequence, allele or signature in an expressed subgenomic interval.

63. The method of paragraph 61, wherein evaluating comprises providing a value for the relative abundance for a sequence, allele or signature in a subgenomic interval and for a sequence, allele or signature in an expressed subgenomic interval.

64. The method of any of paragraphs 1-63, wherein evaluating comprises providing the variability for hypermutation in a locus, e.g., in a V, D, or J segment, in a subject interval.

65. The method of any of paragraphs 1-64, wherein evaluating comprises providing the variability arising from a VD, DJ, or VJ junction, e.g., by the formation of an indel at the junction, in a subject interval.

66. The method of any of paragraphs 1-65, wherein evaluating comprises providing the variability in a CDR, e.g., heavy chain CDR3, in a subgenomic interval.

67. The method of any of paragraphs 1-66, wherein evaluating comprises providing the clonal profile for a sequence from Table 10 (or a cell that comprises the sequence).

68. The method of paragraph 14, comprising acquiring a value for e(i).

69. The method of paragraph 68, wherein the value of (e)(i) comprises a value for the abundance of a sequence, signature, or allele (e.g., a first V segment) in a subject interval relative to a comparison value, e.g., a preselected value, e.g., a value that is a function of the abundance of a second sequence, signature, or allele (e.g., a second V segment).

70. The method of paragraph 68, wherein the value of (e)(i) comprises a value for the abundance of an event, e.g., a sequence, allele, or signature, e.g., a mutation or rearrangement, in a subject interval, relative to a comparison value, e.g., a preselected value, e.g., a value that is a function of the abundance of a sequence lacking the event, e.g., an unmutated or unrearranged sequence in the subject interval.

71. The method of paragraph 68, wherein the value of (e)(i) comprises a value of relative abundance for each of X unique (i.e., different from one another) sequences, signatures, or alleles, at a subject interval.

72. The method of paragraph 71, wherein X is equal to or greater than 3, 4, 5, 6, 7, 8, 9, 10, 20, 30, 40, 50, 100, or 200.

73. The method of paragraph 72, wherein X is equal to or greater than 1,000, 10,000, 100,000, 1,000,000, 10,000,000, or 50,000,000.

74. The method of any of paragraphs 68-73, further comprising displaying the value of (e)(i), e.g., as function of abundance, e.g., relative abundance, e.g., as a histogram.

75. The method of any of paragraphs 68-74, wherein the subject interval comprises: a sequence from an Ig superfamily-receptor, e.g., a T cell receptor or B cell receptor.

76. The method of any of paragraphs 68-75, wherein the subject interval comprises: a sequence from a V segment, a D segment or a J segment.

77. The method of any of paragraphs 68-76, wherein the subject interval comprises a sequence from Table 10.

78. The method of any of paragraphs 68-77, comprising providing the relative abundance for a V segment sequence, signature, or allele.

79. The method of any of paragraphs 68-78, comprising providing the relative abundance for a plurality of V segment sequences, signatures, or alleles.

80. The method of any of paragraphs 68-79, comprising providing the relative abundance for a J segment sequence, signature, or allele.

81. The method of any of paragraphs 68-80, comprising providing the relative abundance for a plurality of J segment sequences, signatures, or alleles.

82. The method of any of paragraphs 68-81, comprising providing the relative abundance for a D segment sequence, signature, or allele.

83. The method of any of paragraphs 68-82, comprising providing the relative abundance for a plurality of D segment sequences, signatures, or alleles.

84. The method of any of paragraphs 68-83, comprising providing the relative abundance for a class switch region sequence, signature, or allele.

85. The method of any of paragraphs 68-84, comprising providing the relative abundance for a plurality of class switch region sequences, signatures, or alleles.

86. The method of paragraph 14, comprising acquiring a value for e(ii).

87. The method of paragraph 86, comprising acquiring a value for variability from a somatic hypermutation.

88. The method of paragraph 86 or 87, comprising acquiring a value for variability arising from at a VD, DJ, or VJ junction, e.g., by the formation of an indel at the junction.

89. The method of any of paragraphs 86-88, comprising acquiring a value for variability arising from a CDR, e.g., heavy chain CDR3, variability.

90. The method of any of paragraphs 86-89, wherein the subject interval comprises a sequence from Table 10.

91. The method of any of paragraphs 86-90, comprising acquiring the sequence of a plurality of unique copies of the subject interval, e.g., a plurality of unique signatures at the subject interval.

92. The method of any of paragraphs 86-91, wherein the value in (e)(ii) comprises a value for the sequence diversity in a plurality of, e.g., X, signatures for the subject interval.

93. The method of any of paragraphs 86-92, wherein the value comprises the number of unique signatures at the subject interval.

94. The method of any of paragraphs 86-93, wherein the value comprises a display, record or listing of the unique signatures at the subject interval.

95. The method of any of paragraphs 86-94, wherein the value comprises a measure of the number of unique copies, e.g., as a function of the total copies of the subject interval.

96. The method of any of paragraphs 92-95, wherein X is equal to or greater than 3, 4, 5, 6, 7, 8, 9, 10, 20, 30, 40, 50, 100, 200, 300, 400, or 500.

97. The method of any of paragraphs 92-96, wherein X is equal to or greater than 1,000, 10,000, 100,000, 1,000,000, 10,000,000, or 50,000,000.

98. The method of any of paragraphs 86-97, wherein the plurality of signatures are all for a single VDJ or VJ combination, and, e.g., provide a value for sequence diversity in a selected VDJ or VJ combination.

99. The method of any of paragraphs 86-98, wherein the variability comprises variability from segment joining, e.g., diversity at a VD, DJ, or VJ junction, e.g., an insertion or deletion at the junction.

100. The method of any of paragraphs 86-99, wherein the variability comprises variability from a somatic hypermutation.

101. The method of any of paragraphs 86-100, wherein each of the plurality of signatures is for a different VDJ or VJ combination.

102. The method of any of paragraphs 86-101, wherein the variability comprises variability from segment joining, e.g., diversity at a VD, DJ, or VJ junction, e.g., an insertion or deletion at the junction.

103. The method of any of paragraphs 86-102, wherein the library is made from B cells, e.g., from a subject comprising a B cell malignancy, e.g., a subject comprising Mantle cell cancer.

104. The method of any of paragraphs 86-103, wherein the subject interval comprises a sequence that encodes a V, D, or J segment, or a VD or DJ junction, from a B cell receptor.

105. The method of any of paragraphs 86-104, further comprising comparing the amount of variability, e.g., somatic hypermutation, with a comparison value, wherein a preselected relationship with the comparison value, e.g., greater than the comparison value, is indicative of outcome, prognosis, or stage of disease.

106. The method of any of paragraphs 14-105, comprising acquiring (e)(i) and (e)(ii).

107. The method of any of paragraphs 1-106, comprising contacting the library with a single bait set.

108. The method of any of paragraphs 1-106, comprising contacting the library with a plurality of bait sets.

109. The method of any of paragraphs 1-108, comprising contacting the library with a bait set which, captures, specifically captures, captures with a preselected efficiency, is optimized to capture, or hybridizes with:
  a sequence at the subject interval;
  a signature at the subject interval; or
  an allele at the subject interval.

110. The method of paragraph 1-109, comprising contacting the library with a second bait set which, captures, specifically captures, captures with a preselected efficiency, is optimized to capture, or hybridizes with:
  a second sequence at the subject interval;
  a second signature at the subject interval; or
  a second allele at the subject interval.

111. The method of any of paragraphs 1-106, comprising contacting with a plurality, e.g., at least X, unique bait sets, wherein each bait set of the plurality, captures, specifically captures, captures with a preselected efficiency, is optimized to capture, or hybridizes with:
  a different sequence from the subject interval;
  a different signature at the subject interval; or
  a different allele at the subject interval,
wherein X is equal to 2, 3, 4, 5, 6, 7, 8, 9, 10, 50, 100, or 200.

112. The method of any of paragraphs 1-111, comprising contacting with a bait set which, captures, specifically captures, captures with a preselected efficiency, is optimized to capture, or hybridizes with:
  a first sequence and a second sequence at the subject interval;
  a first signature and a second signature at the subject interval; or
  a first allele and a second allele at the subject interval.

113. The method of any of paragraphs 1-112, comprising contacting with a bait set which, captures, specifically captures, captures with a preselected efficiency, is optimized to capture, or hybridizes with:
  at least X sequences from the subject interval;
  at least X signatures at the subject interval; or
  at least X alleles at the subject interval,
wherein, X, independently is equal to 2, 3, 4, 5, 6, 7, 8, 9, 10, 50, 100, or 200.

114. The method of any of paragraphs 1-113, comprising contacting with a bait set which, captures, specifically captures, captures with a preselected efficiency, is optimized to capture, or hybridizes with, a first sequence, allele, or signature which is not present at the subject interval in the subject or sample.

115. The method of any of paragraphs 1-114, wherein the subject interval comprises a sequence from Table 10.

116. The method of any of paragraphs 1-115, comprising contacting with a bait set which, captures, specifically captures, captures with a preselected efficiency, is optimized to capture, or hybridizes with, a sequence from a first V, D or J segment and a sequence from a second V, D or J segment.

117. The method of any of paragraphs 1-116, wherein the subject interval comprises a sequence of a V, D or J segment.

118. The method of any of paragraphs 1-117, comprising contacting the library with a bait set that is optimized to capture, or hybridizes with, a V segment (and not a D or J segment).

119. The method of any of paragraphs 1-117, comprising contacting the library with a bait set that is optimized to capture, or hybridizes with, a D segment (and not a V or J segment).

120. The method of any of paragraphs 1-117, comprising contacting the library with a bait set that is optimized to capture, or hybridizes with, a J segment (and not a V or D segment).

121. The method of any of paragraphs 1-117, comprising contacting the library with a bait set that is optimized to capture, or hybridizes with, a V segment.

122. The method of any of paragraphs 1-117 or 121, comprising contacting the library with a bait set that is optimized to capture, or hybridizes with, a D segment.

123. The method of any of paragraphs 1-117, 121, or 122, comprising contacting the library with a bait set that is optimized to capture, or hybridizes with, a J segment.

124. The method of any of paragraphs 1-117 or 121-123, comprising contacting the library with a bait set that comprises bait(s) that span a VD, DJ, or VJ junction.

125. The method of any of paragraphs 1-117 or 121-124, comprising contacting the library with a bait set that comprises bait(s) that span a rearranged VDJ or VJ sequence.

126. The method of any of paragraphs 1-125, comprising contacting the library with a bait set that comprises bait(s) comprising a nucleic acid analog, e.g., locked nucleic acid (LNA), peptide nucleic acid (PNA), or bicyclic nucleic acid (BNA).

127. The method of any of paragraphs 1-126, comprising contacting the library with a bait set that comprises bait(s) that are long enough to be functional but short enough to optimized affinity.

128. The method of any of paragraphs 1-127, wherein the subject interval comprises a subgenomic interval.

129. The method of any of paragraphs 1-127, wherein the subject interval comprises an expressed subgenomic interval.

130. The method of any of paragraphs 1-127, comprising acquiring the sequence of a subgenomic interval and acquiring the sequence of an expressed subgenomic interval.

131. The method of any of paragraphs 1-130, comprising evaluating the clonal profile of a subgenomic interval.

132. The method of any of paragraphs 1-130, comprising evaluating the clonal profile of an expressed subgenomic interval.

133. The method of any of paragraphs 1-130, comprising evaluating the clonal profile of a subgenomic interval and evaluating the clonal profile of an expressed subgenomic interval.

134. The method of any of paragraphs 1-133, comprising evaluating the occurrence or level of expression of a signature present in a subgenomic interval, e.g., where the signature, e.g., a rearrangement, e.g., a translocation, is present in the corresponding subgenomic interval.

135. The method of any of paragraphs 1-134, comprising evaluating the occurrence or level of expression of a signature present in a subgenomic interval, e.g., where the signature, e.g., a rearrangement, e.g., a translocation, as a function of the abundance in the corresponding subgenomic interval.

136. The method of any of paragraphs 1-135, wherein evaluating comprises providing a value for the relative abundance for a sequence, allele or signature in a subgenomic interval and for a sequence, allele or signature in an expressed subgenomic interval.

137. The method of any of paragraphs 1-136, comprising acquiring the sequence of each of a plurality of occurrences of the subject interval;
   wherein one of steps (a), (b) and (c) is performed separately for a first occurrence of the subject interval and for a second occurrence of the subject interval, e.g., wherein one of steps (a), (b) and (c) is performed in a first reaction mixture for the first occurrence and in a second reaction mixture for the second occurrence.

138. The method of paragraph 137, wherein: step(s) (a); (b); (c); (a) and (b); (a) and (c); (b) and (c); or (a), (b), and (c), are performed separately.

139. The method of paragraph 137 or 138, wherein the first copy of the plurality of unique copies of the subject interval comprises a subgenomic interval.

140. The method of any of paragraphs 137-139, wherein the second copy of the plurality of unique copies of the subject interval comprises a subgenomic interval, e.g., an expressed subgenomic interval that corresponds to the subgenomic interval.

141. The method of any of paragraphs 137-140, wherein:
   the first occurrence of the plurality comprises a subgenomic interval, e.g., wherein the subgenomic interval comprises a VDJ sequence, e.g., a VDJ sequence comprising a specific V segment, a specific D segment, and a specific J segment; and
   the second occurrence of the plurality comprises an expressed subgenomic interval, e.g., wherein the expressed subgenomic interval comprises a VDJ sequence, e.g., a VDJ sequence comprising a specific V segment, a specific D segment, and a specific J segment.

142. The method of paragraph 141, wherein the first occurrence of the subject interval comprises an expressed subgenomic interval.

143. The method of paragraph 141 or 142, wherein the second occurrence of the subject interval comprises an expressed subgenomic interval.

144. The method of any of paragraphs 1-136, comprising acquiring the sequence of each of a plurality of occurrences of the subject interval;
   wherein at least one of steps (a), (b) and (c) is performed in the same reaction mixture for a first occurrence of the subject interval and for a second occurrence of the subject interval.

145. The method of paragraph 144, wherein: step(s) (a); (b); (c); (a) and (b); (a) and (c); (b) and (c); or all of steps (a), (b), and (c), are performed in the same reaction mixture.

146. The method of any of paragraphs 137-145, wherein:
   in step (b) the first copy of the plurality of occurrences of the subject interval is contacted with a first bait set; and
   in step (b) the second copy of the plurality of occurrence of the subject interval is contacted with a second bait set, e.g., a second bait set that comprises a bait comprising a different sequence from any bait in the first bait set.

147. The method of any of paragraphs 137-145, wherein:
   in step (b) the first copy of the plurality of unique copies of the subject interval is contacted with a bait set; and
   in step (b) the second copy of the plurality of unique copies of the subject interval is contacted with the same bait set, e.g., wherein both bait sets comprise the same bait(s).

148. The method of any of paragraphs 1-147, comprising acquiring the sequence of a first subject interval and of a second different subject interval (wherein different means from different chromosomal locations)
   wherein one of steps (a), (b) and (c) is performed in a first reaction mixture for the first subject interval and in a second reaction mixture for the second subject interval.

149. The method of paragraph 148, wherein: step(s) (a); (b); (c); (a) and (b); (a) and (c); (b) and (c); or all of steps (a), (b), and (c), are performed separately.

150. The method of paragraph 148 or 149, wherein the first subject interval comprises a subgenomic interval.

151. The method of paragraph 150, wherein the second different subject interval comprises a subgenomic interval.

152. The method of paragraph 148 or 149, wherein the first subject interval comprises an expressed subgenomic interval.

153. The method of paragraph 152, wherein the second different subject interval comprises an expressed subgenomic interval.

154. The method of paragraph 148 or 149, wherein the first subject interval comprises a subgenomic interval and the second different subject interval comprises an expressed subgenomic interval.

155. The method of any of paragraphs 1-154, comprising acquiring the sequence of the subject interval and of a second different subject interval (wherein different means from different chromosomal locations),
wherein at least one of steps (a), (b) and (c) is performed in the same reaction mixture for the first subject interval and for a second subject interval.

156. The method of paragraph 155, wherein: step(s) (a); (b); (c); (a) and (b); (a) and (c); (b) and (c); or all of steps (a), (b), and (c), are performed in the same reaction mixture.

157. The method of paragraph 155 or 156, wherein:
in step (b) a first subject interval is contacted with a first bait set; and
in step (b) a second subject interval is contacted with a second bait set, e.g., a second bait set that comprises a bait comprising a different sequence from any bait in the first bait set.

158. The method of paragraph 155 or 156, wherein:
in step (b) a first subject interval is contacted with a bait set; and
in step (b) a second subject interval is contacted with the same bait set, e.g., wherein both bait sets comprise the same bait(s).

159. The method of any of paragraphs 1-158, comprising repeating steps (a) to (d).

160. The method of paragraph 159, comprising repeating steps (a) to (d) after:
the passage of a preselected period of time;
a change in the genotype of a disorder, e.g., a cancer;
a change in the manifestation of a disorder, e.g., in the case of cancer, a change in aggressiveness or resistance to treatment, e.g., in the case of cancer, development of metastases;
lack of responsiveness to a treatment develops;
progression, relapse, recurrence, or persistence of a disease or disorder.

161. The method of any of paragraphs 1-160, wherein the library is made from chromosomal DNA.

162. The method of any of paragraphs 1-160, wherein the library is made from RNA, e.g., mRNA.

163. The method of any of paragraphs 1-162, comprising:
(a) evaluating the clonal profile of a subgenomic interval from a library made from chromosomal DNA;
(b) evaluating the clonal profile of an expressed subgenomic interval from a library made from RNA, e.g., mRNA; and
optionally, comparing the evaluations provided in steps (a) and (b), e.g., to determine if a selected sequence, allele or signature of an subject interval is expressed.

164. The method of paragraph 163, wherein step (a) and/or (b) comprises acquiring:
(i) a value for the distribution, expression (the occurrence or level of transcribed copies of a subgenomic signature) abundance, or identity, of an allele at the subject interval, e.g., the relative abundance, an allele, or the relative abundance of each of a plurality of alleles, at the subject interval; or
(ii) a value for the distribution, expression (the occurrence or level of transcribed copies of a subgenomic signature) abundance, or identity, of a signature at the subject interval, e.g., the relative abundance, a signature, or the relative abundance of each of a plurality of signatures, at the subject interval; or (iii) a value for variability, e.g., somatic hypermutation, within a signature or subject interval.

165. The method of paragraph 164, wherein:
step (a) comprises (i) and step (b) comprises (i);
step (a) comprises (i) and step (b) comprises (ii);
step (a) comprises (i) and step (b) comprises (iii);
step (a) comprises (ii) and step (b) comprises (i);
step (a) comprises (ii) and step (b) comprises (ii);
step (a) comprises (ii) and step (b) comprises (iii);
step (a) comprises (iii) and step (b) comprises (i);
step (a) comprises (iii) and step (b) comprises (ii); or
step (a) comprises (iii) and step (b) comprises (iii).

166. The method of ay of paragraphs 1-165, wherein the library is made from disease state tissue, e.g., from cancer cells.

167. The method of any of paragraphs 1-165, wherein the library is made from cells from a solid tumor, e.g., a solid tumor described herein.

168. The method of any of paragraphs 1-165, wherein the library is made from cells, e.g., B cells or T cells, that have infiltrated solid tumor, e.g., a solid tumor described herein.

169. The method of any of paragraphs 1-165, wherein the library is made from cells from a hematologic malignancy, e.g., a hematologic malignancy described herein.

170. The method of any of paragraphs 1-165, wherein the library is made from cell free DNA.

171. The method of any of paragraphs 1-165, wherein the library is made from non-disease state tissue.

172. The method of any of paragraphs 1-165, wherein the library is made from peripheral blood, bone marrow, tumor tissue, tumor infiltrate, lymphocytes, B cells, pre-B cells, mature B cells, T cells, or cell free DNA.

173. The method of any of paragraphs 1-165, wherein the library is made from tumor infiltrating cells, e.g., tumor infiltrating B cells, pre-B cells, mature B cells, or T cells.

174. The method of any of paragraphs 1-165, wherein the library is made from peripheral B cells, pre-B cells, mature B cells, or T cells, e.g., CD4+ or CD8+, T cells.

175. The method of any of paragraphs 1-165, comprising evaluating a clonal profile for non-disease-state tissue, e.g., for a cell not associated with a tumor, e.g., a non-tumor cell, or peripheral blood lymphocyte.

176. The method of any of paragraphs 1-165, comprising evaluating a clonal profile for a disease-state tissue, e.g., for a tumor cell or a tumor infiltrating cell, or for a non cancerous disorder.

177. The method of any of paragraphs 1-165, wherein the library is made from T cells and the subgenomic interval comprises sequence that encodes a T cell receptor, e.g., an alpha/beta or delta/gamma, TCR chain.

178. The method of any paragraphs 1-177, comprising:
(a) evaluating the clonal profile of a subject interval from a first cell type, e.g., from a library made from the first cell type, e.g., made from chromosomal DNA, or RNA, e.g., mRNA, from the first cell type;
(b) evaluating the clonal profile of a subject interval from a second cell type, e.g., from a library made from the second cell type, e.g., made from chromosomal DNA, or RNA, e.g., mRNA, from the second cell type; and
optionally, comparing the evaluations provided in steps (a) and (b), e.g., to determine if an allele or signature of an subject interval is expressed.

179. The method of any of paragraphs 1-178, comprising:
(a) evaluating the clonal profile of a subject interval from a first cell type;
(b) evaluating the clonal profile of a subject interval from a second cell type; and optionally, comparing the evaluations provided in steps (a) and (b), e.g., to determine if an allele or signature of an subject interval is expressed.

180. The method of any of paragraphs 1-179, comprising:
(a) evaluating the clonal profile of a subject interval from a library made from chromosomal DNA;
(b) evaluating the clonal profile of a subject interval from a library made from RNA, e.g., mRNA, e.g., cDNA; and
optionally, comparing the evaluations provided in steps (a) and (b), e.g., to determine if an allele or signature of an subject interval is expressed.

181. The method of any of paragraphs 1-180, comprising:
(a) evaluating the clonal profile of a subject interval at a first time period;
(b) evaluating the clonal profile of a subject interval at a second time period; and
optionally, comparing the evaluations provided in steps (a) and (b), e.g., to determine if an allele or signature of an subject interval is expressed.

182. The method of paragraph 181, wherein said first time period is prior to a preselected event and the second time period is after a preselected event, wherein the preselected event can comprise infection, a medical or surgical procedure, e.g., receiving a transplant, a diagnosis, or administration of a treatment, e.g., a first line treatment or a second line treatment, a reoccurrence or relapse or disease.

183. The method of any of paragraphs 1-182, comprising:
evaluating the clonal profile of a sequence, allele, or signature, from a subject interval from a disease state cell; and
evaluating the clonal profile of a sequence, allele, or signature, from the subject interval from a second disease state cell.

184. The method of any of paragraphs 1-183, comprising:
evaluating the clonal profile of a sequence, allele, or signature, from a first subject interval from a disease state cell; and
evaluating the clonal profile of a sequence, allele, or signature, from a second different subject interval from a disease state cell.

185. The method of any of paragraphs 1-184, wherein the subject has cancer.

186. The method of any of paragraphs 1-184, wherein the subject has a hematological-cancer.

187. The method of any of paragraphs 1-184, wherein the subject has a solid tumor.

188. The method of any of paragraphs 1-187, wherein the library is made from B cells and the subject has a B cell malignancy, e.g., mantle cell cancer.

189. The method of any of paragraphs 1-184, wherein the subject has a disorder other than cancer.

190. The method of any of paragraphs 1-184, wherein the subject has an immune disorder, e.g., an autoimmune disorder, an immune deficiency, e.g., an inherited or an acquired immune deficiency, e.g., AIDs or HIV infection.

191. The method of any of paragraphs 1-184, wherein the subject is a graft recipient, e.g., a bone marrow recipient, a solid organ recipient, or a skin graft recipient.

192. The method of any of paragraphs 1-184, wherein the subject has an infection or infectious disease, e.g., a viral, bacterial, protozoan, or fungal infection or disease.

193. The method of any of paragraphs 1-192, wherein the subject interval comprises a nucleotide position, or a junction, or a sequence, representative of a clonal event.

194. The method of any of paragraphs 1-193, wherein the subject interval comprises a nucleotide position, or a junction, or a sequence, representative of a T cell clone or B cell clone.

195. The method of any of paragraphs 1-194, wherein step (c), or the method, does not comprise, amplifying each member, or any member of the plurality, by a method that relies on a sequence specific interaction with target/subject nucleic acid in the member, e.g., by amplifying each member of the plurality with a primer that binds to target/subject nucleic acid in the member.

196. The method of any of paragraphs 1-195, wherein step (d) comprises;
acquiring a read for a subject interval from a member from said library (or library catch);
assigning a nucleotide value from the read for a nucleotide position within the subject interval for each of a plurality of members.

197. The method of any of paragraphs 1-196, comprising, attaching, e.g., ligating, an adaptor sequence to the 5' or 3' end of the nucleic acid from the subject in each member of the plurality of members.

198. The method of any of paragraphs 1-196, comprising, attaching, e.g., ligating, an adaptor sequence to the 5' and 3' ends of the nucleic acid from the subject in each member of the plurality of members.

199. The method of any of paragraphs 1-196, wherein each member of said plurality of members comprises, in the 5' to 3' direction, a 5' adaptor sequence, subject sequence (e.g., genomic or transcribed sequence), and a 3'adaptor.

200. The method of any of paragraphs 1-196, wherein each member of said plurality of members comprises, in the 5' to 3' direction, a 5' adaptor sequence, subject sequence (e.g., genomic or transcribed sequence), and a 3'adaptor, and one of the adaptors comprises an identifier, e.g., a sequence that can function as a bar code.

201. The method of any of paragraphs 1-200, wherein each member of the plurality is amplified with a primer specific for the adaptor sequence.

202. The method of any of paragraphs 1-201, wherein each member of the plurality is amplified with a primer set comprising a primer that binds to the 5' adaptor or a primer that binds to the 3' adaptor.

203. The method of any of paragraphs 1-202, wherein each member of the plurality is amplified with a primer set comprising a primer that binds to the 5' adaptor.

204. The method of any of paragraphs 1-202, wherein each member of the plurality is amplified with a primer set comprising a primer that binds to the 3' adaptor.

205. The method of any of paragraphs 1-200, wherein each member of the plurality is amplified with a primer specific for the adaptor sequence and a primer specific for the target/subject nucleic acid in the member.

206. The method of any of paragraphs 1-205, wherein step (d) comprises:
acquiring a read for a subgenomic interval from a member, e.g., a tumor member from said library or library catch, e.g., by a method comprising sequencing, e.g., with a next generation sequencing method;
aligning said read by an alignment method, e.g., an alignment method described herein; and
assigning a nucleotide value (e.g., calling a mutation, e.g., with a Bayesian method or a method described herein) from said read for the preselected nucleotide position.

207. The method of any of paragraphs 1-206, further comprising;

providing the sequence of a second subject interval, e.g., a subject interval comprising sequence from a gene described herein, e.g., selected from Tables 1-4 or Tables 5A-9.

208. The method of any of paragraphs 1-207, further comprising;
providing the sequence of a second subject interval, e.g., a subject interval comprising sequence encoding an miRNA, a promoter, or other element.

209. The method of any of paragraphs 1-208, further comprising;
providing the sequence of a second subject interval which is from a gene other than a an immunoglobulin or T cell or B cell receptor gene.

210. The method of any of paragraphs 207-209, comprising providing the sequence of a third, or of at least X additional subject intervals, e.g., selected from Tables 1-4 or Tables 5A-9, wherein X is equal to 4, 5, 6, 7, 8, 9, 10, 50, 100, 150, 200, 250, 300, 350, 400, 450 or 500.

211. The method of paragraph 210, wherein the third, or of X additional subject intervals, is from a gene other than an immunoglobulin, B cell receptor, or T cell receptor gene.

212. The method of paragraph 211, wherein X is equal to or greater than, 5, 10, 20, 30, 40, 50, 100, 150, 200, 250, 300, 350, 400, 450, or 500.

213. The method of any of paragraphs 1-212, comprising:
(a) evaluating the clonal profile of a first subject interval, e.g., selected from Table 10, from a first cell type, e.g., from a library made from the first cell type, e.g., a non-cancer cell or a non-malignant cell (e.g., a tumor-infiltrating lymphocyte); and
(b) providing the sequence of a second subject interval, e.g., selected from Tables 1-9, from a second cell type, e.g., from a library made from the second cell type, e.g., a cancer cell or a malignant cell.

214. The method of any of paragraphs 1-212, comprising:
(a) evaluating the clonal profile of a first subject interval, e.g., selected from Table 10, from a first cell type, e.g., from a library made from the first cell type, e.g., a non-cancer cell or a non-malignant cell (e.g., a tumor-infiltrating lymphocyte); and
(b) providing the sequence of a second, a third, or at least X additional subject intervals, e.g., selected from Tables 1-9, wherein X is equal to 4, 5, 6, 7, 8, 9, 10, 50, 100, 150, 200, 250, 300, 350, 400, 450 or 500, from a second cell type, e.g., from a library made from the second cell type, e.g., a cancer cell or a malignant cell.

215. The method of any of paragraphs 1-212, comprising:
(a) evaluating the clonal profile of a first, a second, or at least X additional subject intervals, e.g., selected from Table 10, wherein X is equal to 3, 4, 5, 6, 7, 8, 9, 10, 50, 100, 150, 200, 250, 300, 350, 400, 450 or 500, from a first cell type, e.g., from a library made from the first cell type, e.g., a non-cancer cell or a non-malignant cell (e.g., a tumor-infiltrating lymphocyte); and
(b) providing the sequence of a (X+1)th subject interval, e.g., selected from Tables 1-9, from a second cell type, e.g., from a library made from the second cell type, e.g., a cancer cell or a malignant cell.

216. The method of any of paragraphs 1-212, comprising:
(a) evaluating the clonal profile of one or more (e.g., 2, 3, 4, 5, 6, 7, 8, 9, 10, 50, 100, 150, 200, 250, 300, 350, 400, 450, 500, or more) subject intervals, e.g., selected from Table 10, from a first cell type, e.g., from a library made from the first cell type, e.g., a non-cancer cell or a non-malignant cell (e.g., a tumor-infiltrating lymphocyte); and
(b) providing the sequence of one or more (e.g., 2, 3, 4, 5, 6, 7, 8, 9, 10, 50, 100, 150, 200, 250, 300, 350, 400, 450, 500, or more) subject intervals, e.g., selected from Tables 1-9, from a second cell type, e.g., from a library made from the second cell type, e.g., a cancer cell or a malignant cell.

217. The method of any of paragraphs 213-216, wherein the first cell type, or the library made from the first cell type, is obtained from the same sample as the sample from which the second cell type, or the library made from the second cell type, is obtained.

218. The method of any of paragraphs 213-216, wherein the first cell type, or the library made from the first cell type, is obtained from a different sample than the sample from which the second cell type, or the library made from the second cell type, is obtained.

219. The method of any of paragraphs 207-218, comprising providing the sequence of the second (or subsequent) subject interval by:
(a) acquiring a nucleic acid library comprising a plurality of members, each member of the plurality comprising nucleic acid from the subject e.g., the library of paragraph 1;
(b) contacting the library with a bait set, e.g., under conditions of solution or surface hybridization, to provide a plurality of selected members, each of which comprises the second (or subsequent) subject interval, or a portion thereof (sometimes referred to herein as a library catchy;
(c) amplifying each member of the plurality, e.g., by a method that does not rely on a sequence specific interaction with target/subject nucleic acid in the member, e.g., by amplifying each member of the plurality with a primer that does not bind to target/subject nucleic acid in the member; and
(d) acquiring the sequence of each of the subject interval.

220. The method of paragraph 219, wherein step (d) comprises:
(d)(i) acquiring a read for a subgenomic interval from a member, e.g., a tumor member from said library or library catch, e.g., by a method comprising sequencing, e.g., with a next generation sequencing method;
(d)(ii) aligning said read by an alignment method, e.g., an alignment method described herein; and
(d)(iii) assigning a nucleotide value (e.g., calling a mutation, e.g., with a Bayesian method or a method described herein) from said read for the preselected nucleotide position.

221. A method of evaluating a subject for the occurrence of a whole arm or large rearrangement, e.g., a rearrangement, e.g., a translocation, duplication, insertion, or deletion, comprising, e.g., at least 5, 10, 20, 30, 40, 50, 60, 70, 80, or 90%, or all of a chromosome arm, comprising:
(a) acquiring a nucleic acid library comprising a plurality of members, each member of the plurality comprising nucleic acid from the subject;
(b) contacting the library with a bait set, e.g., under conditions of solution hybridization, to provide a plurality of selected members, each of which comprises a subject interval, or a portion thereof (sometimes referred to herein as a library catchy;
(c) amplifying each member of the plurality, e.g., by a method that does not rely on a sequence specific interaction with target/subject nucleic acid in the member, e.g., by amplifying each member of the plurality with a primer that does not bind to target/subject nucleic acid in the member; and (d) acquiring the sequence of a plurality of subject intervals, wherein said plurality of subject intervals is disposed on a chromosome such as to allow determination of a whole arm or large rearrangement.

222. The method of paragraph 221, wherein the large rearrangement affects, e.g., at least about 5%, 10%, 20%, 30%, 40%, or 50% of a chromosome, or at least about 5%, 10%, 20%, 30%, 40%, 50%, 60%, 70%, 80%, 90%, or 100% of an arm (e.g., a long arm or short arm) of a chromosome.

223. A method of evaluating a subject, comprising:
(a) acquiring a nucleic acid library comprising a plurality of members, each member of the plurality comprising nucleic acid from the subject, e.g., a plurality of tumor members from a hematological-cancer sample;
(b) contacting the library with a bait set, e.g., under conditions of solution hybridization, to provide a plurality of selected members, each of which comprises the subject interval, or a portion thereof (sometimes referred to herein as a library catch);
(c) amplifying each member of the plurality of selected members, e.g., by a method that does not rely on a sequence specific interaction with target/subject nucleic acid in the member, e.g., by amplifying each member of the plurality of selected members with a primer that does not bind to target/subject nucleic acid in the member;
(d) acquiring the sequence of a subgenomic interval and an expressed subgenomic interval;
thereby evaluating the subject,
wherein:
(i) the method comprises contacting the library with a bait set that provides both a subgenomic interval and an expressed subgenomic interval;
(ii) the method comprises contacting the library with a first bait set that provides a subgenomic interval and a second bait set that provides an expressed subgenomic interval;
(iii) wherein the library comprises genomic DNA and is contacted with a bait set that provides a subgenomic interval and the method further comprises a second library which comprises cDNA which is contacted with the bait set to provide an expressed subgenomic interval;
(iv) wherein the library comprises genomic DNA and is contacted with a bait set that provides a subgenomic interval and the method further comprises a second library which comprises cDNA which is contacted with a second bait set to provide an expressed subgenomic interval;
(v) the method comprises performing one of steps (a), (b) and (c) in a first reaction mix to provide a first subject interval, e.g., a subgenomic interval, and on a second reaction mix to provide a second subject interval, e.g., an expressed subgenomic interval, e.g., that corresponds to the subgenomic interval.

224. The method of paragraph 223, wherein step(s) (a); (b); (c); (a) and (b); (a) and (c); (b) and (c); or all of steps (a), (b), and (c), are performed separately.

225. The method of paragraph 223 or 224, wherein the subgenomic interval and expressed subgenomic interval are, independently, selected from Tables 1-4.

226. The method of any of paragraphs 223-225, comprising providing the sequence of at least X subject intervals, wherein X is equal to 2, 3, 4, 5, 10, 20, 30, 40, 50, 100, 150, 200, 250, 300, 350, 400, 450, 500, or greater.

227. The method of any of paragraphs 223-226, wherein the subgenomic interval and the expressed subgenomic interval correspond to the same subject interval, e.g., comprise sequence from the same gene.

A flowchart depiction of an embodiment of a method for multigene analysis of a tumor sample is provided in FIG. 1.

EXEMPLIFICATION

This invention is further illustrated by the following examples which should not be construed as limiting. The contents of all references, figures, sequence listing, patents and published patent applications cited throughout this application are hereby incorporated by reference.

Example 1

Nucleic Acid Isolation from a Tumor Sample

Nucleic acids (DNA and RNA) were isolated from various types of samples, e.g., formalin-fixed, paraffin-embedded (FFPE), blood, and bone marrow aspirate (BMA) samples.

For example, to isolated genomic DNA from an FFPE sample, 3×20 µm sections cut from a paraffin block were mixed with 400 µL Buffer FTL by vortexing and incubated at 90° C. for 15 minutes in a 1.5 mL centrifuge tube. A range of 88-92° C. was acceptable for the incubation. Then, the sample was incubated with 20 µL proteinase K at 55° C. for 6 hours and 10 µL RNase (1 mg/mL) at room temperature for 5 minutes. Next, 460 µL Buffer BL and 500 µL absolute ethanol were added to the sample. The resulting sample solution was kept at room temperature until further use.

To prepare the column for DNA binding, 100 µL Equilibration buffer was added to a MicroElute column and the column was centrifuged at 10,000×g for 30 seconds. 700 µL of the sample solution described above was transferred to the MicroElute column and the column was centrifuged at 10,000×g for 1 minute. The centrifugation step was repeated if fluid did not completely pass through MicroElute column. The remaining sample solution was applied to the MicroElute column in the same way as described above. Then, the MicroElute column was treated with 500 µL Buffer HB and centrifuged at 10,000×g for 1 minute. Next, 700 µL DNA Wash Buffer diluted with ethanol was added into the MicroElute column and the column was centrifuged at 10,000×g for 1 minute. The MicroElute column was washed again using 700 µL DNA Wash Buffer diluted with ethanol, centrifuged at 10,000×g for 1 minute, and centrifuged at >13,000×g for 3 minutes to dry the column. The MicroElute column was placed into a standard 1.5 mL centrifuge tube with the top removed. 50-75 µL Elution Buffer preheated to 70° C. was added into the column and incubated at room temperature for 3 minutes. The column was centrifuged in collection tube at >13,000×g for 1 minute. Another 50-75 µL Elution Buffer preheated to 70° C. was added into the MicroElute column and incubated at room temperature for 3 minutes. The column was centrifuged again in collection tube at >13,000×g for 1 minute. The entire solution was transferred to a fresh 1.5 mL centrifuge tube and stored at −20° C.

FTL buffer, proteinase K, BL Buffer, Equilibration Buffer, MicroElute column, Buffer HB, DNA Wash Buffer, and Elution Buffer were provided in E.Z.N.A.™ FFPE DNA Kit (OMEGA bio-tek, Norcross, GA; Cat. Nos. D3399-00, D3399-01, and D3399-02).

Additional methods to isolate nucleic acids (e.g., DNA) from formaldehyde- or paraformaldehyde-fixed, paraffin-embedded (FFPE) tissues are disclosed, e.g., in Cronin M. et al., (2004) *Am J Pathol.* 164(1):35-42; Masuda N. et al., (1999) *Nucleic Acids Res.* 27(22):4436-4443; Specht K. et al., (2001) *Am J Pathol.* 158(2):419-429, Ambion Recover-All™ Total Nucleic Acid Isolation Protocol (Ambion, Cat. No. AM1975, September 2008), Maxwell® 16 FFPE Plus LEV DNA Purification Kit Technical Manual (Promega Literature #TM349, February 2011), and QIAamp® DNA FFPE Tissue Handbook (Qiagen, Cat. No. 37625, October 2007). RecoverAll™ Total Nucleic Acid Isolation Kit uses xylene at elevated temperatures to solubilize paraffin-embedded samples and a glass-fiber filter to capture nucleic acids. Maxwell® 16 FFPE Plus LEV DNA Purification Kit is used with the Maxwell® 16 Instrument for purification of genomic DNA from 1 to 10 µm sections of FFPE tissue. DNA is purified using silica-clad paramagnetic particles (PMPs), and eluted in low elution volume. QIAamp® DNA FFPE Tissue Kit uses QIAamp® DNA Micro technology for purification of genomic and mitochondrial DNA.

Additional exemplary methods to isolated nucleic acids (e.g., RNA and DNA) from FFPE, blood and bone marrow aspirates are described as follows. RNA from fresh or frozen PAXgene® RNA blood tubes were extracted using Maxwell® 16 LEV simplyRNA Blood Kit for the Maxwell CSC® (Promega Catalog #A1S1311). RNA and DNA from bone marrow aspirates were extracted using Maxwell® 16 LEV simplyRNA Blood Kit for the Maxwell CSC® (Promega Catalog #A1S1311) and Maxwell® 16 Blood DNA Purification Kit for the Maxwell® CSC (Promega Catalog #AS1010), respectively. RNA and DNA from FFPE samples were co-extracted using Maxwell® 16 CSC RNA FFPE kit (Promega Catalog #AS1360) and Maxwell 16 FFPE Tissue LEV DNA kit (Promega Catalog #AS1130), respectively. Deparaffinization of FFPE samples was performed using CitriSolv™ Hybrid Solution (Fisher Scientific Catalog #04-355-121). DNA and RNA from cell lines were purified using Maxwell® 16 LEV simplyRNA Blood kit for the Maxwell CSC® ((Promega Catalog #A1S1311) and Maxwell® 16 Blood DNA Purification Kit for the Maxwell® CSC (Promega Catalog #AS1010), respectively.

Example 2

Quantitation of Isolated Nucleic Acids

Isolated DNA was quantified using Quant-iT™ PicoGreen® dsDNA Reagent (Life Technologies Catalog #P7581). Isolated RNA was quantified using Quant-iT™ RiboGreen® RNA Reagent (Life Technologies Catalog #R11491).

Example 3

Shearing of DNA

Covaris™ E210 instrument with circulating chiller was set to 4° C. The instrument water tank was filled with distilled/deionized water to level "6" on the fill-line. Sono-Lab™ software was launched and the system was allowed to execute homing sequence when prompted. The water in instrument tank was degassed for at least 45 minutes before shearing samples.

To prepare the genomic DNA samples for shearing, samples were first quantified using a PicoGreen® assay (Invitrogen) on a microplate reader (Spectramax M2, Molecular Devices) Based on the concentration, 120 µl desired input DNA (2 ng/µl) with low TE (10 mM Tris, 0.2 mM EDTA, pH 8.0) was used for the experiment. The 100 µl individual samples were pipetted slowly into the Covaris MicroTUBEs (Covaris Cat. #520045) through the septa in the lid of the tube. The Covaris MicroTUBEs were then placed in the Covaris E-series tube rack. For 200 bp shearing, the settings were as follows: 10% duty cycle, 5 Intensity, 200 cycles/burst, time 180 sec, and Frequency Sweeping mode. After shearing, the Covaris MicroTUBEs were briefly spun down using an appropriate adapter in a mini-centrifuge, and the sheared samples were transferred to clean 1.5 ml microcentrifuge tubes. Each sheared DNA sample was purified using a QIAGEN MinElute® column. Briefly, 5× QIAGEN PBI buffer was added to the sample in a 1.5 ml microcentrifuge tube (e.g., 500 µl of PBI buffer was added to 100 µl of sample). Each sample was vortexed, briefly spun down, and transferred to a MinElute spin column. MinElute spin column was centrifuged at 13,000 rpm for 1 minute, and the flow-through was discarded. 750 µl of QIAGEN PE buffer was added to the column, centrifuged at 13,000 rpm for 1 minute, and the flow-through was discarded. The spin column was centrifuged again at 13,000 rpm for 1 minute and transferred to a clean 1.5 ml microcentrifuge tube. The column was air dried for 2-3 minutes. For the first elution, 18 µl of QIAGEN Elution Buffer was added to each column, incubated for 2-3 minutes, and then centrifuged at 13,000 rpm for 1 minute. For the second elution, 15 µl of QIAGEN Elution Buffer was added, incubated for 1 min, and then centrifuged at 13,000 rpm for 1 minute. The eluent was collected and the spin column was discarded.

Typically, 200 ng is used for DNA shearing, but the amount of DNA can range from 20 to 200 ng or higher.

Example 4

Alternative to DNA Shearing

This example describes an alternative method for DNA shearing from Example 3.

A double stranded genomic DNA is first denatured to single stranded DNA, and then mixed with primers, DNA polymerase (e.g., Exo-DNA polymerase), dNTPs, and a small amount of ddNTPs. The primer sequence can be a random hexamer, or a random hexamer tagged with an adaptor sequence at the 5' end. Methods to use tagged random hexamer amplification to clone and sequence minute quantities of DNA are described, e.g., in Wong K. K. et al., *Nucleic Acids Res.* 1996; 24(19):3778-83. The reaction is incubated under the conditions that allow primer-template annealing and DNA synthesis. The DNA synthesis will terminate when a ddNTP is incorporated into the newly synthesized first strand. The length of the synthesized first strand DNA can be controlled by the ratio of dNTPs to ddNTPs. For example, the molar ratio of dNTPs to ddNTP is at least about 1000:1, about 5000:1, or about 10000:1. After first strand synthesis, short fragments (such as primers and synthesized first strand DNA with short length and ddNTPs can be removed by size selection (e.g., using a size selection spin column). The resulting first strand DNA is mixed with primers (e.g., random hexamers or random hesamers tagged with an adaptor sequence), DNA polymerase (e.g., Exo+ DNA polymerase), and dNTPs. An Exo+ DNA polymerase can be used to remove the terminal 3'-ddNTP from the first strand DNA or even to generate blunt ends over the second priming site. The reaction is then incubated under the conditions that allow primer-template annealing and DNA synthesis. After synthesis of the second strand, the resulting double stranded DNA fragments can be purified and used directly in library construction. Alternatively, the double stranded DNA fragments can be PCR amplified using primers containing adaptor sequences if these adaptor sequences have been included in the primers for first- and second-strand synthesis. The primers for PCR amplification can also include the entire sequences and/or bar code sequences.

Example 5 cDNA Synthesis

Prior to library construction, isolated RNA was converted into double-stranded cDNA, which served as input to produce adaptor ligated sequencing libraries.

Double-stranded cDNA was created in a two-step process. First, total RNA was hybridized to a mixture of random hexamer (N6) and oligo-dT DNA primers (Integrated DNA Technologies (IDT)). The hybridized primers were extended by a reverse transcriptase (RT) (Promega Catalog #M3683) which used the RNA strand as a template and generated a single-stranded DNA complementary to the input RNA. The first strand of DNA generated during first strand synthesis (FSS) remained hybridized to the RNA template upon completion of the reaction. Next, second strand synthesis (SSS) occurred when a mixture containing a DNA polymerase, DNA ligase and RNase H was added to the DNA-RNA hybrid (New England BioLabs Catalog #E6111L). The RNase H nicked the RNA bound to the DNA thus creating RNA primers which were used by the DNA polymerase to prime synthesis of the second DNA strand using the first DNA strand as the template. The product of second strand synthesis was a double-stranded DNA compatible with library construction.

The cDNA synthesis protocol was designed to accommodate processing of both high quality (e.g., RNA purified from properly collected and stored fresh frozen inputs (e.g. cell pellets), PAXgene RNA blood tubes, bone marrow aspirates in RNAlater) and low quality (e.g., RNA purified from FFPE) inputs using a semi-automated workflow with minimal differences in assay set-up and execution based upon the quality of the input RNA. The quality of RNA was analyzed on a Bioanalyzer. Clear ribosomal RNA (rRNA) peaks indicated that the mRNA was largely full length.

Typical cDNA fragment length from low quality RNA inputs was between 100 and 500 bp and did not require additional processing (e.g., fragmentation) before starting library construction. Typical cDNA fragment length from high quality RNA inputs generally exceeded 500 bp (up to 2-3 kbp) and the cDNA was fragmented prior to being used as input for library construction. Fragmentation was accomplished by sonication using the same protocol as was used for genomic DNA (Example 3).

Additional exemplary methods to synthesize cDNA from total RNA isolated from FFPE samples are described as follows. For example, cDNA was generated from total RNA extracted from a single 5-10 um FFPE tissue section using the Roche High Pure kit and reverse transcribed to cDNA with random hexamer primers by the SuperScript® III First-Strand Synthesis System (Invitrogen). Double stranded cDNA was made with the NEBNext® mRNA Second Strand Synthesis Module (New England Biolabs) and used as input to library construction, hybrid capture and sequencing as for FFPE DNA samples. Analysis of expression levels was done with a combination of analysis tools.

Example 6

Library Preparation

End Repair Reaction

End-repair reagents (NEB #E6050L) were thawed and an end-repair mastermix was prepared on ice. To prepare 70 µl of mastermix per sample, 55 µl nuclease free water was mixed with 10 µl 10× End Repair reaction buffer and 5 µl End Repair enzyme mix. Then 70 µl of mastermix was added to 30 µl of each sheared DNA sample in a 96 well PCR plate on ice. The reaction was incubated in a thermocycler at 20° C. for 30 minutes. Each sample was purified using a QIAGEN MinElute® column. Briefly, 5× QIAGEN PBI buffer was added to sample (e.g., 500 µl of PBI buffer was added to 100 µl of sample) in a 1.5 ml microcentrifuge tube. Each sample was vortexed, briefly spun down, and transferred to a MinElute spin column. MinElute spin column was centrifuged at 13,000 rpm for 1 minute, and the flow-through was discarded. 750 µl of QIAGEN PE buffer was added to the column, centrifuged at 13,000 rpm for 1 minute, and the flow-through was discarded. The spin column was centrifuged again at 13,000 rpm for 1 minute and transferred to a clean 1.5 ml microcentrifuge tube. The column was air dried for 2-3 minutes. For the first elution, 22 µl of QIAGEN Elution Buffer (10 mM Tris, pH8.5) was added to each column, incubated for 2-3 min, and then centrifuged at 13,000 rpm for 1 minute. For the second elution, 22 µl of QIAGEN Elution Buffer was added, incubated for 1 min, and then centrifuged at 13,000 rpm for 1 minute. The eluent was collected and the spin column was discarded.

3' A-Base Addition

A-base addition reagents (NEB #E6053L) were thawed on ice and an A-base addition mastermix was prepared on ice. To prepare 10 µl of mastermix per sample, 2 µl nuclease-free water was mixed with 5 µl 10× dA-Tailing reaction buffer and 3 µl Klenow Fragment (3'→5' exo-). 10 µl of mastermix was added to 40 µl of each purified end-repaired DNA sample in a 96 well PCR plate on ice. The reaction was incubated in a thermocycler at 37° C. for 30 min. Each sample was purified using a QIAGEN MinElute® column. Briefly, 5× QIAGEN PBI buffer was added to sample (e.g., 250 µl of PBI buffer was added to 50 µl of sample) in a 1.5 ml microcentrifuge tube. Each sample was vortexed, briefly spun down, and transferred to a MinElute spin column. MinElute spin column was centrifuged at 13,000 rpm for 1 minute, and the flow-through was discarded. 750 µl of QIAGEN PE buffer was added to the column, centrifuged at 13,000 rpm for 1 minute, and the flow-through was discarded. The spin column was centrifuged again at 13,000 rpm for 1 minute and transferred to a clean 1.5 ml microcentrifuge tube. The column was air dried for 2-3 min. For the first elution, 13 µl of QIAGEN Elution Buffer (10 mM Tris, pH8.5) was added to each column, incubated for 2-3 min, and then centrifuged at 13,000 rpm for 1 minute. For the second elution, 13 µl of QIAGEN Elution Buffer was added, incubated for 1 min, and then centrifuged at 13,000 rpm for 1 minute. The eluent was collected and the spin column was discarded.

Ligation of Multiplex Adaptors

Ligation reagents (NEB #E6056L) were thawed and a ligation mastermix was prepared on ice. To prepare 36 µl of mastermix per sample, 12 µl 5× Quick Ligation reaction buffer was added to 3.3 µl Illumina Multiplex Adaptor (15 uM, included in Illumina Cat. #PE-400-1001) (3.3 µl adaptor/1 µg starting input DNA was used). For example, for one sample of 500 ng input DNA, the adaptors were first diluted in water (2 µl adaptors plus 2 µl H₂O), then 3.3 µl of this diluted adaptor mix, 15.7 µl of nuclease free water, and 5 µl of Quick T4 DNA ligase were added to the ligation reaction. For >1 µg starting material, >3.3 µl of adaptors were used. Thus, less water was added to keep the total volume of diluted adaptor mix and nuclease free water at 19 µl.

36 µl of mastermix and 24 µl of each dA-tailed DNA sample were added to the wells of a 96 well PCR plate on ice. The reaction was incubated in a thermocycler at 25° C. for 30 min. Each sample was purified using a QIAGEN MinElute® column. Briefly, 5× QIAGEN PBI buffer was added to sample (e.g., 300 µl of PBI buffer was added to 60 µl of sample) in a 1.5 ml microcentrifuge tube. Each sample was vortexed, briefly spun down, and transferred to a MinElute spin column. MinElute spin column was centrifuged at 13,000 rpm for 1 minute, and the flow-through was discarded. 750 µl of QIAGEN PE buffer was added to the column, centrifuged at 13,000 rpm for 1 minute, and the flow-through was discarded. The spin column was centrifuged again at 13,000 rpm for 1 minute and transferred to a clean 1.5 ml microcentrifuge tube. The column was air dried for 2-3 minutes. For the first elution, 20 µl of QIAGEN Elution Buffer (10 mM Tris, pH8.5) was added to each column, incubated for 2-3 minutes, and then centrifuged at 13,000 rpm for 1 minute. For the second elution, 20 µl of QIAGEN Elution Buffer was added, incubated for 1 minute, and then centrifuged at 13,000 rpm for 1 minute. The eluent was collected and the spin column was discarded.

PCR Enrichment

PCR reagents were thawed and a PCR mastermix was prepared on ice. For 62 µl of mastermix per sample, 50 µl of 2× Phusion High Fidelity mastermix with HF Buffer (Finnzyme, NEB Cat. #F-531S), 8 µl nuclease-free water, 2 µl Illumina Primer 1.0 (25 µM), and 2 µl Illumina Primer 2.0 (0.5 µM) were used. Then 62 µl of mastemix was mixed with 2 µl Illumina Index Primer (25 µM, included in Illumina Cat. #PE-400-1001) with appropriate bar code and 36 µl of ligated DNA sample in a 96-well PCR plate. The reaction was incubated in a thermocycler as follows:

| 1 Cycle | 98° C. | 30 sec |
|---|---|---|
| 18 Cycles | 98° C. | 10 sec |
| | 65° C. | 30 sec |
| | 72° C. | 30 sec |
| 1 Cycle | 72° C. | 5 min |
| | 4° C. | hold |

Each PCR reaction was size selected with 1.8× volume of AMPureXP beads (Agencourt; Beckman Coulter Genomics Cat. #A6388). Briefly, 1.8× AMPureXP beads were added to sample (e.g., 180 µl of beads were added to 100 µl of sample) in a 1.5 ml microcentrifuge tube, vortexed, and incubated for 5 minutes with end-over-end rotation mixing. Tubes were placed on a magnet stand until the solution cleared (2 minutes). The supernatant was discarded without disturbing the beads captured on the magnet. 600 µl of freshly-made 70% ethanol was added to the beards, incubated for 1 min followed by removal of the ethanol. A second aliquot of 600 µl freshly-made 70% ethanol was added to the beads, incubated for 1 minute, and the ethanol was removed. The tubes were put back on the magnet stand for 1-2 minutes to re-capture the beads. Any remaining ethanol was removed and the beads were air dried at room temperature for 5-10 minutes. 30 µl of QIAGEN Elution Buffer was added to the beads, vortexed, and incubated for 2 minutes. Tubes were placed back on the magnet stand until the solution cleared (2 minutes). The supernatant was transferred to a fresh 1.5 mL tube and the beads were discarded. The eluted DNA samples were quantified using a Q-PCR assay. These quantifications will allow for equimolar pooling to ensure equal representation of each library within a pooled hybrid capture selection.

Example 7

Hybrid Selection

Pool Indexed Sample Libraries

Pools (up to 12-plex) of libraries that had been indexed, purified, and quantified by Q-PCR were made on ice. Equimolar pools were prepared in 1.5 ml microcentrifuge tubes to ensure that each sample was represented in the hybrid selection process equally. The total input of DNA for each of these pools can range from 2000 ng to 500 ng. Typically, the total input DNA is 2000 ng. Thus, if twelve samples are pooled, 166.67 ng of each can be pooled to achieve a total of 2000 ng. The final volume of a 2000 ng library pool should be 4 µl. Due to varying concentrations of the indexed libraries a pool can be made with any larger volume but then the pool should be dried down by speedvac (using low heat) and reconstituted in 4 µl of nuclease-free water.

The greater the yield in a library construction, the greater the complexity of the library.

Hybridize the Pooled DNA Libraries to Biotinylated-RNA Baits

Agilent SureSelect Target Enrichment Paired End kit (#G3360A-J) was used in this experiment. Hybridization Buffer #3, SureSelect Block #1, SureSelect Block #2, Paired End Primer 1.0 block, Index Primer 1-12 block, RNAse block, and biotinylated-RNA bait were thawed on ice. The following mastermixes were prepared.
  a. Hybridization Buffer Mix (13 µl per reaction):
    i. Hybridization Buffer #1 (Agilent)—25 µl
    ii. Hybridization Buffer #2 (Agilent)—1 µl
    iii. Hybridization Buffer #3 (Agilent)—10 µl
    iv. Hybridization Buffer #4 (Agilent)—13 µl
  b. Blocking Mix (8 µl per reaction):
    i. SureSelect Block #1 (Agilent)—2.5 µl
    ii. SureSelect Block #2 (Agilent)—2.5 µl
    iii. Paired End primer 1.0 block (IDT, resuspended to 200 uM with H₂O)—1.5 µl
    iv. Index Primer 1-12 block (IDT, resuspended to 200 uM with H₂O)—1.5 µl
  c. Dilution of RNase Block
    i. For custom biotinylated RNA-baits with territory<3 Mb: 1 µl of RNase Block (Agilent) was diluted in 9 µl of water.
    ii. For custom baits with a bait territory>3 Mb: 1 µl of RNase block was diluted in 3 µl of water (still 0.5 µl of RNase block per 7 µL capture reaction)
  d. Bait Mix: (7 µl per reaction)
    i. RNA Baits—2 µl (for baits which have a bait territory>3 Mb, 5 µl bait was used)
    ii. Diluted RNase Block—5 µl (for baits which have a bait territory>3 Mb, 2 µl RNase block diluted as indicated above was used)

Once the Hybridization Buffer Mix, Blocking Mix, and Bait Mix(es) were prepared, the hybridization buffer mix was vortexed, spun down, and heated to 65° C. in the heat block. 4 µl of each pooled sample library to be hybrid selected was mixed with 8 µl of the blocking mix in a 96 well PCR plate. The reaction was incubated in a thermocycler at 95° C. for 5 minutes and then held at 65° C. When the pooled sample libraries/blocking mix had been incubating at 95° C. for 5 min and then at 65° C. for 2.5 minutes, the bait mix (=bait/RNAse block mix) were put in the heat block at 65° C. for 2.5 minutes. The hybridization buffer containing tubes were quickly spun down, and then immediately returned to 65° C. heat block. 13 µl of the heated hybridization buffer mix was pipetted into each sample library/block mix while the 96 well plate remained in the thermocycler at 65° C. Once the bait mix had been incubated for 2.5 minutes at 65° C., 7 µl of the bait mix was added to each sample library/block/hybridization buffer mix while the 96 well plate remained in the thermocycler at 65° C. The reaction (total volume was 32 µl) was incubated at 65° C. for 24 hours in a thermocycler.

Preparation of the Magnetic Beads

SureSelect Wash Buffer #2 was prewarmed at 65° C. in the heat block. Dynal MyOne Streptavidin T1 beads (Invitrogen) were vortexed and resuspended. The beads were washed by adding 200 µl of SureSelect Binding Buffer per 50 µl Dynal beads (e.g., 1200 µl of SureSelect Binding Buffer was used to prepare 300 µl of Dynal beads). The beads were vortexed for 5 seconds and spun down briefly. The beads were placed on a magnet stand for about 15 seconds or until all the beads were captured. The supernatant was removed and discarded. Wash was repeated with SureSelect Binding Buffer two more times for a total of three washes. After washing, the beads were resuspended in 200 µl of SureSelect Binding Buffer per 50 µl Dynal beads (e.g., 1200 µl of SureSelect Binding Buffer was used to prepare 300 µl of Dynal beads). The resuspended beads were vortexed and spun down briefly. 200 µl of resuspended beads were aliquoted into individual 1.5 ml microcentrifuge tubes.

Selection of the Hybrid Captured DNA

After 24 hours of incubation, each hybridized sample from the PCR plate in the thermocycler at 65° C. was quickly pipetted into a tube containing 200 µl of prepared beads at room temperature. The mixtures of sample and beads were vortexed for 5 seconds and incubated on a rotator at room temperature for 30 minutes, to ensure proper mixing. Then the tubes were quickly spun down. The beads were captured on a magnet (for 2 minutes) and the supernatant was removed and discarded. The beads were resuspended in 500 µl of SureSelect Wash Buffer #1, for a low stringency wash. The samples were vortexed for 5 seconds and incubated for 15 min at room temperature off the magnet. Samples were vortexed for 5 seconds every 3-5 minutes. The tubes were quickly spun down. The beads were then captured on a magnet stand for 2 minutes and the supernatant was removed and discarded. For a high stringency wash to remove off-target material, the beads were washed with SureSelect Wash Buffer #2 preheated to 65° C. Briefly, the beads were resuspended in 500 µl of prewarmed SureSelect Wash Buffer #2 and mixed on a vortexer for 5 seconds to resuspend the beads. The beads were briefly spun down in a centrifuge and incubated at 65° C. for 10 min in a heat block with occasional vortex mixing for 5 seconds at room temperature. Then the beads were briefly spun down in a centrifuge and captured on a magnet for 2 minutes. Wash was repeated 2 more times with prewarmed SureSelect Wash Buffer #2 at 65° C. for a total of three washes. Then the wash buffer was completely removed and 50 µl of SureSelect Elution Buffer was added to the beads following by vortexing for 5 seconds to mix the beads. The samples were incubated for 10 minutes at room temperature with occasional vortex mixing for 5 seconds. The beads were briefly spun down in a centrifuge and captured on a magnet stand.

The supernatant containing the captured DNA was pipetted to a new 1.5 ml microcentrifuge tube. 50 µl of SureSelect Neutralization Buffer was added to the captured DNA. Samples were vortex for 5 seconds, briefly spun down in a centrifuge, and purified using 1.8× volume of AMPureXP beads. DNA was eluted in 40 µl nuclease-free water.

PCR Enrichment of the Captured DNA

PCR reagents were thawed and a PCR mastermix was prepared on ice. For 60 µl of mastermix per sample, 50 µl 2× Phusion High Fidelity mastermix with HF buffer (NEB #F-531S) was mixed with 8 µl nuclease-free water, 1 µl QPCR Primer1.1 (100 µM in H$_2$O), and 1 µl QPCR Primer2.1 (100 µM in H$_2$O). The primer sequences for Q-PCR are:

```
QPCR Primer1.1 (HPLC-purified from IDT):
                                  (SEQ ID NO: 2)
5'AATGATACGGCGACCACCGAGAT3'

QPCR Primer2.1 (HPLC-purified from IDT):
                                  (SEQ ID NO: 3)
5'CAAGCAGAAGACGGCATACGA3'
```

60 µl of mastermix was added to 40 µl of each purified captured DNA sample in a 96 well PCR plate. The reaction was incubated in a thermocycler as follows:

| 1 Cycle   | 98° C. | 30 sec |
| 12 Cycles | 98° C. | 10 sec |
|           | 65° C. | 30 sec |
|           | 72° C. | 30 sec |
| 1 Cycle   | 72° C. | 5 min  |
|           | 4° C.  | Hold   |

Each 100 µl of PCR reaction was purified with 1.8× volume of AMPureXP beads and eluted in 35 µl of elution buffer (10 mM Tris, pH 8.5). The hybrid selected/captured DNA samples were quantified using a Q-PCR assay. The Q-PCR assay detected the end adaptors and the reads indicated how much of each sample should be loaded on a sequencing flow cell to get the appropriate cluster density.

Example 8

Sequencing Methods

The following exemplifies certain embodiments of the methods and experimental conditions used to identify the alterations according to the Examples. Additional translocation screening can be done using, e.g., either qRT-PCR analysis of cDNA prepared from a pre-selected tumor sample.

Both DNA Sequencing (DNA-seq) and RNA Sequencing (RNA-seq) were performed to identify genetic alterations using nucleic acids isolated from FFPE, blood and bone marrow aspirate samples. For example, massively parallel DNA sequencing was done on hybridization captured, adaptor ligation-based libraries using DNA isolated from archived fixed paraffin-embedded tissue. A combination of analysis tools were used to analyze the data and assign DNA alteration calls. Additional translocation screening was done using either qRT-PCR analysis of cDNA prepared from frozen tumors or IHC assessment of archived FFPE specimens. Massively parallel cDNA sequencing was performed to confirm expression of both novel translocations using RNA isolated from FFPE tissue. Matched normal reference genomic DNA from blood was sequenced for the index NSCLC patient to confirm the somatic origin of the rearrangement.

Genomic DNA Sequencing

Sequencing of 2574 exons of 145 cancer genes was done using DNA from archived formalin fixed paraffin embedded (FFPE) tumor specimens; 24 from NSCLC patients. Sequencing libraries were constructed by the adapter ligation method using genomic DNA followed by hybridization selection with optimized RNA hybridization capture probes (Agilent SureSelect custom kit). Sequencing on the HiSeq2000 instrument (Illumina) was done using 36×36 paired reads to an average depth of 253×. Data processing and mutation assignments for base substitutions, indels, copy number alterations and genomic rearrangements were done using a combination of tools optimized for mutation calling from tumor tissue.

Example 9

Exemplary Selected Genes and Variants for Multiplex Analysis

Exemplary genes, variants and cancer types selected for multiplex analysis are described in Tables 1-9.

Example 10

A Bayesian Approach for Sensitive Detection of Somatic Genomic Alterations from Next-Generation Sequencing of Clinical Cancer Specimens The Bayesian approach described herein was implemented in the following examples.

Figure 2:
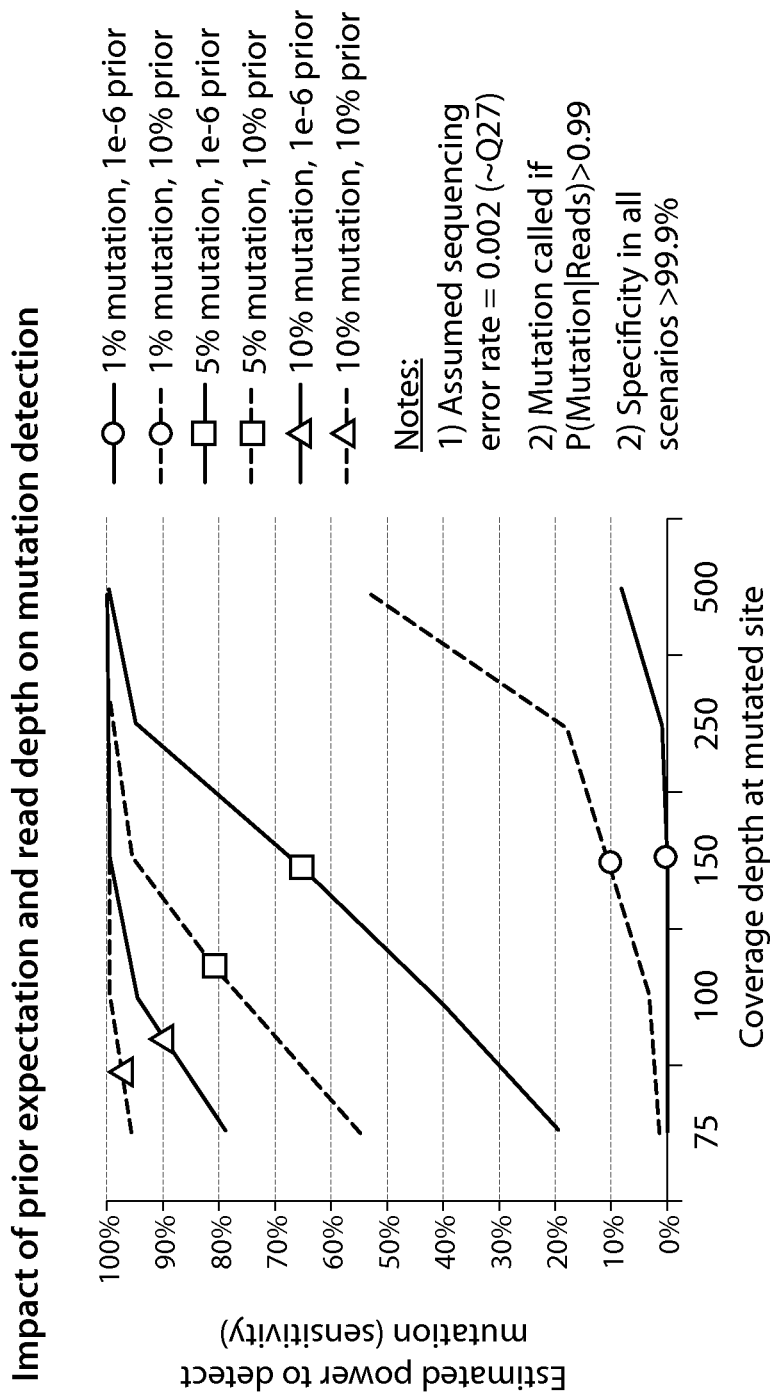
FIG. 2 depicts the impact of prior expectation and read depth on mutation detection.

The utility of this approach is illustrated by power calculations describing the impact of data-driven priors on substitution detection in the lower range of mutation frequencies relevant in the clinical setting. As shown in FIG. 2, the values of prior expectation (e.g., 1e-6 or 10% prior) and mutation frequency (e.g., 1%, 5%, or 15% mutation) correspond to the values described in (i) and (ii) of "A Bayesian Approach for Sensitive Detection of Somatic Genomic Alterations from Next-generation Sequencing of Clinical Cancer Specimens," respectively. FIG. 2 shows that incorporating prior expectations can improve detection power for rarer mutations, e.g., by reducing the required coverage depth at mutated sites, or increasing the estimated power (sensitivity) to detect mutations.

Additional examples that show the applications of the Bayesian approach to various samples (e.g., a constructed low purity multi-clonal sample, lung and colon tumor samples, and breast cancer samples) and to detect infrequent mutations, are disclosed in International Patent Application Publication No. WO2012/092426.

Example 11

High Performance Solution-Based Target Selection Using Individually Synthesized Oligonucleotide Capture Probes The availability of solution-based genomic target selection techniques has enabled rapid development of targeted sequencing applications, some of which have led to the introduction of clinical sequencing tests. Commercialized hybridization capture reagents are based on array-synthesized oligonucleotides, which are converted to biotinylated DNA or RNA probes ("baits"). However, methods of generating these complex pools of probes face performance challenges, for example capturing high-GC content targets.

An alternative approach using individually synthesized, 5'-biotinylated oligonucleotides ("oligo-baits") for capturing a target region of ~130 kb representing 57 clinically relevant and actionable cancer-related genes is described herein. Indexed sequencing libraries selected using these oligo-baits with a 24-hour hybridization procedure yielded 5,000-fold target enrichment. 50M 49×49 paired-end reads generated an average target coverage of 2100× with a standard deviation of 568× (27%). All targets were covered successfully, with 99.95% of the targeted bases covered at >500×. Furthermore, the target coverage had virtually no GC-bias. Targets with GC content>70% averaged 1,975× coverage, and targets with GC content<35% averaged 1,996× coverage.

High performance was retained using even shorter hybridization times: 99.3% of targeted bases were covered at >500× after a 2.5 hour hybridization.

Use of SSPE (Salmon Sperm, PE)/Denhardt's outperformed hyb/wash buffers containing TEACl, TMACl, and/or dextran sulfate.

Oligo-baits can be spiked into array-derived bait pools to increase the coverage of otherwise difficult to capture (e.g., high % GC) regions, or to rapidly add new gene content. This approach offers a highly effective and scalable method for developing high performance targeted clinical sequencing tests.

Exemplary methods of optimizing capture baits and experimental conditions for evaluating bait sets are disclosed in International Patent Application Publication No. WO2012/092426.

Example 12

Routine, Ultra-Deep Sequencing for Sensitive Tumor Profiling Using Low Inputs of DNA Derived from Formalin Fixed Tissue The wide adoption of high-throughput DNA sequencing technologies has facilitated rapid advances in cancer genomics. However, the standard of care in genomic cancer diagnostics still involves testing focused on individual genes and specific mutations. As the number of clinically actionable mutations grows, this single mutation per test paradigm becomes unfeasible, particularly when tissue specimens are limiting as is generally the case with biopsies. To address the clinical need for comprehensive genomic profiling of tumor samples, we have developed a clinical test that delivers massively parallel sequence data for 200+ cancer-related genes. Furthermore, this test was shown to be clinically relevant, producing ultra-deep sequencing data from formalin-fixed paraffin-embedded (FFPE) tissue samples with DNA inputs as low as 50 ng, and from samples as old as eleven years.

To evaluate this test's performance on a wide variety of samples, DNA was isolated from 96 FFPE specimens from an aged-block set, which included 12 tumor/normal pairs from each of breast, colon, lung, and renal tissues evenly distributed for each tissue over the following ages: 1, 3, 5, 7, 9 and 11-years old. 200 ng and/or 50 ng of input DNA was used to construct indexed sequencing libraries, which were then enriched for 200+ cancer-related genes using a solution-based hybrid capture method and sequenced on an Illumina HiSeq™ 2000 platform.

For the 76 samples yielding at least 200 ng of DNA for library construction, sequencing coverage averaged 1,000× after removal of PCR duplicates, with >95% of the samples yielding a median coverage of >350×. For samples where 50 ng was used for library construction, the coverage averaged 450×. Sequencing performance was consistent across all sample tissue types and ages. Such ultra-deep sequencing enables high confidence detection of mutations present at frequencies as low as 5-10%.

Example 13

Profiling the Tumor Genome Using Circulating Tumor Cells

Circulating tumor cells (CTC) provide a unique opportunity to sample human malignancies in a minimally invasive, serial fashion. Use of CTC for molecular characterization of cancer genomes presents two key challenges. First, CTC must be efficiently isolated from blood, where they may be outnumbered $10^7$-fold by non-tumor cells. Second, the limited number of tumor genomes present in a CTC sample must be captured in accessible form while minimizing loss of material and introduction of bias.

Previous CTC genetic analyses have used allele-specific PCR; these methods permit detection of very low copy numbers of specific mutations in ≥$10^4$-fold background of wildtype sequences. While addressing the dual challenges of CTC abundance and capture efficiency, this approach is intrinsically limited to narrow characterizations of select, prespecified variants. To bring molecular CTC analysis into the genomic era, we have coupled a microfluidic rare-cell capture system that allows recovery of CTC with a background of only hundreds, rather than tens of thousands, of white blood cells, with a next-generation platform enabling deep resequencing of more than 200 cancer-associated genes from a single CTC sample.

Using complex mixtures of up to ten cancer cell lines, sensitive mutation detection (~94% for alleles≥10% abundance) from as few as 100 total cells, while largely preserving allele frequencies ($R^2$~0.90). By recapturing cultured cells spiked into whole blood, multi-gene mutation profiles from specimens containing as few as ten cancer cells were obtained. This level of sensitivity places the majority of clinical CTC samples within reach of NGS analysis. In a series of blood samples from breast cancer patients, potential CTC heterogeneity was investigated by comparing frequency of Her2Neu positive cells with the relative abundance of somatic mutation positive DNA.

Example 14

Detection of Cancer-Associated Mutations, Translocations and Changes in Gene Expression Through Integration of Targeted DNA and RNA Deep Sequencing of FFPE Tumor Samples Broad application of personalized therapy to cancer requires comprehensive, sensitive and timely characterization of the diverse aberrations present in the genome and transcriptome of a tumor. The RNA and DNA from most clinical cancer samples, commonly stored as formalin fixed paraffin embedded (FFPE) blocks, are of poor quality and have been difficult to use for molecular profiling. Emerging next-generation DNA sequencing assays work well with damaged DNA and are sufficiently sensitive to detect many types of genomic aberrations. Currently, there is no comparable RNA sequencing protocol for comprehensive analysis of the transcriptome from FFPE tumor samples.

Results:

An FFPE-compatible targeted RNA sequencing and analysis method for sensitive detection of mutations, rearrangements and expression changes in over 200 cancer-associated genes was developed. Protocols were validated on cell line RNA and used to study over 50 FFPE non-small cell lung cancer (NSCLC) tumors. Known mutations and gene fusions (e.g. BCR-ABL1) were detected in cell lines. Technical reproducibility in digital expression profiling exceeded $R^2$=0.99 and >0.9 for cell lines and FFPE RNA, respectively. As expected in cancer genomes, RNA-seq provided evidence of aberrations in the genome including point mutations and novel rearrangements involving known oncogenes. Highly significant differential expression of oncogenes including EGFR, FGFR3, CDH5, KIT and RET was revealed, ranging from 2.5- to 70-fold across different tumors. Combination of RNA and DNA sequencing data on identical FFPE samples corroborated functional consequences of genomic alterations; examples included expression of mutated TP53 alleles and reduced STK11 expression in a tumor which exhibited loss-of-heterozygosity at the DNA level. Application of next generation sequencing technologies to FFPE RNA and integration with extant DNA sequencing methods is anticipated to expand understanding of clinically relevant cancer biology and improve patient care.

Methods:

RNA is extracted from FFPE tissue sections, typically 1 or 2 10 μm curls, using the Roche High Pure Paraffin Kit according to the manufacturer's instructions. Extracted RNA is stored @ −80° C. RNA yield and quality is assessed by RiboGreen (Invitrogen) and a Bioanalyzer RNA Pico Chip (Agilent), respectively, according to the manufacturer's instructions. Typical yields are between 500 ng and 2 μg with a RIN score of less than 4.

The first strand of complimentary DNA (cDNA) is produced from between 100 and 600 ng of FFPE RNA in a 20 μL reaction using SuperScript III (Invitrogen) according to the manufacturer's protocol, with 550 pmols of random hexamer as primer. Second strand synthesis, to generate a fully double-stranded cDNA, is performed immediately after first strand synthesis by addition of 60 μL of a NEBNext Second Strand Synthesis Module (New England Biolabs) master-mix and incubation for 150 minutes at 16° C. according to the manufacturer's protocol. The quality and yield of double-stranded cDNA can be assessed using PicoGreen (Invitrogen) and a Bioanalyzer High Sensitivity Chip (Agilent), respectively. Generally, the entire cDNA synthesis yield is used as input to the standard FMI library construction protocol.

Construction of a paired-end compatible sequencing library and subsequent hybrid selection and sequencing of cDNA generated from FFPE RNA is performed using similar protocols as for FFPE DNA described herein, but starting directly at the End Repair step since the highly fragmented nature of FFPE RNA obviates the need for shearing.

Analysis of sequencing data from FFPE RNA can be performed using methods known in the art. For example, analysis of sequencing data from FFPE RNA can be performed by mapping all of the read pairs to a reference genome sequence (hg19) and/or a reference transcriptome (all of the sequences of known transcripts, e.g. RefSeq). Mapped reads are then used to identify gene fusion, mutations in gene sequences, alternative splicing, and to quantify gene expression as described in the literature, e.g., by Berger et al. (2010) *Genome Res.* 20(4):413-27 (PMID 20179022) and Garber et al. (2011) *Nat Methods.* 8(6):469-77 (PMID 21623353). As demonstrated by Levin et al. (2009) *Genome Biol.* 10(10):R115 (PMID 19835606), targeted RNA-seq can be employed to improve mutation detection and fusion discovery in a selected set of genes, and preserves quantitative information for expression profiling.

Example 15

Sensitive and Accurate Mutation Calling by Ultra-Deep Sequencing of Clinical Tumor Samples Rapid advancement in the understanding of cancer genomics and the growing number of available targeted therapies provide expanding opportunities for effective cancer treatment based on comprehensive tumor profiling. Although significant progress has been made in experimental and computational approaches for analyzing tumor genomes by next-generation sequencing in the research setting, extending these techniques to the clinic poses significant additional challenges. Key among these is the limited purity and heterogeneity of clinical specimens, coupled with the requirement to provide high sensitivity and accuracy for a wide range of potentially clinically-actionable mutations.

To address this challenge we have developed a clinical test that is capable of generating ultra-deep sequence data (>700×) for 200+ cancer-related genes from routine FFPE tumor samples, and computational tools that are capable of exploiting this depth to provide high levels of sensitivity and accuracy for different types of mutations present at low fractions. Our analytical pipeline detects short variants in mapped sequence data accounting for known mutation frequencies, and combines breakpoint detection and local assembly to identify larger insertions and deletions, which are often missed by alternative methods. In addition, copy-number alterations and rearrangements involving key cancer genes are identified.

To validate the analytical performance of our newly-developed methods we designed and implemented an extensive study of sample mixtures as a model for rare events in heterogeneous DNA, including 20 normal HapMap cell-lines and 28 individually characterized cancer cell-lines. We report 100% sensitivity for substitutions and >90% sensitivity for indels of length 1-50 bp present in >10% of a mixture, both with PPV>99%. Application of our test to a cohort of 227 melanoma, prostate, breast, colon, and lung tumor samples revealed 427 known and likely somatic driver mutations, 40% of which were present at sample fractions below 20% and 18% below 10%, underlining the importance of sensitive mutation calling.

Methods for detection of cancer mutations at surgical margins are described in International Patent Application Publication No. WO 2012/092426.

Example 16

Comprehensive Profiling of Immunoglobulin Sequences Using Hybrid Capture-Based Next Generation Sequencing in B-Cell Hematologic Malignancies Sequencing the genes encoding immunoglobulins is critical in detecting clonal cell populations as well as determining prognosis and therapeutic decisions in patients with lymphoid malignancies including B-cell leukemias, lymphomas and multiple myeloma. Current assays for identifying the rearranged immunoglobulin sequence in B-cell malignancies generally rely on sequence specific PCR based amplification of conserved immunoglobulin (IG) regions. This example describes a novel, hybrid capture-based approach to sequencing the immunoglobulin chains that enables identification of the heavy and light chain variable domains, complementarity-determining region (CDR) sequences and somatic hypermutation (SHM) status.

Germline immunoglobin (IG) sequences including variable (V), diversity (D), joining (J) and class segments span over 1 MB on chromosome 14 for the heavy chain, over 344 kb on chromosome 22 for the lambda light chain and over 477 kb on chromosome 2 for the kappa light chain. During VDJ recombination during normal B cell development one single V-D-J (~320 bases) sequence is created. Two main strategies were tested. The first involved baiting only the D, J and class segments. This strategy was shown to be successful in RNA. The second strategy involved baiting in addition or in isolation the V segments. This strategy allowed identification of the IGHV sequence in RNA and DNA.

Methods:

RNA and DNA were successfully extracted from 60 specimens, including 7 mantle cell lymphoma cell (MCL) lines and 53 clinical chronic lymphocytic leukemia (CLL) bone marrow aspirates. Adaptor-ligated DNA and cDNA sequencing libraries were captured by solution hybridization using custom bait-sets targeting the immunoglobulin variable, joining and class segments. All captured libraries were sequenced to high depth (Illumina HiSeq) in a CLIA-certified laboratory (Foundation Medicine).

Paired end sequencing reads are often on the same length scale (~50 bases) as the repetitive regions of the immunoglobin variable domain. The framework and CDR regions of the individual V domains have known homology to each other. Thus, one 50 base pair read to a framework region could potentially map to several different variable segments. In addition, Hg19 reference sequence used in alignment does not contain all the known germline variable segment sequences. For instance, there are four alleles IGHV3-21*01, IGHV3-21*02, IGHV3-21*03, IGHV3-21*04 but Hg19 contains IGHV3-21*01, i.e., the first allele. The analysis method described below was designed to solve these problems.

The analysis for calling the clone and the SHM was done using a program described below. The program includes, e.g., the following steps: (1) selecting chimeric reads to the IG class or junction segments; (2) filtering those reads for reads going to IGHV, IGKV or IGLV segments; (3) building V domain consensus sequence for each candidate V segment in step (2) (e.g., taking each 50 basepair read from the mapped reads to build one ~300 basepair long sequence); and (4) running the sequence built in step (3) through the IgBlast program (this identifies the V domain and give a calculation of the % SHM (www.ncbi.nlm.nih.gov/igblast/). IgBlast is a well-known, validated industry standard tool for the alignment of the sequenced IG chain to the closest germline match VDJ in the IGMT sequence database enabling the SHM % calculation and CDR3 sequence to be identified.

A manual review of each candidate was done to confirm the automated call described above. The manual review (which could also be automated) includes, e.g., the following steps: (1) sorting IgBlast output for alignment length (e.g., not considering any alignment under 200 bases long; and (2) verifying, e.g., the CDR3 sequences are near identical for a given clone, the snps are near identical for a given read cluster, the mapped reads are largely unique, and the reads map to the entire FR1 to CDR3 region ungapped.

As a tumor cell coming from a mature B cell are likely to have rearranged variable and junction segments, this analysis gave strong signal even if tumor purity was relatively low (e.g., about 20% purity).

Results:

The capture-based approach was validated using 7 MCL cell lines and 53 CLL samples profiled using a CLIA-certified commercial PCR-based assay (Invivoscribe). The immunoglobulin sequences derived from the 7 MCL cell lines were 100% concordant with identifying the published heavy and light chain variable domain and percent SHM. Comparison to 53 previously clinically tested samples showed 98% (52/53) concordance for identifying the presence of a clonal population, and 100% (39/39) concordance for identifying the IGHV domain. Comparison to 50 CLL samples previously tested for SHM resulted in 96% (48/50) overall concordance with 94% (31/33) concordant for no SHM and 100% (17/17) concordant for the presence of SHM. Additionally, secondary clones were identified in 11 samples.

Healthy blood samples and enriched blood samples were used as negative controls. These samples should have VDJ rearrangements but no monoclonal populations. For the 3 normal whole blood samples no tumor clones were identified. The enriched B cell population had IGHV clusters called. All were seen to be polyclonal and would not have been called as a tumor clone. There was 100% concordance with the 6 negative tumor clone samples.

Conclusions:

This study demonstrated that hybrid capture-based targeted DNA and RNA sequencing can be used to comprehensively characterize the immunoglobulin sequence of clonal tumor B cell populations. This capability allows for quantification of SHM and identification of the variable domain, CDR3 sequence and class restriction. Integration of this methodology with comprehensive genomic profiling approaches expands the clinical utility of such assays in patients with hematological malignancies and can provide important insights in immune oncology and response of patients to immunotherapies, including patients with solid tumors.

Example 17

Multigene Analysis for Hematological Malignancies Using Targeted DNA Sequencing and RNA Sequencing This example describes highly sensitive and specific detection of various classes of genomic alterations under clinically relevant conditions by combining targeted DNA sequencing (DNA-seq) and RNA sequencing (RNA-seq) on the genomic DNA and total RNA extracted from a number of hematological malignancy samples. The tested genomic alterations include, e.g., base substitutions (Subs), insertions and deletions (Indels), focal copy number alterations (CNAs) and genomic rearrangements. Typical hematological malignancy samples, e.g., FFPE, blood, and bone marrow aspirates, were examined.

The test described in this Example includes a DNA-seq baitset and incorporates a targeted RNA-seq component. The targeted RNA-seq component utilizes RNA converted into complementary DNA (cDNA) rather than gDNA as the input. As compared to DNA-seq alone, an integrated assay combining DNA-seq and RNA-seq offers improved sensitivity for the detection of genomic rearrangements.

Genomic rearrangements include a heterogenous class of alterations which are resulted, e.g., from the joining of two or more different regions of the human genome to produce a non-reference product, e.g., as compared to the hg19 reference human genome assembly, genome sequence and structure. As a result of the rearranged genomic sequence, non-reference sequence RNA transcripts may also be transcribed. Genomic rearrangements can be classified as either occurring outside of reference sequence (RefSeq) genes (i.e., extragenic) or within the introns and exons of genes (i.e., intragenic). For example, extragenic rearrangements, such as the promoter or enhancer associated events involving MYC and IGH, can affect the regulation of the expression of a given mRNA transcript, or pathway, but do not necessarily alter mRNA sequence. Intragenic rearrangements involve the exons and/or introns of two or more genes and can yield chimeric mRNA transcripts comprised of sequence derived from different genes and/or regions of the genome (e.g., different chromosomes, different strands of the same chromosome). Gene fusions can be created by genomic rearrangements which occur in specific, recurrently rearranged introns from 2 or more genes. Introns can be difficult to cover by DNA-seq to sufficient depth due to size (>1 kb) and/or sequence (e.g. repeat structure) constraints. In addition, the relevant break-points may not be known or the gene fusion mRNA transcript could result from a complex rearrangement such that it may not be possible to identify the relevant fusion partners by DNA-seq. RNA-seq improves detection sensitivity by directly characterizing the mRNA products of gene fusions, rather than relying on sequencing introns and extrapolating mRNA structure from DNA sequence data.

As such, an exemplary DNA-seq baitset includes complete exonic coverage of 464 genes (Table 1), coverage of select introns in 31 genes recurrently rearranged in cancer (Table 2), and complete exonic coverage of 91 additional genes (Table 4); and an exemplary RNA-seq component uses an RNA-seq baitset to target exons of 333 genes which are known to be recurrently rearranged in hematological malignancies (Table 3).

Preparation of RNA-Seq and DNA-Seq Baitset Reagents

Bait sequences targeting the genes listed in Tables 1-4 were designed. The baits were synthesized at Integrated DNA Technology (IDT) using its Ultramer synthesis chemistry. An equimolar mix of the appropriate baitset sub-pools received from IDT was prepared to create the RNA-seq and DNA-seq baitset reagents. The baitset reagents were then split into single-use aliquots and stored at −20° C. The performance of the DNA-seq baitset was confirmed by capturing of a HapMap library using a standard, automated hybrid capture protocol. The performance of the RNA-seq baitset was confirmed by capturing of a HapMap library and universal human reference RNA (UHRR) libraries using standard protocols.

DNA-Seq Workflow

The methods of genomic DNA extraction, quantitation, shearing, library construction, hybrid capture and sequencing are described in Examples 1-6.

RNA-Seq Workflow

The RNA workflow was typically run in parallel to the DNA-seq workflow on matched RNA and DNA extracted from the same sample. For example, extracted RNA was first quantified with Ribogreen, a RNA-specific fluorescent dye, and then up to 300 ng of RNA from high quality inputs (e.g., Blood, BMA) or 500 ng of RNA from low quality inputs (e.g., FFPE) was normalized as input for the two-step cDNA synthesis protocol. In the first step of cDNA synthesis, single-stranded DNA strands complementary to the input RNA were generated. In the second step of cDNA synthesis, the single-stranded cDNA was converted to double-stranded DNA. The double-stranded cDNA was then used as input for library construction. If the cDNA was synthesized from high quality RNA, then to ensure that the insert length would be compatible with sequencing, the cDNA was sheared prior to use in library construction. The library construction, hybrid capture, quantitation, and sequencing steps are all performed as for standard DNA-seq libraries, with the exception of using the RNA-seq baitset reagent and associated analysis files and protocols.

Creation of the DNA-Seq Artifact Database

To minimize the calling of false-positive alterations with the DNA-seq workflow, a database of potential sequencing artifacts was created from normal HapMap cell-lines. For example, 200 ng of DNA from 20 individual HapMap cell-lines was used as input for standard library construction. Next, 2 μg of each library was captured with the DNA-seq baitset. After sequencing the captured libraries and processing all of the data through the standard analysis pipeline, an artifact database was created based upon any variant calls present in the genes. Since the samples were derived from normal HapMap cell-lines, any non-SNP alteration detected in the genes was considered to be an artifact, and would be used to filter test data.

Creation of the R2 RNA-Seq Artifact Database

To minimize the detection of false-positive genomic rearrangements with the RNA-seq workflow, a database of potential process related, sequencing, and analysis artifacts in the RNA-seq data was created. For example, 300 ng of RNA from the 8 normal Blood samples was used as input for the High quality cDNA synthesis protocol and 500 ng of RNA from the 6 normal FFPE samples was used as input for the Low quality cDNA synthesis protocol. The entire yield of the cDNA reaction was used as input to library construction. Next, 2 μg of each library was captured with the RNA-seq baitset. After sequencing the captured libraries and processing all of the data through the RNA-seq analysis pipeline, an artifact database of genomic rearrangements was created. Since the blood and FFPE samples were derived from normal donors, any genomic rearrangement detected was considered to be an artifact or germ-line event, and would be used to filter test data.

Validation

The DNA-seq baitset achieved highly uniform coverage and accuracy for the detection of base substitutions, short insertions and deletions and focal copy number alterations with de-identified clinical samples. The integrated results from the DNA-seq and RNA-seq achieved high sensitivity and specificity for the detection of genomic rearrangements/gene fusions in cell-line mixtures. This assay was highly reproducible and the workflow was broadly compatible with routine hematologic oncology clinical samples including FFPE, blood and bone marrow aspirates. The results were also highly concordant with standard-of-care CLIA-certified test results obtained from 76 de-identified clinical samples.

This assay achieved high accuracy in the detection of base substitutions, indels, focal CNAs and genomic rearrangements/gene fusions. The DNA-seq data was highly concordant (>97%) with a CLIA-certified DNA-seq assay for the detection of base subs, indels and focal CNAs across 52 de-identified clinical samples. The integrated results from the DNA-seq and RNA-seq datasets achieved high sensitivity and specificity for the detection of genomic rearrangements across 39 cell-line mixtures. The results were also 99% concordant (100 of 101 alterations) with the base substitutions, indels and genomic rearrangements detected by external reference CLIA-certified tests routinely used to assay clinical samples.

The precision observed with this assay across 5 different runs of 13 samples passed the performance specification; intra-run precision was 97% and inter-run precision was 97%. Precision was assessed based upon the comparison between runs of curated, known and likely base substitutions, indels, focal CNAs and genomic rearrangements/gene fusions for samples passing the coverage specification.

The sensitivity of this assay for base substitutions, indels and CNAs was assessed by comparing DNA-seq results across 52 de-identified clinical samples to those previously obtained with a CLIA-certified DNA-seq assay. The results were 97.7% concordant (167 of 171; 95% CI: 94-99%) with the standard assay results demonstrating that this assay has the same high sensitivity for the detection of base substitutions, indels and CNAs as the standard.

The sensitivity of this assay for genomic rearrangements/gene fusions was determined with a model system comprised of 39 mixtures (10% to 50% mix ratios) of 21 cell-lines with known genomic rearrangements. This assay achieved a very high sensitivity for the detection of genomic rearrangements, detecting 165 of 167 (98.5%; 95% CI: 96-99%) rearrangements across all mixtures and 64 of 66 (97%; 95% CI: 89-99) genomic rearrangements in the 10% mixture.

The specificity of this assay for base substitutions, indels and CNAs was assessed by comparing DNA-seq results across 52 de-identified clinical samples to those previously obtained with a CLIA-certified DNA-seq assay. The results were 97.7% concordant (167 of 171; 95% CI: 94-99%) with the standard assay results demonstrating that this assay has the same high specificity for the detection of base substitutions, indels and CNAs as the standard.

The specificity of this assay for genomic rearrangements/gene fusions was determined with a model system comprised of 39 mixtures (10% to 50% mix ratios) of 21 cell-lines with known genomic rearrangements. This assay achieved a very high specificity for the detection of genomic rearrangements, calling 4 false positive rearrangements out of 165 true positive rearrangements across all mixtures.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web at tigr.org and/or the National Center for Biotechnology Information (NCBI) on the world wide web at ncbi.nlm.nih.gov.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A sequencing method comprising:
   (a) acquiring a nucleic acid library comprising a plurality of members, each member of the plurality comprising a nucleic acid derived from a sample taken from a subject having a solid tumor, wherein the library comprises DNA molecules from a malignant cell of the solid tumor, and RNA molecules or cDNA molecules derived from RNA molecules from a tumor infiltrating lymphocyte from the solid tumor;
   (b) contacting the library with a bait set to provide a library catch comprising a plurality of selected members comprising an expressed subgenomic interval from the tumor infiltrating lymphocyte and a subgenomic interval from the malignant cell, or portions thereof, wherein the bait set comprises a first portion that hybridizes to selected members comprising the expressed subgenomic interval or a portion thereof and a second portion that hybridizes to selected members comprising the subgenomic interval from the malignant cell, and wherein the expressed subgenomic interval is associated with somatic hypermutation or a V(D)J somatic rearrangement and the subgenomic interval from the malignant cell is from a gene other than an immunoglobulin, a T-cell receptor, or a B-cell receptor; and
   (c) sequencing one or more occurrences of both the expressed subgenomic interval and the subgenomic interval from the malignant cell within the library catch.

2. The method of claim 1, wherein the nucleic acid derived from the sample comprises nucleic acid fragments formed by fragmenting nucleic acid molecules from the subject.

3. The method of claim 1, wherein step (b) comprises contacting the library with the bait set under conditions of solution hybridization or surface-based hybridization.

4. The method of claim 1, wherein the subgenomic interval from the malignant cell is chosen from a gene selected from the group consisting of ABCB1, ABCC2, ABCC4, ABCG2, ABI1, ABL1, ABL2, ACSL3, ACSL6, ACTB, ACVR1B, AF15Q14, AF1Q, AF3p21, AF5q31, AFF1, AFF4, AKAP9, AKT1, AKT2, AKT3, ALK, ALPHA, ALO17, ALOX12B, AMER1, APC, APCDD1, APH1A, AR, ARAF, ARFRP1, ARHGAP26, ARHGEF12, ARHH, ARID1A, ARID1B, ARID2, ARNT, ASPSCR1, ASMTL, ASXL1, ATF1, ATG5, ATIC, ATM, ATR, ATRX, ATXN1, AURKA, AURKB, AXIN1, AXL, B2M, BACH1, BAP1, BARD1, BCL10, BCL11A, BCL11B, BCL2, BCL2A1, BCL2L1, BCL2L2, BCL3, BCL5, BCL6, BCL7A, BCL9, BCOR, BCORL1, BCR, BIRC3, BLM, BRAF, BRCA1, BRCA2, BRD3, BRD4, BRIP1, BRSK1, BTG1, BTG2, BTK, BTLA, c1orf144, c11orf30, c12orf9, c15orf21, c17orf39, CAD, CALR, CAMTA1, CANT1, CARD11, CARS, CASP8, CBFA2T1, CBFA2T3, CBFB, CBL, CCND1, CCND2, CCND3, CCNE1, CCT6B, CD22, CD247, CD36, CD58, CD70, CD74, CD79A, CD79B, CDC73, CDH1, CDH11, CDH2, CDH20, CDH5, CDK12, CDK4, CDK6, CDK8, CDKN1B, CDKN2A, CDKN2B, CDKN2C, CDX2, CEBPA, CEP1, CHCHD7, CHD2, CHEK1, CHEK2, CHIC2, CHN1, CHTOP, CHUK, CIC, CIITA, CKS1B, CLP1, CLTC, CLTCL1, CMKOR1, CNTRL, COL1A1, COX6C, CPS1, CRBN, CREB1, CREB3L1, CREB3L2, CREBBP, CRKL, CRLF2, CRTC3, CSF1, CSF1R, CSF3R, CTCF, CTNNA1, CTNNB1, CUL4A, CUL4B, CUX1, CXCR4, CYP1B1, CYP17A1, CYP2C19, CYP2C8, CYP2D6, CYP3A4, CYP3A5, D10S170, DAXX, DDIT3, DDR1, DDR2, DDX5, DDX10, DDX3X, DDX6, DEK, DIS3, DKC1, DLEU2, DNM2, DNMT3A, DOT1L, DPYD, DTX1, DUSP2, DUSP22, DUSP9, DUX4, EBF1, ECT2L, EED, EGFR, EIF4A2, ELF4, ELK4, ELKS, ELL, ELN, ELP2, EML4, EMSY, EP300, EPHA3, EPHA5, EPHA6, EPHA7, EPHB1, EPHB4, EPHB6, EPOR, EPS15, ERBB2, ERBB3, ERBB4, ERCC2, ERG, ESR1, ESR2, ETS1, ETV1, ETV4, ETV5, ETV6, EVI1, EWSR1, EXOSC6, EZH2, FACL6, FAF1, FAM46C, FANCA, FANCC, FANCD2, FANCE, FANCF, FANCG, FANCL, FANG, FANCL, FANCM, FAS, FATS, FBXO11, FBXO31, FBXW7, FCGR2B, FCGR3A, FCRL4, FEV, FGF1, FGF10, FGF12, FGF14, FGF19, FGF23, FGF3, FGF4, FGF6, FGF7, FGFR1, FGFR1OP, FGFR2, FGFR3, FGFR4, FHIT, FIP1L1, FLCN, FLI1, FLT1, FLT3, FLT4, FLU, FLYWCH1, FNBP1, FOP, FOXL2, FOXO1, FOXO3, FOXO3A, FOXO4, FOXO1A, FOXP1, FOXP4, FRS2, FSTL3, FUS, FVT1, GADD45B, GAS7, GATA1, GATA2, GATA3, GID4, GLI1, GLIS2, GMPS, GNA11, GNA12, GNA13, GNAQ, GNAS, GOLGA5, GOPC, GPHN, GPR124, GRAF, GRIN2A, GSK3B, GSTP1, GTSE1, GUCY1A2, H4, HCMOGT-1, HDAC1, HDAC4, HDAC7, HEAB, HEM, HERPUD1, HEY1, HGF, HIP1, HIST1H1A, HIST1H1C, HIST1H1D, HIST1H1E, HIST1H2AC, HIST1H2AG, HIST1H2AL, HIST1H2AM, HIST1H2BC, HIST1H2BJ, HIST1H2BK, HIST1H2BO, HIST1H3B, HIST1H4I, HLA-A, HLF, HLXB9, HMGA1, HMGA2, HNF1A, HNRNPA2B1, HOOKS, HOX11, HOXA11, HOXA13, HOXA3, HOXA9, HOXC11, HOXC13, HOXD11, HOXD13, HRAS, HSP90AA1, HSP90AB1, HSPCA, HSPCB, ICK, ID3, IDH1, IDH2, IGF1, IGF1R, IGF2, IGF2R, IGH, IGK, IGL, IKBKE, IKZF1, IKZF2, IKZF3, IL2, IL21R, IL3, IL7R, INHBA, INPP4B, INPP5D, INSR, IRF1, IRF4, IRF8, IRS2, IRTA1, ITPA, ITK, JAK1, JAK2, JAK3, JARID2, JAZF1, JUN, KAT6A, KDM2B, KDM4C, KDM5A, KDM5C, KDM6A, KDR, KDSR, KEAP1, KIF5B, KIT, KLHL6, KIAA1549, KLK2, KMT2A, KMT2B, KMT2C, KRAS, KTN1, LAF4, LASP1, LCK, LCP1, LCX, LEF1, LHFP, LHX4, LIFR, LMO1, LMO2, LPP, LRP1B, LRP2, LRP6, LRRK2, LTK, LYL1, MAF, MAFB, MAGEA5, MAGED1, MALT1, MAML2, MAN1B1, MAP2K1, MAP2K2, MAP2K4, MAP3K1, MAP3K13, MAP3K14, MAP3K6, MAP3K7, MECT1, MCL1, MDM2, MDM4, MDS1, MDS2, MECOM, MECT1, MED12, MEF2B, MEF2C, MEN1, MET, MHC2TA, MIB1, MITF, MKI67, MKL1, MKL2, MLF1, MLH1, MLL2, MLLT1, MLLT10, MLLT2, MLLT3, MLLT4, MLLT6, MLLT7, MLST8, MN1, MNX1, MORF, MPL, MRE11A, MSF, MSH2, MSH3, MSH6, MSI2, MSN, MTAP, MTCP1, MTHFR, MTOR, MUC1, MUTYH, MYB, MYC, MYCL, MYCL1, MYCN, MYD88, MYH11, MYH9, MYO18A, MYST3, MYST4, NACA, NBEAP1, NBN, NCOA1, NCOA2, NCOA4, NCOR1, NCOR2, NCSTN, NDRG1, NF1, NF2, NFE2L2, NFIB, NFKBIA, NFKB1, NFKB2, NFKBIE, NIN, NKX2-1, NOD1, NONO, NOTCH1, NOTCH2, NOTCH3, NOTCH4, NPM1, NQO1, NR4A3, NRP2, NRAS, NSD1, NT5C2, NTRK1, NTRK2, NTRK3, NUMA1, NUP214, NUP93, NUP98, NUT, NUTM2A, OLIG2, OMD, P2RY8, PAFAH1B2, PAG1, PAK3, PAK7, PALB2, PARP1, PARP2, PARP3, PARP4, PALB2, PASK, PAX3, PAX5, PAX7, PAX8, PBRM1, PBX1, PC, PCBP1, PCLO, PCM1, PCSK7, PDCD1, PDCD11, PDCD1LG2, PDE4DIP, PDGFB, PDGFRA, PDGFRB, PDK1, PDL1, PER1, PHF1, PHF6, PHLPP2, PHOX2B, PICALM, PIK3C2G, PIK3C3, PIK3CA, PIK3CG, PIK3R1, PIK3R2, PIM1, PKHD1, PLAG1, PLCG1, PLCG2, PML, PMS2, PMX1, PNRC1, PNUTL1, POT1, POU2AF1, POU5F1, PPARG, PPP1CB, PPP2R1A, PRCC, PRDM1, PRDM16, PRKAR1A, PRKDC, PRRX1, PRO1073, PRSS8, PSIP1, PSIP2, PTCH1, PTCH2, PTEN, PTK2, PTK2B, PTK7, PTPN11, PTPN2, PTPN6, PTPRD, PTPRO, RAB5EP, RABEP1, RAD21, RAD50, RAD51, RAD51B, RAD51C, RAD51D, RAD51L1, RAD52, RAD54L, RAF1, RALGDS, RANBP17, RAP1GDS1, RARA, RASGEF1A, RB1, RBM15, RCOR1, REL, RELN, RET, RHEB, RHOA, RHOH, RICTOR, RMRP, RNF213, RNF43, ROCK1, ROS1, RPA1, RPL11, RPL13, RPL15, RPL22, RPL35A, RPN1, RPS14, RPS15, RPS19, RPS26, RPTOR, RUNX1, RUNX1T1, RUNX2, RUNXBP2, RUNXT1, S1PR2, SBDS, SDHA, SDHB, SDHC, SDHD, SEC31A, SEPT5, SEPT6, SEPT9, SERP2, SET, SETBP1, SETD2, SF3B1, SFPQ, SFRS3, SGK1, SH2B3, SH3GL1, SIL, SLC1A2, SLC19A1, SLC22A2, SLC45A3, SLCO1B3, SMAD2, SMAD3, SMAD4, SMARCA1, SMARCA4, SMARCB1, SMARCD1, SMC1A, SMC3, SMO, SNX29, SPOP, SOCS1, SOCS2, SOCS3, SOD2, SOX10, SOX2, SPEN, SPOP, SRC, SRGAP3, SRSF2, SRSF3, SS18, SS18L1, SSH3BP1, SSX1, SSX2, SSX4, STAG2, STAT5, STAT4, STAT5A, STAT5B, STAT6, STK11, STK12, STL, SUFU, SULT1A1, SUZ12, SYK, TAF1, TAF15, TAL1, TAL2, TBL1XR1, TBX22, TBX23, TBX3, TCEA1, TCF12, TCF3, TCL1A, TCL6, TEC, TET1, TET2, TFE3, TFEB, TFG, TFPT, TFRC, TGFBR2, THRAP3, TIF1, TIPARP, TLL2, TLX1, TLX3, TMEM30A, TMPRSS2, TMSB4XP8, TNFAIP3, TNFRSF11A, TNFRSF14, TNFRSF17, TNFSF9, TNKS, TNKS2, TOP1, TP53, TP63, TPM3, TPM4, TPMT, TPR, TRA, TRAF2, TRAF3, TRAF5, TRB, TRD, TRG, TRIM24, TRIM27, TRIM33, TRIP11, TRRAP, TSC, TSC1, TSC2, TSHR, TTL, TUSC3, TYK2, TYMS, U2AF1, U2AF2, UG T1A1, UMPS, USP6, USP9X, VHL, WDR90, WHSC1, WHSC1L1, WISPS, WT1, XBP1, XPO1, XRCC3, YPEL5, YY1AP1, ZBTB16, ZMYM2, ZMYM3, ZNF145, ZNF198, ZNF217, ZNF24, ZNF278, ZNF331, ZNF384, ZNF521, ZNF703, ZNF9, ZNFN1A1, ZRSR2, and an MHC gene.

5. The method of claim 1, wherein step (c) comprises:
sequencing a plurality of occurrences of the subgenomic interval and the expressed subgenomic interval.

6. The method of claim 1, wherein a clonal profile for a clone of a cancer is provided.

7. The method of claim 1, wherein a clonal profile for a first V segment, or a first V segment and a second V segment, is provided.

8. The method of claim 1, wherein a clonal profile for a first D segment, or a first D segment and a second D segment, is provided.

9. The method of claim 1, wherein a clonal profile for a first J segment, or a first J segment and a second J segment, is provided.

10. The method of claim 1, wherein a clonal profile for a first VDJ or VJ combination, or a second VDJ or VJ combination, is provided.

11. The method of claim 1, wherein a clonal profile for an antibody light chain, or an antibody light chain and an antibody heavy chain, is provided.

12. The method of claim 1, wherein a clonal profile for a sequence, allele, or signature in a subgenomic interval, or an expressed subgenomic interval, is provided.

13. The method of claim 1, wherein a clonal profile is provided, and wherein the clonal profile comprises:
   (i) variability for hypermutation in a locus chosen from a V, D, or J segment in the expressed subgenomic interval;
   (ii) variability arising from a VD, DJ, or VJ junction by a formation of an indel at the junction in the expressed subgenomic interval; or
   (iii) variability in a CDR in the expressed subgenomic interval.

14. The method of claim 1, wherein the expressed subgenomic interval comprises a sequence encoding an antibody; an antibody light chain; an antibody heavy chain; a variable region; a heavy chain variable region; a light chain variable region; a constant region; a heavy chain constant region; a light chain constant region; a kappa light chain sequence; a lambda light chain sequence; a portion of a constant region that can distinguish one or more Ig classes or subclasses; a CDR; a light chain CDR1; a light chain CDR2; a light chain CDR3; a heavy chain CDR1; a heavy chain CDR2; a heavy chain CDR3; a T cell receptor; an alpha chain of a T cell receptor; a beta chain of a T cell receptor; a delta chain of a T cell receptor; a gamma chain of a T cell receptor; a sequence encoding an antibody variable region; a sequence encoding a B cell receptor variable region; a sequence encoding a T cell receptor variable region; a sequence encoding an antibody diversity region; a sequence encoding a B cell receptor diversity region; a sequence encoding a T cell receptor diversity region; a sequence encoding an antibody joining region; a sequence encoding a B cell receptor joining region; a sequence encoding a T cell receptor joining region; a sequence encoding an antibody switch region; a sequence encoding a B cell receptor switch region; a sequence encoding a T cell receptor switch region; a sequence encoding an antibody constant region; a sequence encoding a B cell receptor constant region; a sequence encoding a T cell receptor constant region; a sequence encoding a V segment, prior to rearrangement, of an antibody; a sequence encoding a V segment, prior to rearrangement, of an Ig superfamily-receptor; a sequence encoding a V segment, prior to rearrangement, of an immunoglobulin gene; a sequence encoding a V segment, prior to rearrangement, of a T cell receptor; a sequence encoding a V segment, prior to rearrangement, of a B cell receptor; a sequence encoding a V segment, after rearrangement, of an antibody; a sequence encoding a V segment, after rearrangement, of an Ig superfamily-receptor; a sequence encoding a V segment, after rearrangement, of an immunoglobulin gene; a sequence encoding a V segment, after rearrangement, of a T cell receptor; a sequence encoding a V segment, after rearrangement, of a B cell receptor; a sequence encoding a D segment, prior to rearrangement, of an antibody; a sequence encoding a D segment, prior to rearrangement, of an Ig superfamily-receptor; a sequence encoding a D segment, prior to rearrangement, of an immunoglobulin gene; a sequence encoding a D segment, prior to rearrangement, of a T cell receptor; a sequence encoding a D segment, prior to rearrangement, of a B cell receptor; a sequence encoding a D segment, after rearrangement, of an antibody; a sequence encoding a D segment, after rearrangement, of an Ig superfamily-receptor; a sequence encoding a D segment, after rearrangement, of an immunoglobulin gene; a sequence encoding a D segment, after rearrangement, of a T cell receptor; a sequence encoding a D segment, after rearrangement, of a B cell receptor; a sequence encoding a J segment, prior to rearrangement, of an antibody; a sequence encoding a J segment, prior to rearrangement, of an Ig superfamily-receptor; a sequence encoding a J segment, prior to rearrangement, of an immunoglobulin gene; a sequence encoding a J segment, prior to rearrangement, of a T cell receptor; a sequence encoding a J segment, prior to rearrangement, of a B cell receptor; a sequence encoding a J segment, after rearrangement, of an antibody; a sequence encoding a J segment, after rearrangement, of an Ig superfamily-receptor; a sequence encoding a J segment, after rearrangement, of an immunoglobulin gene; a sequence encoding a J segment, after rearrangement, of a T cell receptor; a sequence encoding a J segment, after rearrangement, of a B cell receptor; a sequence encoding V, D, and J segments, prior to rearrangement, of an antibody; a sequence encoding V, D, and J segments, prior to rearrangement, of an Ig superfamily-receptor; a sequence encoding V, D, and J segments, prior to rearrangement, of an immunoglobulin gene; a sequence encoding V, D, and J segments, prior to rearrangement, of a T cell receptor; a sequence encoding V, D, and J segments, prior to rearrangement, of a B cell receptor; a sequence encoding V, D, and J segments, after rearrangement, of an antibody; a sequence encoding V, D, and J segments, after rearrangement, of an Ig superfamily-receptor; a sequence encoding V, D, and J segments, after rearrangement, of an immunoglobulin gene; a sequence encoding V, D, and J segments, after rearrangement, of a T cell receptor; a sequence encoding V, D, and J segments, after rearrangement, of a B cell receptor; a sequence encoding V and J segments, prior to rearrangement, of an antibody; a sequence encoding V and J segments, prior to rearrangement, of an Ig superfamily-receptor; a sequence encoding V and J segments, prior to rearrangement, of an immunoglobulin gene; a sequence encoding V and J segments, prior to rearrangement, of a T cell receptor; a sequence encoding V and J segments, prior to rearrangement, of a B cell receptor; a sequence encoding V and J segments, after rearrangement, of an antibody; a sequence encoding V and J segments, after rearrangement, of an Ig superfamily-receptor; a sequence encoding V and J segments, after rearrangement, of an immunoglobulin gene; a sequence encoding V and J segments, after rearrangement, of a T cell receptor; a sequence encoding V and J segments, after rearrangement, of a B cell receptor; a sequence comprising a VD junction of an Ig superfamily receptor; a sequence comprising a VD junction of an immunoglobulin gene; a sequence comprising a VD junction of a T cell receptor; a sequence comprising a VD junction of a B cell receptor; a sequence comprising a DJ junction of an Ig superfamily receptor; a sequence comprising a DJ junction of an immunoglobulin gene; a sequence comprising a DJ junction of a T cell receptor; a sequence comprising a DJ junction of a B cell receptor; a sequence comprising a VJ junction of an Ig superfamily receptor; a sequence comprising a VJ junction of an immunoglobulin gene; a sequence comprising a VJ junction of a T cell receptor; or a sequence comprising a VJ junction of a B cell receptor.

15. The method of claim 1, wherein the expressed subgenomic interval comprises a V, D, or J segment.

16. The method of claim 1, wherein the first portion of the bait set:
(i) is configured to capture or hybridize with a V segment and not a D or J segment; a D segment and not a V or J segment; a J segment and not a V or D segment; a V segment; a D segment; or a J segment; or
(ii) comprises one or more baits that span a VD junction, a DJ junction, a VJ junction, a rearranged VDJ sequence, or a rearranged VJ sequence.

17. The method of claim 1,
wherein one of steps (a), (b) and (c) is performed separately for the subgenomic interval and for the expressed subgenomic interval.

18. The method of claim 1, wherein one of steps (a), (b) and (c) is performed in a first reaction mixture for the expressed subgenomic interval and in a second reaction mixture for the subgenomic interval.

19. The method of claim 1, further comprising acquiring a sequence of a second different subgenomic interval for the malignant cell, wherein at least one of steps (a), (b) and (c) is performed in the same reaction mixture for the subgenomic interval and for a second subgenomic interval.

20. The method of claim 1, comprising repeating steps (a) to (c).

21. The method of claim 1, wherein the library is made from: a disease state tissue, cancer cells, a solid tumor, B cells or T cells that have infiltrated a solid tumor, a hematologic malignancy, cell free DNA, a non-disease state tissue, peripheral blood, bone marrow, tumor tissue, tumor infiltrate, lymphocytes, B cells, peripheral B cells, pre-B cells, mature B cells, T cells, or tumor infiltrating cells.

22. The method of claim 1, wherein the expressed subgenomic interval comprises a nucleotide position, or a junction, or a sequence, representative of: a clonal event, a T cell clone or B cell clone.

23. The method of claim 1, comprising attaching an adaptor sequence to the 5' or 3' end of the nucleic acid from the subject in each member of the plurality of members.

24. The method of claim 1, further comprising providing a sequence of the subgenomic interval.

25. The method of claim 1, further comprising amplifying each member of the plurality of selected members.

* * * * *